US009057083B2

(12) United States Patent
Yadav et al.

(10) Patent No.: US 9,057,083 B2
(45) Date of Patent: Jun. 16, 2015

(54) FUNGAL Δ-12 DESATURASE AND Δ-15 DESATURASE MOTIFS

(75) Inventors: Narendra S. Yadav, Wilmington, DE (US); Hongxiang Zhang, Chadds Ford, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 854 days.

(21) Appl. No.: 12/396,845

(22) Filed: Mar. 3, 2009

(65) Prior Publication Data
US 2009/0186362 A1 Jul. 23, 2009

Related U.S. Application Data

(62) Division of application No. 11/740,298, filed on Apr. 26, 2007, now abandoned.

(60) Provisional application No. 60/796,637, filed on May 1, 2006.

(51) Int. Cl.
C12N 9/02 (2006.01)
C12P 7/64 (2006.01)
C12Q 1/26 (2006.01)
C07H 21/04 (2006.01)
C12Q 1/68 (2006.01)

(52) U.S. Cl.
CPC ............... *C12P 7/6427* (2013.01); *C12N 9/001* (2013.01); *C12N 9/0083* (2013.01); *C12P 7/6472* (2013.01); *C12Q 1/6895* (2013.01)

(58) Field of Classification Search
CPC ........... C12N 15/8247; C12N 15/8243; C12N 15/1034; C12N 9/0004; C12N 15/80; C12N 15/81; C12P 7/6427; C12P 7/6472; C12P 7/6463; C12P 7/6409; C12P 7/64; A23V 2002/00; A23V 2250/1874; C07K 2319/71; C07K 14/39; C07K 14/37
See application file for complete search history.

(56) References Cited

U.S. PATENT DOCUMENTS

| | | | |
|---|---|---|---|
| 5,952,544 | A | 9/1999 | Browse et al. |
| 6,342,658 | B1 | 1/2002 | DeBonte et al. |
| 7,125,672 | B2 | 10/2006 | Picatagglo et al. |
| 7,189,559 | B2 | 3/2007 | Damude et al. |
| 7,192,762 | B2 | 3/2007 | Macool et al. |
| 7,198,937 | B2 | 4/2007 | Xue et al. |
| 7,202,356 | B2 | 4/2007 | Pollak et al. |
| 2003/0196217 | A1 | 10/2003 | Mukerji et al. |
| 2003/0233675 | A1* | 12/2003 | Cao et al. ............ 800/279 |
| 2006/0156435 | A1 | 7/2006 | Ursin et al. |

FOREIGN PATENT DOCUMENTS

| | | |
|---|---|---|
| EP | 1790720 A1 | 5/2007 |
| WO | 03099216 A2 | 12/2003 |
| WO | WO 03/099216 A2 | 12/2003 |
| WO | WO 2005/047479 A2 | 5/2005 |
| WO | WO 2005/047480 A2 | 5/2005 |
| WO | WO 2005/047485 A2 | 5/2005 |
| WO | WO 2005/083093 A2 | 9/2005 |
| WO | WO 2006/019192 A1 | 2/2006 |

OTHER PUBLICATIONS

Oura et al. *Saccharomyces kluyveri* FAD3 encodes an omega3 fatty acid desaturase, 2004, 150: 1983-1990.*
Chica et al. Semi-rational approaches to engineering enzyme activity: combining the benefits of directed evolution and rational design, Curr Opin Biotechnol. Aug. 2005;16(4):378-84. Review.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Jones et al. (PNAS 101: 7329-7334, Apr. 26, 2005).*
Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36)11643-50.*
Wei, Dongsheng et al., Identification and characterization of a novel delta12-fatty acid desaturase gene from *Rhizopus arrhizus*, FEB Letters, 2004, pp. 45-50, vol. 573, Elsevier B. V.
Jones, Ted et al., The diploid genome sequence of *Candida albicans*, Proceedings of the National Academy of Sciences of the USA, May 11, 2004, pp. 7329-7334, vol. 101, No. 19, The National Academy of Sciences of the USA.
Dujon, Bernard et al., Genome evolution in yeasts, Nature, Jul. 1, 2004, pp. 35-44, vol. 430, Nature Publishing Group.
Pain, Arnab et al., Insight into the genome of *Aspergillus fumigatus*: analysis of a 922 kb region encompassing the nitrate assimilation gene cluster, Fungal Genetics and Biology, 2004, pp. 443-453, vol. 41, Elsevier Inc.
Kelder, Bruce et al., Expression of fungal desaturase genes in cultured mammalian cells, Molecular and Cellular Biochemistry, 2001, pp. 7-11, vol. 219, Kluwer Academic Publishers.
Jones T. et al., Database EBI Accession No. Q5AL44, Likely delta-12 fatty acid desaturase, Apr. 26, 2005.
Jones T. et al., Database EBI Accession No. Q59WT3, Likely delta-12 fatty acid desaturase, Apr. 26, 2005.

(Continued)

*Primary Examiner* — Iqbal H Chowdhury

(57) ABSTRACT

The present invention relates to fungal Δ12 desaturases (responsible for conversion of oleic acid to linoleic acid (18:2, LA)) and Δ15 fatty acid desaturases (responsible for conversion of LA to α-linolenic acid (18:3, ALA)). Amino acid motifs diagnostic of Δ12 desaturases and Δ15 desaturases are also provided. Methods of altering enzyme specificity towards Δ12 desaturation or towards Δ15 desaturation and/or increasing production of specific ω-3 and ω-6 fatty acids by over-expression of the fungal desaturases are also described.

2 Claims, 8 Drawing Sheets

(56) References Cited

OTHER PUBLICATIONS

Figure 1A:
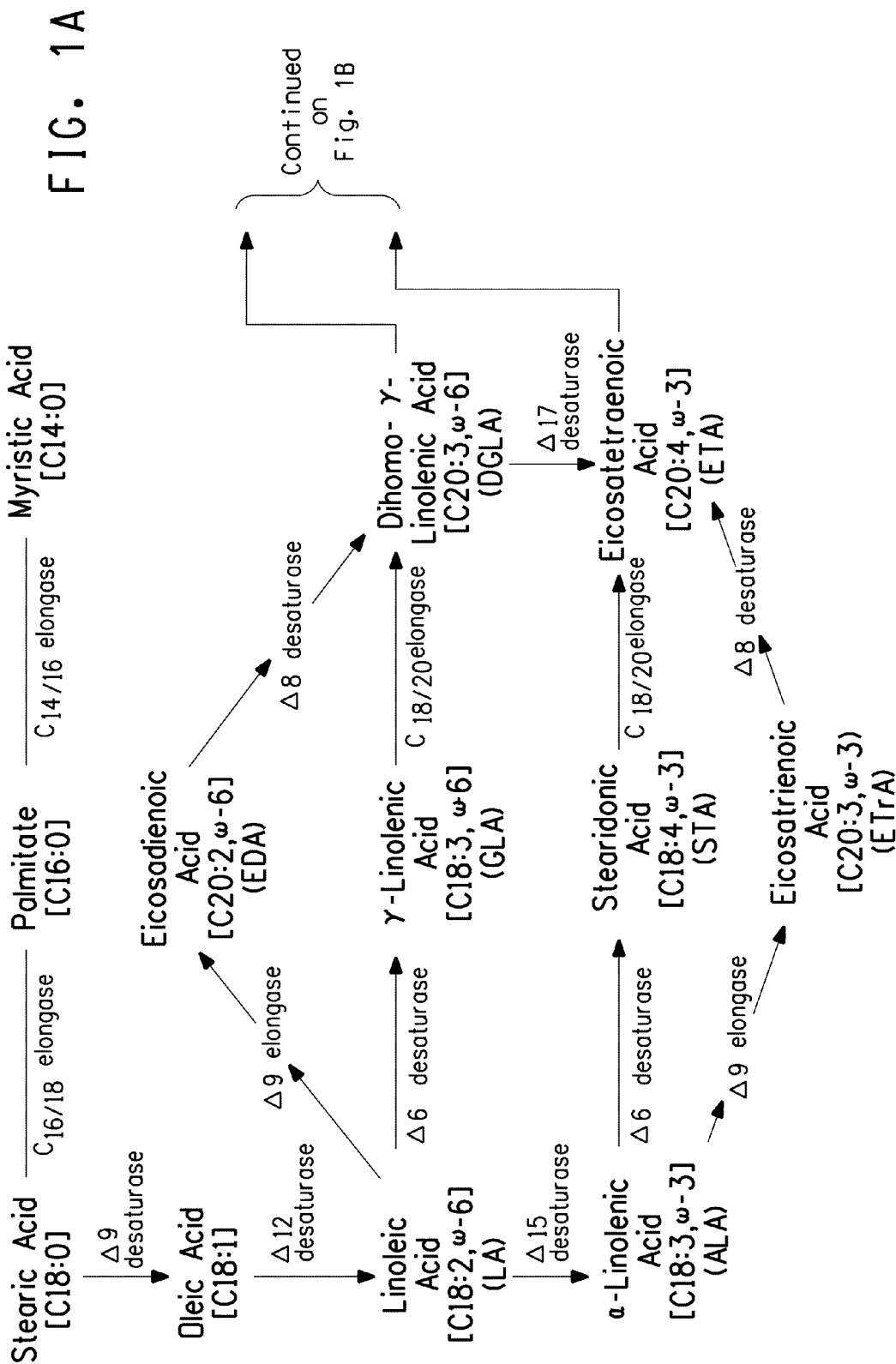

Dujon, B. et al., Database EBI Accession No. Q6BJ43, Similar to CA0482 | IPF14763 *Candida albicans* IPF14763 delta-12 fatty acid desaturase, Aug. 16, 2004.
Dujon, B. et al., Database EBI Accession No. Q6CWY8, Similar to ca | CA3604 | IPF12942 *Candida albicans* delta-12 fatty acid desaturase, Aug. 16, 2004.
Dujon, B. et al., Database EBI Accession No. Q6CKY7, Similar to ca | CA0482 | IPF14763 *Candida albicans* delta-12 fatty acid desaturase, Aug. 16, 2004.
Dujon, B. et al., Database EBI Accession No. Q6BPD2, Similar to CA3604 | IPF12942 *Candida albicans* IPF12942 delta-12 fatty acid desaturase, Aug. 16, 2004.
Pain, A. et al., Database EBI Accession No. Q6MYN1, Oleate delta-12 desaturase, Jul. 5, 2004.
International Search Report, International Application No. PCT/US2007/010256, International Filing Date Apr. 26, 2007.
Birren, B. W. et al., Database Uniprot Accession No. Q2H780, Putative uncharacterized protein, Mar. 21, 2006.
Machida, M. et al., Database Uniprot Accession No. Q2TW42, Fatty acid desaturase, Jan. 24, 2006.
Machida, M. et al., Genome sequencing and analysis of *Aspergillus oryzae*, Nature, Dec. 2005, pp. 1157-1161, vol. 438, 22/29, Nature Publishing Group.
International Search Report dated Mar. 13, 2008, International Application No. PCT/US2007/010256.
International Preliminary Report on Patentability and Written Opinion in corresponding PCT application No. PCT/US2007/011717, dated Nov. 27, 2008.
U.S. Appl. No. 10/840,579, filed May 6, 2004, Stephen Picataggio et al.
U.S. Appl. No. 10/840,325, filed May 6, 2004, Narendra S. Yadav et al.
U.S. Appl. No. 10/869,630, filed Jun. 16, 2004, Stephen Picataggio et al.
U.S. Appl. No. 10/882,760, filed Jul. 1, 2004, Narendra S. Yadav et al.
U.S. Appl. No. 10/985,254, filed Nov. 10, 2004, Narendra S. Yadav et al.
U.S. Appl. No. 10/985,691, filed Nov. 10, 2004, Narendra S. Yadav et al.
U.S. Appl. No. 11/024,544, filed Dec. 29, 2004, Narendra S. Yadav et al.
U.S. Appl. No. 11/166,993, filed Jun. 24, 2005, Howard Glenn Damude et al.
U.S. Appl. No. 11/183,664, filed Jul. 18, 2005, Stephen Picataggio et al.
U.S. Appl. No. 11/185,301, filed Jul. 20, 2005, Zhixiong Xue et al.
U.S. Appl. No. 11/190,750, filed Jul. 27, 2005, Stephen Picataggio et al.
U.S. Appl. No. 11/198,975, filed Aug. 8, 2005, Quinn Qun Zhu et al.
U.S. Appl. No. 11/225,354, filed Sep. 13, 2005, Zhixiong Xue et al.
U.S. Appl. No. 11/253,882, filed Oct. 19, 2005, Daniel Joseph Macool et al.
U.S. Appl. No. 11/264,784, filed Nov. 1, 2005, Howard Glenn Damude et al.
U.S. Appl. No. 11/264,737, filed Nov. 1, 2005, Howard Glenn Damude et al.
U.S. Appl. No. 11/265,761, filed Nov. 2, 2005, Howard Glenn Damude et al.
U.S. Appl. No. 60/795,810, filed Apr. 28, 2006, Howard Glenn Damude et al.
U.S. Appl. No. 60/793,575, filed Apr. 20, 2006, Zhixiong Xue et al.
U.S. Appl. No. 60/796,637, filed May 1, 2006, Narendra S. Yadav et al.
U.S. Appl. No. 60/801,172, filed May 17, 2006, Howard Glenn Damude et al.
U.S. Appl. No. 60/801,119, filed May 17, 2006, Howard Glenn Damude et al.
U.S. Appl. No. 60/853,563, filed Oct. 23, 2006, Howard Glenn Damude et al.
U.S. Appl. No. 60/855,177, filed Oct. 30, 2006, Zhixiong Xue et al.
U.S. Appl. No. 11/601,563, filed Nov. 16, 2006, Howard Glenn Damude et al.
U.S. Appl. No. 11/601,564, filed Nov. 16, 2006, Howard Glenn Damude et al.
U.S. Appl. No. 11/635,258, filed Dec. 7, 2006, Howard Glenn Damude et al.
U.S. Appl. No. 11/613,420, filed Dec. 20, 2006, John E. Seip et al.
J. Dyerberg et al., Fatty Acid Composition of the Plasma Lipids in Greenland Eskimos, Amer. J. Clin. Nutr., 1975, vol. 28:958-966.
J. Dyerberg et al., Eicosapentaenoic Acid and Prevention of Thrombosis and Atherosclerosis?, Lancet, 1978, vol. 2:117-119.
H. Shimokawa, Beneficial Effects of Eicosapentaenoic Acid on Endothelial Vasodilator Functions in Animals and Humans, World Rev. Nutr. Diet, 2001, vol. 88:100-108.
C. vonSchacky et al., Fatty Acids From Eskimos to Clinical Cardiology—What Took Us So Long?, World Rev. Nutr. Diet, 2001, vol. 88:90-99.
Kainou et al., Isolation of 12 and 3 Fatty Acid Desaturase Genes From the Yeast *Kluyveromyces lactis* and Their Heterologous Expression to Produce Linoleic and X-Linolenic Acids in *Saccharomyces cerevisiae*, Yeast, 2006, vol. 23:605-612.
Murayama et al., Construction and Functional Analysis of Fatty Acids Desaturase Gene Disruptants in *Candida albicans*, Microbiol., 2006, vol. 152:1551-1558.
National Center for Biotechnology Information General Identifier No. 44885796, Oct. 7, 2006, Oura et al., *Saccharomyces kluyveri* FAD3 ENcodes on Omega3 Fatty Acid Desaaturase, Accession No. BAD11952.
Oura et al., *Saccharomyces Kluyveri* FAD3 Encodes an 3 Fatty Acid Desaturase, Microbiol., 2004, vol. 150:1983-1990.
National Center for Biotechnology Information General Identifier No. 62084355, Mar. 26, 2005, E. Sakuradani et al., A Novel Fungal Omega3-Desaturase With Wide Substrate Specificity From Arachidonic Acid-Producing Mortierella Alpina 1S-4, Accession No. AB182163.
Sakuradani et al., A Novel Fungal W3-Desaturase With Wide Substrate Specificity From Arachidonic Acid-Producing Mortierella Alpina 1S-4, Appl. Microbiol. Biotechnol., 2005, vol. 66:648-654.
National Center for Biotechnology Information General Identifier No. 41529188, Jul. 17, 2004, K. Watanabe et al., Yeast Delta 12 Fatty Acid Desaturase: Gene Cloning Expression, and Function, Accession No. BAD08375.
Watanabe et al., Yeast 12 Fatty Acid Desaturase: Gene Cloning, Expression, and Function, Biosci. Biotech. Biochem., 2004, vol. 68:721-727.
National Center for Biotechnology Information General Identifier No. 5257239, Jun. 26, 1999, E. Sakuradani et al., Identification of Delta12-Fatty Acid Desaturase From Arachidonic Acid-Producing *Mortierella* Fungus by Heterologous Expression in the Yeast *Saccharomyces cerevisiae* and the Fungus *Aspergillus oryzae*, Accession No. BAA81754.
Sakuradani et al., Identification of 12 Fatty Acid Desaturase From Arachidonic Acid-Producing *Mortierella* Fungus by Heterologous Expression in the Yeast *Saccharomyces cerevisiae* and the Fungus *Aspergillus oryzae*, Eur. J. Biochem., 1999, vol. 261:812-820.
National Center for Biotechnology Information General Identifier No. 82658702, Jun. 21, 2006, H.G. Damude et al., Identification of Biofunctional (Delta) 12/Omega 3 to Omega 6 Fatty Acids in Microbes and Plants, Accession No. DQ272515.
National Center for Biotechnology Information General Identifier No. 67517709, Sep. 29, 2005, B. Birren et al., Accession No. XM658641.
National Center for Biotechnology Information General Identifier No. 145604939, R.A. Dean et al., The Genome Sequence of the Rice BLST Fungus *Magnaporthe*, Genbank XP365283.
National Center for Biotechnology Information General Identifier No. 32418755, J.E. Galagan et al., Accession No. XP329856.
National Center for Biotechnology Information General Identifier No. 42553016, Feb. 13, 2004, B. Birren et al., Genome Sequence of *Fusarium graminearum*, Accession No. EAA75859.

(56) References Cited

OTHER PUBLICATIONS

Pereira et al., A Novel 3 Fatty Acid Desaturase Involved in the Biosynthesis of Eicosapentaenoic Acid, Biochem. J., 2004, vol. 378:665-671.

Damude et al., Identification of Bifunctional 12/3 Fatty Acid Desaturases for Improving the Ratio of w3 to w6 Fatty Acids in Microbes and Plants, PNAS, 2006, vol. 103:9446-9451.

* cited by examiner

| | Af. d12 | Af. d15 | An. d12 | An. d15 | Ca. d12 | Ca. d15 | Cg. d12 | Cg. d15 | Cl. d12 | Cl. d15 | Ct. d12 | Ct. d15 | Dh. d12 | Dh. d15 | Fg. d12 | Fg. d15 | Fm. d12 | Fm. d15 | Kl. d12 |
|---|---|---|---|---|---|---|---|---|---|---|---|---|---|---|---|---|---|---|---|
| Af.d12 | *** | 36.2 | 82.7 | 35.2 | 47.3 | 44.1 | 45.0 | 39.9 | 47.8 | 36.2 | 39.7 | 36.9 | 44.6 | 43.1 | 60.1 | 35.6 | 61.8 | 36.2 | 45.4 |
| Af.d15 | 100.7 | *** | 42.7 | 55.3 | 38.1 | 42.4 | 36.9 | 40.2 | 39.4 | 36.9 | 35.9 | 36.4 | 36.9 | 39.1 | 41.7 | 46.0 | 41.9 | 47.7 | 41.4 |
| An.d12 | 19.7 | 101.5 | *** | 33.7 | 48.7 | 44.5 | 45.1 | 40.7 | 48.3 | 35.8 | 41.1 | 37.3 | 43.4 | 44.3 | 59.1 | 37.1 | 61.4 | 37.1 | 45.3 |
| An.d15 | 105.4 | 63.8 | 110.9 | *** | 40.1 | 36.4 | 36.7 | 36.2 | 38.9 | 33.9 | 34.9 | 32.4 | 35.7 | 37.2 | 40.1 | 44.9 | 39.4 | 45.4 | 38.2 |
| Ca.d12 | 75 | 114.5 | 70.7 | 103.3 | *** | 56.9 | 65.8 | 50.7 | 67.2 | 46.1 | 67.7 | 47.5 | 66.3 | 56.7 | 46.3 | 36.9 | 46.6 | 38.3 | 59.6 |
| Ca.d15 | 82.7 | 99.4 | 81.1 | 120.1 | 59.1 | *** | 53.1 | 68.4 | 54.7 | 62.8 | 47.8 | 69.5 | 54.7 | 77.1 | 47.8 | 36.5 | 48.5 | 36.7 | 53.8 |
| Cg.d12 | 77.6 | 119.7 | 76.4 | 117.4 | 40.2 | 66.2 | *** | 53.6 | 66.7 | 47.1 | 58.1 | 48.3 | 73.4 | 56.7 | 46.7 | 37.8 | 45.9 | 38.8 | 58.6 |
| Cg.15 | 77 | 98.1 | 73.5 | 111.3 | 54.4 | 23.6 | 52.8 | *** | 61.2 | 70.6 | 54.2 | 74.4 | 59.6 | 81.7 | 52.0 | 41.5 | 52.3 | 41.5 | 61.2 |
| Cl.d12 | 70.1 | 108.8 | 67.9 | 107.6 | 38.4 | 63.0 | 43.0 | 50.9 | *** | 49.2 | 58.5 | 48.9 | 68.5 | 57.8 | 49.6 | 38.7 | 48.4 | 40.3 | 61.6 |
| Cl.d15 | 80.6 | 97.1 | 81.4 | 108.8 | 56.9 | 25.2 | 59.4 | 27.1 | 53.6 | *** | 56.8 | 80.7 | 55.9 | 76.1 | 52.7 | 39.8 | 51.9 | 40.1 | 60.2 |
| Ct.d12 | 68.5 | 100.7 | 63.2 | 103.6 | 14.6 | 54.1 | 35.9 | 55.5 | 34.6 | 59.0 | *** | 61.0 | 70.1 | 58.7 | 52.2 | 44.0 | 51.6 | 45.2 | 65.4 |
| Ct.d15 | 79.5 | 100.4 | 77.2 | 117.0 | 54.4 | 15.2 | 57.4 | 22.4 | 55.2 | 22.4 | 53.5 | *** | 57.1 | 79.7 | 50.9 | 39.7 | 50.9 | 40.0 | 58.0 |
| Dh.d12 | 77.9 | 119.3 | 80.5 | 120.5 | 39.1 | 62.1 | 31.2 | 54.4 | 38.8 | 59.8 | 36.1 | 57.2 | *** | 58.4 | 46.4 | 35.8 | 45.7 | 37.5 | 63.2 |
| Dh.d15 | 86.7 | 111.3 | 82.4 | 116.9 | 60.2 | 27.3 | 62.4 | 21.1 | 60.4 | 28.5 | 58.3 | 23.4 | 59.3 | *** | 47.4 | 35.6 | 47.6 | 36.3 | 55.9 |
| Fg.d12 | 51.3 | 102.8 | 52.8 | 108.3 | 88.0 | 82.7 | 87.3 | 72.8 | 79.2 | 71.0 | 73.8 | 75.7 | 88.0 | 84.0 | *** | 36.8 | 47.6 | 37.3 | 44.7 |
| Fg.d15 | 104.7 | 88.1 | 97.9 | 89.7 | 105.2 | 109.6 | 106.9 | 100.3 | 102.8 | 103.1 | 90.3 | 103.3 | 115.3 | 112.4 | 102.4 | *** | 95.0 | 88.8 | 38.2 |
| Fm.d12 | 52.9 | 104.1 | 53.4 | 111.9 | 88.9 | 82.1 | 91.1 | 72.2 | 83.8 | 73.1 | 75.7 | 75.7 | 91.9 | 84.6 | 5.2 | 106.5 | *** | 34.8 | 42.8 |
| Fm.d15 | 101.7 | 82.7 | 97.6 | 87.8 | 99.5 | 108.2 | 102.8 | 100.3 | 96.3 | 102.0 | 86.7 | 102.3 | 108.0 | 109.2 | 100.3 | 11.9 | 105.2 | *** | 40.3 |

FIG. 3A

| Kl. d15 | Ma. d12 | Ma. d15 | Mg. d12 | Mg. d15 | Nc. d12 | Nc. d15 | Sk. d12 | Sk. d15 | Ro. d12 | Cc. d12 | Mc. d12 | Mr. d12 | Cn. d12 | Chg. d15 | Chg. d12 | Ao. d15 | Ao. d12 | |
|---|---|---|---|---|---|---|---|---|---|---|---|---|---|---|---|---|---|---|
| 43.5 | 37.1 | 33.7 | 67.4 | 34.8 | 66.3 | 35.0 | 45.8 | 42.9 | 37.1 | 38.8 | 35.0 | 31.1 | 38.4 | 36.0 | 45.6 | 36.2 | 86.1 | Af.d12 |
| 38.9 | 37.9 | 36.1 | 43.4 | 47.5 | 42.7 | 49.5 | 42.2 | 37.4 | 35.9 | 38.9 | 36.1 | 32.3 | 37.9 | 49.2 | 30.1 | 78.5 | 42.7 | Af.d15 |
| 44.3 | 35.8 | 33.3 | 65.7 | 36.2 | 67.2 | 35.0 | 46.4 | 43.9 | 36.4 | 38.6 | 35.4 | 31.6 | 38.3 | 37.1 | 44.1 | 35.6 | 83.5 | An.d12 |
| 37.9 | 35.9 | 33.9 | 40.9 | 45.6 | 42.1 | 49.1 | 38.9 | 35.7 | 34.9 | 37.2 | 35.9 | 33.9 | 37.9 | 50.1 | 28.4 | 52.1 | 39.2 | An.d15 |
| 54.8 | 36.2 | 32.1 | 49.3 | 36.0 | 50.9 | 36.9 | 59.4 | 51.8 | 36.9 | 41.1 | 37.2 | 33.3 | 42.2 | 38.5 | 31.4 | 35.6 | 51.6 | Ca.d12 |
| 64.9 | 34.2 | 32.6 | 49.7 | 37.0 | 49.2 | 34.2 | 53.1 | 61.7 | 34.4 | 38.3 | 34.4 | 31.6 | 40.0 | 37.0 | 32.1 | 36.5 | 46.4 | Ca.d15 |
| 52.9 | 36.8 | 33.0 | 48.6 | 35.4 | 52.6 | 35.2 | 59.8 | 52.6 | 38.3 | 40.7 | 37.1 | 32.1 | 41.4 | 36.6 | 32.5 | 33.5 | 51.9 | Cg.d12 |
| 70.9 | 37.2 | 37.2 | 54.4 | 42.6 | 53.6 | 39.4 | 61.2 | 69.0 | 38.0 | 46.1 | 37.5 | 34.0 | 44.7 | 40.4 | 33.7 | 41.0 | 50.9 | Cg.15 |
| 57.3 | 37.9 | 33.7 | 52.0 | 39.6 | 52.0 | 39.4 | 62.5 | 57.3 | 39.9 | 43.2 | 37.7 | 34.1 | 43.4 | 40.1 | 33.4 | 37.7 | 54.4 | Cl.d12 |
| 68.9 | 36.9 | 35.2 | 53.6 | 40.6 | 52.4 | 40.1 | 57.9 | 66.0 | 38.0 | 43.8 | 38.0 | 34.6 | 42.9 | 40.3 | 30.8 | 40.3 | 48.4 | Cl.d15 |
| 58.9 | 43.4 | 37.2 | 54.0 | 41.3 | 56.3 | 42.5 | 64.5 | 54.8 | 41.6 | 46.3 | 41.3 | 37.0 | 47.5 | 42.5 | 32.3 | 41.6 | 54.8 | Ct.d12 |
| 71.7 | 37.7 | 35.4 | 51.1 | 39.1 | 50.3 | 38.3 | 57.4 | 67.1 | 36.0 | 43.4 | 36.6 | 33.7 | 43.4 | 40.0 | 28.9 | 40.0 | 49.1 | Ct.d15 |
| 57.2 | 36.8 | 33.4 | 49.0 | 36.5 | 51.0 | 37.3 | 62.3 | 55.0 | 38.2 | 40.6 | 37.0 | 32.0 | 40.4 | 37.5 | 32.2 | 35.1 | 50.0 | Dh.d12 |
| 63.4 | 34.5 | 32.9 | 49.0 | 36.8 | 49.2 | 35.9 | 54.0 | 61.1 | 33.8 | 40.0 | 33.6 | 30.6 | 39.3 | 37.0 | 32.9 | 35.2 | 47.1 | Dh.d15 |
| 45.2 | 36.4 | 36.0 | 71.3 | 37.3 | 69.3 | 35.1 | 46.5 | 43.0 | 34.9 | 40.8 | 35.3 | 31.6 | 38.4 | 35.7 | 47.8 | 35.7 | 62.1 | Fg.d12 |
| 39.0 | 36.2 | 31.8 | 42.7 | 59.3 | 42.2 | 58.6 | 39.5 | 37.7 | 31.5 | 37.5 | 32.3 | 29.5 | 39.0 | 58.6 | 30.0 | 46.4 | 41.4 | Fg.d15 |
| 43.0 | 34.4 | 34.0 | 69.6 | 35.8 | 67.9 | 33.8 | 44.7 | 40.9 | 33.1 | 39.6 | 33.8 | 30.0 | 37.5 | 34.2 | 47.0 | 33.8 | 60.6 | Fm.d12 |
| 38.3 | 37.1 | 32.1 | 42.0 | 60.7 | 42.0 | 58.7 | 40.5 | 37.3 | 32.6 | 37.1 | 32.8 | 30.3 | 38.8 | 58.5 | 29.6 | 47.0 | 42.3 | Fm.d15 |

FIG. 3B

|         | Af. d12 | Af. d15 | An. d12 | An. d15 | Ca. d12 | Ca. d15 | Cg. d12 | Cg. d15 | Cl. d12 | Cl. d15 | Ct. d12 | Ct. d15 | Dh. d12 | Dh. d15 | Fg. d12 | Fg. d15 | Fm. d12 | Fm. d15 | Kl. d12 |
|---------|---------|---------|---------|---------|---------|---------|---------|---------|---------|---------|---------|---------|---------|---------|---------|---------|---------|---------|---------|
| Kl.d12  | 73.8    | 99.1    | 73.2    | 109.3   | 48.1    | 62.4    | 55.6    | 52.5    | 48.7    | 54.0    | 45.9    | 58.6    | 45.3    | 57.2    | 78.5    | 108.3   | 79.9    | 100.9   | ***     |
| Kl.d15  | 80.2    | 109.1   | 77.3    | 110.3   | 60.4    | 42.1    | 68.4    | 34.7    | 58.7    | 37.1    | 56.6    | 32.2    | 58.8    | 44.2    | 80.2    | 106.2   | 80.8    | 108.7   | 52.5    |
| Ma.d12  | 95.5    | 111.9   | 99.7    | 115.7   | 109.6   | 118.8   | 113.0   | 114.5   | 107.8   | 111.5   | 91.3    | 108.3   | 113.6   | 116.7   | 100.8   | 117.6   | 104.4   | 114.1   | 111.9   |
| Ma.d15  | 109.2   | 118.8   | 110.1   | 124.2   | 128.0   | 126.0   | 130.0   | 114.5   | 126.0   | 118.8   | 113.6   | 117.8   | 128.4   | 123.8   | 102.1   | 138.6   | 105.8   | 136.9   | 124.7   |
| Mg.d12  | 42.7    | 99.3    | 45.7    | 106.7   | 81.4    | 79.2    | 83.8    | 67.0    | 74.6    | 68.9    | 69.9    | 75.0    | 82.5    | 81.1    | 36.2    | 100.8   | 38.9    | 103.0   | 76.6    |
| Mg.d15  | 103.8   | 82.0    | 97.2    | 85.3    | 105.5   | 104.2   | 113.1   | 95.4    | 95.9    | 98.6    | 97.7    | 104.1   | 108.7   | 104.2   | 96.6    | 54.0    | 97.2    | 51.2    | 95.7    |
| Nc.d12  | 44.6    | 101.9   | 43.1    | 102.2   | 77.4    | 80.5    | 73.1    | 68.9    | 74.6    | 71.7    | 64.5    | 77.2    | 77.3    | 80.5    | 39.4    | 102.5   | 41.8    | 103.0   | 70.6    |
| Nc.d15  | 115.1   | 80.5    | 114.6   | 79.9    | 114.7   | 128.7   | 126.7   | 110.6   | 108.0   | 104.7   | 98.1    | 111.5   | 118.6   | 120.7   | 118.6   | 59.6    | 119.5   | 59.2    | 113.8   |
| Sk.d12  | 74.2    | 99.5    | 71.8    | 108.4   | 50.3    | 66.5    | 54.6    | 52.9    | 48.7    | 58.4    | 46.8    | 59.5    | 48.9    | 63.7    | 75.1    | 106.3   | 75.8    | 102.3   | 33.3    |
| Sk.d15  | 83.1    | 115.1   | 79.9    | 119.6   | 68.1    | 48.1    | 69.7    | 37.7    | 59.3    | 42.4    | 66.7    | 40.1    | 63.9    | 48.6    | 87.6    | 111.1   | 88.9    | 112.7   | 57.7    |
| Ro.d12  | 92.9    | 117.0   | 94.6    | 116.6   | 104.5   | 115.3   | 104.6   | 111.3   | 98.4    | 106.9   | 97.2    | 115.3   | 105.5   | 117.4   | 104.4   | 136.8   | 107.2   | 131.6   | 108.7   |
| Cc.d12  | 97.3    | 111.9   | 97.9    | 114.9   | 97.9    | 109.3   | 104.3   | 89.1    | 94.9    | 95.2    | 89.0    | 96.5    | 103.0   | 102.3   | 91.8    | 114.5   | 92.6    | 116.1   | 98.8    |
| Mc.d12  | 103.3   | 118.4   | 100.6   | 114.8   | 106.2   | 117.7   | 111.7   | 113.4   | 108.8   | 106.9   | 98.2    | 112.9   | 112.7   | 120.9   | 104.8   | 135.5   | 106.8   | 132.6   | 114.5   |
| Mr.d12  | 120.5   | 135.9   | 117.3   | 123.3   | 122.8   | 130.7   | 134.4   | 128.4   | 123.8   | 121.0   | 114.3   | 125.1   | 135.7   | 135.7   | 121.4   | 150.5   | 124.6   | 145.6   | 136.0   |
| Cn.d12  | 98.1    | 115.9   | 98.0    | 111.9   | 94.0    | 102.8   | 101.4   | 93.2    | 93.8    | 97.6    | 85.1    | 96.0    | 103.8   | 104.5   | 100.4   | 108.6   | 100.0   | 109.1   | 98.4    |
| Chg.d12 | 102.2   | 78.5    | 97.2    | 73.5    | 99.0    | 107.3   | 111.7   | 103.7   | 97.2    | 100.5   | 94.6    | 101.9   | 108.4   | 106.4   | 105.7   | 57.7    | 107.6   | 57.9    | 98.7    |
| Chg.d15 | 49      | 102.0   | 52.8    | 106.1   | 97.8    | 91.6    | 91.4    | 79.9    | 87.8    | 83.6    | 78.6    | 92.1    | 94.4    | 88.6    | 42.1    | 103.6   | 45.7    | 107.1   | 82.7    |
| Ao.d12  | 99.2    | 23.7    | 100.9   | 70.4    | 108.5   | 107.6   | 124.7   | 104.7   | 105.3   | 104.1   | 100.7   | 105.4   | 117.6   | 112.5   | 104.5   | 83.4    | 107.1   | 81.6    | 105.1   |
| Ao.d15  | 14.7    | 101.1   | 17.3    | 112.8   | 72.6    | 86.1    | 73.9    | 75.6    | 67.6    | 82.2    | 67.4    | 80.2    | 78.6    | 84.0    | 50.3    | 104.0   | 52.5    | 101.0   | 75.1    |

FIG. 3C

| 59.8 | 37.1 | 34.1 | 51.0 | 40.0 | 53.4 | 38.0 | 72.4 | 57.6 | 37.6 | 42.4 | 36.3 | 31.7 | 42.4 | 40.0 | 33.9 | 38.3 | 51.5 | Kl.d12 |
|---|---|---|---|---|---|---|---|---|---|---|---|---|---|---|---|---|---|---|
| *** | 35.2 | 33.7 | 51.1 | 37.8 | 51.1 | 36.6 | 57.6 | 79.3 | 34.5 | 41.7 | 35.7 | 31.6 | 41.4 | 37.8 | 32.3 | 37.3 | 48.9 | Kl.d15 |
| 117.6 | *** | 51.4 | 43.9 | 35.3 | 44.1 | 34.6 | 38.3 | 35.8 | 52.4 | 44.1 | 56.4 | 49.9 | 43.9 | 38.6 | 29.8 | 38.1 | 42.1 | Ma.d12 |
| 123.8 | 75.9 | *** | 40.7 | 33.3 | 41.7 | 33.3 | 35.7 | 34.5 | 47.9 | 38.2 | 48.4 | 43.9 | 39.7 | 33.5 | 28.3 | 35.2 | 38.7 | Ma.d15 |
| 76.7 | 95.4 | 104.4 | *** | 30.3 | 60.3 | 30.9 | 39.2 | 37.0 | 31.9 | 34.3 | 32.1 | 29.4 | 32.8 | 30.3 | 44.1 | 31.0 | 55.7 | Mg.d12 |
| 103.1 | 121.0 | 128.8 | 101.0 | *** | 44.4 | 60.9 | 41.4 | 38.3 | 34.3 | 37.1 | 33.5 | 29.7 | 37.1 | 66.0 | 29.2 | 47.0 | 40.9 | Mg.d15 |
| 76.7 | 94.6 | 100.9 | 39.9 | 94.3 | *** | 33.6 | 43.8 | 41.5 | 37.1 | 38.6 | 37.3 | 33.8 | 37.3 | 35.3 | 51.9 | 33.8 | 65.1 | Nc.d12 |
| 119.8 | 130.8 | 135.3 | 111.5 | 54.1 | 118.9 | *** | 36.8 | 34.7 | 32.4 | 33.3 | 31.9 | 29.4 | 31.9 | 62.5 | 27.3 | 46.6 | 38.2 | Nc.d15 |
| 58.3 | 113.6 | 122.7 | 73.9 | 99.2 | 77.0 | 114.5 | *** | 57.5 | 35.3 | 40.6 | 35.6 | 31.2 | 41.6 | 39.9 | 33.4 | 39.7 | 50.7 | Sk.d12 |
| 24.3 | 120.9 | 125.0 | 83.1 | 108.9 | 85.8 | 122.9 | 58.3 | *** | 34.8 | 40.1 | 33.4 | 29.8 | 39.4 | 36.8 | 29.6 | 35.8 | 47.7 | Sk.d15 |
| 118.4 | 70.4 | 80.9 | 91.7 | 124.5 | 89.4 | 126.3 | 117.4 | 115.2 | *** | 46.3 | 81.7 | 70.7 | 46.3 | 35.2 | 29.0 | 35.7 | 44.5 | Ro.d12 |
| 98.5 | 97.1 | 116.6 | 96.3 | 117.2 | 95.5 | 129.1 | 105.9 | 104.2 | 90.4 | *** | 40.8 | 36.5 | 70.0 | 34.3 | 26.0 | 32.7 | 39.7 | Cc.d12 |
| 115.5 | 63.0 | 81.2 | 93.5 | 130.8 | 91.1 | 131.2 | 118.4 | 124.3 | 21.0 | 91.0 | *** | 86.6 | 48.0 | 36.1 | 27.8 | 35.4 | 42.7 | Mc.d12 |
| 134.7 | 78.5 | 94.2 | 105.8 | 151.2 | 104.9 | 145.0 | 139.1 | 142.7 | 36.8 | 106.4 | 14.5 | *** | 42.2 | 32.6 | 24.0 | 31.6 | 37.9 | Mr.d12 |
| 99.0 | 97.9 | 110.7 | 103.2 | 117.2 | 99.9 | 136.2 | 102.1 | 106.5 | 90.4 | 37.8 | 85.4 | 103.2 | *** | 34.8 | 25.9 | 32.1 | 39.5 | Cn.d12 |
| 105.8 | 109.5 | 129.7 | 104.3 | 43.9 | 101.7 | 43.4 | 99.6 | 108.7 | 124.3 | 112.9 | 120.1 | 136.4 | 109.9 | *** | 29.5 | 47.8 | 41.5 | Chg.d15 |
| 92.5 | 104.0 | 109.9 | 38.6 | 105.9 | 34.0 | 118.4 | 87.0 | 103.6 | 107.4 | 112.5 | 115.3 | 138.4 | 112.5 | 105.8 | *** | 34.8 | 61.5 | Chg.d12 |
| 107.4 | 108.3 | 118.2 | 98.7 | 83.1 | 105.7 | 76.5 | 99.8 | 112.3 | 118.6 | 117.6 | 120.0 | 138.1 | 119.8 | 79.9 | 96.4 | *** | 43.1 | Ao.d15 |
| 80.2 | 100.2 | 110.7 | 45.3 | 104.8 | 42.7 | 114.4 | 76.4 | 82.8 | 93.4 | 100.6 | 98.6 | 115.9 | 99.9 | 104.1 | 48.3 | 100.0 | *** | Ao.d12 |
| Kl. d15 | Ma. d12 | Ma. d15 | Mg. d12 | Mg. d15 | Nc. d12 | Nc. d15 | Sk. d12 | Sk. d15 | Ro. d12 | Cc. d12 | Mc. d12 | Mr. d12 | Cn. d12 | Chg. d15 | Chg. d12 | Ao. d15 | Ao. d12 | |

FIG. 3D

US 9,057,083 B2

FUNGAL Δ-12 DESATURASE AND Δ-15 DESATURASE MOTIFS

CROSS REFERENCE TO RELATED APPLICATIONS

This application is a divisional of U.S. patent application Ser. No. 11/740,298, filed on 26 Apr. 2007 now abandoned, which claims benefit of U.S. Prov. App. No. 60/796,637, filed 1 May 2006, and now expired.

FIELD OF THE INVENTION

This invention is in the field of biotechnology. More specifically, this invention pertains to the identification of nucleic acid fragments encoding fungal motifs indicative of Δ15 fatty acid desaturase enzymes and Δ12 fatty acid desaturase enzymes.

BACKGROUND OF THE INVENTION

The importance of long chain polyunsaturated fatty acids (PUFAs) is undisputed. For example, certain PUFAs are important biological components of healthy cells and are recognized as: "essential" fatty acids that cannot be synthesized de novo in mammals and instead must be obtained either in the diet or derived by further desaturation and elongation of linoleic acid (LA; 18:2 ω-6) or α-linolenic acid (ALA; 18:3 ω-3); constituents of plasma membranes of cells, where they may be found in such forms as phospholipids or triacylglycerols; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain ω-3 PUFAs produces cardiovascular protective effects (Dyerberg, J. et al., Amer. J. Clin Nutr., 28:958-966 (1975); Dyerberg, J. et al., Lancet, 2(8081):117-119 (Jul. 15, 1978); Shimokawa, H., World Rev. Nutr. Diet, 88:100-108 (2001); von Schacky, C. and Dyerberg, J., World Rev. Nutr. Diet, 88:90-99 (2001)). And, numerous other studies document wide-ranging health benefits conferred by administration of ω-3 and/or ω-6 PUFAs against a variety of symptoms and diseases (e.g., asthma, psoriasis, eczema, diabetes, cancer).

A variety of different hosts including plants, algae, fungi and yeast are being investigated as means for commercial PUFA production. Genetic engineering has demonstrated that the natural abilities of some hosts (even those natively limited to LA and ALA fatty acid production) can be substantially altered to result in high level production of e.g., arachidonic acid (ARA; 20:4 ω-6), eicosapentaenoic acid (EPA; 20:5 ω-3) and docosahexaenoic acid (DHA; 22:6 ω-3) PUFAs. Whether ω-3/ω-6 PUFA production is the result of natural abilities or recombinant technology, both strategies may require conversion of oleic acid (18:1) to LA by the action of a Δ12 desaturase; ω-3 PUFA production is typically enhanced by the conversion of LA to ALA by the action of a Δ15 desaturase. Subsequent longer-chain PUFAs are generally synthesized via either the Δ6 desaturase/Δ6 elongase pathway (which is predominantly found in algae, mosses, fungi, nematodes and humans and which is characterized by production of γ-linoleic acid (GLA; 18:3 ω-6) and/or stearidonic acid (STA; 18:4 ω-3)) or the Δ9 elongase/Δ8 desaturase pathway (which operates in some organisms, such as euglenoid species and which is characterized by production of eicosadienoic acid (EDA; 20:2 ω-6) and/or eicosatrienoic acid (ETrA; 20:3 ω-3)) (FIG. 1).

Based on the role that Δ12 desaturase and Δ15 desaturase enzymes play to thereby effectively "push" carbon into the ω-3/ω-6 PUFA biosynthetic pathway, there has been considerable effort to identify and characterize these enzymes from various sources. Although a variety of fungal Δ12 desaturases have been publically disclosed, a limited number of fungal Δ15 desaturases with an unexpectedly high degree of sequence homology to fungal Δ12 desaturases have been described only recently. More specifically, many fungal Δ15 desaturases were initially described as a "Δ12 desaturase-like" protein or polypeptide, based on their significant similarity with known fungal Δ12 desaturases (PCT Publications No. WO 2005/047485 and No. WO 2005/047480).

PCT Publication No. WO 2003/099216 (Monsanto Technology, LLC) teaches fungal sequences and their expression, and specifically includes data supporting the functional characterization of desaturases having Δ15 activity from *Neurospora crassa* and *Aspergillus nidulans*, as well as some amino acid motifs derived thereof; a putative "Δ15 desaturase" sequence from *Botrytis cinerea* is also disclosed. PCT Publication No. WO 2006/019192 describes the Δ15 desaturase of *Mortierella alpina*. Additionally, Kainou et al. (*Yeast*, 23(8): 605-612 (2006)) and Murayama et al. (*Microbiol.*, 152(5): 1551-1558 (2006)) independently characterized Δ12 and Δ15 desaturases from *Kluyveromyces lactis* and *Candida albicans*, respectively. Kainou et al. suggests amino acid alterations responsible for the substrate preferences between the *Kluyveromyces lactis* Δ12 and Δ15 desaturase.

Relatively few fungal Δ15 desaturases are known. Additionally, no facile sequence-based method is available to facilitate the distinction between Δ15 and Δ12 desaturase sequences. The problem to be solved, therefore, is to provide a sequence-based method that easily distinguishes polypeptides having Δ15 desaturase activity as opposed to Δ12 desaturase activity. Applicants have solved the stated problem via a sequence of empirical steps comprising: (1) isolating a pool of Δ12/Δ15 desaturase-like polypeptides of fungal origin; (2) developing a sequence-based means to distinguish fungal Δ12 desaturases from fungal Δ15 desaturases; and, (3) identifying a specific amino acid residue(s) that enables one to alter fungal desaturase enzyme activity, substrate specificity and Δ12/Δ15 regiospecificity.

SUMMARY OF THE INVENTION

The invention relates to the discovery of motifs present in desaturases enzymes having either Δ12 or Δ15 desaturase activity. The Δ12 desaturase motifs are diagnostic for Δ12 desaturase activity; and conversely, the Δ15 desaturase motifs are diagnostic for Δ15 desaturase activity. Additionally the invention describes specific amino acid residues that, when altered, have the effect of altering the Δ12 or Δ15 desaturase specificity.

Accordingly the invention provides a fungal Δ12 desaturase motif having an amino acid sequence as set forth in SEQ ID NO:5. Other preferred Δ12 desaturase motifs are encompassed by the amino acid sequences of SEQ ID NOs:3 and 4. Similarly the invention provides a fungal Δ15 desaturase motif having an amino acid sequence as set forth in SEQ ID NO:48, where other preferred motifs have the amino acid motifs set forth in SEQ ID NOs:46 and 47.

In another embodiment the invention provides a method for identifying a fungal polypeptide having Δ12 desaturase activity from a pool of Δ12/Δ15 desaturase-like polypeptides comprising:

a) identifying a fungal Δ12/Δ15 desaturase-like polypeptide of; and,
b) confirming the presence of a Δ12 desaturase motif in the Δ12/Δ15 desaturase-like polypeptide, wherein the Δ12 desaturase motif is selected from the group consisting of SEQ ID NOs:3, 4 and 5 and wherein the presence of the Δ12 desaturase motif is indicative of Δ12 desaturase activity.

In another embodiment the invention provides a method for identifying a fungal polypeptide having Δ15 desaturase activity from a pool of Δ12/Δ15 desaturase-like polypeptides comprising:
a) identifying a fungal Δ12/Δ15 desaturase-like polypeptide; and,
b) confirming the presence of a Δ15 desaturase motif in the Δ12/Δ15 desaturase-like polypeptide, wherein the Δ15 desaturase motif is selected from the group consisting of SEQ ID NOs:46, 47 and 48 and wherein the presence of the Δ15 desaturase motif is indicative of Δ15 desaturase activity.

In a related embodiment the invention provides a fungal polypeptide having Δ12 desaturase activity isolated by the methods of the invention, excluding Δ12 desaturase polypeptides isolated from the following species: *Saccharomyces kluyveri, Mortierella alpina, Fusarium graminearum, Fusarium moniliforme, Magnaporthe grisea, Neurospora crassa, Aspergillus nidulans, Mortierella isabellina, Pichia pastoris, Aspergillus parasiticus, Cryptococcus curvatus, Saprolegnia diclina, Yarrowia lipolytica, Lentinula edodes, Mucor circinelloides, Mucor rouxii, Rhizopus oryzae, Botrytis cinerea* and *Aspergillus flavus.*

In a similar embodiment the invention provides an isolated fungal polypeptide having Δ15 desaturase activity isolated by the methods of the invention, excluding Δ15 desaturase polypeptides isolated from the following species: *Saccharomyces kluyveri, Mortierella alpina, Aspergillus nidulans, Neurospora crassa, Fusarium graminearum, Fusarium moniliforme* and *Magnaporthe grisea.*

In a related embodiment the invention provides methods for obtaining nucleic acid molecules encoding the Δ12 and Δ15 desaturase polypeptides of the invention using primer directed amplification protocols or nucleic acid hybridization methods in combination with primers or probes having sequence homology based on the motifs disclosed herein against fungal libraries or genomic DNA.

In another embodiment the invention provides a method for increasing the ability of a bifunctional fungal Δ15 desaturase enzyme to act on a Δ12 desaturase substrate comprising:
a) providing a nucleic acid molecule encoding a polypeptide having bifunctional Δ15 desaturase activity and comprising a Δ15 desaturase motif having an amino acid sequence selected from the group consisting of SEQ ID NOs:46, 47 and 48, wherein each of the motif sequences comprises an isoleucine at amino acid residue 4; and,
b) altering the nucleic acid molecule of (a) such that it encodes a mutant polypeptide comprising a mutant Δ15 desaturase motif of (a) wherein the isoleucine at amino acid residue 4 is replaced with valine, wherein the mutant polypeptide having Δ15 desaturase activity has an increased ability to act on a Δ12 desaturase substrate.

Similarly the invention provides a method for increasing the ability of a bifunctional fungal Δ12 desaturase enzyme to act on a Δ15 desaturase substrate comprising:
a) providing a nucleic acid molecule encoding a polypeptide having bifunctional Δ12 desaturase activity and comprising a Δ12 desaturase motif having an amino acid sequence selected from the group consisting of SEQ ID NOs:3, 4 and 5, wherein each of the motif sequences comprises a valine at amino acid residue 4; and,
b) altering the nucleic acid molecule of (a) such that it encodes a mutant polypeptide comprising a mutant Δ12 desaturase motif of (a) wherein the valine at amino acid residue 4 is replaced with isoleucine, wherein the mutant polypeptide having Δ12 desaturase activity has an increased ability to act on a Δ15 desaturase substrate.

In another embodiment the invention provides a method for the production of linoleic acid comprising:
a.) providing a host cell comprising:
i.) an isolated nucleic acid fragment encoding a desaturase polypeptide comprising a fungal Δ12 desaturase motif selected from the group consisting of SEQ ID NOs:3, 4 and 5; and,
ii.) a source of oleic acid;
b.) growing the host cell of step (a) under conditions wherein the nucleic acid fragment encoding the desaturase polypeptide is expressed and the oleic acid is converted to linoleic acid; and,
c.) optionally recovering the linoleic acid of step (b).

In a similar embodiment the invention provides a method for the production of α-linolenic acid comprising:
a.) providing a host cell comprising:
i.) an isolated nucleic acid fragment encoding a desaturase polypeptide comprising a fungal Δ15 desaturase motif selected from the group consisting of SEQ ID NOs:46, 47 and 48; and,
ii.) a source of linoleic acid;
b.) growing the host cell of step (a) under conditions wherein the nucleic acid fragment encoding the desaturase protein is expressed and the linoleic acid is converted to α-linolenic acid; and,
c.) optionally recovering the α-linolenic acid of step (b).

In another embodiment the invention provides a method for identifying a polynucleotide sequence encoding a fungal polypeptide having Δ15 desaturase activity comprising:
a) providing at least one polynucleotide sequence encoding a Δ15 desaturase motif selected from the group consisting of SEQ ID NOs:46, 47 and 48, on a computer-readable format;
b) comparing on the computer-readable format the at least one polynucleotide sequence of (a) with at least on e polynucleotide sequence of at least one fungal genome; and
c) identifying a fungal sequence comprising the at least one polynucleotide sequence encoding a Δ15 desaturase motif;
wherein the fungal sequences of (c) comprising the at least one polynucleotide sequences encoding a Δ15 desaturase motif encode a Δ15 desaturase polypeptide having Δ15 desaturase activity.

Similarly the invention provides a method for identifying an amino acid sequence of fungal polypeptide having Δ15 desaturase activity comprising:
a) providing at least one amino acid sequence of a Δ15 desaturase motif selected from the group consisting of SEQ ID NOs:46, 47 and 48, on a computer-readable format;
b) comparing, on the computer-readable format, the at least one amino acid sequence of (a) with at least one amino acid sequence of at least one fungal genome;
c) identifying a fungal sequence comprising the at least one amino acid sequence of a Δ15 desaturase motif;

wherein the fungal sequence of (c) comprising the at least one amino acid sequence of a Δ15 desaturase motif define a Δ15 desaturase polypeptide having Δ15 desaturase activity.

In a related embodiment the invention provides a method for identifying a polynucleotide sequence encoding a fungal polypeptide having Δ12 desaturase activity comprising:

a) providing at least one polynucleotide sequence encoding a Δ12 desaturase motif selected from the group consisting of SEQ ID NOs:3, 4 and 5, on a computer-readable format;

b) comparing, on the computer-readable format the at least one polynucleotide sequence of (a) with at least one polynucleotide sequence of at least one fungal genome; and c) identifying a fungal sequence comprising the at least one polynucleotide sequence encoding a Δ12 desaturase motif;

wherein the fungal sequences of (c) comprising the at least one polynucleotide sequences encoding a Δ12 desaturase motif encode a Δ12 desaturase polypeptide having Δ12 desaturase activity.

Similarly the invention provides a method for identifying an amino acid sequence of fungal polypeptide having Δ12 desaturase activity comprising:

a) providing at least one amino acid sequence of a Δ12 desaturase motif selected from the group consisting of SEQ ID NOs:3, 4 and 5, on a computer-readable format;

b) comparing, on the computer-readable format, the at least one amino acid sequence of (a) with at least one amino acid sequence of at least one fungal genome;

c) identifying a fungal sequence comprising the at least one amino acid sequence of a Δ12 desaturase motif;

wherein the fungal sequences of (c) comprising the at least one amino acid sequence of a Δ12 desaturase motif define a Δ12 desaturase polypeptide having Δ12 desaturase activity.

BRIEF DESCRIPTION OF THE DRAWINGS AND SEQUENCE DESCRIPTIONS

Figure 1B:
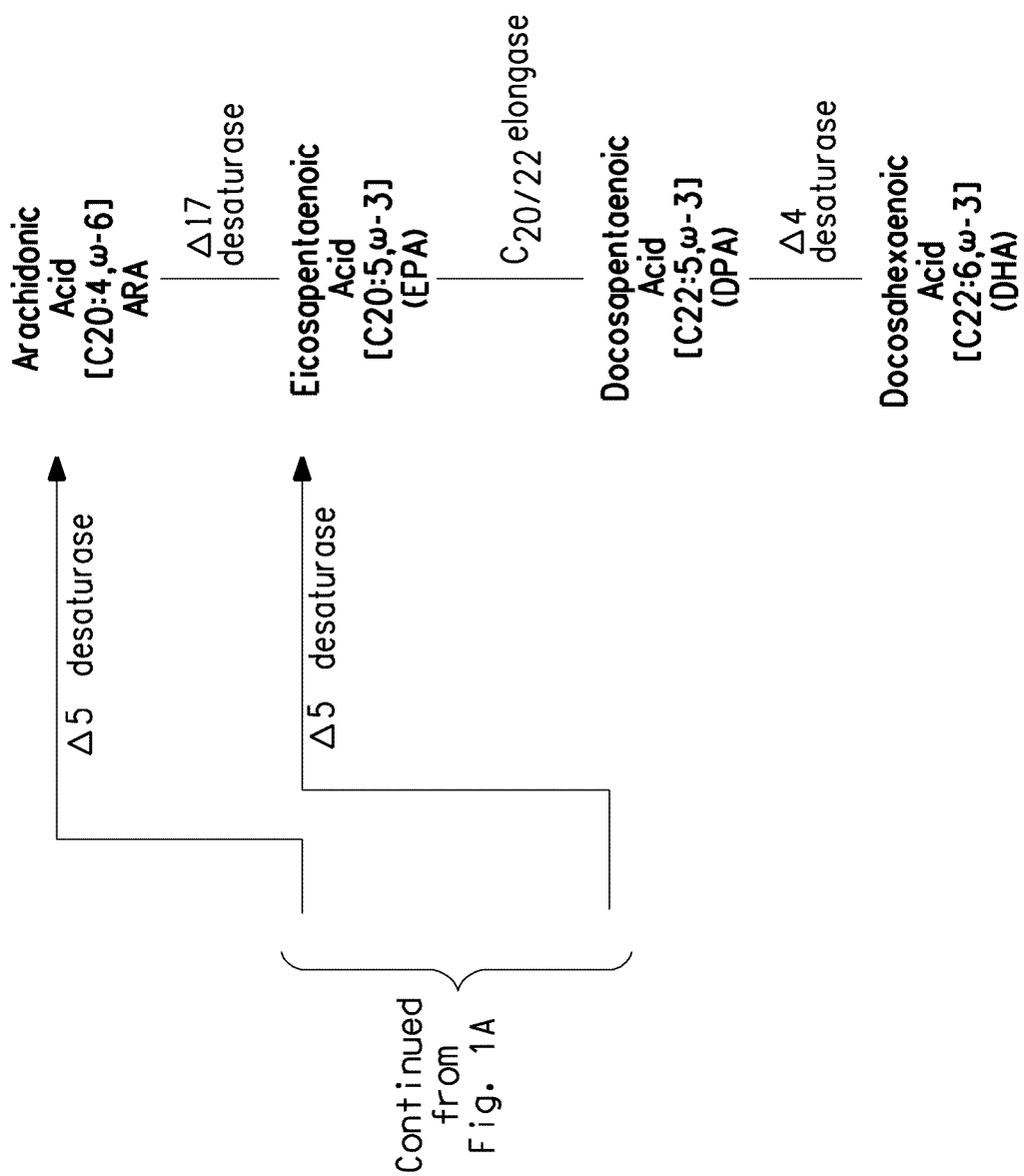

FIG. 1 consists of FIG. 1A and FIG. 1B, which together illustrates the ω-3/ω-6 fatty acid biosynthetic pathway, and should be viewed together when considering the description of this pathway.

Figure 2:
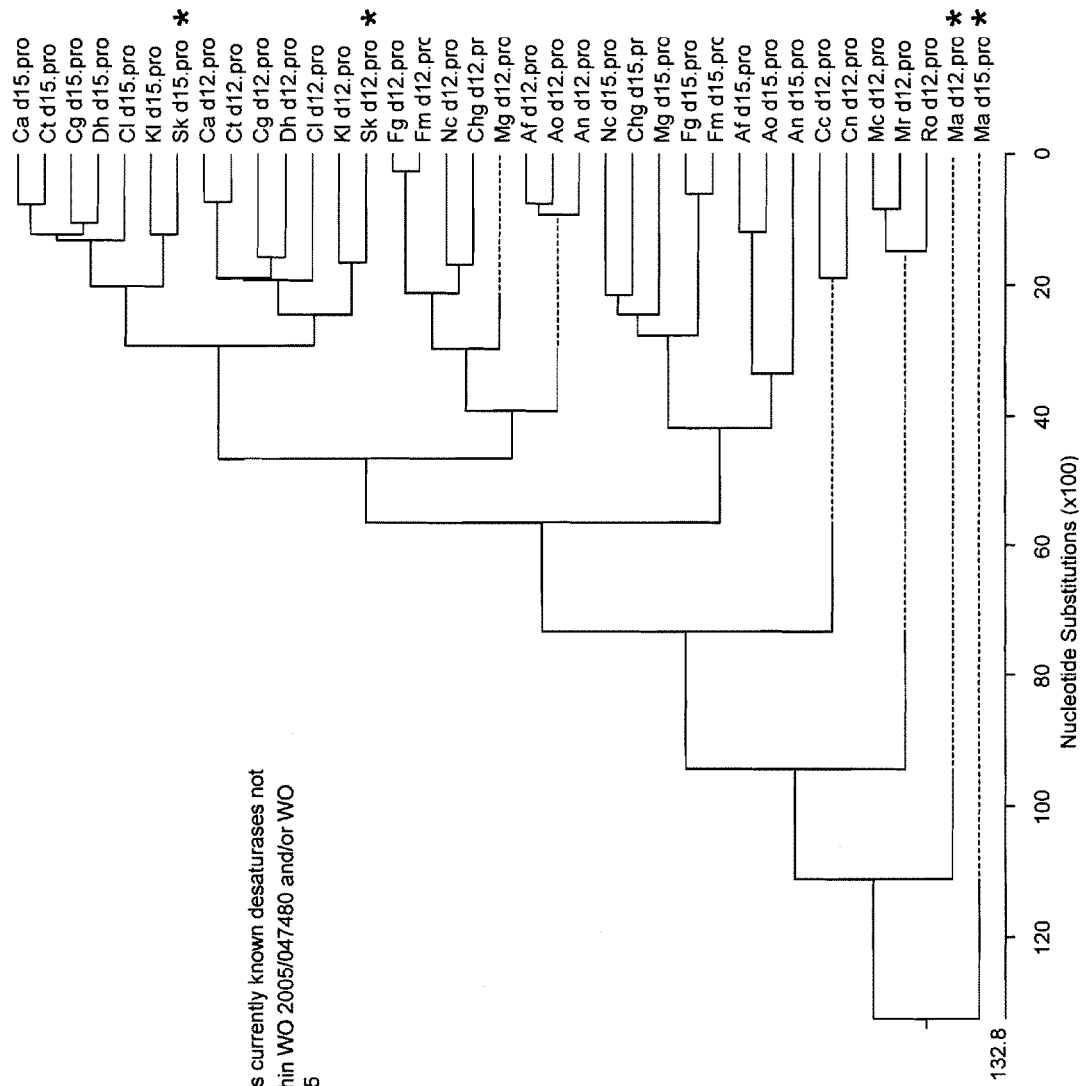

FIG. 2 shows a phylogenetic tree of fungal Δ12 desaturase and fungal Δ15 desaturase proteins, created using the MegAlign™ program of DNASTAR software.

FIG. 3 consists of FIG. 3A, FIG. 3B, FIG. 3C and FIG. 3D, which together create a single FIGURE showing a pairwise comparison (% Identity) between and among proteins from different fungi using a Clustal W analysis (MegAlign™ program of DNASTAR software). More specifically, FIG. 3A corresponds to the left upper quadrant of the assembled figure, FIG. 3B corresponds to the right upper quadrant, FIG. 3C corresponds to the left lower quadrant and FIG. 3D corresponds to the right lower quadrant of the assembled figure. A series of asterisks divide the composite table into an upper triangle, which reports percent similarity between each pair of proteins, and a lower triangle, which reports percent divergence between each pair of proteins.

FIG. 4 provides plasmid maps for the following: (A) pY137; and, (B) pY117.

The invention can be more fully understood from the following detailed description and the accompanying sequence descriptions, which form a part of this application.

The following sequences comply with 37 C.F.R. §1.821-1.825 ("Requirements for patent applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

A Sequence Listing is provided herewith on Compact Disk. The contents of the Compact Disk containing the Sequence Listing are hereby incorporated by reference in compliance with 37 C.F.R. §1.52(e). The Compact Disks are submitted in triplicate and are identical to one another.

SEQ ID NOs:1-30 and 46-95 are motifs, regions of conserved amino acids or proteins encoding desaturases, as identified in Table 1.

TABLE 1

Summary Of Protein SEQ ID Numbers

| Description and Abbreviation | Protein SEQ ID NO. |
|---|---|
| Fungal Δ12 Desaturase Motif "A" | 1 |
| Fungal Δ12 Desaturase Motif "B" | 2 |
| Fungal Δ12 Desaturase Motif "C" | 3 |
| Fungal Δ12 Desaturase Motif "D" | 4 |
| Fungal Δ12 Desaturase Motif "E" | 5 |
| Fungal Δ15 Desaturase Motif "A" | 46 |
| Fungal Δ15 Desaturase Motif "B" | 47 |
| Fungal Δ15 Desaturase Motif "C" | 48 |
| HIS Box I motif | 6 |
| Fungal Δ12 Desaturase Conserved Region #1 | 7 |
| Fungal Δ12 Desaturase Conserved Region #2 | 8 |
| Fungal Δ12 Desaturase Conserved Region #3 | 9 |
| Fungal Δ12 Desaturase Conserved Region #4 | 10 |
| Fungal Δ12 Desaturase Conserved Region #5 | 11 |
| Fungal Δ12 Desaturase Conserved Region #6 | 12 |
| Fungal Δ12 Desaturase Conserved Region #7 | 13 |
| Fungal Δ12 Desaturase Conserved Region #8 | 14 |
| Fungal Δ12 Desaturase Conserved Region #9 | 15 |
| Fungal Δ12 Desaturase Conserved Region #10 | 16 |
| Fungal Δ12 Desaturase Conserved Region #11 | 17 |
| Fungal Δ12 Desaturase Conserved Region #12 | 18 |
| Fungal Δ12 Desaturase Conserved Region #13 | 19 |
| Fungal Δ12 Desaturase Conserved Region #14 | 20 |
| Fungal Δ12 Desaturase Conserved Region #15 | 21 |
| Fungal Δ15 Desaturase Conserved Region #1 | 22 |
| Fungal Δ15 Desaturase Conserved Region #2 | 23 |
| Fungal Δ15 Desaturase Conserved Region #3 | 24 |
| Fungal Δ15 Desaturase Conserved Region #4 | 25 |
| Fungal Δ15 Desaturase Conserved Region #5 | 26 |
| Fungal Δ15 Desaturase Conserved Region #6 | 27 |
| Fungal Δ15 Desaturase Conserved Region #7 | 28 |
| Fungal Δ15 Desaturase Conserved Region #8 | 29 |
| Fungal Δ15 Desaturase Conserved Region #9 | 30 |
| *Gibberella fujikuroi* Δ12 desaturase (GenBank Accession No. DQ272515) | 49 (477 AA) |
| *Gibberella fujikuroi* Δ15 desaturase (GenBank Accession No. DQ272516) | 50 (402 AA) |
| *Aspergillus nidulans* FGSC A4 Δ12 desaturase (GenBank Accession No. XP_658641) | 51 (426 AA) |
| *Aspergillus nidulans* FGSC A4 Δ15 desaturase (GenBank Accession No. XP_664808) | 52 (394 AA) |
| *Magnaporthe grisea* 70-15 Δ12 desaturase (GenBank Accession No. XP_365283) | 53 (551 AA) |
| *Magnaporthe grisea* 70-15 Δ15 desaturase (GenBank Accession No. XP_362963) | 54 (394 AA) |
| *Neurospora crassa* Δ15 desaturase (GenBank Accession No. XP_329856) | 55 (429 AA) |
| *Neurospora crassa* Δ12 desaturase (GenBank Accession No. XP_330985) | 56 (481 AA) |
| *Gibberella zeae* PH-1 Δ12 desaturase (GenBank Accession No. EAA75859) | 57 (475 AA) |

TABLE 1-continued

Summary Of Protein SEQ ID Numbers

| Description and Abbreviation | Protein SEQ ID NO. |
|---|---|
| *Gibberella zeae* Δ15 desaturase (GenBank Accession No. BAA33772) | 58 (193 AA) |
| *Mortierella alpina* Δ12 desaturase (GenBank Accession No. BAA81754) | 59 (400 AA) |
| *Mortierella alpina* Δ15 desaturase (GenBank Accession No. AB182163) | 60 (403 AA) |
| *Saccharomyces kluyveri* Δ12 desaturase (GenBank Accession No. BAD08375) | 61 (416 AA) |
| *Saccharomyces kluyveri* Δ15 desaturase (GenBank Accession No. BAD11952) | 62 (419 AA) |
| *Kluyveromyces lactis* Δ12 desaturase (GenBank Accession No. XP_455402) | 63 (410 AA) |
| *Kluyveromyces lactis* Δ15 desaturase (GenBank Accession No. XP_451551) | 64 (415 AA) |
| *Candida albicans* SC5314 Δ12 desaturase (GenBank Accession No. EAK94955) | 65 (436 AA) |
| *Candida albicans* SC5314 Δ15 desaturase (GenBank Accession No. EAL03493) | 66 (433 AA) |
| *Candida guilliermondii* Δ12 desaturase | 67 (417 AA) |
| *Candida guilliermondii* Δ15 desaturase | 68 (370 AA) |
| *Candida tropicalis* Δ12 desaturase | 69 (340 AA) |
| *Candida tropicalis* Δ15 desaturase | 70 (349 AA) |
| *Candida lusitaniae* Δ12 desaturase | 71 (418 AA) |
| *Candida lusitaniae* Δ15 desaturase | 72 (346 AA) |
| *Debaryomyces hanseni i* CBS767 Δ12 desaturase (GenBank Accession No. CAG90237) | 73 (416 AA) |
| *Debaryomyces hansenii* CBS767 Δ15 desaturase (GenBank Accession No. CAG88182) | 74 (435 AA) |
| *Aspergillus fumigatus* Af293 Δ12 desaturase (GenBank Accession No. EAL90585) | 75 (469 AA) |
| *Aspergillus fumigatus* Af293 Δ15 desaturase (GenBank Accession No. EAL85733) | 76 (396 AA) |
| *Aspergillus oryzae* Δ12 desaturase (GenBank Accession No. BAD04850) | 77 (466 AA) |
| *Aspergillus oryzae* Δ15 desaturase (GenBank Accession No. BAE66531) | 78 (392 AA) |
| *Chaetomium globosum* CBS 148.51 Δ12 desaturase (GenBank Accession No. EAQ83131) | 79 (348 AA) |
| *Chaetomium globosum* CBS 148.51 Δ15 desaturase (GenBank Accession No. EAQ88866) | 80 (400 AA) |
| *Mortierella isabellina* Δ12 desaturase (GenBank Accession No. AAL13301) | 81 (400 AA) |
| *Coccidioides immitis* RS Δ12 desaturase (GenBank Accession No. EAS31392) | 82 (445 AA) |
| *Pichia pastoris* Δ12 desaturase (GenBank Accession No. AAX20125) | 83 (420 AA) |
| *Ashbya gossypii* [ATCC #10895] Δ12 desaturase (GenBank Accession No. AAS53960) | 84 (413 AA) |
| *Aspergillus parasiticus* Δ12 desaturase (GenBank Accession No. AAP23194) | 85 (466 AA) |
| *Cryptococcus curvatus* Δ12 desaturase (GenBank Accession No. AAU12575) | 86 (446 AA) |
| *Cryptococcus neoformans* var. *neoformans* B3501A Δ12 desaturase (GenBank Accession No. EAL21306) | 87 (448 AA) |
| *Saprolegnia diclina* Δ12 desaturase (GenBank Accession No. AAR20443) | 88 (393 AA) |
| *Yarrowia lipolytica* CLIB122 Δ12 desaturase (GenBank Accession No. CAG82952) | 89 (419 AA) |
| *Lentinula edodes* Δ12 desaturase (GenBank Accession No. BAD51484) | 90 (435 AA) |
| *Ustilago maydis* 521 Δ12 desaturase (GenBank Accession No. XP_757193) | 91 (553 AA) |
| *Mucor circinelloides* Δ12 desaturase (GenBank Accession No. BAB69056) | 92 (396 AA) |
| *Mucor rouxii* Δ12 desaturase (GenBank Accession No. AAD55982) | 93 (396 AA) |
| *Rhizopus oryzae* Δ12 desaturase (GenBank Accession No. AAT58363) | 94 (389 AA) |
| *Aspergillus flavus* Δ12 desaturase (GenBank Accession No. AAP33789) | 95 (466 AA) |

SEQ ID NOs:31-32 correspond to primers 513 and 514, respectively, used to PCR amplify Kl.d15 from *Kluyveromyces lactis* NRRL Y-1140.

SEQ ID NOs:33-34 correspond to primers 519 and 520, respectively, used to PCR amplify Sk.d15 from *Saccharomyces kluyveri*.

SEQ ID NOs:35-36 correspond to primers 521 and 522, respectively, used to PCR amplify Dh.d15 from *Debaryomyces hansenii* CBS767.

SEQ ID NO:37 provides the amino acid sequence of the *Saccharomyces kluyveri* Δ15 desaturase (i.e., Sk.d15) in plasmid pY107 Skd15.

SEQ ID NO:38 shows the DNA sequence of the *Fusarium moniliforme* Δ15 desaturase gene, while SEQ ID NO:39 shows the corresponding amino acid sequence of the *F. moniliforme* Δ15 desaturase (i.e., Fm.d15).

SEQ ID NO:40 shows the DNA sequence of the *Fusarium moniliforme* Δ12 desaturase gene, while SEQ ID NO:41 shows the corresponding amino acid sequence of the *F. moniliforme* Δ12 desaturase (i.e., Fm.d12).

SEQ ID NOs:42-45 correspond to primers 515, 516, 517 and 518, respectively, used during site-directed mutagenesis of Fm.d12 and Fm.d15, respectively.

SEQ ID NOs:96 and 97 correspond to primers 631 and 632, respectively, used during site-directed mutagenesis of Sk.d15.

SEQ ID NO:98 provides the 9,099 bp nucleotide sequence of plasmid pY28.

SEQ ID NOs:99 and 100 correspond to primers 633 and 634, respectively, used during site-directed mutagenesis of Yl.d12.

SEQ ID NO:101 provides the 6,267 bp nucleotide sequence of plasmid pY137.

SEQ ID NO:102 provides the 9,570 bp nucleotide sequence of plasmid pY117.

SEQ ID NO:103 provides the nucleic acid sequence of the *Saccharomyces kluyveri* Δ15 desaturase (i.e., Sk.d15) in plasmid pY107 Skd15.

DETAILED DESCRIPTION OF THE INVENTION

All patents, patent applications, and publications cited herein are incorporated by reference in their entirety. This specifically includes the following Applicants' Assignee's co-pending applications: U.S. Pat. Nos. 7,125,672, 7,189, 559, 7,192,762, 7,198,937, 7,202,356, U.S. patent application Ser. Nos. 10/840,579 and 10/840,325 (filed May 6, 2004), U.S. patent application Ser. No. 10/869,630 (filed Jun. 16, 2004), U.S. patent application Ser. No. 10/882,760 (filed Jul. 1, 2004), U.S. patent application Ser. Nos. 10/985,254 and 10/985,691 (filed Nov. 10, 2004), U.S. patent application Ser. No. 11/024,544 (filed Dec. 29, 2004), U.S. patent application Ser. No. 11/166,993 (filed Jun. 24, 2005), U.S. patent application Ser. No. 11/183,664 (filed Jul. 18, 2005), U.S. patent application Ser. No. 11/185,301 (filed Jul. 20, 2005), U.S. patent application Ser. No. 11/190,750 (filed Jul. 27, 2005), U.S. patent application Ser. No. 11/198,975 (filed Aug. 8, 2005), U.S. patent application Ser. No. 11/225,354 (filed Sep. 13, 2005), U.S. patent application Ser. No. 11/253,882 (filed Oct. 19, 2005), U.S. patent application Ser. No. 11/264, 784 and 11/264,737 (filed Nov. 1, 2005), U.S. patent application Ser. No. 11/265,761 (filed Nov. 2, 2005), U.S. Patent Application No. 60/795,810 (filed Apr. 28, 2006), U.S. Patent Application No. 60/793,575 (filed Apr. 20, 2006), U.S. Patent Application No. 60/796,637 (filed May 2, 2006), U.S. patent application Ser. Nos. 60/801,172 and 60/801,119 (filed May 17, 2006), U.S. Patent Application No. 60/853,563 (filed Oct. 23, 2006), U.S. Patent Application No. 60/855,177 (filed Oct. 30, 2006), U.S. patent application Ser. Nos. 11/601,563 and 11/601,564 (filed Nov. 16, 2006), U.S. patent application Ser.

No. 11/635,258 (filed Dec. 7, 2006) and U.S. patent application Ser. No. 11/613,420 (filed Dec. 20, 2006).

Applicants have identified Δ15 desaturases from *Kluyveromyces lactis*, *Candida albicans*, *C. guilliermondii*, *C. tropicalis*, *C. lusitaniae*, *Debaryomyces hansenii* CBS767, *Aspergillus fumigatus*, *A. oryzae* and *Chaetomium globosum*. Methods are also provided to readily distinguish fungal protein sequences having Δ15 desaturase activity as opposed to Δ12 desaturase activity, based on a single isoleucine/valine amino acid. Mutation of this specific residue has proven an effective means to alter enzyme substrate specificity or regioselectivity, such as towards Δ12 desaturation or towards Δ15 desaturation.

The invention relates to novel fungal Δ12 and Δ15 desaturase enzymes and genes encoding the same that may be used for the manipulation of biochemical pathways for the production of healthful PUFAs. Thus, the subject invention finds many applications. PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary).

Supplementation of humans or animals with PUFAs produced by recombinant means can result in increased levels of the added PUFAs, as well as their metabolic progeny. For example, treatment with EPA can result not only in increased levels of EPA, but also downstream products of EPA such as eicosanoids (i.e., prostaglandins, leukotrienes, thromboxanes). Complex regulatory mechanisms can make it desirable to combine various PUFAs, or add different conjugates of PUFAs, in order to prevent, control or overcome such mechanisms to achieve the desired levels of specific PUFAs in an individual.

Definitions

In this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Triacylglycerols" are abbreviated TAGs.

The term "*Fusarium moniliforme*" is synonymous with "*Fusarium verticillioides*" and is also synonymous with "*Gibberella fujikuroi*". More specifically, the *Fusarium moniliforme* Δ12 desaturase described herein as SEQ ID NO:41 (Fm.d12) is identical to the *Gibberella fujikuroi* Δ12 desaturase described as GenBank Accession No. DQ272515 (SEQ ID NO:49 herein). Similarly, the *Fusarium moniliforme* Δ15 desaturase described herein as SEQ ID NO:39 (Fm.d15) is identical to the *Gibberella fujikuroi* Δ15 desaturase described as GenBank Accession No. DQ272516 (SEQ ID NO:50 herein).

The term "*Fusarium graminearium*" is synonymous with "*Gibberella zeae*". More specifically, the *Fusarium graminearium* Δ12 desaturase described herein as Fg.d12 is identical to the *Gibberella zeae* Δ12 desaturase described as GenBank Accession No. EAA75859 (SEQ ID NO:57 herein). Similarly, the *Fusarium graminearium* Δ15 desaturase described herein as Fg.d15 is identical to the partial *Gibberella zeae* Δ15 desaturase fragment described as GenBank Accession No. BAA33772 (SEQ ID NO:58 herein).

The term "invention" or "present invention" as used herein is not meant to be limiting to any one specific embodiment of the invention but applies generally to any and all embodiments of the invention as described in the claims and specification.

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in PCT Publication No. WO 2004/101757.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the specification and each compounds' chemical name.

TABLE 2

Nomenclature of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| γ-Linoleic | GLA | cis-6,9,12-octadecatrienoic | 18:3 ω-6 |
| Eicosadienoic | EDA | cis-11,14-eicosadienoic | 20:2 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosa-tetraenoic | ETA | cis-8,11,14,17-eicosatetraenoic | 20:4 ω-3 |
| Eicosa-pentaenoic | EPA | cis-5,8,11,14,17-eicosapentaenoic | 20:5 ω-3 |
| Docosa-pentaenoic | DPA | cis-7,10,13,16,19-docosapentaenoic | 22:5 ω-3 |
| Docosa-hexaenoic | DHA | cis-4,7,10,13,16,19-docosahexaenoic | 22:6 ω-3 |

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see PCT Publication No. WO2006/052870). Briefly, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzymes" refer to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase, a Δ8 desaturase, a Δ9 elongase, a $C_{14/16}$ elongase, a $C_{16/18}$ elongase, a $C_{18/20}$ elongase and/or a $C_{20/22}$ elongase.

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode PUFA biosynthetic pathway enzymes. A representative pathway is illustrated in FIG. 1, providing for the conversion of myristic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids. That portion that only generates ω-3 fatty acids will be referred to herein as the ω-3 fatty acid biosynthetic pathway, whereas that portion that generates only ω-6 fatty acids will be referred to herein as the ω-6 fatty acid biosynthetic pathway.

The term "amplification" refers to the process in which "replication" is repeated in cyclic process such that the number of copies of the nucleic acid sequence is increased in either a linear or logarithmic fashion. Such replication processes may include but are not limited to, for example, Polymerase Chain Reaction (PCR) [(see, Thein and Wallace, "The use of oligonucleotide as specific hybridization probes in the Diagnosis of Genetic Disorders", in *Human Genetic Diseases: A Practical Approach*, K. E. Davis Ed., (1986) pp 33-50, IRL: Herndon, Va.); and Rychlik, W. In, *Methods in Molecular Biology*, PCR Protocols: Current Methods and Applications. White, B. A., Ed. (1993), Vol. 15, pp 31-39, Humania: Totowa, N.J.).], Ligase Chain Reaction (LCR) Strand Displacement Amplification (SDA) [Walker et al. (*Proc. Natl. Acad. Sci. U.S.A.*, 89:392 (1992))], or other such enzymatic reactions.

The term "primer directed nucleic acid amplification" or "primer-directed amplification" refers to any method known in the art wherein primers are used to sponsor replication of nucleic acid sequences in the linear or logarithmic amplification of nucleic acid molecules. Applicants contemplate that primer-directed amplification may be accomplished by any of several schemes known in this art, including but not limited to the polymerase chain reaction (PCR), ligase chain reaction (LCR) or strand-displacement amplification (SDA).

The term "amplification product" refers to portions of nucleic acid fragments that are produced during a primer directed amplification reaction. Typical methods of primer directed amplification include polymerase chain reaction (PCR), ligase chain reaction (LCR) or Strand displacement Amplification (SDA). If PCR methodology is selected, the replication composition would include for example, nucleotide triphosphates, two primers with appropriate sequences, DNA or RNA polymerase and proteins. These reagents and details describing procedures for their use in amplifying nucleic acids are provided in U.S. Pat. No. 4,683,202 (1987, Mullis, et al.) and U.S. Pat. No. 4,683,195 (1986, Mullis, et al.). If LCR methodology is selected, then the nucleic acid replication compositions would comprise, for example, a thermostable ligase, e.g., *T. aquaticus* ligase, two sets of adjacent oligonucleotides wherein one member of each set is complementary to each of the target strands, Tris HCl buffer, KCl, EDTA, NAD, dithiothreitol and salmon sperm DNA. See, for example, Tabor et al., *Proc. Acad. Sci. U.S.A.*, 82, 1074-1078 (1985)).

The term "functional" as used herein in context with the ω-3/ω-6 fatty acid biosynthetic pathway means that some (or all of) the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all the genes listed in the above paragraph are required, as a number of fatty acid products will only require the expression of a subset of the genes of this pathway.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of interest herein are: 1.) Δ17 desaturases that desaturate a fatty acid between the $17^{th}$ and $18^{th}$ carbon atom numbered from the carboxyl-terminal end of the molecule and which, for example, catalyze the conversion of ARA to EPA and/or DGLA to ETA; 2.) Δ6 desaturases that catalyze the conversion of LA to GLA and/or ALA to STA; 3.) Δ5 desaturases that catalyze the conversion of DGLA to ARA and/or ETA to EPA; 4.) Δ4 desaturases that catalyze the conversion of DPA to DHA; 5.) Δ8 desaturases that catalyze the conversion of EDA to DGLA and/or ETrA to ETA; 6.) Δ9 desaturases that catalyze the conversion of palmitate to palmitoleic acid (16:1) and/or stearate to oleic acid; 7.) Δ12 desaturases that catalyze the conversion of oleic acid to LA; and 8.) Δ15 desaturases that catalyze the conversion of LA to ALA and/or GLA to STA. In the art, Δ15 and Δ17 desaturases are also occasionally referred to as "omega-3 desaturases", "w-3 desaturases" and/or "ω-3 desaturases", based on their ability to convert ω-6 fatty acids into their ω-3 counterparts (e.g., conversion of LA into ALA and ARA into EPA, respectively).

Of particular interest herein, however, are Δ12 desaturases and Δ15 desaturases. These enzymes are further classified with respect to only Δ12 and Δ15 desaturase activities as being either "monofunctional" or "bifunctional" Δ12 or Δ15 desaturases.

More specifically, Δ12 desaturases are defined as those fatty acid desaturases having monofunctional or bifunctional Δ12 desaturase activity, wherein Δ12 desaturase activity is the conversion of oleic acid to LA. The term "monofunctional Δ12 desaturase", "monofunctional Δ12 desaturase activity" or "exclusive Δ12 desaturase activity" refers to a Δ12 desaturase that is capable of converting oleic acid to LA but that is not capable of converting LA to ALA. In contrast, "bifunctional Δ12 desaturase", "bifunctional Δ12 desaturase activity" or "primary Δ12 desaturase activity" refers to a Δ12 desaturase that preferentially converts oleic acid to LA but additionally has limited ability to convert LA into ALA. One example of a bifunctional Δ12 desaturase is the *Fusarium moniliforme* Δ12 desaturase, Fm.d12 (SEQ ID NOs:41 and 49; PCT Publications No. WO 2005/047485 and No. WO 2005/047480).

Similarly, Δ15 desaturases are defined as those fatty acid desaturases having monofunctional or bifunctional Δ15 desaturase activity, wherein Δ15 desaturase activity is the conversion of LA to ALA. The term "monofunctional Δ15 desaturase", "monofunctional Δ15 desaturase activity" or "exclusive Δ15 desaturase activity" refers to a Δ15 desaturase that is capable of converting LA to ALA but that is not capable of converting oleic acid to LA. In contrast, "bifunctional Δ15 desaturase", "bifunctional Δ15 desaturase activity" or "primary Δ15 desaturase activity" refers to a Δ15 desaturase that preferentially converts LA into ALA but additionally has limited ability to convert oleic acid to LA; one example of a bifunctional Δ15 desaturase is the *Fusarium moniliforme* Δ15 desaturase, Fm.d15 (SEQ ID NOs:39 and 50; PCT Publications No. WO 2005/047485 and No. WO 2005/047480).

It should be noted that Δ12 and Δ15 desaturases can have specificities other than Δ12 and Δ15 desaturation that are not relevant in the present classification. It should also be noted that the distinction between monofunctional and bifunctional Δ12 or Δ15 desaturases is a practical one and not absolute in fungi; the same enzyme can function with e.g., either monofunctional or bifunctional Δ12 desaturase activity, depending on the level of its expression, growth condition, etc. For example, in some fungi, such as *Yarrowia lipolytica* and *Mortierella alpina*, the native Δ12 desaturases appear monofunctional but their overexpression in *Yarrowia lipolytica* under a heterologus promoter, such as the *Yarrowia* glyceraldehyde-3-phosphate dehydrogenase (GPD) promoter, reveals bifunctionalty (see Example 4). Similarly, over-expression an apparently monofunctional Δ15 desaturase may reveal bifunctional Δ15 desaturase activity. Furthermore, in some cases, determination of an enzyme's desaturase activity as monofunctional or bifunctional will depend on the methodology used to analyze fatty acid profile and the sensitivity of the equipment to detect extremely low levels of fatty acid conversion.

By "enzymatic substrate" it is meant that the desaturase polypeptide binds the substrate at an active site and acts upon it in a reactive manner. In some embodiments, it is most desirable to empirically determine the specificity of a fatty acid desaturase by transforming a suitable host with the gene for the fatty acid desaturase and determining its effect on the fatty acid profile of the host.

The term "Δ12/Δ15 desaturase-like polypeptide" in the context of this invention refers to a fungal protein that has homology to known fungal Δ12 and/or Δ15 desaturases. More specifically, "Δ12/Δ15 desaturase-like polypeptides" include those "hits" identified when performing a computer-automated sequence comparison using a known fungal Δ12 desaturase or fungal Δ15 desaturase as the query sequence and using an algorithm such as BLAST (Basic Local Alignment Search Tool; Altschul, S. F., et al., *J. Mol. Biol.*, 215: 403-410 (1993)), along with default search parameters. Conversely, "Δ12/Δ15 desaturase-like polypeptides" also include those proteins, which when used as a query make hits to a known fungal Δ12 desaturase and/or fungal Δ15 desaturase. Thus, "Δ12/Δ15 desaturase-like polypeptides" include both fungal Δ12 and Δ15 desaturases as exemplified by *Fusarium moniliforme, Aspergillus nidulans, Magnaporthe grisea, Neurospora crassa* and *Fusarium* graminearium Δ12 desaturases and Δ15 desaturases (i.e., Fm.d12, Fm.d15, An.d12, An.d15, Mg.d12, Mg.d15, Nc.d12, Nc.d15, Fg.d12 and Fg.d15, as described in PCT Publications No. WO 2005/047485 and No. WO 2005/047480 and corresponding herein to SEQ ID NOs:41 [or 49], 39 [or 50], 51, 52, 53, 54, 56, 55, 57 and 58, respectively). As demonstrated in the invention herein, once a pair of "Δ12/Δ15 desaturase-like polypeptides" are identified in a fungus, phylogenetic analysis frequently suggests that one protein encodes a Δ15 desaturase while the other protein encodes a Δ12 desaturase (especially when the organism from which the pair of proteins are identified belongs to a fungal group that comprises a second fungal organism with a known Δ15 desaturase). Although not to be construed as limiting to the invention herein, the homology exhibited by the novel "Δ12/Δ15 desaturase-like polypeptides" of the invention to Fm.d12, Fm.d15, An.d12, An.d15, Mg.d12, Mg.d15, Nc.d12, Nc.d15, Fg.d12, Fg.d15, Sk.d12, Sk.d15, Ma.d12, Ma.d15, Af.d12, Ro.d12, Cc.d12, Mc.d12, Mr.d12 and Cn.d12 ranged from about 24.0%-95% identical (see Table 12 for additional desaturase abbreviations). Thus, other suitable nucleic acid fragments (isolated polynucleotides) encoding "Δ12/Δ15 desaturase-like polypeptides" will be at least about 24-35% identical, preferably at least about 35-45% identical, and more preferably at least about 45-55% identical to Fm.d12, Fm.d15, An.d12, An.d15, Mg.d12, Mg.d15, Nc.d12, Nc.d15, Fg.d12, Fg.d15, Sk.d12, Sk.d15, Ma.d12, Ma.d15, Kl.d12, Kl.d15, Ca.d12, Ca.d15, Cg.d12, Cg.d15, Ct.d12, Ct.d15, Cl.d12, Cl.d15, Dh.d12, Dh.d15, Af.d12, Af.d15, Ao.d12, Ao.d15, Chg.d12, Chg.d15, Ro.d12, Cc.d12, Mc.d12, Mr.d12 and Cn.d12 (i.e., SEQ ID NOs:41[or 49], 39[or 50], 51, 52, 53, 54, 56, 55, 57, 58, 61, 62, 59, 60, 63, 64, 65, 66, 67, 68, 69, 70, 71, 72, 73, 74, 75, 76, 77, 78, 79, 80, 94, 86, 92, 93 and 87, respectively). Preferred nucleic acid fragments encode amino acid sequences that are at least about 55-65% identical, more preferred nucleic acid fragments encode amino acid sequences that are at least about 65-85% identical, and most preferred are nucleic acid fragments that encode amino acid sequences that are at least about 85-95% identical to Fm.d12, Fm.d15, An.d12, An.d15, Mg.d12, Mg.d15, Nc.d12, Nc.d15, Fg.d12, Fg.d15, Sk.d12, Sk.d15, Ma.d12, Ma.d15, Kl.d12, Kl.d15, Ca.d12, Ca.d15, Cg.d12, Cg.d15, Ct.d12, Ct.d15, Cl.d12, Cl.d15, Dh.d12, Dh.d15, Af.d12, Af.d15, Ao.d12, Ao.d15, Chg.d12, Chg.d15, Ro.d12, Cc.d12, Mc.d12, Mr.d12 and Cn.d12 (i.e., SEQ ID NOs:41[or 49 ], 39 [or 50 ], 51, 52, 53, 54, 56, 55, 57, 58, 61, 62, 59, 60, 63, 64, 65, 66, 67, 68, 69, 70, 71, 72, 73, 74, 75, 76, 77, 78, 79, 80, 94, 86, 92, 93 and 87, respectively). Suitable nucleic acid fragments not only have the above homologies but typically encode a "Δ12/Δ15 desaturase-like polypeptide" having at least 50 amino acids, preferably at least 100 amino acids, more preferably at least 150 amino acids, still more preferably at least 200 amino acids, and most preferably at least 250 amino acids.

Concisely stated then, a "Δ12/Δ15 desaturase-like polypeptide" may be viewed as one that falls into any one or all of the following descriptions:
  i. a fungal polypeptide that is identified as a "hit" when performing BLAST analysis using a known fungal desaturase as the query sequence and default search parameters, wherein the known fungal desaturase is selected from the group consisting of Δ12 desaturases and Δ15 desaturases;
  ii. a fungal polypeptide that has primary "hits" to known fungal desaturases when used as a query sequence in a BLAST analysis using default search parameters, wherein the known fungal desaturase is selected from the group consisting of Δ12 desaturases and Δ15 desaturases;
  iii. a fungal polypeptide that has at least 27.3% identity with a known fungal Δ12 desaturase or Δ15 desaturase based on the Clustal W method of alignment;
  iv. a fungal polypeptide having a motif selected from the group consisting of SEQ ID NOs:3, 4 and 5 that has at least 24.0% identity with a known fungal Δ12 desaturase based on the Clustal W method of alignment; and/or,
  vii. a fungal polypeptide having a motif selected from the group consisting of SEQ ID NOs:46, 47 and 48 that has at least 31.8% identity with a known fungal Δ15 desaturase based on the Clustal W method of alignment.

It will be apparent to the skilled person that the methods of the invention may make use of a computer readable format to store electronic information representing the amino acid and encoding polynucleotide sequences of Δ12 desaturase and Δ15 desaturase motifs as well as Δ12/Δ15 desaturase-like polypeptides. As used herein "computer readable format" will mean any medium for the storage and access of electronic data and information including but not limited to computer disks, compact disks, flash drives, hard drivers, servers or the like.

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it. More specifically, Δ12 percent substrate conversion is calculated according to the following formula: ([18:2+18:3]/[18:1+18:2+18:3])*100; relatedly, Δ15 percent substrate conversion is calculated according to the following formula: ([18:3]/[18:2+18:3])*100.

The term "increased ability to act on a Δ12 desaturase substrate" refers to improved Δ12 desaturase substrate conversion; similarly, the term "increased ability to act on a Δ15 desaturase substrate" refers to improved Δ15 desaturase substrate conversion.

The term "Δ12/Δ15 desaturase specificity" is calculated as: (Δ12 percent substrate conversion)/(Δ15 percent substrate conversion). The term "Δ15/Δ12 desaturase specificity" is calculated as: (Δ15 percent substrate conversion)/(Δ12 percent substrate conversion).

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, as described in PCT Publication No. WO 2005/047480. Examples of reactions catalyzed by elongase systems are the conversion of GLA to DGLA, STA to ETA and EPA to DPA. In general, the substrate selectivity of elongases is somewhat broad but segregated by both chain length and the degree and type of unsaturation. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase (also known as a Δ6 elongase as the terms can be used interchangeably) will utilize a $C_{18}$ substrate (e.g., GLA, STA) and a $C_{20/22}$ elongase will utilize a $C_{20}$ substrate (e.g., EPA). In like manner, a Δ9 elongase is able to catalyze the conversion of LA and ALA to EDA and ETrA, respectively. It is important to note that some elongases have broad specificity and thus a single enzyme may be capable of catalyzing several elongase reactions (e.g., thereby acting as both a $C_{16/18}$ elongase and a $C_{18/20}$ elongase).

The term "oleaginous" refers to those organisms that tend to store their energy source in the form of lipid (Weete, In: Fungal Lipid Biochemistry, $2^{nd}$ Ed., Plenum, 1980). The term "oleaginous yeast" refers to those microorganisms classified as yeasts that can make oil. Generally, the cellular oil or TAG content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "fungi" as used herein includes the phyla Ascomycota, Basidiomycota, Chytridiomycota and Zygomycota, as well as the Oomycota and all mitosporic fungi (Hawksworth et al., In: Ainsworth and Bisby's Dictionary of The Fungi, $8^{th}$ ed., 1995, CAB International, University:Cambridge, UK). Representative groups of Ascomycota include, e.g., *Neurospora, Eupenicillium* (i.e., *Penicillium*), *Emericella* (i.e., *Aspergillus*), Eurotiun (i.e., *Aspergillus*) and the true yeasts (e.g., *Candida, Kluyveromyces, Saccharomyces, Schizosaccharomyces, Pichia* and *Yarrowia*). Examples of Basidiomycota include mushrooms, rusts and smuts. Representative groups of Chytridiomycota include e.g., Allomyces, Blastocladiella, Coelomomyces and aquatic fungi. Representative groups of Zygomycota include, e.g., *Rhizopus* and *Mucor*. Representative groups of Oomycota include, e.g., Saprolegniomycetous aquatic fungi (water molds) such as *Achlya*. Non-limiting examples of mitosporic fungi include *Aspergillus, Penicilliun, Candida* and *Alternaria*.

The term "genome" as it applies to a fungal cells encompasses not only chromosomal DNA found within the nucleus, but organelle DNA found within subcellular components (e.g., mitochondrial, Woronin bodies) of the cell.

As used herein, an "isolated nucleic acid fragment" or "isolated nucleic acid molecule" or "genetic construct" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual, $2^{nd}$* ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., J. Mol. Biol., 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine.

The terms "homology" and "homologous" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that homologous nucleic acid sequences encompassed by this invention are also defined by their ability to hybridize, under moderately stringent conditions (e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequences" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; PCT Publication No. WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragments of the invention. Expression may also refer to translation of mRNA into a polypeptide.

"Mature" protein refers to a post-translationally processed polypeptide, i.e., one from which any pre- or propeptides present in the primary translation product have been removed. "Precursor" protein refers to the primary product of translation of mRNA, i.e., with pre- and propeptides still present. Pre- and propeptides may be (but are not limited to) intracellular localization signals.

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Expression cassette" refers to a specific vector containing a foreign gene and having elements in addition to the foreign gene that allow for enhanced expression of that gene in a foreign host.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computa-*

*tional Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al., *Comput. Appl. Biosci.,* 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191 (1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 24%, 30%, 35%, 40%, 45%, 50%, 55%, 60%, 65%, 70%, 75%, 80%, 85%, 90%, or 95%, or any integer percentage from 24% to 100% may be useful in describing the present invention, such as 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family. For the purposes herein, the following Table describes motifs of the present invention which are indicative of a fungal protein having Δ12 desaturase activity or Δ15 desaturase activity, respectively.

TABLE 3

Summary Of Fungal Desaturase Motifs

| Description | Sequence | Protein SEQ ID NO. |
|---|---|---|
| Fungal Δ12 Desaturase Motif "A" | G (I/L/V) W V (L/I) A H E C G H (Q/G/L) (A/S) F S | 1 |
| Fungal Δ12 Desaturase Motif "B" | G X W V X A H E C G H X X F S | 2 |
| Fungal Δ12 Desaturase Motif "C" | G (I/L/V) W V (L/I/V) (A/G) H F (A/C) G H (Q/G/L) (A/S) (F/Y) S | 3 |
| Fungal Δ12 Desaturase Motif "D" | G X W V X (A/G) H E (A/C) G H X X (F/Y) S | 4 |
| Fungal Δ12 Desaturase Motif "E" | G X W V X X H E X G H X X X S | 5 |
| Fungal Δ15 Desaturase Motif "A" | G (I/L/V/M/P) W I L (A/G/S) H E (A/C) G H (G/S) A F S | 46 |
| Fungal Δ15 Desaturase Motif "B" | G X W I L X H E (A/C) G H X A F S | 47 |

TABLE 3-continued

Summary Of Fungal Desaturase Motifs

| Description | Sequence | Protein SEQ ID NO. |
|---|---|---|
| Fungal Δ15 Desaturase Motif "C" | G X W I X X H E X G H X X X S | 48 |

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.,* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

An Overview Microbial Biosynthesis of Fatty Acids and Triacylglycerols

In general, lipid accumulation in oleaginous microorganisms is triggered in response to the overall carbon to nitrogen ratio present in the growth medium. This process, leading to the de novo synthesis of free:palmitate (16:0) in oleaginous microorganisms, is described in detail in PCT Publication No. WO 2004/101757. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: 1.) the esterification of one molecule of acyl-CoA to glycerol-3-phosphate via an acyltransferase to produce lysophosphatidic acid; 2.) the esterification of a second molecule of acyl-CoA via an acyltransferase to yield 1,2-diacylglycerol phosphate (commonly identified as phosphatidic acid); 3.) removal of a phosphate by phosphatidic acid phosphatase to yield 1,2-diacylglycerol (DAG); and 4.) the addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to ω-3/ω-6 fatty acids involves elongation of the carbon chain through the addition of carbon atoms and desaturation of the molecule through the addition of double bonds. This requires a series of special desaturation and elongation enzymes present in the endoplasmic reticulim membrane. However, as seen in FIG. 1 and as described below, there are often multiple alternate pathways for production of a specific ω-3/ω-6 fatty acid.

Specifically, all pathways require the initial conversion of oleic acid to LA, the first of the ω-6 fatty acids, by a Δ12 desaturase. Then, using the "Δ6 desaturase/Δ6 elongase pathway", ω-6 fatty acids are formed as follows: (1) LA is converted to GLA by a Δ6 desaturase; (2) GLA is converted to DGLA by a $C_{18/20}$ elongase; and, (3) DGLA is converted to ARA by a Δ5 desaturase. Alternatively, the "Δ6 desaturase/Δ6 elongase pathway" can be utilized for formation of ω-3 fatty acids as follows: (1) LA is converted to ALA, the first of the ω-3 fatty acids, by a Δ15 desaturase; (2) ALA is converted to STA by a Δ6 desaturase; (3) STA is converted to ETA by a $C_{18/20}$ elongase; (4) ETA is converted to EPA by a Δ5 desaturase; (5) EPA is converted to DPA by a $C_{20/22}$ elongase; and, (6) DPA is converted to DHA by a Δ4 desaturase. Optionally, other ω-6 fatty acids may be converted to ω-3 fatty acids; for example, ETA and EPA are produced from DGLA and ARA, respectively, by Δ17 desaturase activity.

Alternate pathways for the biosynthesis of ω-3/ω-6 fatty acids utilize a Δ9 elongase and Δ8 desaturase. More specifically, LA and ALA may be converted to EDA and ETrA, respectively, by a Δ9 elongase; then, a Δ8 desaturase converts EDA to DGLA and/or ETrA to ETA.

It is contemplated that the particular functionalities required to be expressed in a specific host organism for production of ω-3/ω-6 fatty acids will depend on the host cell (and its native PUFA profile and/or desaturase/elongase profile), the availability of substrate, and the desired end product(s). One skilled in the art will be able to identify various candidate genes encoding each of the enzymes desired for ω-3/ω-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; and/or, 4.) co-factors required by the polypeptide. The expressed polypeptide preferably has parameters compatible with the biochemical environment of its location in the host cell (see PCT Publication No. WO 2004/101757 for additional details).

In additional embodiments, it will also be useful to consider the conversion efficiency of each particular desaturase and/or elongase. More specifically, since each enzyme rarely functions with 100% efficiency to convert substrate to product, the final lipid profile of un-purified oils produced in a host cell will typically be a mixture of various PUFAs consisting of the desired ω-3/ω-6 fatty acid, as well as various upstream intermediary PUFAs. Thus, each enzyme's conversion efficiency is also a variable to consider when optimizing biosynthesis of a desired fatty acid.

With each of the considerations above in mind, candidate genes having the appropriate desaturase and elongase activities (e.g., Δ6 desaturases, $C_{18/20}$ elongases, Δ5 desaturases, Δ17 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Identification of Fungal Δ12 and Δ15 Desaturases

Public sources have long contained a variety of Δ12 desaturase sequences from fungal sources (e.g., the *Mortierella alpina* Δ12 desaturase [SEQ ID NO:59] isolated by Sakuradani, E., et al., *Eur. J. Biochem.*, 261(3):812-820 (1999)); in contrast, however, the identification of Δ15 desaturases has been much more elusive to researchers. Although Δ15 desaturases from photosynthetic organisms (e.g., plants [PCT Publication No. WO 94/11516]) and *Caenorhabditis elegans* were available in the public literature, the first published disclosure of fungal Δ15 desaturases was not until PCT Publication No. WO 03/099216. Although WO 2003/099216 includes expression data to support the functional characterization of desaturases having Δ15 activity from *Neurospora crassa* and *Aspergillus nidulans*, no corresponding data is presented to support the putative annotation therein of the *Botrytis cinerea* desaturase as a "Δ15 desaturase".

A Δ12 desaturase from *Yarrowia lipolytica* (PCT Publication No. WO 2004/104167; SEQ ID NO:89) was used as a query against a proprietary DuPont expressed sequence tag (EST) library of *Fusarium moniliforme* strain M-8114 (E.I. du Pont de Nemours and Co., Inc., Wilmington, Del.) as well as against public databases of the filamentous fungi *Aspergillus nidulans, Magnaporthe grisea, Neurospora crassa* and *Fusarium graminearium*. Remarkedly, these searches identified two homologs within each species of the filamentous fungi (i.e., "pairs of Δ12/Δ15 desaturase-like polypeptides"); and, the sequences from each species fell into one of two "sub-families" based on phylogenetic analyses (PCT Publications No. WO 2005/047480 and No. WO 2005/047485).

Since *Yarrowia lipolytica* was only able to synthesize 18:2 (but not 18:3) while each of the filamentous fungi described above could make both 18:2 and ALA, and since *Yarrowia* had a single Δ12 desaturase while each of the filamentous fungi had two homologs to the *Yarrowia* Δ12 desaturase, the Applicants postulated that one of the sub-families of desaturases in these organisms represented Δ12 desaturases and the other represented Δ15 desaturases. This hypothesis was confirmed by expression analysis of the two *Fusarium moniliforme* homologs, which positively characterized "Fm2" as a Δ12 desaturase (i.e., Fm.d12; SEQ ID NOs:41 and 49) while "Fm1" was characterized as a Δ15 desaturase additionally having some Δ12 desaturase activity (i.e., Fm.d15; SEQ ID NOs:39 and 50) (PCT Publications No. WO 2005/047480 and No. WO 2005/047485). Subsequent expression analysis also proved that one of the Δ12/Δ15 desaturase-like polypeptides in *Fusarium graminearum* and one of the Δ12/Δ15 desaturase-like polypeptides in *Magnaporthe grisea* encoded a Δ15 desaturase, additionally having some Δ12 desaturase activity (PCT Publication No. WO 2005/047480).

Identification of Fungal Δ12 and Δ15 Desaturases Via Identification of "Pairs" of Δ12/Δ15 Desaturase-Like Polypeptides Two additional Δ15 desaturases have recently been reported. Specifically, the *Saccharomyces kluyveri* Δ15 desaturase (GenBank Accession No. BAD11952; Sk.d15) was described in Oura et al. (*Microbiol.*, 150:1983-1990 (2004)), while that from *Mortierella alpina* (GenBank Accession No. AB182163; Ma.d15) was described by Sakuradani et al. (*Appl. Microbiol. Biotechnol.*, 66:648-654 (2005); PCT Publication No. WO 2006/019192). Since both sequences were identified in part based on their close homology to the previously identified *S. kluyveri* Δ12 desaturase (Sk.d12; GenBank Accession No. BAD08375; Watanabe et al., *Biosci. Biotech. Biochem.*, 68(3):721-727 (2004)) and *M. alpina* Δ12 desaturase (Ma.d12; GenBank Accession No. BAA81754; Sakuradani et al., *Eur. J. Biochem.*, 261(3):812-820 (1999)), respectively, followed by a determination of their functional activity, these two pairs of proteins provided additional examples of closely related fungal Δ12 and Δ15 desaturases similar to those of *Fusarium moniliforme, Aspergillus nidulans, Magnaporthe grisea, Neurospora crassa* and *Fusarium graminearium* (PCT Publications No. WO 2005/047480 and No. WO 2005/047485). This suggested that "pairs" of fungal Δ12/Δ15 desaturase-like polypeptide sequences may comprise one protein having Δ15 desaturase activity and one protein having Δ12 desaturase activity.

Accordingly similar "pairs" of Δ12/Δ15 desaturase-like polypeptides were analyzed in publicly available genomic databases from fungi. This search resulted in the identification of additional "pairs" of Δ12/Δ15 desaturase-like polypeptides in *Kluyveromyces lactis, Candida albicans, C. guilliermondii, C. tropicalis, C. Iusitaniae, Debaryomyces hansenii* CBS767, *Aspergillus fumigatus, A. oryzae* and *Chaetomium globosum*. One member of each pair aligned more closely to the previously identified fungal Δ12 desaturases (i.e., Sk.d12, Nc.d12, An.d12) and the other more closely to fungal Δ15 desaturases (i.e., Sk.d15, Fm.d15), as shown in FIG. 2. Details concerning these previously characterized and putative desaturases are summarized in Table 4 below.

TABLE 4

Previously Characterized And Putative Fungal Δ12 And Δ15 Desaturases

| Organism | Δ12 Desaturase Abbreviation | Reference | Δ15 Desaturase Abbreviation | Reference |
|---|---|---|---|---|
| *Fusarium moniliforme* | Fm.d12 (SEQ ID NOs: 41 and 49) | PCT Publication No. WO 2005/047485; GenBank Accession No. DQ272515 | Fm.d15 (SEQ ID NOs: 39 and 50) | PCT Publication No. WO 2005/047480; GenBank Accession No. DQ272516 |

TABLE 4-continued

Previously Characterized And Putative Fungal Δ12 And Δ15 Desaturases

| Organism | Δ12 Desaturase Abbreviation | Reference | Δ15 Desaturase Abbreviation | Reference |
|---|---|---|---|---|
| *Aspergillus nidulans* | An.d12 (SEQ ID NO: 51) | PCT Publication No. WO 2005/047485; Contig 1.15 (scaffold 1) in the *A. nidulans* genome project; GenBank Accession No. XP_658641 | An.d15 (SEQ ID NO: 52) | PCT Publications No. WO 2005/047480 and No. WO 2003/099216; Contig 1.122 (scaffold 9) in the *A. nidulans* genome project; GenBank Accession No. XP_664808 |
| *Magnaporthe grisea* | Mg.d12 (SEQ ID NO: 53) | PCT Publication No. WO 2005/047485; Locus MG01985.1 in contig 2.375 in the *M. grisea* genome project; GenBank Accession No. XP_365283 | Mg.d15 (SEQ ID NO: 54) | PCT Publication No. WO 2005/047480; Locus MG08474.1 in contig 2.1597 in the *M. grisea* genome project; GenBank XP_362963 |
| *Neurospora crassa* | Nc.d12 (SEQ ID NO: 56) | PCT Publication No. WO 2005/047485; GenBank Accession No. XP_330985 | Nc.d15 (SEQ ID NO: 55) | PCT Publications No. WO 2005/047480 and No. WO 2003/099216; GenBank Accession No. XP_329856 |
| *Fusarium graminearium* | Fg.d12 (SEQ ID NO: 57) | PCT Publication No. WO 2005/047485; Contig 1.233 in the *F. graminearium* genome project; GenBank Accession No. EAA75859 | Fg.d15 (SEQ ID NO: 58) | PCT Publication No. WO 2005/047480; Contig 1.320 in the *F. graminearium* genome project; GenBank Accession No. BAA33772.1 (partial sequence) |
| *Mortierella alpina* | Ma.d12 (SEQ ID NO: 59) | GenBank Accession No. BAA81754; Sakuradani et al., Eur. J. Biochem., 261(3): 812-820 (1999) | Ma.d15 (SEQ ID NO: 60) | GenBank Accession No. AB182163; Sakuradani et al., Appl. Microbiol. Biotechnol., 66: 648-654 (2005); PCT Publication No. WO 2006/019192 |
| *Saccharomyces kluyveri* | Sk.d12 (SEQ ID NO: 61) | GenBank Accession No. BAD08375; Watanabe et al., Biosci. Biotech. Biochem., 68(3): 721-727 (2004) | Sk.d15 (SEQ ID NO: 62) | GenBank Accession No. BAD11952; Oura et al., Microbiol., 150: 1983-1990 (2004) |
| *Kluyveromyces lactis* NRRL Y-1140 | Kl.d12 (SEQ ID NO: 63) | GenBank Accession No. XP_455402; Kainou, K. et al., Yeast, 23(8): 605-612 (2006) | Kl.d15 (SEQ ID NO: 64) | GenBank Accession No. XP_451551; Kainou, K. et al., Yeast, 23(8): 605-612 (2006) |
| *Candida albicans* SC5314 | Ca.d12 (SEQ ID NO: 65) | GenBank Accession No. EAK94955; Murayama et al., Microbiol., 152(5): 1551-1558 (2006) | Ca.d15 (SEQ ID NO: 66) | GenBank Accession No. EAL03493; Murayama et al., Microbiol., 152(5): 1551-1558 (2006) |
| *Candida guilliermondii* | Cg.d12 (SEQ ID NO: 67) | DNA [1122100, 1123500] (complement): *Candida guilliermondii* supercontig 1.3 | Cg.d15 (SEQ ID NO: 68) | DNA [680800, 682000] (complement): *Candida guilliermondii* supercontig 1.4 |
| *Candida tropicalis* | Ct.d12 (SEQ ID NO: 69) | DNA [123300, 124400] (complement): *Candida tropicalis* supercontig 1.10 | Ct.d15 (SEQ ID NO: 70) | DNA [1709400, 1710700] (complement): *Candida tropicalis* supercontig 1.3 |
| *Candida Vlusitaniae* | Cl.d12 (SEQ ID NO: 71) | DNA [738900, 740200] (complement): *Candida lusitaniae* supercontig 1.2 | Cl.d15 (SEQ ID NO: 72) | DNA [2095200, 2096600] (complement): *Candida lusitaniae* supercontig 1.2 |
| *Debaryomyces hansenii* CBS767 | Dh.d12 (SEQ ID NO: 73) | GenBank Accession No. CAG90237 | Dh.d15 (SEQ ID NO: 74) | GenBank Accession No. CAG88182 |
| *Aspergillus fumigatus* | Af.d12 (SEQ ID NO: 75) | PCT Publication No. WO 2005/047485; GenBank Accession No. EAL90585 | Af.d15 (SEQ ID NO: 76) | GenBank Accession No. EAL85733 |
| *Aspergillus oryzae* | Ao.d12 (SEQ ID NO: 77) | GenBank Accession No. BAD04850 | Ao.d15 (SEQ ID NO: 78) | GenBank Accession No. BAE66531 |
| *Chaetomium globosum* CBS 148.51 | Chg. d12 (SEQ ID NO: 79) | GenBank Accession No. EAQ83131 | Chg. d15 (SEQ ID NO: 80) | GenBank Accession No. EAQ88866 |

Notes:
All *Candida* genome sequences are sponsored by The Fungal Genome Initiative (FGI), Broad Institute of MIT and Harvard (Cambridge, MA). The *Aspergillus nidulans* genome project is sponsored by the Center for Genome Research (CGR), Cambridge, MA; the *M. grisea* genome project is sponsored by the CGR and International Rice Blast Genome Consortium; the *F. graminearium* genome project is sponsored by the CGR and the International *Gibberella zeae* Genomics Consortium (IGGR).
As is well-known to one of skill in the art, the "nr" database (comprising all GenBank, EMBL, DDBJ and PDB sequences) contains some redundant accession numbers, as a result of the significant computational costs of maintaining a non-redundant database. For brevity, these redundancies are not included in the citations above. For example, GenBank Accession No. AB020033 (*Mortierella alpina* mRNA for Δ12 fatty acid desaturase, complete cds) includes the full nucleotide and protein sequence of a Δ12 fatty acid desaturase; the protein sequence of GenBank Accession No. AB020033 is 100% identical to that provided in GenBank Accession No. BAA81754. Similarly, some Δ12 desaturases have been isolated from various strains within a particular species (e.g., the *M. alpina* Δ12 desaturases from ATCC #32221, ATCC #16266 and strain IS-4, corresponding to GenBank Accession Nos. AAF08684, AAL13300 and BAA81754); sequences corresponding to these slight strain variations are not included above.

Given the teachings herein, one will be able to use similar methodology to identify other orthologous Δ12 desaturase and Δ15 desaturase proteins which are substantially identical to the instant desaturase sequences (i.e., Fm.d12, An.d12, Mg.d12, Nc.d12, Fg.d12, Ma.d12, Sk.d12, Kl.d12, Ca.d12, Cg.d12, Ct.d12, Cl.d12, Dh.d12, Af.d12, Ao.d12, Chg.d12, Fm.d15, An.d15, Mg.d15, Nc.d15, Fg.d15, Ma.d15, Sk.d15, Kl.d15, Ca.d15, Cg.d15, Ct.d15, Cl.d15, Dh.d15, Af.d15, Ao.d15 and/or Chg.d15, corresponding to SEQ ID NOs:41 [or 49], 51, 53, 56, 57, 59, 61, 63, 65, 67, 69, 71, 73, 75, 77, 79, 39 [or 50], 52, 54, 55, 58, 60, 62, 64, 66, 68, 70, 72, 74, 76, 78 and 80, respectively). By "substantially identical" is intended an amino acid sequence or nucleic acid sequence exhibiting in order of increasing preference at least about 70%, 80%, 90% or 95% homology to the selected polypeptides, or nucleic acid sequences encoding the amino acid sequence. For polypeptides, the length of comparison sequences generally is at least 16 amino acids, preferably at least 20 amino acids or most preferably at least 35 amino acids. For nucleic acids, the length of comparison sequences generally is at least 50 nucleotides, preferably at least 60 nucleotides, more preferably at least 75 nucleotides, and most preferably at least 110 nucleotides.

Identification of Fungal Δ12 and Δ15 Desaturases Via Motifs

In additional embodiments herein, the Applicants have identified a means to readily distinguish fungal Δ12/Δ15 desaturase-like polypeptide sequences having Δ15 desaturase activity as opposed to Δ12 desaturase activity. Specifically, when an amino acid sequence alignment was analyzed that comprised Fm.d12, An.d12, Mg.d12, Nc.d12, Fg.d12, Ma.d12, Sk.d12, Kl.d12, Ca.d12, Cg.d12, Ct.d12, Cl.d12, Dh.d12, Af.d12, Ao.d12, Chg.d12, Fm.d15, An.d15, Mg.d15, Nc.d15, Fg.d15, Ma.d15, Sk.d15, Kl.d15, Ca.d15, Cg.d15, Ct.d15, Cl.d15, Dh.d15, Af.d15, Ao.d15 and Chg.d15 (abbreviations provided above in Table 4), it became apparent that all of the 32 fungal Δ15 or Δ12 desaturases contained either an Ile or Val amino acid residue, respectively, at the position that is only three amino acid residues away from the conserved His Box I ("HE[C/A]GH"; SEQ ID NO:6) (Table 5). Furthermore, the amino acid region spanning from 6 residues upstream of the His Box I to 4 residues downstream of the His Box I (i.e., a region comprising a total of 15 amino acid residues) was also significantly conserved.

Although 7 different sequence variants exist within this region in the Δ12 desaturases (i.e., SEQ ID NOs:7, 8, 9, 10, 11, 12 and 13), a motif that was representative of all sixteen of the fungal Δ12 desaturases was identified as: G (I/L/V) W V (L/I) A H E C G H (Q/G/L) (A/S) F S (SEQ ID NO:1; "Fungal Δ12 Desaturase Motif A"). More broadly, this motif was defined as: G X W V X A H E C G H X X F S (SEQ ID NO:2; "Fungal Δ12 Desaturase Motif B"), while in a more preferred embodiment, this motif was defined as: G X W V X X H E X G H X X X S (SEQ ID NO:5; "Fungal Δ12 Desaturase Motif E").

Similarly, although 9 different variants exist within the Δ15 desaturases (i.e., SEQ ID NOs:22, 23, 24, 25, 26, 27, 28, 29 and 30), a motif that was representative of all sixteen of the fungal Δ15 desaturases is: G (I/L/V/M/P) W I L (A/G/S) H E (A/C) G H (G/S) A F S (SEQ ID NO:46; "Fungal Δ15 Desaturase Motif A"). In a preferred embodiment, this motif was defined as: G X W I L X H E (A/C) G H X A F S (SEQ ID NO:47; "Fungal Δ15 Desaturase Motif B"), while in a more preferred embodiment, this motif was defined as: G X W I X X H E X G H X X X S (SEQ ID NO:48; "Fungal Δ15 Desaturase Motif C").

TABLE 5

Amino Acid Alignment Around The His Box I Of Fungal Δ12 And Δ15 Desaturases

| Amino Acid Residue* | Conserved Region Around the His Box I | SEQ ID NO: Of The Conserved Region | Desaturase |
|---|---|---|---|
| 134 | GIWVLAHECGHQAFS | 7 | Ca.d12 (SEQ ID NO: 65) |
| 115 | GLWVLAHECGHLAFS | 10 | Cg.d12 (SEQ ID NO: 67) |
| 118 | GIWVLAHECGHQAFS | 7 | Cl.d12 (SEQ ID NO: 71) |
| 38 | GIWVLAHECGHQAFS | 7 | Ct.d12 (SEQ ID NO: 69) |
| 119 | GLWVLAHECGHQAFS | 11 | Dh.d12 (SEQ ID NO: 73) |
| 105 | GLWVLAHECGHQAFS | 11 | Kl.d12 (SEQ ID NO: 63) |
| 115 | GIWVLAHECGHQAFS | 7 | Sk.d12 (SEQ ID NO: 61) |
| 106 | GIWVLAHECGHQSFS | 8 | Ma.d12 (SEQ ID NO: 59) |
| 142 | GIWVLAHECGHQAFS | 7 | An.d12 (SEQ ID NO: 51) |
| 129 | GLWVIAHECGHGAFS | 9 | Fg.d12 (SEQ ID NO: 57) |
| 148 | GLWVIAHECGHGAFS | 9 | Fm.d12 (SEQ ID NOs: 41 and 49) |
| 159 | GIWVLAHECGHQAFS | 7 | Mg.d12 (SEQ ID NO: 53) |
| 152 | GLWVLAHECGHQAFS | 11 | Nc.d12 (SEQ ID NO: 56) |
| 139 | GVWVLAHECGHQAFS | 13 | Ao.d12 (SEQ ID NO: 77) |
| 141 | GVWVLAHECGHQAFS | 13 | Af.d12 (SEQ ID NO: 75) |
| 154 | GLWVLAHECGHGAFS | 12 | Chg.d12 (SEQ ID NO: 79) |

TABLE 5-continued

Amino Acid Alignment Around The His Box I Of Fungal Δ12 And Δ15 Desaturases

| Amino Acid Residue* | Conserved Region Around the His Box I | SEQ ID NO: Of The Conserved Region | Desaturase |
|---|---|---|---|
| 129 | GLWILAHECGHGAFS | 22 | Ca.d15 (SEQ ID NO: 66) |
| 75 | GLWILAHECGHGAFS | 22 | Cg.d15 (SEQ ID NO: 68) |
| 46 | GLWILAHECGHGAFS | 22 | Cl.d15 (SEQ ID NO: 72) |
| 46 | GLWILAHECGHGAFS | 22 | Ct.d15 (SEQ ID NO: 70) |
| 131 | GLWILAHECGHGAFS | 22 | Dh.d15 (SEQ ID NO: 74) |
| 116 | GLWILAHECGHGAFS | 22 | Kl.d15 (SEQ ID NO: 64) |
| 116 | GLWILAHECGHSAFS | 25 | Sk.d15 (SEQ ID NO: 62) |
| 104 | GPWILAHECGHGAFS | 24 | Ma.d15 (SEQ ID NO: 60) |
| 87 | GIWILAHECGHGAFS | 23 | An.d15 (SEQ ID NO: 52) |
| 100 | GIWILGHECGHGAFS | 27 | Fg.d15 (SEQ ID NO: 58) |
| 99 | GVWILAHECGHGAFS | 26 | Fm.d15 (SEQ ID NOs: 39 and 50) |
| 94 | GLWILAHECGHGAFS | 22 | Mg.d15 (SEQ ID NO: 54) |
| 118 | GIWILAHECGHGAFS | 23 | Nc.d15 (SEQ ID NO: 55) |
| 87 | GIWILSHECGHGAFS | 29 | Ao.d15 (SEQ ID NO: 78) |
| 93 | GMWILAHECGHGAFS | 28 | Af.d15 (SEQ ID NO: 76) |
| 101 | GIWILAHEAGHGAFS | 30 | Chg.d15 (SEQ ID NO: 80) |

*"Amino Acid Residue" refers to the location of the first glycine within the conserved region around the His Box I (defined above), with respect to the full-length desaturase protein sequence. For example, the conserved region around the His Box I is located between amino acids 134-148 of the *Candida albicans* Δ12 desaturase (i.e., Ca.d12; SEQ ID NO: 65); thus, the amino acid residue corresponding to the initial glycine within the conserved region in this particular protein is residue 134.
**Shaded text highlights the His Box I.

Given this teaching it is apparent that the Ile and Val amino acid residues located three amino acid residues upstream from the first histidine in the conserved His Box I are a determinant of Δ15 and Δ12 desaturase specificity, respectively, in fungal Δ12/Δ15 desaturase-like polypeptides. It is therefore contemplated that any fungal Δ12/Δ15 desaturase-like polypeptide with Ile at the corresponding residue(s) (i.e., or the Fungal Δ15 Desaturase Motif A, B or C [SEQ ID NOs:46, 47 and 48, respectively]) will be a Δ15 desaturase and any fungal Δ12/Δ15 desaturase-like polypeptide with Val at the corresponding residue(s) (i.e., or the Fungal Δ12 Desaturase Motif A, B or E [SEQ ID NOs:1, 2 and 5, respectively]) will be a Δ12 desaturase. Thus, this single isoleucine/valine amino acid is expected to play a pivotal role in the determination of Δ12 or Δ15 desaturase activity.

This methodology will be particularly important as novel fungal Δ12/Δ15 desaturase-like polypeptide sequences are identified within species belonging to fungal groups from which a Δ15 desaturase has not previously been identified. Based on the teachings herein, it is expected that classification of any novel Δ12/Δ15 desaturase-like polypeptide as either a Δ12 desaturase or Δ15 desaturase by phylogenetic means alone will be possible. Prior to this teaching, identification of the Δ12 desaturase versus the Δ15 desaturase within the pair of *Mortierella* alpina Δ12/Δ15 desaturase-like polypeptides was possible only by experimentation (Sakuradani et al., *Eur. J. Biochem.*, 261(3):812-820 (1999) and *Appl. Microbiol. Biotechnol.*, 66:648-654 (2005)), since phylogentic analysis was not sufficient to distinguish enzymatic function.

Identification and Isolation of Homologs

Any of the instant desaturase sequences (i.e., Fm.d12, An.d12, Mg.d12, Nc.d12, Fg.d12, Ma.d12, Sk.d12, Kl.d12, Ca.d12, Cg.d12, Ct.d12, Cl.d12, Dh.d12, Af.d12, Ao.d12, Chg.d12, Fm.d15, An.d15, Mg.d15, Nc.d15, Fg.d15, Ma.d15, Sk.d15, Kl.d15, Ca.d15, Cg.d15, Ct.d15, Cl.d15, Dh.d15, Af.d15, Ao.d15 and/or Chg.d15, corresponding to SEQ ID NOs:41 [or 49], 51, 53, 56, 57, 59, 61, 63, 65, 67, 69, 71, 73, 75, 77, 79, 39 [or 50], 52, 54, 55, 58, 60, 62, 64, 66, 68, 70, 72, 74, 76, 78 and 80, respectively) or portions thereof may be used to search for Δ12 and Δ15 desaturase homologs in the same or other bacterial, algal, fungal or plant species using sequence analysis software. In general, such computer software matches similar sequences by assigning degrees of homology to various substitutions, deletions, and other modifications.

Alternatively, any of the instant desaturase sequences or portions thereof may also be employed as hybridization reagents for the identification of Δ12 desaturase and Δ15 desaturase homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the Δ12 desaturase and/or Δ15 desaturase nucleic acid fragments of the instant invention (or any homologs identified thereof) may be used to isolate genes encoding homologous proteins from the same or other bacterial, algal, fungal or plant species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. U.S.A.*, 82:1074 (1985); or strand displacement amplification (SDA), Walker, et al., *Proc. Natl. Acad. Sci. U.S.A.*, 89:392 (1992)]; and 3.) methods of library construction and screening by complementation.

For example, genes encoding similar proteins or polypeptides to the Δ12 and/or Δ15 desaturases described herein could be isolated directly by using all or a portion of the instant nucleic acid fragments as DNA hybridization probes to screen libraries from any desired yeast or fungus using methodology well known to those skilled in the art (wherein those yeast or fungus producing LA or ALA [or LA and/or ALA-derivatives] would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *Proc. Acad. Sci. U.S.A.*, 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *Proc. Acad. Sci. U.S.A.*, 86:5673 (1989); Loh et al., *Science*, 243:217 (1989)).

It will be apparent that probes and/or primers corresponding to the nucleic acids of the invention (SEQ ID NOs:1, 2, 5, 46, 47 and/or 48) will be useful for the identification and isolation of Δ12 desaturase and/or Δ15 desaturase enzymes, respectively.

The validity of using the above methodologies for the identification of other Δ12 and Δ15 desaturases of fungal origin is well-supported herein. For example, the utility of Fungal Δ12 Desaturase Motif B (SEQ ID NO:2) as a means to identity other Δ12 desaturases was confirmed via homology searching using the motif as a query in a BLASTP program of analysis; specifically, the top results of the search included other known fungal Δ12 desaturases available in GenBank, all which shared the motif of SEQ ID NO:2 or a variant thereof (wherein the V residue was invariant): Accession No. CAG82952 (*Yarrowia lipolytica*; SEQ ID NO:89), Accession No. AAL13301 (*Mortierella isabellina*; SEQ ID NO:81), Accession No. AAP23194 (*Aspergillus parasiticus*; SEQ ID NO:85), Accession No. AAX20125 (*Pichia pastoris*; SEQ ID NO:83), Accession No. BAB69056 (*Mucor circinelloides*; "Mc.d12"; SEQ ID NO:92), Accession No. AAD55982 (*Mucor rouxii*; "Mr.d12"; SEQ ID NO:93), Accession No. AAT58363 (*Rhizopus oryzae*; "Ro.d12"; SEQ ID NO:94), Accession No. BAD51484 (*Lentinula edodes*; SEQ ID NO:90), Accession No. AAU12575 (*Cryptococcus curvatus*; "Cc.d12"; SEQ ID NO:86), Accession No. AAR20443 (*Saprolegnia diclina*; SEQ ID NO:88) and Accession No. AAP33789 (*Aspergillus flavus*; SEQ ID NO:95). Furthermore, four additional hypothetical fungal proteins were identified (having the Fungal Δ12 Desaturase Motif B or a variant thereof) that are hypothesized herein to encode Δ12 desaturases: Accession No. AAS53960 (*Ashbya gossypii* ATCC 10895; SEQ ID NO:84), Accession No. XP_757193 (*Ustilago maydis* 521; SEQ ID NO:91), Accession No. EAS31392 (*Coccidioides immitis* RS; SEQ ID NO:82) and Accession No. EAL21306 (*Cryptococcus neoformans* var. *neoformans* B-3501A; "Cn.d12"; SEQ ID NO:87). Based on analysis of the conserved region surrounding the His Box I of each of these additional known and putative Δ12 desaturase proteins, an additional fungal Δ12 desaturase motif was defined as: G (I/L/V) W V (L/I/V) (A/G) H E (A/C) G H (Q/G/L) (A/S) (F/Y) S (SEQ ID NO:3; "Fungal Δ12 Desaturase Motif C"). In a preferred embodiment, this motif was defined as: G X W V X (A/G) H E (A/C) G H X X (F/Y) S (SEQ ID NO:4; "Fungal Δ12 Desaturase Motif D"), while in a more preferred embodiment, this motif was defined as: G X W V X X H E X G H X X X S (SEQ ID NO:5; "Fungal Δ12 Desaturase Motif E"). The motifs of SEQ ID NOs:3, 4 and 5 are thus representative of all of the fungal Δ12 desaturases described in the present application (i.e., Fm.d12, An.d12, Mg.d12, Nc.d12, Fg.d12, Ma.d12, Sk.d12, Kl.d12, Ca.d12, Cg.d12, Ct.d12, Cl.d12, Dh.d12, Af.d12, Ao.d12, Chg.d12, as well as the known and putative Δ12 desaturases described above).

Analysis of select Δ12 desaturase and Δ15 desaturase proteins (i.e., Fm.d12, An.d12, Mg.d12, Nc.d12, Fg.d12, Ma.d12, Sk.d12, Kl.d12, Ca.d12, Cg.d12, Ct.d12, Cl.d12, Dh.d12, Af.d12, Ao.d12, Chg.d12, Cc.d12, Mr.d12, Mc.d12, Ro.d12, Cn.d12, Fm.d15, An.d15, Mg.d15, Nc.d15, Fg.d15, Ma.d15, Sk.d15, Kl.d15, Ca.d15, Cg.d15, Ct.d15, Cl.d15, Dh.d15, Af.d15, Ao.d15 and Chg.d15, corresponding to SEQ ID NOs:41 [or 49], 51, 53, 56, 57, 59, 61, 63, 65, 67, 69, 71, 73, 75, 77, 79, 86, 93, 92, 94, 87, 39 [or 50], 52, 54, 55, 58, 60, 62, 64, 66, 68, 70, 72, 74, 76, 78 and 80, respectively) revealed that the Δ12 desaturase proteins shared between 27.3%-61.2% identity with the Δ15 desaturase proteins, according to the Clustal W (MegAlign™ program of DNASTAR software) method of alignment (FIG. 3). Within the twenty-one Δ12 desaturases the percent identity ranged from 24.0%-95%, while within the sixteen Δ15 desaturases the percent identity ranged from 31.8%-88.8%. Finally, the percent identity between the Δ12 desaturase and the Δ15 desaturase within the same organism ranged between 29.5%-61.0% identity.

It is within the context of the invention therefore to provide a method for identifying a fungal polypeptide having Δ12 desaturase activity from a pool of Δ12/Δ15 desaturase-like polypeptides comprising:
  a) identifying a Δ12/Δ15 desaturase-like polypeptide of fungal origin; and,
  b) confirming the presence of a Δ12 desaturase motif in the Δ12/Δ5 desaturase-like polypeptide, wherein the Δ12 desaturase motif is selected from the group consisting of SEQ ID NOs:3, 4 and 5, and wherein the presence of the Δ12 desaturase motif is indicative of Δ12 desaturase activity.

It will be expected that the Δ12/Δ15 desaturase-like polypeptide of fungal origin has either Δ12 or Δ15 desaturase activity and the Δ12/Δ15 desaturase-like polypeptide of fungal origin will have at least 27.3% identity with a known fungal Δ12 desaturase or Δ15 desaturase based on the Clustal W method of alignment, using the default parameters of GAP PENALTY=10, GAP LENGTH PENALTY=0.1, and Gonnet 250 series of protein weight matrix. Upon identification of a fungal polypeptide having Δ12 desaturase activity according to the methodology above, it will be expected that the Δ12 desaturase will have either "monofunctional Δ12 desaturase activity" (wherein the desaturase is only capable of using oleic acid as enzymatic substrate) or "bifunctional Δ12 desaturase activity" (wherein the desaturase prefers oleic acid as its enzymatic substrate but additionally has limited ability to use LA such that the enzyme is a "bifunctional" Δ12 desaturase). Additionally, it will be expected that the Δ12 desaturase identified above will have at least 24.0% identity with a known fungal Δ12 desaturase based on the Clustal W method of alignment, using the default parameters of GAP PENALTY=10, GAP LENGTH PENALTY=0.1, and Gonnet 250 series of protein weight matrix.

Similarly it will be understood that the invention provides a method for identifying a fungal polypeptide having Δ15 desaturase activity from a pool of Δ12/Δ15 desaturase-like polypeptides comprising:
  a) identifying a Δ12/Δ15 desaturase-like polypeptide of fungal origin; and,
  b) confirming the presence of a Δ15 desaturase motif in the Δ12/Δ15 desaturase-like polypeptide, wherein the Δ15 desaturase motif is selected from the group consisting of SEQ ID NOs:46, 47 and 48, and wherein the presence of the Δ15 desaturase motif is indicative of Δ15 desaturase activity.

It will be expected therefore that the Δ12/Δ15 desaturase-like polypeptide of fungal origin has either Δ12 or Δ15 desaturase activity and the Δ12/Δ15 desaturase-like polypeptide of fungal origin will have at least 27.3% identity with a known fungal Δ12 desaturase or Δ15 desaturase based on the Clustal W method of alignment, using the default parameters of GAP PENALTY=10, GAP LENGTH PENALTY=0.1, and Gonnet 250 series of protein weight matrix. Upon identification of a fungal polypeptide having Δ15 desaturase activity according to the methodology above, it will be expected that the Δ15 desaturase will have either "monofunctional Δ15 desaturase activity" (wherein the desaturase is only capable of using LA as enzymatic substrate) or "bifunctional Δ15 desaturase activity" (wherein the desaturase prefers LA as its enzymatic substrate but additionally has limited ability to use oleic acid such that the enzyme is a "bifunctional" Δ15 desaturase). Additionally, it will be expected that the Δ15 desaturase identified above will have at least 31.8% identity with a known fungal Δ15 desaturase based on the Clustal W method of alignment, using the default parameters of GAP PENALTY=10, GAP LENGTH PENALTY=0.1, and Gonnet 250 series of protein weight matrix.

Modification of Fungal Δ12 and Δ15 Desaturase Activity and Specificity

The present analysis teaches that mutation(s) that result in a Ile-to-Val change three amino acid residues upstream from the first histidine in the conserved His Box I of a bifunctional fungal Δ15 desaturase-like polypeptide will alter enzyme specificity towards Δ12 desaturation (thereby producing a mutant desaturase having improved Δ12 substrate conversion); and, conversely, those mutations that result in a Val-to-Ile change in the same position will alter enzyme specificity towards Δ15 desaturation (thereby producing a mutant desaturase having improved Δ15 substrate conversion).

Mutant variants based on the *Fusarium moniliforme* bifunctional homologs, i.e., Fm.d12 (characterized as a Δ12 desaturase with a trace level of Δ15 desaturase activity) and Fm.d15 (characterized as a primarily a Δ15 desaturase, additionally having some Δ12 desaturase activity), were constructed. Specifically, the native Val at position 151 of Fm.d12 was changed to Ile by site-specific mutation (i.e., V151I mutation), while the native Ile at position 102 of Fm.d15 was similarly changed to Val by site-specific mutation (i.e., I102V mutation). Fatty acid composition within a Δ12 desaturase-disrupted strain of *Yarrowia lipolytica* transformed with plasmids expressing the mutant desaturases showed that the I102V mutation in Fm.d15 resulted in improved Δ12 desaturation, poorer Δ15 desaturation and a ratio of Δ15 substrate conversion to Δ12 substrate conversion of ca. 46-55% compared to the wild type enzyme. Conversely, the V151I mutation in Fm.d12 resulted in poorer Δ12 desaturation, improved Δ15 desaturation and ca. 381-401% improvement in the ratio of Δ15 substrate conversion to Δ12 substrate conversion compared to the wild type enzyme. The experimental results clearly confirmed that the Ile or Val amino acid residue, respectively, that is only three amino acid residues upstream of the conserved His Box I is a determinant of Δ12 or Δ15 specificity in the Δ12 and Δ15 desaturases of fungi.

Similarly, a V118I mutation in the bifunctional Yl.d12 desaturase improves its Δ15/Δ12 specificity.

In contrast, a I119V mutation in the monofunctional Sk.d15 desaturase was found to reduce Δ15 substrate conversion by ca. 17%. No Δ12 desaturase activity was detectable.

Therefore, it is within the context of the present invention to provide a method for increasing the ability of a bifunctional fungal Δ15 desaturase enzyme to act on a Δ12 desaturase substrate comprising:

a) providing a nucleic acid molecule encoding a polypeptide having bifunctional Δ15 desaturase activity and comprising a Δ15 desaturase motif having an amino acid sequence selected from the group consisting of SEQ ID NOs:46, 47 and 48, wherein each of the motif sequences comprises an isoleucine at amino acid residue 4; and, b) altering the nucleic acid molecule of (a) such that it encodes a mutant polypeptide comprising a mutant Δ15 desaturase motif of (a) wherein the isoleucine at amino acid residue 4 is replaced with valine, wherein the mutant polypeptide has an increased ability to act on a Δ12 desaturase substrate.

Conversely the invention describes a method for increasing the ability of a bifunctional fungal Δ12 desaturase enzyme to act on a Δ15 desaturase substrate comprising:

a) providing a nucleic acid molecule encoding a polypeptide having bifunctional Δ12 desaturase activity and comprising a Δ12 desaturase motif having an amino acid sequence selected from the group consisting of SEQ ID NOs:3, 4 and 5, wherein each of the motif sequences comprises a valine at amino acid residue 4; and, b) altering the nucleic acid molecule of (a) such that it encodes a mutant polypeptide comprising a mutant Δ12 desaturase motif of (a) wherein the valine at amino acid residue 4 is replaced with isoleucine, wherein the mutant polypeptide has an increased ability to act on a Δ15 desaturase substrate.

Although the techniques described herein made use of site-directed mutagenesis to alter the *Fusarium moniliforme* Δ12 and Δ15 desaturase, the *Yarrowia lipolytica* Δ12 desaturase and the *Saccharomyces kluyveri* Δ15 desaturase catalytic activity and specificity, it is well known in the art that in vitro mutagenesis and selection, chemical mutagenesis, "gene shuffling" methods or other means can be employed to obtain mutations of naturally occurring desaturase genes. This would permit production of various polypeptides having altered Δ12 and/or Δ15 desaturase activity, that possessed a Val-to-Ile mutation or a Ile-to-Val mutation, respectively, three amino acid residues upstream from the first histidine in the conserved His Box I (SEQ ID NO:6).

Methods for Production of Various ω-3 and/or ω-6 Fatty Acids

It is expected that introduction of chimeric genes encoding the Δ12 desaturases and Δ15 desaturases described herein (i.e., wildtype enzymes, mutant enzymes, codon-optimized enzymes or homologs thereof), under the control of the appropriate promoters will result in increased production of LA and ALA in the transformed host organism, respectively. As such, the present invention encompasses a method for the direct production of PUFAs comprising exposing a fatty acid substrate (i.e., oleic acid or LA) to the desaturase enzymes described herein (e.g., Ca.d12 or Kl.d15), such that the substrate is converted to the desired fatty acid product (i.e., LA or ALA).

Specifically the methods described here contemplate production of α-linolenic acid comprising the steps of:

a.) providing a host cell comprising:

i.) an isolated nucleic acid fragment encoding a polypeptide having Δ15 desaturase activity and comprising a Δ15 desaturase motif having an amino acid sequence selected from the group consisting of SEQ ID NOs: 46, 47 and 48; and, ii.) a source of linoleic acid;
b.) growing the host cell of step (a) under conditions wherein the nucleic acid fragment encoding the polypeptide is expressed and the linoleic acid is converted to α-linolenic acid; and,
c.) optionally recovering the α-linolenic acid of step (b).

In the alternative, linoleic acid may be made in a process comprising the steps of:
a.) providing a host cell comprising:
   i.) an isolated nucleic acid fragment encoding a polypeptide having Δ12 desaturase activity and comprising a Δ12 desaturase motif having an amino acid sequence selected from the group consisting of SEQ ID NOs:3, 4 and 5; and,
   ii.) a source of oleic acid;
b.) growing the host cell of step (a) under conditions wherein the nucleic acid fragment encoding the polypeptide is expressed and the oleic acid is converted to linoleic acid; and,
c.) optionally recovering the linoleic acid of step (b).

Alternatively, each PUFA gene and its corresponding enzyme product described herein can be used indirectly for the production of ω-3/ω-6 PUFAs (see PCT Publications No. WO 2005/047480 and No. WO2005/047485). Indirect production of ω-3/ω-6 PUFAs occurs wherein the fatty acid substrate is converted indirectly into the desired fatty acid product, via means of an intermediate step(s) or pathway intermediate(s). Thus, it is contemplated that the Δ12 desaturases and/or the Δ15 desaturases described herein (i.e., wild-type enzymes, mutant enzymes, codon-optimized enzymes or homologs thereof) may be expressed in conjunction with additional genes encoding enzymes of the PUFA biosynthetic pathway to result in higher levels of production of longer-chain ω-3/ω-6 fatty acids (e.g., ARA, EPA and DHA). The particular genes included within a particular expression cassette will depend on the host cell (and its PUFA profile and/or desaturase/elongase profile), the availability of substrate and the desired end product(s).

In alternative embodiments, it may be useful to disrupt a host organism's native Δ12 desaturase or Δ15 desaturase, based on the complete sequences described herein, the complement of those complete sequences, substantial portions of those sequences, codon-optimized desaturases derived therefrom and those sequences that are substantially homologous thereto. For example, the targeted disruption of the Δ15 desaturase in a host organism produces a mutant strain that is unable to synthesize ALA. This mutant strain could be useful for the production of "pure" ω-6 fatty acids (without co-synthesis of ω-3 fatty acids).

In preferred embodiments for the production of linoleic acid nucleic acids encoding the following desaturase polypeptides may be used:
a.) a polypeptide selected from the group consisting of the following GenBank Accession Nos: XP_455402 (*Kluyveromyces lactis* [SEQ ID NO:63]), EAK94955 (*Candida albicans* [SEQ ID NO:65]), CAG90237 (*Debaryomyces hansenii* CBS767 [SEQ ID NO:73]), EAL90585 (*Aspergillus fumigatus* [SEQ ID NO:75]), BAD04850 (*Aspergillus oryzae* [SEQ ID NO:77]), EAQ83131 (*Chaetomium globosum* [SEQ ID NO:79]), EAS31392 (*Coccidioides immitis* RS [SEQ ID NO:82]), AAS53960 (*Ashbya gossypii* ATCC 10895 [SEQ ID NO:84]), XP_757193 (*Ustilago maydis* 521 [SEQ ID NO:91]) and EAL 21306 (*Cryptococcus neoformans* var. *neoformans* B-3501 A [SEQ ID NO:87]); and,
b.) a polypeptide whose amino acid sequence is selected from the group consisting of the following genomic sequence ORFs:
   i.) [1122100, 1123500] (complement) within *Candida guilliermondii* supercontig 1.3 [SEQ ID NO:67];
   ii.) [123300, 124400] (complement) within *Candida tropicalis* supercontig 1.10 [SEQ ID NO:69]; and
   iii.) [738900, 740200] (complement) within *Candida lusitaniae* supercontig 1.2 [SEQ ID NO:71].

Similarly In preferred embodiments for the production of α-linolenic acid nucleic acids encoding the following desaturase polypeptides may be used:
a.) a polypeptide selected from the group consisting of the following GenBank Accession Nos: XP_451551 (*Kluyveromyces lactis* [SEQ ID NO:64]), EAL03493 (*Candida albicans* [SEQ ID NO:66]), CAG88182 (*Debaryomyces hansenii* CBS767 [SEQ ID NO:74]), EAL85733 (*Aspergillus fumigatus* [SEQ ID NO:76]), BAE66531 (*Aspergillus oryzae* [SEQ ID NO:78]) and EAQ88866 (*Chaetomium globosum* [SEQ ID NO:80]); and,
b.) a polypeptide whose amino acid sequence is selected from the group consisting of the following genomic sequence ORFs:
   i.) [680800, 682000] (complement) within *Candida guilliermondii* supercontig 1.4 [SEQ ID NO:68];
   ii.) [1709400, 1710700] (complement) within *Candida tropicalis* supercontig 1.3 [SEQ ID NO:70]; and,
   iii.) [2095200, 2096600] (complement) within *Candida lusitaniae* supercontig 1.2 [SEQ ID NO:72].

Expression Systems, Cassettes and Vectors

The genes and gene products of the instant sequences described herein may be expressed in heterologous host cells. Expression in recombinant hosts may be useful for the production of various PUFA pathway intermediates, or for the modulation of PUFA pathways already existing in the host for the synthesis of new products heretofore not possible using the host.

Expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate host cells via transformation to provide high-level expression of the encoded enzymes.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed host cell, although it is to be understood that such control regions need not be derived from the genes native to the specific species chosen as a production host.

Initiation control regions or promoters which are useful to drive expression of the instant ORFs in the desired host cell are numerous and familiar to those skilled in the art. Virtually any promoter capable of directing expression of these genes in the selected host cell is suitable for the present invention. Expression in a host cell can be accomplished in a transient or stable fashion. Transient expression can be accomplished by inducing the activity of a regulatable promoter operably linked to the gene of interest. Stable expression can be achieved by the use of a constituitive promoter operably linked to the gene of interest. As an example, when the host cell is yeast, transcriptional and translational regions functional in yeast cells are provided, particularly from the host species (e.g., see PCT Publication No. WO 2006/052870 for preferred transcriptional initiation regulatory regions for use in Yarrowia lipolytica). Any one of a number of regulatory sequences can be used, depending upon whether constitutive or induced transcription is desired, the efficiency of the promoter in expressing the ORF of interest, the ease of construction and the like.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation and correct folding of the protein in the host organism; 5.) the intrinsic stability of the mRNA and protein of the cloned gene within the host cell; and, 6.) the codon usage within the cloned gene, such that its frequency approaches the frequency of preferred codon usage of the host cell. Each of these types of modifications are encompassed in the present invention, as means to further optimize expression of the $\Delta 12$ and $\Delta 15$ desaturases described herein.

For example, codon-optimized genes encoding desaturases that are substantially identical to Fm.d12, An.d12, Mg.d12, Nc.d12, Fg.d12, Ma.d12, Sk.d12, Kl.d12, Ca.d12, Cg.d12, Ct.d12, Cl.d12, Dh.d12, Af.d12, Ao.d12, Chg.d12, Fm.d15, An.d15, Mg.d15, Nc.d15, Fg.d15, Ma.d15, Sk.d15, Kl.d15, Ca.d15, Cg.d15, Ct.d15, Cl.d15, Dh.d15, Af.d15, Ao.d15 and/or Chg.d15(i.e., SEQ ID NOs:41 [or 49], 51, 53, 56, 57, 59, 61, 63, 65, 67, 69, 71, 73, 75, 77, 79, 39[or 50], 52, 54, 55, 58, 60, 62, 64, 66, 68, 70, 72, 74, 76, 78 and 80, respectively) could be utilized as a means to increase expression of the heterologous genes in an alternate host (see, e.g., PCT Publication No. WO 2004/101757 for details concerning means to identify host-preferred codons and optimize codon usage of heterologous proteins in Yarrowia lipolytica).
Transformation of Host Cells Once the DNA encoding a polypeptide suitable for expression in an appropriate host cell has been obtained, it is placed in a plasmid vector capable of autonomous replication in the host cell, or it is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [Methods in Enzymology, 194:186-187 (1991)]), protoplast fusion, biolistic impact, electroporation, microinjection, or any other method that introduces the gene of interest into the host cell.

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by various selection techniques, as described in PCT Publications No. WO 2004/101757, No. WO 2005/003310 and No. WO 2006/052870.

Following transformation, substrates suitable for the instant $\Delta 12$ and/or $\Delta 15$ desaturases (and, optionally other PUFA enzymes that are co-expressed within the host cell) may be produced by the host either naturally or transgenically, or they may be provided exogenously.
Metabolic Engineering of ω-3 and/or ω-6 Fatty Acid Biosynthesis Knowledge of the sequences of the present $\Delta 12$ and $\Delta 15$ desaturases will be useful for manipulating ω-3 and/or ω-6 fatty acid biosynthesis in various host cells. This may require metabolic engineering directly within the PUFA biosynthetic pathway or additional manipulation of pathways that contribute carbon to the PUFA biosynthetic pathway. Methods useful for up-regulating desirable biochemical pathways and down-regulating undesirable biochemical pathways are well known to those skilled in the art. For example, biochemical pathways competing with the ω-3 and/or ω-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in PCT Publication No. WO 2006/055322 [U.S. Patent Publication No. 2006-0094092-A1], PCT Publication No. WO 2006/052870 [U.S. Patent Publication No. 2006-0115881-A1] and PCT Publication No. WO 2006/052871 [U.S. Patent Publication No. 2006-0110806-A1], respectively, as are desirable manipulations in the TAG biosynthetic pathway and the TAG degradation pathway (and associated techniques thereof).

Preferred Hosts for Recombinant Expression of Δ12 and Δ15 Desaturases

Host cells for expression of the instant genes and nucleic acid fragments may include microbial hosts that grow on a variety of feedstocks, including simple or complex carbohydrates, fatty acids, organic acids, oils, alcohols, and/or hydrocarbons over a wide range of temperature and pH values. Based on the needs of the Applicants' Assignee, the genes described in the instant invention were initially isolated for expression in an oleaginous yeast (and in particular *Yarrowia lipolytica*); however, it is contemplated that because transcription, translation and the protein biosynthetic apparatus are highly conserved, any bacteria, yeast, algae and/or fungus will be a suitable host for expression of the present nucleic acid fragments.

Preferred hosts are oleaginous organisms, such as oleaginous yeast. These oleaginous organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #76982, ATCC #20362, ATCC #8862, ATCC #18944 and/or LGAM S(7)1 (Papanikolaou S., and Aggelis G., *Bioresour. Technol.*, 82(1):43-9 (2002)).

Specific teachings applicable for engineering GLA, ARA, EPA and DHA in *Y. lipolytica* are provided in U.S. patent application Ser. Nos. 11/198,975 (PCT Publication No. WO 2006/033723), No. 11/264,784 (PCT Publication No. WO 2006/055322), No. 11/265,761 (PCT Publication No. WO 2006/052870) and No. 11/264,737 (PCT Publication No. WO 2006/052871), respectively. Detailed means for the synthesis and transformation of expression vectors comprising Δ12 and Δ15 desaturases in oleaginous yeast (i.e., *Yarrowia lipolytica*) are provided in PCT Publications No. WO 2005/047480 and No. WO 2005/047485. The preferred method of expressing genes in this yeast is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene locus (GenBank Accession No. M34929), the Aco2 gene locus (GenBank Accession No. AJO01300), the Pox3 gene locus (Pox3: GenBank Accession No. XP_503244; or, Aco3: GenBank Accession No. AJO01301), the Δ12 desaturase gene locus (PCT Publication No. WO 2004/104167), the Lip1 gene locus (GenBank Accession No. Z50020) and/or the Lip2 gene locus (GenBank Accession No. AJ012632)].

Preferred selection methods for use in *Yarrowia lipolytica* are resistance to kanamycin, hygromycin and the amino glycoside G418, as well as ability to grow on media lacking uracil, leucine, lysine, tryptophan or histidine. In alternate embodiments, 5-fluoroorotic acid (5-fluorouracil-6-carboxylic acid monohydrate; "5-FOA") is used for selection of yeast Ura-mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of Ura⁻ mutant yeast strains (Bartel, P. L. and Fields, S., Yeast 2-Hybrid System, Oxford University: New York, v. 7, pp 109-147, 1997).

Other preferred microbial hosts include oleaginous bacteria, algae and other fungi; and, within this broad group of microbial hosts, of particular interest are microorganisms that synthesize ω-3/ω-6 fatty acids. Thus, for example, transformation of *Mortierella alpina* (which is commercially used for production of ARA) with any of the present Δ15 desaturase genes under the control of inducible or regulated promoters could yield a transformant organism capable of synthesizing EPA. Furthermore, one could improve the ratio of ω-3 to ω-6 fatty acids in this genetically engineered organism by transforming those strains having a disruption or mutation in their native Δ12 desaturase (e.g., by introducing any of the present Δ15 desaturases into the locus of the native Δ12 gene, using means well known in the art). The method of transformation of *M. alpina* is described by Mackenzie et al. (*Appl. Environ. Microbiol.*, 66:4655 (2000)). Similarly, methods for transformation of Thraustochytriales microorganisms are disclosed in U.S. Pat. No. 7,001,772.

In alternate preferred embodiments, the present invention provides a variety of plant hosts for transformation with the Δ12 and Δ15 desaturases described herein. Plants so transformed can be monocotyledonous plants or dicotyledonous plants, and preferably they belong to a class of plants identified as oleaginous (e.g., oilseed plants). Examples of preferred oilseed plant hosts include, but are not limited to: soybean (Glycine and *Soja* sp.), corn (*Zea mays*), flax (*Linum* sp.), rapeseed (*Brassica* sp.), primrose, canola, maize, safflower (*Carthamus* sp.) and sunflower (*Helianthus* sp.). Means for overexpression of the instant Δ12 and Δ15 desaturases in oilseed plants (e.g., construction of expression cassettes, transformation, selection, etc.) are described in PCT Publications No. WO 2005/047479 and No. WO 2005/047480.

No matter what particular host is selected for expression of the Δ12 and Δ15 desaturases described herein, multiple transformants must be screened in order to obtain a strain displaying the desired expression level and pattern. Such screening may be accomplished by Southern analysis of DNA blots (Southern, *J. Mol. Biol.*, 98:503 (1975)), Northern analysis of mRNA expression (Kroczek, *J. Chromatogr. Biomed. Appl.*, 618 (1-2):133-145 (1993)), Western and/or Elisa analyses of protein expression, phenotypic analysis or GC analysis of the PUFA products.

Fermentation Processes for Omega Fatty Acid Production in Microbes

The transformed microbial host cell is grown under conditions that optimize expression of chimeric desaturase genes and produce the greatest and most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. *Yarrowia lipolytica* are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources are taught in PCT Publication No. WO 2005/047480. Although it is contemplated that the source of carbon utilized in the present invention may encompass a wide variety of carbon-containing sources, preferred carbon sources are sugars, glycerol and/or fatty acids. Most preferred is glucose and/or fatty acids containing between 10-22 carbons.

Nitrogen may be supplied from an inorganic (e.g., (NH$_4$)$_2$SO$_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., Fe$^{+2}$, Cu$^{+2}$, Mn$^{+2}$, Co$^{+2}$, Zn$^{+2}$, Mg$^{+2}$) that promote synthesis of lipids and PUFAs (Nakahara, T. et al., Ind. Appl. Single Cell Oils, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in *Yarrowia lipolytica*. This approach is described in PCT Publication No. WO 2004/101757, as are various suitable fermentation process designs (i.e., batch, fed-batch and continuous) and considerations during growth.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by:
1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience, Hoboken, N.J. (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994); or by Thomas D. Brock in Biotechnology: A Textbook of Industrial Microbiology, 2 ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified. *E. coli* (XL1-Blue) competent cells were purchased from the Stratagene Company (San Diego, Calif.). *E. coli* strains were typically grown at 37° C. on Luria Bertani (LB) plates.

General molecular cloning was performed according to standard methods (Sambrook et al., supra).

DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR, Inc., Madison, Wis.).

Percent identity between desaturase-related proteins were performed by multiple sequence alignment by the slow-accurate method Clustal W method using the MegAlign™ program of LASERGENE (Windows 32 MegAlign™ 5.06 1993-2003; DNASTAR Inc.). The parameters included GAP PENALTY=10, GAP LENGTH PENALTY=0.1, Protein Weight Matrix of Gonnet 250 series, and Delay Divergent Seqs(%) of 30%.

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "pmole" mean micromole(s), "g" means gram(s), "µg" means microgram(s), "ng" means nanogram(s), "U" means unit(s), "bp" means base pair(s), and "kB" means kilobase(s).

*Yarrowia lipolytica* Plasmids

The synthesis of the *Yarrowia* expression vector identified herein as pY35 was described in PCT Publication No. WO 2005/047485. The vector comprised the *Fusarium moniliforme* Δ12 desaturase (i.e., Fm.d12 or Fm2) under the control of the *Yarrowia lipolytica* translation elongation factor-1α (TEF) promoter (Muller, S., et al., Yeast 14:1267-1283 (1998); GenBank Accession No. AF054508) and a terminator comprising ~100 bp of the 3' region of the *Yarrowia* Xprgene (GenBank Accession No. M17741) [i.e., a TEF::Fm.d12::XPR chimeric gene].

The synthesis of the *Yarrowia* expression vector identified herein as pY34 was described in PCT Publication No. WO 2005/047480. The vector comprised the *Fusarium moniliforme* bifunctional Δ15 desaturase (i.e., Fm.d15 or Fm1) under the control of the *Yarrowia* glyceraldehyde phosphate dehydrogenase promoter (GPD; PCT Publication No. WO 2005/003310) [i.e., a GPD::Fm.d15::XPR chimeric gene].

Both pY34 and pY35 additionally contained: the ARS18 *Yarrowia* autonomous replication sequence; a ColE1 plasmid origin of replication; an ampicillin resistance gene (AmpR)

for selection in *E. coli*; the *E. coli* 'f1' replication origin; and the *Yarrowia* LEU2 gene for selection in *Yarrowia*.

Yarrowia LiPolytica Strains

*Yarrowia lipolytica* strains ATCC #20362, #76982 and #90812 were purchased from the American Type Culture Collection (Rockville, Md.).

Two separate Δ12 desaturase-disrupted [Δ12 knockout (KO)] strains of *Yarrowia lipolytica* ATCC #76982 were utilized herein: strain Q-d12D and strain L38. Both strains will be generically referred to as a "d12KO" strain and are phenotypically identical. Strain "Q-d12D" was previously described in PCT Publication No. WO 2004/104167; briefly, this d12KO strain was derived from *Y. lipolytica* #76982, following a Δ12 desaturase knockout created via homologous recombination-mediated replacement of the Δ12 desaturase gene with a targeting cassette comprising a truncated and disrupted version of the wildtype Δ12 desaturase. Strain "L38" is a Δ12 desaturase-disrupted strain of *Yarrowia lipolytica* similar to strain Q-d12D (supra). It will be described in Example 1, infra.

Transformation and Cultivation of *Yarrowia lipolytica*

*Y. lipolytica* strains were usually grown at 28° C. on YPD agar (1% yeast extract, 2% bactopeptone, 2% glucose, 2% agar).

For selection of transformants, minimal medium ("MM") was generally used; the composition of liquid MM is as follows: 0.17% yeast nitrogen base (DIFCO Laboratories, Detroit, Mich.) without ammonium sulfate or amino acids, 2% glucose, 0.1% proline, pH 6.1), whereas MM plates additionally contained 20 g/L agar.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.*, 37:911-917 (1959)). Fatty acid methyl esters were prepared by transesterification of the lipid extract with sodium methoxide (Roughan, G. and Nishida I., *Arch Biochem Biophys.*, 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μl of 1%) was added to the sample, and then the sample was vortexed and rocked for 20 min. After adding 3 drops of 1 M NaCl and 400 μl hexane, the sample was vortexed and spun. The upper layer was removed and analyzed by GC as described above.

Example 1

Description of Δ12 Knockout *Yarrowia* Strain L38

Strain L38 is a Δ12 desaturase-disrupted strain of *Yarrowia lipolytica* similar to the d12KO strain described as Q-d12D (PCT Publication No. WO 2004/10416). It was also derived from *Y. lipolytica* ATCC #76982 following disruption of its only native Δ12 desaturase gene by replacement with a disrupted version via homologous recombination.

Selection Method Theory

The methodology used to create the d12KO strain identified herein as L38 relied on site-specific recombinase systems. Briefly, the site-specific recombination system consists of two elements: (1) a recombination site having a characteristic DNA sequence [e.g., LoxP]; and, (2) a recombinase enzyme that binds to the DNA sequence specifically and catalyzes recombination (i.e., excision) between DNA sequences when two or more of the recombination sites are oriented in the same direction at a given interval on the same DNA molecule [e.g., Cre]. For the purposes herein, an integration construct was created comprising a target gene that was desirable to insert into the host genome (i.e., a first selection marker [i.e., Leu2]) that was flanked by recombination sites. Following transformation and selection of the transformants, the first selection marker was excised from the chromosome by the introduction of a replicating plasmid carrying a second selection marker (i.e., sulfonylurea resistance [AHAS]) and a recombinase suitable to recognize the site-specific recombination sites introduced into the genome (i.e., Cre). Upon selection of those transformants carrying the second marker, the replicating plasmid was then cured from the host in the absence of selection and excision of the first selection marker from the cured strain's host genome was confirmed by loss of Leu prototrophy. This produced a transformant that possessed neither the first nor second selection marker, and thus the cured strain was available for another round of transformation using the first selection marker. Additional details concerning site-specific recombinase based methodology for use in *Yarrowia lipolytica* is described in PCT Publication No. WO 2006/052870.

The second selection marker gene utilized was a native *Yarrowia lipolytica* acetohydroxyacid synthase (AHAS or acetolactate synthase; E.C. 4.1.3.18; GenBank Accession No. XM_501277) containing a single amino acid change (W497L) that confers sulfonyl urea herbicide resistance ($SU^R$; described in PCT Publication No. WO 2006/052870). AHAS is the first common enzyme in the pathway for the biosynthesis of branched-chain amino acids and it is the target of the sulfonylurea and imidazolinone herbicides.

Experimental Methodology

*Yarrowia lipolytica* ATCC #76982 was transformed with SphI and AscI linearized plasmid pY137. The sequence of plasmid pY137 (labeled as pY137.YID12ko.Leu2 in FIG. 4A) is disclosed as SEQ ID NO:101 and pY137 Is described in the table below.

TABLE 6

Description of pY137 (SEQ ID NO: 101)

| RE Sites And Nucleotides Within SEQ ID NO: 101 | Description Of Fragment And Chimeric Gene Components |
| --- | --- |
| PacI-BgIII [digestion with PacI-SaI releases LoxP::Leu2] | Contains LoxP::Leu2::LoxP, comprising: LoxP (28-61 bp) *Yarrowia* LEU2 gene (68-2228 bp) (GenBank Accession No. AF260230) LoxP (2308-2341) |
| BgIII-AscI | Contains 3' portion of *Yarrowia lipolytica* Δ12 desaturase ORF (2357-2950 bp) that corresponds to 661-1254 bp of GenBank Accession No. XM_500707) |
| AscI-SphI | Contains ColE1 plasmid origin of replication (3003-3883), ampicillin resistance gene ($Amp^R$; 3941-4801) for selection in *E. coli*, *E. coli* f1 origin of replication (5009-5409) |
| SphI-PacI | Contains 5' portion of *Yarrowia lipolytica* Δ12 desaturase ORF (5662-6262 bp) that corresponds to 1-601 bp of GenBank Accession No. XM_500707 |

Eleven LEU prototrophic pY137 transformants were analyzed by GC and four were identified as Δ12 knockout (d12KO) strains by the absence of detectable 18:2 (LA) upon GC analysis. One of these was designated strain L37.

The LEU2 gene in d12KO strain L37 was excised by transient expression of Cre recombinase under the control of Yarrowia glycerol-3-phosphate acyltransferase (GPAT) promoter. Specifically, strain L37 was transformed with plasmid pY117. The mutated Yarrowia AHAS enzyme in plasmid pY117 conferred $SU^R$, which was used as a positive screening marker.

Figures 4A, 4B:
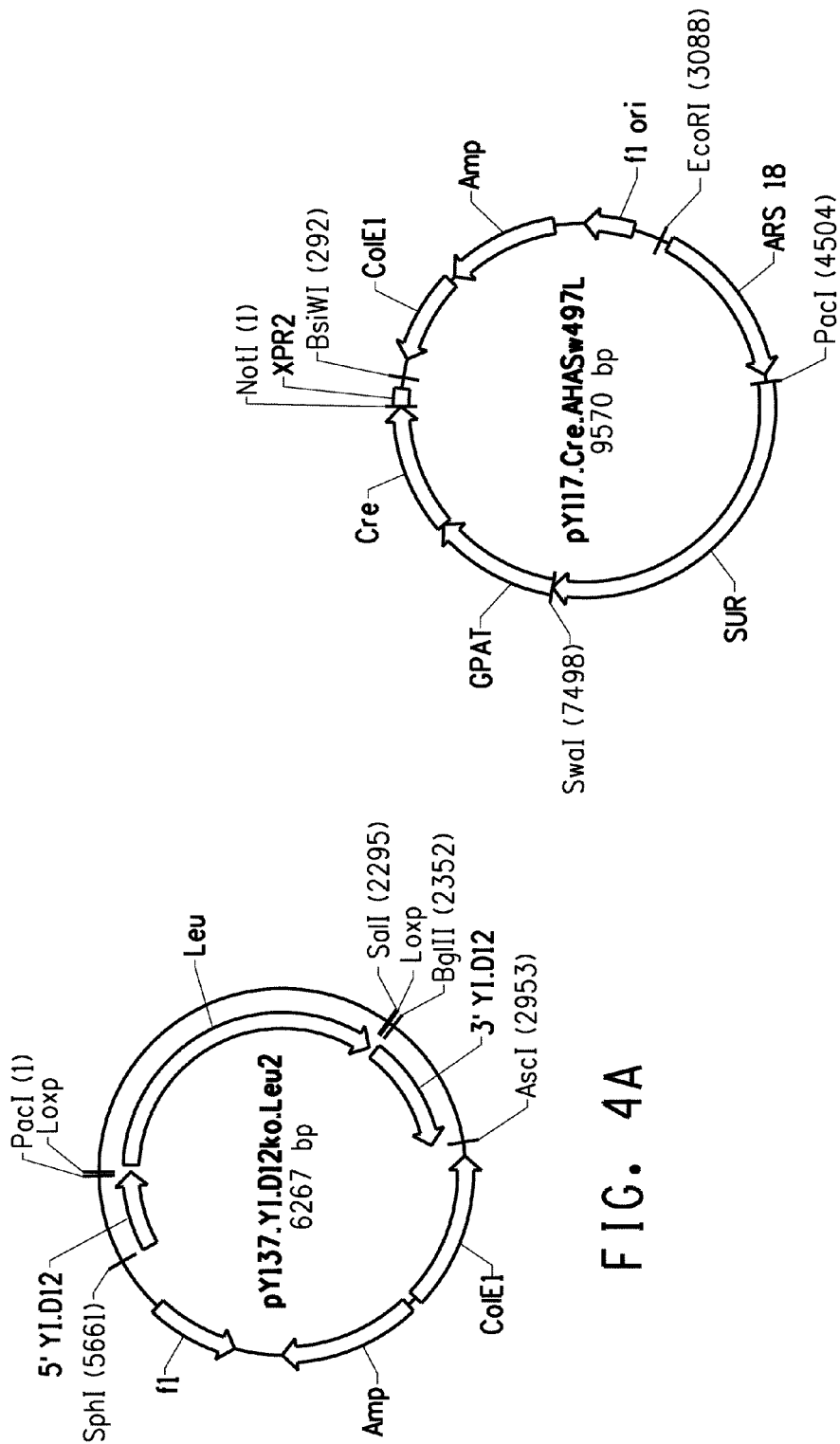

Plasmid pY117 was derived from plasmid pY116 (described in U.S. patent application Ser. No. 11/635,258) by inserting the mutant AHAS gene flanked by PacI-SwaI sites into PacI-SwaI digested pY116 thereby replacing the LEU selectable marker with the sulfonylurea marker. Plasmid pY117 (SEQ ID NO:102) is represented in FIG. 4B (labeled therein as pY117.Cre.AHASw497L) and is described in Table 7 below.

TABLE 7

Description of pY117 (SEQ ID NO: 102)

| RE Sites And Nucleotides Within SEQ ID NO: 102 | Description Of Fragment And Chimeric Gene Components |
|---|---|
| BsiWI-Eco RI | Contains ColE1 plasmid origin of replication (448-1328), ampicillin resistance gene ($Amp^R$; 1328-2258, complementary) for selection in E. coli, and E. coli f1 origin of replication (2438-2838) |
| Eco RI-PacI | Yarrowia autonomous replication sequence (ARS18; GenBank Accession No. A17608) (3157-4461 bp) |
| PacI-SwaI | Contains Yarrowia lipolytica AHAS gene (corresponding to 27040-30026 bp [complementary] in Genbank Accession No. CR382129) comprising a W497L mutation (3157-4461 bp) |
| Swa I/BsiWI [digestion with SwaI-NotI releases GPAT::Cre] | Contains GPAT::Cre::XPR2 comprising: GPAT: Yarrowia lipolytica GPAT promoter (PCT Publication No. WO 2006/031937) (7498-8535 bp) Cre: Enterobacteria phage P1 Cre ORF for recombinase protein (GenBank Accession No. X03453) (8537-9570 bp) except for single base change (T4G) resulting in a single amino acid change (S2A) to create a NcoI site for cloning convenience XPR: ~170 bp of the 3' region of the Yarrowia Xpr gene (GenBank Accession No. M17741) |

L37 transformed by pY117 were plated on minimal plates containing Leu and 280 μg/mL sulfonyurea (chlorimuron ethyl, E. I. duPont de Nemours & Co., Inc., Wilmington, Del.). To cure the strains of pY117, two $SU^R$ colonies were used to inoculate 3 mL YPD. After overnight growth at 30° C., 100 μl of 1:250,000 diluted cultures were plated on YPD plates. After overnight growth at 30° C., 6 single colonies were streaked on both YPD and MM plates. All grew on YPD but not on MM plates, confirming their Leu auxotrophy. One of these was designated as strain L38.

Example 2

Identification of Fungal Sequences Encoding Δ15 Desaturases

"Pairs" of Δ12/Δ15 desaturase-like polypeptides have previously been identified in the following filamentous fungi: Fusarium moniliforme, Fusarium graminearum, Magneporthe grisea, Neurospora crassa, Aspergillus nidulans, Mortirerella alpina and Saccharomyces kluveromyces. In each case, one protein was subsequently determined (or predicted) to possess Δ12 desaturase activity while the other protein was determined to possess Δ15 desaturase activity (PCT Publication No. WO 2005/047480; PCT Publication No. WO 2005/047485; Sakuradani et al., Appl. Microbiol. Biotechnol., 66:648-654(2005); Oura, T. and Kajiwara, S., Microbiology (Reading, Engl.), 150(6):1983-1990(2004); Sakuradani, E., et al., Eur. J. Biochem., 261(3):812-820 (1999); Watanabe, K., et al., Biosci. Biotechnol. Biochem., 68(3):721-727 (2004)). More specifically, the following proteins were previously characterized as Δ15 desaturases: Fm.d15 (SEQ ID NOs:39 and 50), Fg.d15 (SEQ ID NO:58), Mg.d15 (SEQ ID NO:54), Nc.d15 (SEQ ID NO:55), An.d15 (SEQ ID NO:52), Ma.d15 (SEQ ID NO:60) and Sk.d15 (SEQ ID NO:62); and, the following proteins were previously characterized as, or predicted to be, Δ12 desaturases: Fm.d12 (SEQ ID NOs:41 and 49), Fg.d12 (SEQ ID NO:57), Mg.d12 (SEQ ID NO:53), Nc.d12 (SEQ ID NO:-56), An.d12 (SEQ ID NO:51), Ma.d12 (SEQ ID NO:59) and Sk.d12 (SEQ ID NO:61) (see Table 4, supra, for additional details).

Publically available sequences from other fungal species were searched to identify similar "pairs" of Δ12/Δ15 desaturase-like polypeptides as a means to identify novel Δ15 desaturases. Specifically, "pairs" of Δ12/Δ15 desaturase-like polypeptides were identified by performing standard BLAST searches against public databases (e.g., NCBI) using known fungal Δ12 desaturases, such as the Fusarium moniliforme and Yarrowia lipolytica Δ12 desaturases (SEQ ID NOs:41 [or 49] and 89, respectively).

Following the identification of nine different "pairs" of Δ12/Δ15 desaturase-like polypeptides, phylogenetic analysis of the sequences was performed using the Clustal W method (slow/accurate Gonnet) by DNASTAR MegAlign™ 6.1 (FIG. 2). Desaturases whose functions were biochemically characterized in published literature other than PCT Publications No. WO 2005/047485 or No. WO 2005/047480 are identified with a black star (i.e., *).

As shown in FIG. 2, this phylogenetic analysis confirmed that one member of each "pair" of Δ12/Δ15 desaturase-like polypeptides was more closely related to a known fungal Δ15 desaturase (i.e., Sk.d15, Fm.d15), while the other was more closely related to a known fungal Δ12 desaturase (i.e., Sk.d12, Nc.d12, An.d12). This enabled the Applicants to differentiate one protein as a putative Δ15 desaturase (i.e., d15) and the other as a putative Δ12 desaturase (i.e., d12) within each "pair" of Δ12/Δ15 desaturase-like polypeptides as indicated in Table 8 below in the column labeled as "ORF Designation". Additional details concerning each "pair" of Δ12/Δ15 desaturase-like polypeptides are also provided in Table 8, including the putative function of the protein as annotated in public sources (i.e., GenBank).

TABLE 8

"Pairs" Of Fungal Δ12/Δ15 Desaturase-Like Polypeptides

| ORF Designation | Organism | Locus | SEQ ID NO | Annotation |
|---|---|---|---|---|
| Ca.d12 | Candida albicans SC5314 | GenBank Accession No. EAK94955 | 65 | Δ12-like; Ode 1 |
| Ca.d15 | Candida albicans SC5314 | GenBank Accession No. EAL03493 | 66 | Likely Δ12 fatty acid desaturase |
| Cg.d12 | Candida guilliermondii | DNA [1122100, 1123500] (complement): Candida | 67 | — |

TABLE 8-continued

"Pairs" Of Fungal Δ12/Δ15 Desaturase-Like Polypeptides

| ORF Designation | Organism | Locus | SEQ ID NO | Annotation |
|---|---|---|---|---|
| Cg.d15 | Candida guilliermondii | guilliermondii supercontig 1.3 DNA [680800, 682000] (complement): Candida guilliermondii supercontig 1.4 | 68 | — |
| Cl.d12 | Candida lusitaniae | DNA [738900, 740200] (complement): Candida lusitaniae supercontig 1.2 | 71 | — |
| Cl.d15 | Candida lusitaniae | DNA [2095200, 2096600] (complement): Candida lusitaniae supercontig 1.2 | 72 | — |
| Ct.d12 | Candida tropicalis | DNA [123300, 124400] (complement): Candida tropicalis supercontig 1.10 | 69 | — |
| Ct.d15 | Candida tropicalis | DNA [1709400, 1710700] (complement): Candida tropicalis supercontig 1.3 | 70 | — |
| Dh.d12 | Debaryomyces hansenii CBS767 | GenBank Accession No. CAG90237 | 73 | Unnamed protein product |
| Dh.d15 | Debaryomyces hansenii CBS767 | GenBank Accession No. CAG88182 | 74 | Unnamed protein product |
| Kl.d12 | Kluyveromyces lactis NRRL Y-1140 | GenBank Accession No. XP_455402 | 63 | Unnamed protein product |
| Kl.d15 | Kluyveromyces lactis NRRL Y-1140 | GenBank Accession No. XP_451551 | 64 | Unnamed protein product |
| Af.d12 | Aspergillus fumigatus | GenBank Accession No. EAL90585 | 75 | Oleate Δ12 desaturase |
| Af.d15 | Aspergillus fumigatus | GenBank Accession No. EAL85733 | 76 | Oleate Δ12 desaturase |
| Ao.d12 | Aspergillus oryzae | GenBank Accession No. BAD04850 | 77 | Oleate Δ12 desaturase |
| Ao.d15 | Aspergillus oryzae | GenBank Accession No. BAE66531 | 78 | Unnamed protein product; Fatty acid desaturase |
| Chg.d12 | Chaetomium globosum CBS 148.51 | GenBank Accession No. EAQ83131 | 79 | Hypothetical protein CHGG10949; Fatty acid desaturase |
| Chg.d15 | Chaetomium globosum CBS 148.51 | GenBank Accession No. EAQ88866 | 80 | Hypothetical protein CHGG05485; Fatty acid desaturase |

Note:
All *Candida* genome sequences were sponsored by The Fungal Genome Initiative (FGI), Broad Institute of MIT and Harvard (Cambridge, MA).

Confirmation of Predicted Fungal Δ15 Desaturase Activity by Analysis of Fatty Acid Composition Prior to functional characterization of the putative Δ15 desaturases by over-expression in an alternate host, two of the yeast strains were analyzed to confirm the presence of ALA, i.e., the fatty acid product of the putative Δ15 desaturase. Specifically, *Kluyveromyces lactis* NRRL-Y-1140 (designated "Kl Y12651" herein) and *Debaromyces hansenii* CBS767 (designated "DhY7426" herein) were obtained from the Agriculture Research Service (ARS) Culture Collection (National Center for Agricultural Utilization Research, Peoria, Illinois). Additionally, *Saccharomyces kluyveri* NRRL Y-12651 (designated "Sk Y12651" herein) was also obtained from the ARS Culture Collection as a means to confirm Oura et al.'s identification of a Δ15 desaturase within that strain (*Microbiol.*, 150:1983-1990 (2004)).

Each yeast strain was grown for 2 days on YPD plates and the fatty acid composition was determined by analyzing a loop full of cells, as described in the General Methods. All three strains were confirmed to make a significant amount of the Δ15 desaturation product, ALA. More specifically, the fatty acid profile of each strain is shown below in Table 9. Fatty acids are identified as 16:0 (palmitate), 16:1 (palmitoleic acid), 18:0, 18:1 (oleic acid), 18:2 (LA) and 18:3 (ALA) and the composition of each is presented as a % of the total fatty acids. "Δ12% SC" was calculated according to the following formula: ([18:2+18:3]/[18:1+18:2+18:3])*100 and represents percent substrate conversion to 18:2. "Δ15% SC" was calculated according to the following formula: ([18:3]/[18:2+18:3])*100 and represents percent substrate conversion to ALA.

TABLE 9

Fatty Acid Composition (% Total Fatty Acids) Of Yeast Strains

| Yeast Species | 16:0 | 16:1 | 18:0 | 18:1 | 18:2 | ALA | Δ12 % SC | Δ15 % SC |
|---|---|---|---|---|---|---|---|---|
| Sk Y12651 | 14 | 28 | 2 | 28 | 16 | 11 | 50 | 41 |
| Kl Y1140 | 12 | 22 | 2 | 14 | 31 | 18 | 77 | 37 |
| Dh Y7426 | 15 | 2 | 3 | 43 | 22 | 15 | 46 | 41 |

Functional Characterization of Predicted Fungal Δ15 Desaturases by Expression in *Yarrowia lipolytica*

To experimentally confirm the activity of Kl.d15 (SEQ ID NO:64) and Dh.d15 (SEQ ID NO:74) as Δ15 desaturases, and to comparatively evaluate the function of these ORFs with respect to Sk.d15 (SEQ ID NO:62), all three ORFs were subsequently expressed in wild-type (WT) and Δ12 desaturase knockout (Δ12d KO) strains of *Yarrowia lipolytica* ATCC #76982.

First, genomic DNA from all three strains was extracted by the YeaStar Genomic DNA Kit™ (Zymo Research Corporation, Orange, Calif.). For this, 1.5 mL of yeast cultures were harvested by spinning. Supernatant was removed and 120 μl of YD Digestion Buffer and 5 μl of R-Zymolyase™ added. Each pellet was resuspended by vortexing and incubated at 37° C. for 60 min. Then, 120 μl of YD Lysis Buffer was added and mixed by gentle vortexing. Lysates were centrifuged in a table-top centrifuge at >10,000 rpm for 2 min and the supernatant loaded onto the Zymo-spin III column and centrifuged at >10,000 rpm for 1 min. The column was washed by 300 μl of DNA Wash Buffer and centrifuged for 1 min at 10,000 rpm. Another 300 μl of DNA Wash Buffer was added to repeat the wash and centrifuged for 1 min. The Zymo-spin III column was transferred to a new 1.5 mL centrifuge tube and the genomic DNAs were eluted with 60 μl of water.

Next, the isolated genomic DNAs were used to clone the predicted Δ15 desaturase ORFs. Since each ORF lacked an intron, the genomic DNA was used for cloning the entire ORF by PCR using the following upper primer and lower primer combinations:

TABLE 10

Primers Used for Amplification of Predicted Δ15 Desaturase ORFs

| ORF | Upper Primer | Lower Primer |
|---|---|---|
| Kl.d15 | Primer 513 (SEQ ID NO: 31) | Primer 514 (SEQ ID NO: 32) |
| Sk.d15 | Primer 519 (SEQ ID NO: 33) | Primer 520 (SEQ ID NO: 34) |
| Dh.d15 | Primer 521 (SEQ ID NO: 35) | Primer 522 (SEQ ID NO: 36) |

The primers were designed to allow direct cloning of the ORFs without use of restriction sites using in-fusion cloning (Clontech Laboratories, Inc., Mountain View, Calif.).

PCR was performed using standard conditions in a 25 μl total volume containing: 100 ng genomic DNA, 200 μM each deoxyribonucleotide triphosphate, 10 pmole of each primer, 2.5 μl 10×PfuUltra™ high-fidelity reaction buffer and 1 μl PfuUltra™ high-fidelity DNA polymerase (Stratagene, San Diego, Calif.). Amplification was carried out via initial denaturation at 95° C. for 3 min, followed by 30 cycles of the following: 95° C. for 1 min, 55° C. for 30 sec and 72° C. for 1 min. A final extension cycle of 72° C. for 10 min was carried out, followed by reaction termination at 4° C. PCR products were run on an agarose gel and products of the expected length were obtained, gel purified, and cloned by the in-fusion method (Clontech, Catalog No. PT3650-2) into plasmid pY35 linearized with NcoI/NotI digestion (PCT Publication No. WO 2005/047485).

The in-fusion reaction was transformed into E. coli XL1-Blue competent cells (Stratagene) and the cells were plated on LB/Amp selection plates. Correct transformants were screened by digesting miniprep DNA with SalI/NcoI and then performing agarose gel electrophoresis for product analysis.

The resultant plasmids comprising the K. lactis, D. hansenii and S. kluyveri ORFs (i.e., KI.d15, Dh.d15, and Sk.d15, respectively) were designated "pY104 KId15", "pY106 Dhd15" and "pY107 Skd15", respectively. Kl.d15 and Dh.d15 in plasmids pY104 KId15 and pY106 Dhd15, respectively, were sequenced and confirmed to be identical to the public sequences (i.e., GenBank Accession No. XP_451551 and No. CAG88182, corresponding to SEQ ID NOs:64 and 74, respectively). Surprisingly, however, ORF Sk.d15 in plasmid pY107 Skd15 had 29 bp substitutions (97.7% identity) that resulted in 5 amino acid substitutions (98.8% identity), when compared to the public sequence (i.e., GenBank Accession No. BAD11952; SEQ ID NO:62). The differences presumably arose from strain differences. The nucleotide sequence of ORF Sk.d15 in plasmid pY107 Skd15 is provided herein as SEQ ID NO:103, while the amino acid sequence of ORF Sk.d15 in plasmid pY107 Skd15 is provided herein as SEQ ID NO:37.

Plasmids pY104 KId15, pY106 Dhd15 and pY107 Skd15 were then transformed into wild type (WT) Y. lipolytica ATCC #76982 and the d12KO strain referred to as "Q-d12D" (General Methods; PCT Publication No. WO 2004/104167). Additionally, plasmid pY34 (PCT Publication No. WO 2005/047480) was used as a positive control, comprising the Fusarium moniliforme Δ15 desaturase (i.e., Fm.d15 [SEQ ID NOs:39 and 50], which additionally possessed some Δ12 desaturase activity). Plasmids pY34 and pY35 shared the same vector background to allow direct comparison of expression results.

One strain from each transformation was selected and grown in duplicate in 3 mL MM at 30° C. for 2 days before determining the fatty acid composition, as described in the General Methods. The average fatty acid composition of the transformants is shown in Table 11. Fatty acids are identified as 16:0 (palmitate), 16:1 (palmitoleic acid), 18:0, 18:1 (oleic acid), 18:2 (LA) and 18:3 (ALA) and the composition of each is presented as a % of the total fatty acids. "Δ12% SC" was calculated according to the following formula: ([18:2+18:3]/[18:1+18:2+18:3])*100 and represents percent substrate conversion to 18:2. "Δ15% SC" was calculated according to the following formula: ([18:3]/[18:2+18:3])*100 and represents percent substrate conversion to ALA.

TABLE 11

Fatty Acid Composition (% Total Fatty Acids) In Yarrowia Transformants

| Host strain | Plasmid | 16:0 | 16:1 | 18:0 | 18:1 | 18:2 | ALA | Δ12 % SC | Δ15 % SC |
|---|---|---|---|---|---|---|---|---|---|
| WT | pY34 Fm.d15 | 5.8 | 8.8 | 2.0 | 46.7 | 9.3 | 17.7 | 36.6 | 65.7 |
| WT | pY104 Kld15 | 7.2 | 8.6 | 2.6 | 44.5 | 25.1 | 0.8 | 36.8 | 3.1 |
| WT | pY106 Dhd15 | 7.0 | 8.7 | 2.6 | 42.7 | 28.1 | 0.2 | 39.8 | 0.6 |
| WT | pY107 Skd15 | 6.9 | 8.8 | 2.8 | 44.9 | 23.3 | 2.7 | 36.7 | 10.4 |
| d12KO | pY34 Fm.d15 | 5.2 | 9.3 | 2.4 | 63.8 | 0.5 | 9.1 | 13.1 | 95.0 |
| d12KO | pY104 Kld15 | 4.3 | 7.7 | 2.2 | 70.1 | 0.0 | 0.0 | 0.0 | 0.0 |
| d12KO | pY106 Dhd15 | 4.3 | 7.8 | 2.1 | 70.0 | 0.0 | 0.0 | 0.0 | 0.0 |
| d12KO | pY107 Skd15 | 4.9 | 9.3 | 2.7 | 72.9 | 0.0 | 0.0 | 0.0 | 0.0 |

In WT cells, all transformants resulted in the presence of a new fatty acid methyl ester with a retention time that was identical to that for ALA. Thus, both Kl.d15 (SEQ ID NO:64) and Dh.d15 (SEQ ID NO:74) were shown to positively encode proteins having Δ15 desaturase activity. Additionally, Sk.d15 (SEQ ID NO:37) was also confirmed to have Δ15 desaturase activity when expressed in Yarrowia lipolytica. The amount of ALA varied from 0.2 to 2.7% (of total fatty acids); the relatively low level of ALA, compared to the levels seen in the source organisms (Table 9, wherein the amount of ALA varied from 11 to 18%) likely reflects differences in growth conditions and codon usage of the heterologous genes that were not codon optimized for expression in Yarrowia.

In the d12KO strain, ALA was observed only with Fm.d15. This was not unexpected, since Fm.d15 is a bifunctional Δ15 desaturase having primarily Δ15 desaturase activity and some Δ12 desaturase activity. In contrast, none of the d12KO transformants expressing KI.d 5, Dh.d15 or Sk.d15 possessed Δ12 desaturase activity in addition to Δ15 desaturase activity; thus, these desaturases can not be characterized as bifunctional Δ15 desaturases but should instead be classified as monofunctional Δ15 desaturases.

Example 3

Amino Acids Motifs for Identification of Fungal Δ12 and Δ15 Desaturases

Comparison of the different fungal Δ12/Δ15 desaturase-like polypeptides (i.e., including both known and putative Δ12 and Δ15 desaturase sequences) from sixteen different fungal species (Table 4, supra) enabled the identification of regions of significant homology between the genes, such as the 15 amino acids surrounding and including the conserved His Box I ("HE[C/A]GH"; SEQ ID NO:6). More specifically, a total of 7 different sequence variants within this region (i.e., from 6 residues upstream of the His Box I to 4 residues downstream of the His Box I) were identified within the Δ12 desaturases (i.e., SEQ ID NOs:7, 8, 9, 10, 11, 12 and 13), while a total of 9 different sequence variants within this region were identified within the Δ15 desaturases (i.e., SEQ ID NOs:22, 23, 24, 25, 26, 27, 28, 29 and 30). These conserved sequences are summarized below in Tables 12 and 13 (wherein the shaded portion of the sequence corresponds to the His Box I), and led to the identification of SEQ ID NOs:1 and 2 as motifs that were representative of the fungal Δ12 desaturases and the identification of SEQ ID NOs:46, 47 and 48 as motifs that were representative of the fungal Δ15 desaturases.

TABLE 12

Amino Acid Alignment Around The His Box I Of Fungal Δ12/Δ15 Desaturase-Like Polypeptides Identified As Δ12 Desaturases

| Conserved Region Around the His Box I | SEQ ID NO: Of The Conserved Region | Desaturases Sharing Conserved Region |
|---|---|---|
| GIWVLAHECGHQAFS | 7 | Ca.d12 (SEQ ID NO: 65), Cl.d12 (SEQ ID NO: 71), Ct.d12 (SEQ ID NO: 69), Sk.d12 (SEQ ID NO: 61), An.d12 (SEQ ID NO: 51), Mg.d12 (SEQ ID NO: 53) |
| GVWVLAHECGHQSFS | 8 | Ma.d12 (SEQ ID NO: 59) |
| GLWVIAHECGHGAFS | 9 | Fm.d12 (SEQ ID NOs: 41 and 49), Fg.d12 (SEQ ID NO: 57) |
| GLWVLAHECGHLAFS | 10 | Cg.d12 (SEQ ID NO: 67) |
| GLWVLAHECGHQAFS | 11 | Dh.d12 (SEQ ID NO: 73), Kl.d12 (SEQ ID NO: 63), Nc.d12 (SEQ ID NO: 56) |
| GLWVLAHECGHGAFS | 12 | Chg.d12 (SEQ ID NO: 79) |
| GVWVLAHECGHQAFS | 13 | Af.d12 (SEQ ID NO: 75), Ao.d12 (SEQ ID NO: 77) |
| G(I/L/V)WV(L/I)AHECGH(Q/G/L)(A/S)FS | 1 | Fungal Δ12 Desaturase Motif "A" |
| GXWVXAHECGHXXFS | 2 | Fungal Δ12 Desaturase Motif "B" |

TABLE 13

Amino Acid Alignment Around The His Box I Of Fungal Δ12/Δ15 Desaturase-Like Polypeptides Identified As Δ15 Desaturases

| Conserved Region Around the His Box 1 | SEQ ID NO: Of The Conserved Region | Desaturases Sharing Conserved Region |
|---|---|---|
| GLWILAHECGHGAFS | 22 | Ca.d15 (SEQ ID NO: 66), Cg.d15 (SEQ ID NO: 68), Cl.d15 (SEQ ID NO: 72), Ct.d15 (SEQ ID NO: 70), Dh.d15 (SEQ ID NO: 74), |

TABLE 13-continued

Amino Acid Alignment Around The His Box I Of
Fungal Δ12/Δ15 Desaturase-Like Polypeptides
Identified As Δ15 Desaturases

| Conserved Region Around the His Box 1 | SEQ ID NO: Of The Conserved Region | Desaturases Sharing Conserved Region |
|---|---|---|
| | | Kl.d15 (SEQ ID NO: 64), Mg.d15 (SEQ ID NO: 54) |
| GIWILAHECGHGAFS | 23 | An.d15 (SEQ ID NO: 52), Nc.d15 (SEQ ID NO: 55) |
| GPWILAHECGHGAFS | 24 | Ma.d15 (SEQ ID NO: 60) |
| GLWILAHECGHSAFS | 25 | Sk.d15 (SEQ ID NOs: 62 and 37) |
| GVWILGHECGHGAFS | 26 | Fm.d15 (SEQ ID NOs: 39 and 50) |
| GIWILGHECGHGAFS | 27 | Fg.d15 (SEQ ID NO: 58) |
| GMWILAHECGHGAFS | 28 | Af.d15 (SEQ ID NO: 76) |
| GIWILSHECGHGAFS | 29 | Ao.d15 (SEQ ID NO: 78) |
| GIWILAHEAGHGAFS | 30 | Chg.d15 (SEQ ID NO: 80) |
| G(I/L/V/M/P)WIL(A/G/S)H E(A/C)GH(G/S)AFS | 46 | Fungal Δ15 Desaturase Motif "A" |
| GXWILXHE(A/C)GH XAFS | 47 | Fungal Δ15 Desaturase Motif "B" |
| GXWIXXHEXGH XXXS | 48 | Fungal Δ15 Desaturase Motif "C" |

The most significant residue within SEQ ID NOs:1, 2, 46, 47 and 48 is the invariant Val or Ile, respectively, which is located three amino acid residues upstream from the first histidine in the conserved His Box I. This amino acid residue was hypothesized to be a determinant of Δ12 and Δ15 desaturase specificity, respectively, in fungal Δ12/Δ15 desaturase-like polypeptides.

Following the identification of the Δ15 and Δ12 desaturase fungal motifs, above, the Fungal Δ12 Desaturase Motif of SEQ ID NO:2 was used as a means to identity other fungal Δ12 desaturases using the BLASTP program of analysis (Basic Local Alignment Search Tool; Altschul, S. F., et al., *J. Mol. Biol.*, 215:403-410 (1993) and *Nucleic Acids Res.*, 25:3389-3402 (1997)), with hits limited to fungal organisms. These searches resulted in the identification of the following known and putative Δ12 desaturases, all of which comprised the fungal Δ12 desaturase fungal motif of SEQ ID NO:2, or a variant thereof (see Table 14, infra); some additional hits were drawn to those Δ12 and Δ15 desaturases previously described in Table 4. It is important to note that none of the organisms in Table 14 possessed a "pair" of Δ12/Δ15 desaturase-like polypeptide sequences and thus either lack Δ15 desaturase or their Δ15 desaturase is yet to be identified. Significantly, all of the additional known and putative Δ12 desaturases identified below in Table 14 share an invariant Val residue which is located three amino acid residues upstream from the first histidine in the conserved His Box I, thus lending support that this amino acid is a determinant of Δ12 desaturase specificity in fungal desaturases.

TABLE 14

Additional Δ12 Desaturases Comprising Fungal Δ12 Desaturase Motif "B" (SEQ ID NO: 2) Or A Variant Thereof

| Desat. SEQ ID NO: | Desat. Abbreviation | Organism | GenBank Accession No. | Amino Acid Residue * | Conserved Region Around the His Box1 | SEQ ID NO: Of The Conserved Region | Annotation As Reported In GenBank |
|---|---|---|---|---|---|---|---|
| 81 | — | *Mortierella isabellina* | AAL13301 | 106 | GIWVLAHECGHQSFA | 8 | Δ12 fatty acid desaturase |
| 82 | — | *Coccidioides immitis* RS | EAS31392 | 112 | GIWVLAHECGHQSFS | 8 | Hypothetical protein CIMG 06871; Fatty acid desaturase |

TABLE 14-continued

Additional Δ12 Desaturases Comprising Fungal Δ12 Desaturase Motif "B" (SEQ ID NO: 2) Or A Variant Thereof

| Desat. SEQ ID NO: | Desat. Abbreviation | Organism | GenBank Accession No. | Amino Acid Residue* | Conserved Region Around the His Box1 | SEQ ID NO: Of The Conserved Region | Annotation As Reported In GenBank |
|---|---|---|---|---|---|---|---|
| 83 | — | Pichia pastoris | AAX20125 | 120 | GLWVLAHECGHQAFS | 11 | Δ12 fatty acid desaturase |
| 84 | — | Ashbya gossypii ATCC 10895 | AAS53960 | 107 | GLWVLAHECGHQAFS | 11 | AFR589Cp; Fatty acid desaturase |
| 85 | — | Aspergillus parasiticus | AAP23194 | 139 | GVWVLAHECGHQAFS | 13 | Oleate Δ12 desaturase |
| 95 | — | Aspergillus flavus | AAP33789 | 139 | GVWVLAHECGHQAFS | 13 | Oleate Δ12 desaturase |
| 86 | Cc.d12 | Cryptococcus curvatus | AAU12575 | 119 | GIWVIAHECGHQAYS | 14 | Δ12 fatty acid desaturase |
| 87 | Cn.d12 | Cryptococcus neoformans var. neoformans B-3501A | EAL21306 | 119 | GIWVIAHEAGHQAYS | 15 | Hypothetical protein CNBD3600; Fatty acid desaturase |
| 88 | — | Saprolegnia diclina | AAR20443 | 104 | GIWVIAHECGHQAFS | 16 | Δ12 desaturase |
| 89 | — | Yarrowia lipolytica | CAG82952 | 115 | GLWVLAHECGHSAFS | 17 | Unnamed protein product; fatty acid desaturase (see, however, characterization as Δ12 fatty acid desaturase in PCT Publication No. WO2004/104167) |
| 90 | — | Lentinula edodes | BAD51484 | 99 | GLWVVAHECGHQAFS | 18 | Δ12 fatty acid desaturase |
| 91 | — | Ustilago maydis 521 | XP_757193 | 210 | GVWVIAHECGHQSFS | 19 | Hypothetical protein UM01046.1; Fatty acid desaturase |
| 92 | Mc.d12 | Mucor circinelloides | BAB69056 | 106 | GVWVIGHECGHQAFS | 20 | Δ12 fatty acid desaturase |
| 93 | Mr.d12 | Mucor rouxii | AAD55982 | 106 | GVWVIGHECGHQAFS | 20 | Δ12 desaturase |
| 94 | Ro.d12 | Rhizopus oryzae | AAT58363 | 99 | GVWVVGHECGHQAFS | 21 | Δ12 fatty acid desaturase |

Fungal Δ12 Desaturase Motif "B": G X W V X A H E C G H X X F S (SEQ ID NO: 2)

* "Amino Acid Residue" refers to the location of the first glycine within the conserved region around the His Box I, with respect to the full-length desaturase protein sequence. For example, the conserved region around the His Box I is located between amino acids 106-120 of the *Mortierella isabellina* Δ12 desaturase; thus, the amino acid residue corresponding to the initial glycine within the conserved region in this particular protein is residue 106.
** Shaded text highlights the His Box I.

Based on the residues that were variant with respect to Fungal Δ12 Desaturase Motif "B" (shown in bold text in Table 14), a third Fungal Δ12 Desaturase Motif "C" motif was defined as: G (I/L/V) W V (L/I/V) (A/G) H E (A/C) G H (QIGIL) (A/S) (F/Y) S (SEQ ID NO:3). Since Motif "C" is representative of all of the fungal Δ12 desaturases described in Table 14, in addition to Fm.d12, An.d12, Mg.d12, Nc.d12, Fg.d12, Ma.d12, Sk.d12, Kl.d12, Ca.d12, Cg.d12, Ct.d12, Cl.d12, Dh.d12, Af.d12, Ao.d12 and Chg.d12 (i.e., SEQ ID NOs:41 [or 49], 51, 53, 56, 57, 59, 61, 63, 65, 67, 69, 71, 73, 75, 77 and 79, respectively), this motif is preferred (relative to either SEQ ID NO:1 or SEQ ID NO:2) for the identification of fungal polypeptides having Δ12 desaturase activity, wherein the presence of Fungal Δ12 Desaturase Motif "C" motif is indicative of Δ12 desaturase activity. More broadly, a motif indicative of Δ12 desaturase activity was defined as: G X W V X (A/G) H E (A/C) G H X X (F/Y) S (SEQ ID NO:4; "Fungal Δ12 Desaturase Motif D"), while even more broadly, this motif was defined as: G X W V X X H E X G H X X X S (SEQ ID NO:5; "Fungal Δ12 Desaturase Motif E").

The desaturase proteins identified above as Cc.d12 (SEQ ID NO:86), Ro.d12 (SEQ ID NO:94), Mc.d12 (SEQ ID NO:92), Mr.d12 (SEQ ID NO:93) and Cn.d12 (SEQ ID NO:87), in addition to the Δ15 desaturases identified as Fm.d15, An.d15, Mg.d15, Nc.d15, Fg.d15, Ma.d15, Sk.d15, Kl.d15, Ca.d15, Cg.d15, Ct.d15, Cl.d15, Dh.d15, Af.d15, Ao.d15 and/or Chg.d15 (i.e., SEQ ID NOs:39[or 50], 52, 54, 55, 58, 60, 62, 64, 66, 68, 70, 72, 74, 76, 78 and 80, respectively) and the Δ12 desaturases identified as Fm.d12, An.d12, Mg.d12, Nc.d12, Fg.d12, Ma.d12, Sk.d12, Kl.d12, Ca.d12, Cg.d12, Ct.d12, Cl.d12, Dh.d12, Af.d12, Ao.d12 and Chg.d12 (i.e., SEQ ID NOs:41 [or 49], 51, 53, 56, 57, 59, 61, 63, 65, 57, 59, 71, 73, 75, 77 and 79, respectively) were then aligned using the method of Clustal W (slow, accurate, Gonnet option; Thompson et al., Nucleic Acids Res., 22:4673-4680 (1994)) of the MegAlign™ program of DNASTAR software. This resulted in creation of FIG. 3, where percent similarity is shown in the large upper triangle of the Figure while percent divergence is shown in the large lower triangle.

The percent identities revealed by this method allowed determination of: 1.) the percent identity between each of the fungal Δ12 and Δ15 desaturases (of putative and known function); 2.) the percent identity among the putative and known fungal Δ12 desaturase proteins; and 3.) the percent identity among the putative and known fungal Δ15 desaturase proteins. Specifically, comparison of the fungal Δ12 desaturases (putative and confirmed) to the fungal Δ15 desaturases (putative and confirmed) determined that the sequences collectively shared between 27.3%-61.2% identity; minimum identity was between Chg.d12 and Nc.d15, while the maximum identity was between Cl.d12 and Cg.d15 (61.2% identity), Kl.d12 and Cg.d15 (61.2% identity), and Sk.d12 and Cg.d15 (61.2% identity). Within the twenty-one Δ12 desaturases, the percent identity ranged from 24.0% to 95%; minimum identity was between Chg.d12 and Mr.d12, while maximum identity was between Fm.d12 and Fg.d12. Similarly, within the sixteen Δ15 desaturases, the percent identity ranged from 31.8% to 88.8%; minimum identity was between Fg.d15 and Ma.d15, while maximum identity was between Fg.d15 and Fm.d15. Boxes in FIG. 3 corresponding to the specific maximum and minimum interspecies percent identities described above are outlined in bold.

The percent identity between the Δ12 desaturase and the Δ15 desaturase within the same organism ranged between 29.5%-61.0% identity.

Example 4

Method of Altering Δ12/Δ15 Desaturase Specificity of Bifunctional Fungal Desaturases Based on the Applicant's observation that a single amino acid was sufficient to distinguish all known and putative fungal Δ12 desaturases from all known and putative fungal Δ15 desaturases (Tables 12, 13 and 14, supra), the work described below was undertaken as a means to confirm the desaturase specificity conveyed by this diagnostic Val or Ile amino acid residue located three amino acid residues upstream from the first histidine in the conserved His Box I. More specifically, the present Example demonstrates that a Val-to-Ile mutation within the Fungal Δ12 Desaturase Motif (SEQ ID NO:3, 4 or 5) of a bifunctional Δ12 desaturase or a Ile-to-Val mutation within the Fungal Δ15 Desaturase Motif (SEQ ID NO:46, 47 or 48) of a bifunctional Δ15 desaturase is an effective means to alter the Δ12/Δ15 specificity of fungal Δ12 and Δ15 desaturases, respectively.

Site-Directed Mutagenesis within Fm.d12 And Fm.d15

The Δ12 desaturase (Fm.d12; SEQ ID NOs:40 and 41 [or 49] herein) and Δ15 desaturase (Fm.d15; SEQ ID NOs:38 and 39 [or 50] herein) from *Fusarium monoliforme* have been well-characterized in PCT Publications No. WO 2005/047485 and No. WO 2005/047480, respectively. Briefly, wild type Fm.d12 is a bifunctional Δ12 desaturase having only a trace level of Δ15 desaturase activity, while wild type Fm.d15 is a bifunctional Δ15 desaturase, wherein the polypeptide prefers LA as its enzymatic substrate but additionally has some ability to utilize oleic acid as substrate. The activity of these wildtype enzymes were compared to mutant enzymes, created via site-directed mutagenesis. Specifically, single nucleotide base pair changes resulting in single amino acid substitutions of V-to-I in Fm.d12 and I-to-V in Fm.d15 were engineered. Then, both mutant enzymes were evaluated according to: 1.) their Δ12 activity; 2.) their Δ15 activity; and 3.) the ratio of Δ15 to Δ12 substrate conversion.

Site directed mutagenesis was carried out using Stratagene's QuikChange® XL Site-Directed Mutagenesis kit, per the manufacturer's instructions. Nucleotide 'G' at position 451 of Fm.d12 was changed to 'A', resulting in a V-to-I substitution at amino acid residue 151 (i.e., a V151I mutation). Plasmid pY35 (comprising a TEF::Fm.d12 chimeric gene) was used as the template with sense and antisense mutant primers 515 and 516 (SEQ ID NOs:42 and 43), respectively. Similarly, nucleotide 'A' at position 304 of Fm.d15 was changed to 'G', resulting in an I-to-V substitution at amino acid residue 102 (i.e., a I102V mutation). Plasmid pY34 (comprising a GPD::Fm.d15 chimeric gene) was used as the template with sense and antisense mutant primers 517 and 518 (SEQ ID NOs:44 and 45), respectively.

QuickChange reactions were transformed into *E. coli* GOLD XL competent cells (BRL, Bethesda, Md.). Ten transformants each were sequenced; of those mutants, clone pY34M #1 was identified as a Fm.d12 mutant containing only a V151I mutation, while clone pY35M #20 was identified as a Fm.d15 mutant containing only a I102V mutation.

Analysis of Lipid Composition in Transformant *Y. lipholytica* Over-Expressing Mutant Fm.d12 and Fm.d15 Desaturases Plasmids pY34M #1 and pY35M #20 were transformed into wild type (WT) transformed into wild type (WT) *Y. lipolytica* ATCC #76982 and the d12KO strain referred to as "Q-d12D" (General Methods; PCT Publication No. WO 2004/104167) using standard lithium acetate methods and plated onto MM selection plates. After 3-4 days selection on MM plates, four colonies from each transformation were streaked onto fresh MM plates. After incubation at 30° C. overnight, cells from each plate were used to inoculate 3 mL MM liquid medium and grown on a shaker at 30° C. for 2 days. As controls, wild type (WT) and d12KO *Yarrowia lipolytica* ATCC #76982 strains transformed with parental plasmids pY34 and pY35 were also similarly grown. The cells were collected by centrifugation, total lipids were extracted, and fatty acid methyl esters were prepared by transesterification, and subsequently analyzed with a Hewlett-Packard 6890 GC as described in the General Methods.

Fatty acid composition of the single culture of each WT was compared to that of the average of 4 independent transformants of each mutation ("Experiment #1"). Alternatively, the experimental work described above was repeated in "Experiment 2"; and, fatty acid composition of duplicate cultures of both WT were compared to that of duplicate cultures of a single transformant out of the original four independent transformants of each mutation.

The results of the two experiments are combined in Table 15. Fatty acid composition as % of the total fatty acids is shown for each strain. Fatty acids are identified as 16:0 (palmitate), 16:1 (palmitoleic acid), 18:0, 18:1 (oleic acid), 18:2 (LA) and 18:3 (ALA). In the column titled "Desaturase", the amino acid residue of the mutant enzyme is specified. The number in bracket following the enzyme description indicates the number of samples tested. "Δ12% SC" was calculated according to the following formula: ([18:2+18:3]/[18:1+18:2+18:3])*100 and represents percent substrate conversion ("SC") to 18:2. "Δ15% SC" was calculated according to the following formula: ([18:3]/[18:2+18:3])*100 and represents percent substrate conversion to ALA. Δ15/Δ12 SC is calculated as Δ15% SC/Δ12% SC; Δ12/Δ15 SC is calculated as Δ12% SC/Δ15% SC; Δ15/Δ12 SC % WT is calculated as ([Δ15/Δ12 SC of the mutant enzyme]/[Δ15/Δ12 SC of the wild type enzyme])*100; and Δ12/Δ15 SC %

WT is calculated as ([Δ12/Δ15 SC of the mutant enzyme]/[Δ12/Δ15 SC of the wild type enzyme])*100.

Ro.d12 (SEQ ID NO:94), Cc.d12 (SEQ ID NO:86), Mc.d12 (SEQ ID NO:92), Mr.d12 (SEQ ID NO:93) and/or Cn.d12

TABLE 15

Effect Of Site Directed Mutations On Δ12/Δ15 Desaturation Specificity In Bifunctional Fusarium moniliforme Δ12 And Δ15 Desaturases

| Experiment No. | Host | Desaturase | % 16:0 | % 16:1 | % 18:0 | % 18:1 | % 18:2 | % ALA | Δ12 % SC | Δ15 % SC | Δ15/ Δ12 SC | Δ15/ Δ12 SC % WT | Δ12/ Δ15 SC | Δ12/ Δ15 SC % WT |
|---|---|---|---|---|---|---|---|---|---|---|---|---|---|---|
| 1 | WT | Fm.d15 WT (1) | 8 | 9 | 7 | 43 | 7 | 20.1 | 39 | 74.8 | 1.9 | | 0.5 | |
| 1 | WT | Fm.d15 I102V (4) | 8 | 9 | 7 | 34 | 13 | 23.2 | 52 | 64.1 | 1.2 | 64 | 0.8 | 156 |
| 2 | WT | Fm.d15 WT (2) | 6 | 9 | 2 | 47 | 9 | 17.7 | 37 | 65.7 | 1.8 | | 0.6 | |
| 2 | WT | Fm.d15 I102V (2) | 7 | 9 | 3 | 43 | 16 | 14.3 | 42 | 47.1 | 1.1 | 63 | 0.9 | 159 |
| 1 | d12KO | Fm.d15 WT (1) | 7 | 9 | 10 | 53 | 1 | 12.6 | 20 | 95.1 | 4.8 | | 0.2 | |
| 1 | d12KO | Fm.d15 I102V (4) | 7 | 9 | 8 | 50 | 5 | 14.4 | 28 | 73.6 | 2.6 | 55 | 0.4 | 182 |
| 2 | d12KO | Fm.d15 WT (2) | 5 | 9 | 2 | 64 | 0 | 9.1 | 13 | 95.0 | 7.2 | | 0.1 | |
| 2 | d12KO | Fm.d15 I102V (2) | 5 | 7 | 2 | 59 | 5 | 7.8 | 18 | 59.7 | 3.3 | 46 | 0.3 | 219 |
| 1 | WT | Fm.d12 WT (1) | 12 | 4 | 11 | 12 | 57 | 0.4 | 82 | 0.8 | 0.0 | | 108.3 | |
| 1 | WT | Fm.d12 V151I (4) | 11 | 5 | 8 | 17 | 55 | 1.8 | 77 | 3.1 | 0.0 | 433 | 25.0 | 23 |
| 2 | WT | Fm.d12 WT (2) | 10 | 4 | 3 | 15 | 64 | 0.6 | 81 | 0.9 | 0.0 | | 95.1 | |
| 2 | WT | Fm.d12 V151I (2) | 10 | 4 | 3 | 20 | 55 | 1.8 | 74 | 3.1 | 0.0 | 394 | 24.1 | 25 |
| 1 | d12KO | Fm.d12 WT (1) | 11 | 4 | 9 | 21 | 51 | 0.4 | 71 | 0.8 | 0.0 | | 84.2 | |
| 1 | d12KO | Fm.d12 V151I (4) | 10 | 4 | 9 | 23 | 49 | 1.6 | 69 | 3.3 | 0.0 | 401 | 21.0 | 25 |
| 2 | d12KO | Fm.d12 WT (2) | 9 | 4 | 2 | 22 | 56 | 0.5 | 72 | 0.9 | 0.0 | | 80.5 | |
| 2 | d12KO | Fm.d12 V151I (2) | 9 | 5 | 2 | 27 | 51 | 1.6 | 66 | 3.1 | 0.05 | 381 | 21.2 | 26 |

Results showed that I102V mutation in Fm.d15 resulted in a mutant enzyme with improved Δ12 desaturation and poorer Δ15 desaturation. Specifically, in the Δ12 desaturase-disrupted strain, the I102V mutant had a ratio of Δ15/Δ12 SC of 46% (Experiment 2) to 55% (Experiment 1), as compared to the wild type enzyme. Conversely, the V151I mutation in Fm.d12 resulted in poorer Δ12 desaturation and improved Δ15 desaturation. Specifically, in the Δ12 desaturase-disrupted strain, the V151I mutant had a 381% (Experiment 2) to 401% (Experiment 1) improvement in Δ15/Δ12 SC, as compared to the wild type enzyme. This showed that the catalytic activity and specificity of the Fusarium monoliforme desaturases can be improved by the mutations.

Thus, in summary, the present work demonstrated that an Ile-to-Val mutation within the Fungal Δ15 Desaturase Motif (SEQ ID NO:46, 47 or 48) in the Δ15 desaturase of Fusarium moniliforme (i.e., a I102V mutation in the Δ15 desaturase having bifunctional Δ15 desaturase activity) decreased the enzyme's Δ15/Δ12 specificity. In contrast, a Val-to-Ile mutation within the Fungal Δ12 Desaturase Motif (SEQ ID NO:3, 4 or 5) in the Δ12 desaturase of Fusarium moniliforme (i.e., a V151I mutation in the Δ12 desaturase having bifunctional Δ12 desaturase activity) increased the enzyme's Δ15/Δ12 specificity.

Modification of Δ12/Δ15 desaturase-like polypeptides having Δ12 and/or Δ15 desaturase activity could be achieved using the methodology described in the present Example in e.g., An.d12 (SEQ ID NO:51), Mg.d12 (SEQ ID NO:53), Nc.d12 (SEQ ID NO:56), Fg.d12 (SEQ ID NO:57), Ma.d12 (SEQ ID NO:59), Sk.d12 (SEQ ID NO:61), Kl.d12 (SEQ ID NO:63), Ca.d12 (SEQ ID NO:65), Cg.d12 (SEQ ID NO:67), Ct.d12 (SEQ ID NO:69), Cl.d12 (SEQ ID NO:71), Dh.d12 (SEQ ID NO:73), Af.d12 (SEQ ID NO:75), Ao.d12 (SEQ ID NO:77), Chg.d12 (SEQ ID NO:79), An.d15 (SEQ ID NO:52), Mg.d15 (SEQ ID NO:54), Nc.d15 (SEQ ID NO: 55), Fg.d15 (SEQ ID NO:58), Ma.d15 (SEQ ID NO:60), Sk.d15 (SEQ ID NO:62), Kl.d15 (SEQ ID NO:64), Ca.d15 (SEQ ID NO:66), Cg.d15 (SEQ ID NO:68), Ct.d15 (SEQ ID NO:70), Cl.d15 (SEQ ID NO:72), Dh.d15 (SEQ ID NO:74), Af.d15 (SEQ ID NO:76), Ao.d15 (SEQ ID NO:78), Chg.d15 (SEQ ID NO:80), (SEQ ID NO:87), or wildtype enzymes, mutant enzymes, codon-optimized enzymes or homologs thereof.

Example 5

Method of Altering Δ12/Δ15 Desaturase Specificity of Monofunctional Fungal Desaturases Based on the Applicant's demonstration that a Val-to-Ile mutation within the Fungal Δ12 Desaturase Motif (SEQ ID NO:3, 4 or 5) of a desaturase having bifunctional Δ12 desaturase activity increased the enzyme's Δ15/Δ12 specificity, while a Ile-to-Val mutation within the Fungal Δ15 Desaturase Motif (SEQ ID NO:46, 47 or 48) of a desaturase having bifunctional Δ15 desaturase activity decreased the enzyme's Δ15/Δ12 specificity, comparable mutations were made in the present Example in monofunctional fungal Δ12 and Δ15 desaturases. Specifically, the Applicant made the corresponding mutations in the monofunctional Δ15 desaturase (Sk.d15) from Saccharomyces kluyveri and the apparently monofunctional Δ12 desaturase (Yl.d12) from Yarrowia lipolytica. Both mutant enzymes were compared to their parent controls with respect to: 1.) their Δ12 activity; 2.) their Δ15 activity; and 3.) the ratio of Δ15 to Δ12 substrate conversion.

Site-Directed Mutagenesis in Sk.d15

Plasmid pY107 Skd15, comprising a TEF::Sk.d12 chimeric gene, described in Example 2, was used as the template with sense and antisense mutant primers 631 and 632 (SEQ ID NOs:96 and 97), respectively, for site-directed mutagenesis using Stratagene's QuikChange® XL Site-Directed Mutagenesis kit, per the manufacturer's instructions. These primers were designed to change nucleotide 'A' at position 355 of Sk.d15 ORF to 'G' (i.e., a Δ355G mutation) resulting in an I-to-V substitution at amino acid residue 119 (i.e., a I119V mutation).

The QuickChange reaction was transformed into E. coli GOLD XL competent cells (BRL, Bethesda, Md.). Several transformants were sequenced. Plasmid pY123 #5 was identified as a Sk.d15 mutant containing only the desired Δ355G mutation resulting in a I119V mutation. To ensure that there were no mutations in the unsequenced portion of pY123 #5, the sequenced region of pY123 #5 between SphI and NcoI was isolated and used to replace the corresponding sequence of the parent pY107. This resulted in plasmid pY125 that contained Sk.d15 with I119V as the sole mutation.

Site-Directed Mutagenesis in Yl.d12

Plasmid pY28 comprising a GPD::Yl.d12 chimeric gene, is derived from plasmid pY34 (described in PCT Publication No. WO 2005/047480). Plasmid pY28 is described in Table 16 and its 9099 bp sequence disclosed in SEQ ID NO:98.

TABLE 16

Description of Plasmid pY28 (SEQ ID NO: 98)

| RE Sites And Nucleotides Within SEQ ID NO: 98 | Description Of Fragment And Chimeric Gene Components |
|---|---|
| SalI/NcoI (1-971) | Yarrowia lipolytica GPD promoter (WO 2005/003310; GenBank Accession No. XM_501515) (corresponding to 825835-826763 bp in GenBank Accession No. CR382129, except for a single bp change (C826238T) made to destroy the NcoI for cloning convenience, a single A insertion at position 826161 and a 37 bp direct repeat of nucleotides 825884-825922) |
| NcoI/NotI (971-2234) | Yarrowia lipolytica Δ12 desaturase (WO 2004/104167; GenBank Accession No. CR382128) (SEQ ID NO: X) |
| NotI (2234)-2561 | Lip1: Lip1 terminator sequence from Yarrowia Lip1 gene (GenBank Accession No. Z50020) |
| 2562-2635 | ~100 bp of the 3' region of the Yarrowia Xpr gene (GenBank Accession No. M17741) |
| 2636-SalI (1) | E. coli/Yarrowia shuttle vector backbone, including: E. coli replication origin, 'ColE1' (2878-3758) E. coli replication origin, 'f1' (4868-5268) Yarrowia autonomous replication sequence (ARS18) sequence (5587-6864) Yarrowia LEU2 gene for selection in Yarrowia (6873-1) (GenBank Accession No. AF260230) |

Plasmid pY6 was derived from plasmid pY28 by removal of the Yl.d12 ORF. It served as an empty vector control.

Plasmid pY28 was used as the template with sense and antisense mutant primers 633 and 634 (SEQ ID NOs:99 and 100), respectively, for site-directed mutagenesis using Stratagene's QuikChange® XL Site-Directed Mutagenesis kit, per the manufacturer's instructions. These primers were designed to change nucleotide 'G' at position 352 of the Yl.d12 ORF to 'A' (i.e., a G352A mutation) resulting in a V-to-I substitution at amino acid residue 118 (i.e., a V118I mutation).

The QuickChange reaction was transformed into E. coli GOLD XL competent cells (BRL, Bethesda, Md.). Several transformants were sequenced to identify mutant enzymes. Plasmid pY124 #7 was identified as a Yl.d12 desaturase mutant containing only the desired G352A mutation resulting in a V118I mutation. In addition, plasmid pY124 #9 was also identified with an inadvertent Yl.d12 desaturase mutant containing a G352T mutation resulting in a V118F mutation.

To ensure that there were no mutations in the unsequenced portion of the Yl.d12 mutants, the mutant Yl.d12 ORFs were isolated from pY124 #7 and pY124 #9, and used to replace the Yl.d12 WT ORF in the parental plasmid pY28 resulting in plasmids pY128 (Yl.d12 V118I mutant) and pY127 (Yl.d12 V118F mutant), respectively.

Analysis of Lipid Composition in Transformant Y. lipolytica Over-Expressing Mutant Sk.d15 and Yl.d12 Desaturases Experiment 1: Plasmids pY5-13 (vector control) (Damude et al., Proc. Nat. Acad. Sci. U.S.A., 103:9446 (2006)), pY107 (Sk.d15 WT), pY125 (Sk.d15 I119V mutant), pY28 (Yl.d12 WT), pY128 (Yl.d12 V118I mutant) and pY127 (Yl.d12 V118F mutant) were transformed into wild type (WT) Y. lipolytica ATCC #76982 and the d12KO strain referred to as "Q-d12D" (General Methods; PCT Publication No. WO 2004/104167), using standard lithium acetate methods and plated onto MM selection plates. After 3-4 days selection on MM plates, three colonies from each transformation were streaked onto fresh MM plates. After incubation at 30° C. overnight, cells from each plate were used to inoculate 3 mL MM liquid medium and grown on a shaker at 30° C. for 2 days. The cells were collected by centrifugation, total lipids were extracted, and fatty acid methyl esters were prepared by trans-esterification, and subsequently analyzed with a Hewlett-Packard 6890 GC as described in the General Methods.

Experiment 2: Plasmid pY129, comprising a Y. lipolytica GPD promoter and the Mortierella alpina Δ12 desaturase (Ma.d12; GenBank Accession No. AF417244) was created as follows. First, the Ma.d12 ORF was cloned by PCR from a M. alpina cDNA library with 5' NcoI and 3' NotI. The encoded Δ12 desaturase protein was identical to the sequence in GenBank Accession No. AF417244, except for a H392Q mutation. Then, the NcoI/NotI fragment carrying the Ma.d12 ORF was used to replace the NcoI/NotI fragment carrying the Yl.d12 ORF in plasmid pY28, resulting in plasmid pY129 comprising a chimeric GPD::Ma.d12 ORF gene.

Plasmids pY6 (empty vector control), pY28 (Yl.d12 WT), pY128 (Yl.d12 V118I mutant), pY127 (Yl.d12 V118F mutant), and pY129 (Ma.d12 WT) were transformed into wild type (WT) Y. lipolytica ATCC #76982 and the d12KO strain referred to as "L38" (Example 1) using standard lithium acetate methods and plated onto MM selection plates.

After 3-4 days selection on MM plates, four transformant colonies from each transformation were streaked onto fresh MM plates. After incubation at room temperature for 3 days, cells from each plate were used to separately inoculate three 3 mL MM liquid medium and grown on a shaker at 30° C. for 2 days. Each culture (2 mL) was collected by centrifugation, total lipids were extracted, and fatty acid methyl esters were prepared by trans-esterification, and subsequently analyzed with a Hewlett-Packard 6890 GC as described in the General Methods.

Tables 17 and 18 show fatty acid composition (% of the total fatty acids) with standard deviation ("SD") in experiments 1 and 2, respectively. Fatty acids are identified as 16:0 (palmitate), 16:1 (palmitoleic acid), 18:0, 18:1 (oleic acid), 18:2 (c9,12) (LA) and 18:3 (c9,12,15) (ALA). In the column titled "Desaturase", the amino acid residue of the mutant enzyme is specified. "Δ12% SC" was calculated according to the following formula: ([18:2+18:3]/[18:1+18:2+18:3])*100 and represents percent substrate conversion ("SC") to 18:2. "Δ15% SC" was calculated according to the following formula: ([18:3]/[18:2+18:3])*100 and represents percent substrate conversion to ALA. Δ15/Δ12 SC is calculated as Δ15% SC/Δ12% SC. Fatty acid composition in Table 17 is the average of triplicate cultures of all samples, except WT host transformed with pY124, which was the average of duplicate cultures. Fatty acid composition in Table 18 is the average of quadruplicate cultures of all samples, except the d12KO host transformed with pY28, which was the average of triplicate cultures.

TABLE 17

Fatty Acid Composition (% Total Fatty Acids) In *Yarrowia* Transformants (Experiment 1)

| Host strain | Plasmid | Desaturase | | % 16:0 | % 16:1 | % 18:0 | % 18:1 | % LA | % ALA | Δ12 % SC | Δ15 % SC | Δ15/Δ12 SC |
|---|---|---|---|---|---|---|---|---|---|---|---|---|
| WT | pY5-13 | Vector control | avg | 10.3 | 10.5 | 5.8 | 39.8 | 30.4 | 0.000 | 43.3 | 0.0 | |
| | | | SD | 0.3 | 0.2 | 0.3 | 0.6 | 0.4 | 0.0 | 0.6 | 0.0 | |
| WT | pY28 | Yld12 WT | avg | 11.2 | 6.7 | 6.2 | 25.2 | 46.3 | 0.977 | 65.2 | 2.1 | 0.03 |
| | | | SD | 0.2 | 0.1 | 0.4 | 0.4 | 0.6 | 0.1 | 0.6 | 0.2 | 0.00 |
| WT | pY127 | Yld12 V118F mutant | avg | 10.5 | 9.5 | 6.6 | 39.0 | 30.3 | 0.063 | 43.8 | 0.2 | 0.00 |
| | | | SD | 0.8 | 1.3 | 1.1 | 1.5 | 1.2 | 0.1 | 1.9 | 0.3 | 0.01 |
| WT | pY128 | Yld12 V118I mutant | avg | 10.1 | 7.5 | 6.3 | 28.7 | 39.7 | 2.976 | 59.7 | 6.7 | 0.11 |
| | | | SD | | | | | | | | | |
| WT | pY107 | Skd15 WT | avg | 9.8 | 9.6 | 5.7 | 43.4 | 20.9 | 6.588 | 38.8 | 24.0 | 0.62 |
| | | | SD | 0.2 | 0.2 | 0.2 | 0.4 | 0.5 | 0.2 | 0.5 | 0.9 | 0.03 |
| WT | pY125 | Skd15 I119V mutant | avg | 9.5 | 9.4 | 5.4 | 42.7 | 22.9 | 5.652 | 40.1 | 19.8 | 0.49 |
| | | | SD | 0.4 | 0.1 | 0.3 | 0.5 | 0.6 | 0.1 | 0.8 | 0.2 | 0.01 |
| d12KO | pY5-13 | Vector control | avg | 8.6 | 11.5 | 5.2 | 70.9 | 0.0 | 0.000 | 0.0 | 0.0 | |
| | | | SD | 0.5 | 0.1 | 0.7 | 0.2 | 0.0 | 0.0 | 0.0 | 0.0 | |
| d12KO | pY28 | Yld12 WT | avg | 10.5 | 6.6 | 6.1 | 32.8 | 38.8 | 1.104 | 54.8 | 2.8 | 0.05 |
| | | | SD | 0.1 | 0.1 | 0.0 | 0.3 | 0.3 | 0.1 | 0.4 | 0.2 | 0.00 |
| d12KO | pY127 | Yld12 V118F mutant | avg | 7.8 | 12.1 | 4.3 | 69.7 | 0.000 | 0.000 | 0.0 | 0.0 | |
| | | | SD | 0.0 | 0.3 | 0.5 | 0.5 | 0.0 | 0.0 | 0.0 | 0.0 | |
| d12KO | pY128 | Yld12 V118I mutant | avg | 10.1 | 6.9 | 5.7 | 35.9 | 33.0 | 4.738 | 51.2 | 12.6 | 0.25 |
| | | | SD | 0.1 | 0.1 | 0.1 | 0.2 | 0.2 | 0.1 | 0.3 | 0.2 | 0.00 |
| d12KO | pY107 | Skd15 WT | avg | 7.7 | 10.3 | 4.2 | 71.9 | 0.000 | 0.000 | 0.00 | 0.00 | |
| | | | SD | 0.3 | 0.4 | 0.4 | 0.9 | 0.0 | 0.0 | 0.00 | 0.00 | |
| d12KO | pY125 | Skd15 I119V mutant | avg | 7.7 | 9.9 | 4.5 | 72.0 | 0.000 | 0.000 | 0.00 | 0.00 | |
| | | | SD | 0.3 | 0.3 | 0.4 | 0.6 | 0.0 | 0.0 | 0.00 | 0.00 | |

TABLE 18

Fatty Acid Composition (% Total Fatty Acids) In *Yarrowia* Transformants (Experiment 2)

| Host | Plasmid | Desaturase | | % 16:0 | % 16:1 | % 18:0 | % 18:1 | % LA | % ALA | Δ12 % SC | Δ15 % SC | Δ15/Δ12 SC |
|---|---|---|---|---|---|---|---|---|---|---|---|---|
| WT | pY6 | empty vector | avg | 10.1 | 9.4 | 2.4 | 28.4 | 36.90 | 0.00 | 56.5 | 0.0 | |
| | | | SD | 0.2 | 0.3 | 0.1 | 1.1 | 1.8 | 0.0 | | | |
| WT | pY28 | Yl D12d WT | avg | 10.5 | 5.1 | 2.0 | 14.4 | 51.30 | 1.90 | 78.7 | 3.6 | 0.045 |
| | | | SD | 0.0 | 0.5 | 0.3 | 1.7 | 3.0 | 0.2 | | | |
| WT | pY127 | Yld12 V118F mutant | avg | 11.0 | 9.8 | 2.2 | 22.9 | 45.70 | 0.10 | 66.7 | 0.2 | 0.003 |
| | | | SD | 1.0 | 1.2 | 0.4 | 5.1 | 8.8 | 0.1 | | | |
| WT | pY128 | Yld12 V118I mutant | avg | 10.4 | 4.9 | 1.4 | 12.2 | 50.80 | 9.70 | 83.2 | 16.0 | 0.193 |
| | | | SD | 0.2 | 0.1 | 0.1 | 0.4 | 0.2 | 0.2 | | | |
| WT | pY129 | Ma D12d | avg | 10.9 | 6.1 | 2.2 | 12.8 | 54.60 | 0.80 | 81.2 | 1.4 | 0.018 |
| | | | SD | 0.3 | 0.8 | 0.8 | 1.5 | 3.7 | 0.5 | | | |
| d12KO | pY6 | empty vector | avg | 6.7 | 10.8 | 2.1 | 71.4 | 0.000 | 0.000 | 0.0 | | |
| | | | SD | 0.3 | 0.3 | 0.3 | 1.2 | 0.0 | 0.0 | | | |
| d12KO | pY28 | Yl D12d WT | avg | 9.8 | 7.1 | 2.3 | 27.9 | 44.97 | 1.14 | 62.3 | 2.5 | 0.040 |
| | | | SD | 0.1 | 0.0 | 0.3 | 1.0 | 1.3 | 0.0 | 1.5 | 0.0 | |
| d12KO | pY127 | Yld12 V118F mutant | avg | 5.8 | 12.5 | 1.4 | 70.0 | 0.000 | 0.000 | 0.0 | | |
| | | | SD | 0.4 | 0.9 | 0.2 | 0.9 | 0.0 | 0.0 | | | |
| d12KO | pY128 | Yld12 V118I mutant | avg | 9.3 | 7.2 | 1.9 | 31.3 | 37.10 | 6.35 | 58.2 | 14.6 | 0.251 |
| | | | SD | 0.3 | 0.1 | 0.1 | 0.6 | 0.8 | 0.4 | 1.1 | 0.5 | |
| d12KO | pY129 | Ma D12d | avg | 11.6 | 6.0 | 3.5 | 22.9 | 49.53 | 1.15 | 68.9 | 2.3 | 0.033 |
| | | | SD | 0.2 | 0.1 | 0.2 | 0.5 | 0.8 | 0.0 | 0.8 | 0.0 | |

Results in Table 17 showed that the I119V mutation in the monofunctional Δ15 (ω3) desaturase of *Saccharomyces kluyveri* reduced Δ15 desaturase conversion efficiency (SC) by ca. 17% without detectable Δ12 desaturase activity.

Results in Tables 17 and 18 showed that WT and d12KO *Yarrowia* transformed with empty vector lack detectable ALA. Thus, expression of the native chromosomal Yl.d12 gene results in an apparently monofunctional Δ12 desaturase, i.e., without detectable Δ15 desaturase activity. However, WT and d12KO *Yarrowia* transformed with pY28 (Yl.d12 WT) showed traces of ALA, as confirmed by GC-MS. Thus, plasmid-based expression of the Yl.d12 ORF under control of the GPD promoter in *Yarrowia* resulted in a bifunctional Δ12 desaturase, i.e., with trace Δ15 desaturase activity. It is likely that overexpression of Yl.d12 desaturase confers or reveals Δ12/Δ15 bifunctional desaturase activity to an apparently monofunctional Δ12 desaturase enzyme. Applicants postulate that all fungal Δ12 desaturases that appear monofunctional in their native species are bifunctional when so overexpressed. This postulate is also supported by the expression of the *Mortierella alpina* Δ12 desaturase (GenBank Accession No. AF417244) that appears monofunctional under its native promoter (Sakuradani, E. et al., *European J. Biochem.*, 261(3):812-820 (1999)) and bifunctional when overexpressed in *Y. lipolytica* under the control of the *Y. lipolytica* GPD promoter in plasmid pY129 (Table 18).

Nevertheless, results in Tables 17 and 18 showed that, as expected, transformants of plasmid pY128 carrying Yl.d12 V118I mutant demonstrated improved Δ15/Δ12 SC compared to transformants carrying the parental control plasmid, pY28. For example, d12KO transformant carrying plasmid pY128 showed 6.3 fold improvement in Δ15/Δ12 specificity (Δ15/Δ12 SC) over that of pY28 (Table 18). Thus, this result with the Yl.d12 V118I mutant is qualitatively similar to that of the Fm.d12 V151I mutant (Example 4), which showed ca. 4 fold improvement in Δ15/Δ12 specificity.

Results showed no Δ12 desaturase activity in the d12KO strain transformed with plasmid pY127 carrying the Yl.d12 V118F mutant; thus, residue 118 of Yl.d12 desaturase is important for enzyme activity.

Modification of Δ12/Δ15 desaturase-like polypeptides having Δ12 and/or Δ15 desaturase activity could be achieved using the methodology described in the present Example in e.g., An.d12 (SEQ ID NO:51), Mg.d12 (SEQ ID NO:53), Nc.d12 (SEQ ID NO:56), Fg.d12 (SEQ ID NO:57), Ma.d12 (SEQ ID NO:59), Sk.d12 (SEQ ID NO:61), Kl.d12 (SEQ ID NO:63), Ca.d12 (SEQ ID NO:65), Cg.d12 (SEQ ID NO:67), Ct.d12 (SEQ ID NO:69), Cl.d12 (SEQ ID NO:71), Dh.d12 (SEQ ID NO:73), Af.d12 (SEQ ID NO:75), Ao.d12 (SEQ ID NO:77), Chg.d12 (SEQ ID NO:79), An.d15 (SEQ ID NO:52), Mg.d15 (SEQ ID NO:54), Nc.d15 (SEQ ID NO:55), Fg.d15 (SEQ ID NO:58), Ma.d15 (SEQ ID NO:60), Kl.d15 (SEQ ID NO:64), Ca.d15 (SEQ ID NO:66), Cg.d15 (SEQ ID NO:68), Ct.d15 (SEQ ID NO:70), Cl.d15 (SEQ ID NO:72), Dh.d15 (SEQ ID NO:74), Af.d15 (SEQ ID NO:76), Ao.d15 (SEQ ID NO:78), Chg.d15 (SEQ ID NO:80), Ro.d12 (SEQ ID NO:94), Cc.d12 (SEQ ID NO:86), Mc.d12 (SEQ ID NO:92), Mr.d12 (SEQ ID NO:93) and/or Cn.d12 (SEQ ID NO:87), or wild-type enzymes, mutant enzymes, codon-optimized enzymes or homologs thereof.

What is claimed is:

1. An isolated fungal polypeptide having delta-15 desaturase activity comprising:

(a) an amino acid sequence that is at least 90% identical with SEQ ID NO:52, 54, 55, 58, 60, or 62, based on the Clustal W method of alignment, using the default parameters of GAP PENALTY=10, GAP LENGTH PENALTY=0.1, and Gonnet 250 series of protein weight matrix, wherein the amino acid sequence is not SEQ ID NO:50, 52, 54, 55, 58, 60, or 62; and (b) a delta-15 desaturase motif as set forth in SEQ ID NO:46.

2. A method for producing alpha-linolenic acid comprising:

(a) providing a host cell comprising:
  (i) an isolated nucleic acid fragment encoding the fungal polypeptide according to claim 1; and
  (ii) a source of linoleic acid;
(b) growing the host cell of step (a) under conditions wherein the nucleic acid fragment encoding the fungal polypeptide is expressed and the linoleic acid is converted to alpha-linolenic acid; and
(c) optionally recovering the alpha-linolenic acid of step (b).

* * * * *

```
                          SEQUENCE LISTING

<160> NUMBER OF SEQ ID NOS: 103

<210> SEQ ID NO 1
<211> LENGTH: 15
<212> TYPE: PRT
<213> ORGANISM: Artificial Sequence
<220> FEATURE:
<223> OTHER INFORMATION: Fungal Delta-12 Desaturase Motif "A"
<220> FEATURE:
<221> NAME/KEY: MISC_FEATURE
<222> LOCATION: (2)..(2)
<223> OTHER INFORMATION: Xaa = Ile or Leu or Val
<220> FEATURE:
<221> NAME/KEY: MISC_FEATURE
<222> LOCATION: (5)..(5)
<223> OTHER INFORMATION: Xaa = Ile or Leu
<220> FEATURE:
<221> NAME/KEY: MISC_FEATURE
<222> LOCATION: (12)..(12)
<223> OTHER INFORMATION: Xaa = Gln or Gly or Leu
<220> FEATURE:
<221> NAME/KEY: MISC_FEATURE
<222> LOCATION: (13)..(13)
<223> OTHER INFORMATION: Xaa = Ala or Ser

<400> SEQUENCE: 1

Gly Xaa Trp Val Xaa Ala His Glu Cys Gly His Xaa Xaa Phe Ser
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Fungal Delta-12 Desaturase Motif "B"
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid

<400> SEQUENCE: 2

Gly Xaa Trp Val Xaa Ala His Glu Cys Gly His Xaa Xaa Phe Ser
1               5                   10                  15

<210> SEQ ID NO 3
<211> LENGTH: 15
```

```
<212> TYPE: PRT
<213> ORGANISM: Artificial Sequence
<220> FEATURE:
<223> OTHER INFORMATION: Fungal Delta-12 Desaturase Motif "C"
<220> FEATURE:
<221> NAME/KEY: MISC_FEATURE
<222> LOCATION: (2)..(2)
<223> OTHER INFORMATION: Xaa = Ile or Leu or Val
<220> FEATURE:
<221> NAME/KEY: MISC_FEATURE
<222> LOCATION: (5)..(5)
<223> OTHER INFORMATION: Xaa = Ile or Leu or Val
<220> FEATURE:
<221> NAME/KEY: MISC_FEATURE
<222> LOCATION: (6)..(6)
<223> OTHER INFORMATION: Xaa = Ala or Gly
<220> FEATURE:
<221> NAME/KEY: MISC_FEATURE
<222> LOCATION: (9)..(9)
<223> OTHER INFORMATION: Xaa = Ala or Cys
<220> FEATURE:
<221> NAME/KEY: MISC_FEATURE
<222> LOCATION: (12)..(12)
<223> OTHER INFORMATION: Xaa = Gln or Gly or Leu
<220> FEATURE:
<221> NAME/KEY: MISC_FEATURE
<222> LOCATION: (13)..(13)
<223> OTHER INFORMATION: Xaa = Ala or Ser
<220> FEATURE:
<221> NAME/KEY: MISC_FEATURE
<222> LOCATION: (14)..(14)
<223> OTHER INFORMATION: Xaa = Phe or Tyr

<400> SEQUENCE: 3

Gly Xaa Trp Val Xaa Xaa His Glu Xaa Gly His Xaa Xaa Xaa Ser
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Fungal Delta-12 Desaturase Motif "D"
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa = Ala or Gly
<220> FEATURE:
<221> NAME/KEY: MISC_FEATURE
<222> LOCATION: (9)..(9)
<223> OTHER INFORMATION: Xaa = Ala or Cys
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa = Phe or Tyr

<400> SEQUENCE: 4

Gly Xaa Trp Val Xaa Xaa His Glu Xaa Gly His Xaa Xaa Xaa Ser
1               5                   10                  15

<210> SEQ ID NO 5
<211> LENGTH: 15
<212> TYPE: PRT
```

```
<213> ORGANISM: Artificial Sequence
<220> FEATURE:
<223> OTHER INFORMATION: Fungal Delta-12 Desaturase Motif "E"
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid

<400> SEQUENCE: 5

Gly Xaa Trp Val Xaa Xaa His Glu Xaa Gly His Xaa Xaa Xaa Ser
1               5                   10                  15

<210> SEQ ID NO 6
<211> LENGTH: 5
<212> TYPE: PRT
<213> ORGANISM: Artificial Sequence
<220> FEATURE:
<223> OTHER INFORMATION: His Box I
<220> FEATURE:
<221> NAME/KEY: MISC_FEATURE
<222> LOCATION: (3)..(3)
<223> OTHER INFORMATION: Xaa = Ala or Cys

<400> SEQUENCE: 6

His Glu Xaa Gly His
1               5

<210> SEQ ID NO 7
<211> LENGTH: 15
<212> TYPE: PRT
<213> ORGANISM: Artificial Sequence
<220> FEATURE:
<223> OTHER INFORMATION: Fungal delta-12 conserved region #1

<400> SEQUENCE: 7

Gly Ile Trp Val Leu Ala His Glu Cys Gly His Gln Ala Phe Ser
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Fungal delta-12 conserved region #2

<400> SEQUENCE: 8

Gly Ile Trp Val Leu Ala His Glu Cys Gly His Gln Ser Phe Ser
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Fungal delta-12 conserved region #3

<400> SEQUENCE: 9

Gly Leu Trp Val Ile Ala His Glu Cys Gly His Gly Ala Phe Ser
```

```
<210> SEQ ID NO 10
<211> LENGTH: 15
<212> TYPE: PRT
<213> ORGANISM: Artificial Sequence
<220> FEATURE:
<223> OTHER INFORMATION: Fungal delta-12 conserved region #4

<400> SEQUENCE: 10

Gly Leu Trp Val Leu Ala His Glu Cys Gly His Leu Ala Phe Ser
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Fungal delta-12 conserved region #5

<400> SEQUENCE: 11

Gly Leu Trp Val Leu Ala His Glu Cys Gly His Gln Ala Phe Ser
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Fungal delta-12 conserved region #6

<400> SEQUENCE: 12

Gly Leu Trp Val Leu Ala His Glu Cys Gly His Gly Ala Phe Ser
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Fungal delta-12 conserved region #7

<400> SEQUENCE: 13

Gly Val Trp Val Leu Ala His Glu Cys Gly His Gln Ala Phe Ser
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Fungal delta-12 conserved region #8

<400> SEQUENCE: 14

Gly Ile Trp Val Ile Ala His Glu Cys Gly His Gln Ala Tyr Ser
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Fungal delta-12 conserved region #9

<400> SEQUENCE: 15

Gly Ile Trp Val Ile Ala His Glu Ala Gly His Gln Ala Tyr Ser
1               5                   10                  15
```

```
<210> SEQ ID NO 16
<211> LENGTH: 15
<212> TYPE: PRT
<213> ORGANISM: Artificial Sequence
<220> FEATURE:
<223> OTHER INFORMATION: Fungal delta-12 conserved region #10

<400> SEQUENCE: 16

Gly Ile Trp Val Ile Ala His Glu Cys Gly His Gln Ala Phe Ser
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Fungal delta-12 conserved region #11

<400> SEQUENCE: 17

Gly Leu Trp Val Leu Ala His Glu Cys Gly His Ser Ala Phe Ser
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Fungal delta-12 conserved region #12

<400> SEQUENCE: 18

Gly Leu Trp Val Val Ala His Glu Cys Gly His Gln Ala Phe Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Fungal delta-12 conserved region #13

<400> SEQUENCE: 19

Gly Val Trp Val Ile Ala His Glu Cys Gly His Gln Ser Phe Ser
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Fungal delta-12 conserved region #14

<400> SEQUENCE: 20

Gly Val Trp Val Ile Gly His Glu Cys Gly His Gln Ala Phe Ser
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Fungal delta-12 conserved region #15

<400> SEQUENCE: 21

Gly Val Trp Val Val Gly His Glu Cys Gly His Gln Ala Phe Ser
1               5                   10                  15
```

```
<210> SEQ ID NO 22
<211> LENGTH: 15
<212> TYPE: PRT
<213> ORGANISM: Artificial Sequence
<220> FEATURE:
<223> OTHER INFORMATION: Fungal delta-15 conserved region #1

<400> SEQUENCE: 22

Gly Leu Trp Ile Leu Ala His Glu Cys Gly His Gly Ala Phe Ser
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Fungal delta-15 conserved region #2

<400> SEQUENCE: 23

Gly Ile Trp Ile Leu Ala His Glu Cys Gly His Gly Ala Phe Ser
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Fungal delta-15 conserved region #3

<400> SEQUENCE: 24

Gly Pro Trp Ile Leu Ala His Glu Cys Gly His Gly Ala Phe Ser
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Fungal delta-15 conserved region #4

<400> SEQUENCE: 25

Gly Leu Trp Ile Leu Ala His Glu Cys Gly His Ser Ala Phe Ser
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Fungal delta-15 conserved region #5

<400> SEQUENCE: 26

Gly Val Trp Ile Leu Gly His Glu Cys Gly His Gly Ala Phe Ser
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Fungal delta-15 conserved region #6

<400> SEQUENCE: 27

Gly Ile Trp Ile Leu Gly His Glu Cys Gly His Gly Ala Phe Ser
1               5                   10                  15
```

```
<210> SEQ ID NO 28
<211> LENGTH: 15
<212> TYPE: PRT
<213> ORGANISM: Artificial Sequence
<220> FEATURE:
<223> OTHER INFORMATION: Fungal delta-15 conserved region #7

<400> SEQUENCE: 28

Gly Met Trp Ile Leu Ala His Glu Cys Gly His Gly Ala Phe Ser
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Fungal delta-15 conserved region #8

<400> SEQUENCE: 29

Gly Ile Trp Ile Leu Ser His Glu Cys Gly His Gly Ala Phe Ser
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Fungal delta-15 conserved region #9

<400> SEQUENCE: 30

Gly Ile Trp Ile Leu Ala His Glu Ala Gly His Gly Ala Phe Ser
1               5                   10                  15

<210> SEQ ID NO 31
<211> LENGTH: 40
<212> TYPE: DNA
<213> ORGANISM: Artificial Sequence
<220> FEATURE:
<223> OTHER INFORMATION: Primer 513

<400> SEQUENCE: 31
gtataagaat cattcaccat gagcaaaagc accggcgtcg                              40

<210> SEQ ID NO 32
<211> LENGTH: 40
<212> TYPE: DNA
<213> ORGANISM: Artificial Sequence
<220> FEATURE:
<223> OTHER INFORMATION: Primer 514

<400> SEQUENCE: 32
ggccgcggtg gcggccgctc attcttgaca tggtgctccg                              40

<210> SEQ ID NO 33
<211> LENGTH: 45
<212> TYPE: DNA
<213> ORGANISM: Artificial Sequence
<220> FEATURE:
<223> OTHER INFORMATION: Primer 519

<400> SEQUENCE: 33
gtataagaat cattcaccat gtctattgaa acagtcggat catcg                        45

<210> SEQ ID NO 34
<211> LENGTH: 45
<212> TYPE: DNA
<213> ORGANISM: Artificial Sequence
```

```
<220> FEATURE:
<223> OTHER INFORMATION: Primer 520

<400> SEQUENCE: 34
gggccgcggt ggcggcctca ttgactggaa ccatcttccg gcttg                    45

<210> SEQ ID NO 35
<211> LENGTH: 43
<212> TYPE: DNA
<213> ORGANISM: Artificial Sequence
<220> FEATURE:
<223> OTHER INFORMATION: Primer 521

<400> SEQUENCE: 35
gagtataaga atcattcacc atgtcagtcg ttgaccttac cag                      43

<210> SEQ ID NO 36
<211> LENGTH: 42
<212> TYPE: DNA
<213> ORGANISM: Artificial Sequence
<220> FEATURE:
<223> OTHER INFORMATION: Primer 522

<400> SEQUENCE: 36
gccgcggtgg cggccgctta atctattggc ttaactggac ct                       42

<210> SEQ ID NO 37
<211> LENGTH: 419
<212> TYPE: PRT
<213> ORGANISM: Saccharomyces kluyveri
<220> FEATURE:
<221> NAME/KEY: MISC_FEATURE
<222> LOCATION: (1)..(419)
<223> OTHER INFORMATION: Delta-15 desaturase

<400> SEQUENCE: 37

Met Ser Ile Glu Thr Val Gly Ser Ser Gly Val Ala Ile Asn Ser
1               5                   10                  15

Lys Ala Val Ser Ser Thr Ala Thr Ala Val Val Gln Pro Lys Thr Ala
            20                  25                  30

Ile Asp Thr Asn Gly Asn Val Phe Lys Val Pro Asp Tyr Thr Ile Lys
        35                  40                  45

Asp Ile Leu Ser Ala Ile Pro Lys Glu Cys Tyr Lys Arg Asp Thr Leu
    50                  55                  60

Trp Ser Leu His Tyr Val Val Arg Asp Ile Ala Ala Ile Leu Val Ile
65              70                  75                  80

Gly Tyr Ile Gly Thr Asn Tyr Ile Pro Val Leu Phe Pro Asn Ser Ala
                85                  90                  95

Leu Leu Arg Gly Ile Ala Tyr Ala Ile Gln Ser Tyr Leu Ile Gly Leu
            100                 105                 110

Phe Gly Phe Gly Leu Trp Ile Leu Ala His Glu Cys Gly His Ser Ala
        115                 120                 125

Phe Ser Glu Ser Asn Thr Val Asn Asp Thr Val Gly Trp Val Leu His
    130                 135                 140

Ser Trp Trp Met Val Pro Tyr Phe Ser Trp Lys Phe Ser His Ser Lys
145                 150                 155                 160

His His Lys Ala Thr Gly His Met Thr Arg Asp Met Val Phe Ile Pro
                165                 170                 175

Tyr Thr Lys Asp Glu Phe Ile Thr Met Lys Lys Ser Lys Leu Ala
            180                 185                 190
```

```
Glu Ile Thr Glu Glu Ala Pro Val Met Thr Leu Phe Asn Leu Ile Ala
            195                 200                 205

Gln Gln Val Gly Gly Leu Gln Leu Tyr Leu Ala Thr Asn Ala Thr Gly
        210                 215                 220

Gln Pro Tyr Pro Gly Val Lys Lys Phe Phe Lys Ser His Tyr Trp Pro
225                 230                 235                 240

Thr Ser Pro Val Phe Asp Ala Lys Asp Phe Trp Trp Ile Ile Met Ser
                245                 250                 255

Asp Ile Gly Ile Val Ser Thr Leu Leu Ile Asn Tyr Leu Trp Tyr Arg
            260                 265                 270

Ala Tyr Gly Ala His Val Val Leu Ile Asn Trp Phe Ile Pro Trp Leu
        275                 280                 285

Trp Val Asn His Trp Leu Val Phe Val Thr Phe Leu Gln His Thr Asp
290                 295                 300

Pro Thr Met Pro His Tyr Asp Ala Glu Glu Trp Thr Phe Ala Lys Gly
305                 310                 315                 320

Ala Ala Ala Thr Ile Asp Arg Asn Phe Gly Phe Val Gly Gln His Ile
                325                 330                 335

Phe His Asp Ile Ile Glu Thr His Val Leu His His Tyr Cys Ser Arg
            340                 345                 350

Ile Pro Phe Tyr Asn Ala Arg Lys Ala Thr Ser Ala Ile Lys Glu Val
        355                 360                 365

Met Gly Gln His Tyr Arg Tyr Glu Gly Glu Asn Met Trp Lys Ser Leu
        370                 375                 380

Trp Lys Val Ala Arg Ser Cys Gln Tyr Val Glu Gly Asp Asn Gly Val
385                 390                 395                 400

Arg Met Phe Arg Asn Thr Asn Gly Val Gly Val Lys Pro Glu Asp Gly
                405                 410                 415

Ser Ser Gln

<210> SEQ ID NO 38
<211> LENGTH: 1209
<212> TYPE: DNA
<213> ORGANISM: Fusarium monoliforme
<220> FEATURE:
<221> NAME/KEY: misc_feature
<222> LOCATION: (1)..(1209)
<223> OTHER INFORMATION: delta-15 desaturase

<400> SEQUENCE: 38
atggcgactc gacagcgaac tgccaccact gttgtggtcg aggaccttcc caaggtcact      60
cttgaggcca agtctgaacc tgtgttcccc gatatcaaga ccatcaagga tgccattccc     120
gcgcactgct tccagccctc gctcgtcacc tcattctact acgtcttccg cgattttgcc     180
atggtctctg ccctcgtctg ggctgctctc acctacatcc ccagcatccc cgaccagacc     240
ctccgcgtcg cagcttggat ggtctacggc ttcgtccagg tctgttctg caccggtgtc     300 tggattctcg gccatgagtg cggccacggt gctttctctc ccacggaaa ggtcaacaat     360 gtgaccggct ggttcctcca ctcgttcctc ctcgtccct acttcagctg aagtactct     420 caccaccgcc accaccgctt caccggccac atggatctcg acatggcttt cgtcccaag     480 actgagccca agccctccaa gtcgctcatg attgctggca ttgacgtcgc cgagcttgtt     540
gaggacaccc ccgctgctca gatggtcaag ctcatcttcc accagctttt cggatggcag     600
gcgtacctct tcttcaacgc tagctctggc aagggcagca agcagtggga gcccaagact     660
ggcctctcca gtggttccg agtcagtcac ttcgagccta ccagcgctgt cttccgcccc     720
```

```
aacgaggcca tcttcatcct catctccgat atcggtcttg ctctaatggg aactgctctg    780
tactttgctt ccaagcaagt tggtgtttcg accattctct tcctctacct tgttccctac    840
ctgtgggttc accactggct cgttgccatt acctacctcc accaccacca caccgagctc    900
cctcactaca ccgctgaggg ctggacctac gtcaagggag ctctcgccac tgtcgaccgt    960
gagtttggct tcatcggaaa gcacctcttc cacggtatca ttgagaagca cgttgttcac   1020
catctcttcc ctaagatccc cttctacaag gctgacgagg ccaccgaggc catcaagccc   1080
gtcattggcg accactactg ccacgacgac cgaagcttcc tgggccagct gtggaccatc   1140
ttcggcacgc tcaagtacgt cgagcacgac cctgcccgac ccggtgccat gcgatggaac   1200
aaggactag                                                           1209

<210> SEQ ID NO 39
<211> LENGTH: 402
<212> TYPE: PRT
<213> ORGANISM: Fusarium monoliforme

<400> SEQUENCE: 39
```

Met Ala Thr Arg Gln Arg Thr Ala Thr Thr Val Val Glu Asp Leu
1               5                  10                  15

Pro Lys Val Thr Leu Glu Ala Lys Ser Glu Pro Val Phe Pro Asp Ile
            20                  25                  30

Lys Thr Ile Lys Asp Ala Ile Pro Ala His Cys Phe Gln Pro Ser Leu
        35                  40                  45

Val Thr Ser Phe Tyr Tyr Val Phe Arg Asp Phe Ala Met Val Ser Ala
    50                  55                  60

Leu Val Trp Ala Ala Leu Thr Tyr Ile Pro Ser Ile Pro Asp Gln Thr
65                  70                  75                  80

Leu Arg Val Ala Ala Trp Met Val Tyr Gly Phe Val Gln Gly Leu Phe
                85                  90                  95

Cys Thr Gly Val Trp Ile Leu Gly His Glu Cys Gly His Gly Ala Phe
            100                 105                 110

Ser Leu His Gly Lys Val Asn Asn Val Thr Gly Trp Phe Leu His Ser
        115                 120                 125

Phe Leu Leu Val Pro Tyr Phe Ser Trp Lys Tyr Ser His His Arg His
    130                 135                 140

His Arg Phe Thr Gly His Met Asp Leu Asp Met Ala Phe Val Pro Lys
145                 150                 155                 160

Thr Glu Pro Lys Pro Ser Lys Ser Leu Met Ile Ala Gly Ile Asp Val
                165                 170                 175

Ala Glu Leu Val Glu Asp Thr Pro Ala Ala Gln Met Val Lys Leu Ile
            180                 185                 190

Phe His Gln Leu Phe Gly Trp Gln Ala Tyr Leu Phe Phe Asn Ala Ser
        195                 200                 205

Ser Gly Lys Gly Ser Lys Gln Trp Glu Pro Lys Thr Gly Leu Ser Lys
    210                 215                 220

Trp Phe Arg Val Ser His Phe Glu Pro Thr Ser Ala Val Phe Arg Pro
225                 230                 235                 240

Asn Glu Ala Ile Phe Ile Leu Ile Ser Asp Ile Gly Leu Ala Leu Met
                245                 250                 255

Gly Thr Ala Leu Tyr Phe Ala Ser Lys Gln Val Gly Val Ser Thr Ile
            260                 265                 270

Leu Phe Leu Tyr Leu Val Pro Tyr Leu Trp Val His His Trp Leu Val

|  |  |  | 275 |  |  | 280 |  |  |  | 285 |  |
|---|---|---|---|---|---|---|---|---|---|---|---|
| Ala | Ile | Thr | Tyr | Leu | His | His | His | Thr | Glu | Leu | Pro | His | Tyr | Thr |
|  |  |  | 290 |  |  |  |  | 295 |  |  |  | 300 |  |  |

Ala Glu Gly Trp Thr Tyr Val Lys Gly Ala Leu Ala Thr Val Asp Arg
305                310                315                320

Glu Phe Gly Phe Ile Gly Lys His Leu Phe His Gly Ile Ile Glu Lys
                325                330                335

His Val Val His His Leu Phe Pro Lys Ile Pro Phe Tyr Lys Ala Asp
            340                345                350

Glu Ala Thr Glu Ala Ile Lys Pro Val Ile Gly Asp His Tyr Cys His
        355                360                365

Asp Arg Ser Phe Leu Gly Gln Leu Trp Thr Ile Phe Gly Thr Leu
    370                375                380

Lys Tyr Val Glu His Asp Pro Ala Arg Pro Gly Ala Met Arg Trp Asn
385                390                395                400

Lys Asp

```
<210> SEQ ID NO 40
<211> LENGTH: 1434
<212> TYPE: DNA
<213> ORGANISM: Fusarium monoliforme
<220> FEATURE:
<221> NAME/KEY: misc_feature
<222> LOCATION: (1)..(1434)
<223> OTHER INFORMATION: delta-12 desaturase

<400> SEQUENCE: 40
```

| atggcgtcca cttcggctct gcccaagcag aaccctgcgc ttagacgcac cgtcacctca | 60 |
|---|---|
| actactgtga cggattctga gtctgccgcc gtctctcctt cagactctcc ccgccactcg | 120 |
| gcctcttcca catcgctctc gtccatgtcc gaggttgata tcgccaagcc caagtccgag | 180 |
| tatggtgtca tgctcgacac ctacggcaac cagttcgagg ttcccgactt taccatcaag | 240 |
| gacatctaca atgccatccc taagcactgc ttcaagcgct ccgctctcaa gggatacggt | 300 |
| tatatcctcc gcgacattgt cctcctgact accactttca gcatctggta caactttgtg | 360 |
| accccccgaat atatccccctc caccccgcc cgcgctggtc tgtgggccgt gtacaccgtt | 420 |
| cttcagggtc ttttcggtac tggtctctgg gttattgccc atgagtgcgg tcacggtgct | 480 |
| ttctccgatt ctcgcatcat caacgacatt actggctggg ttcttcactc ttccctcctt | 540 |
| gtcccctact tcagctggca aatctcccac cgaaagcacc acaaggccac tggcaacatg | 600 |
| gagcgtgaca tggtcttcgt tccccgaacc cgcgagcagc aggctactcg tctcggaaag | 660 |
| atgacccacg agctcgctca tcttactgag gagacccccg ctttcactct tctcatgctc | 720 |
| gtccttcagc agctcgttgg ctggcccaac tacctcatca ccaatgttac cggccacaac | 780 |
| taccacgagc gccagcgtga gggtcgcggc aagggcaagc ataacggcct cggcggtggt | 840 |
| gttaaccact cgatccccg cagccctctg tacgagaaca gtgacgctaa gctcatcgtc | 900 |
| ctcagcgata ttggtatcgg tctgatggcc actgctctgt acttcctcgt tcagaagttc | 960 |
| ggtttctaca acatggccat ctggtacttt gttccctacc tctgggttaa ccactggctc | 1020 |
| gttgccatca ccttcctcca gcacaccgac cctaccttc cccactacac caacgacgag | 1080 |
| tggaacttcg tcgtggtgc cgctgctacc attgaccgtg agatgggctt catcggccgc | 1140 |
| caccttctcc acggcatcat cgagactcat gtcctccacc actacgtcag cagcatcccc | 1200 |
| ttctacaacg cggacgaggc caccgaggcc attaagccca tcatgggcaa gcactaccgg | 1260 |

```
gctgatgtcc aggatggtcc tcgtggcttc atccgcgcca tgtaccgcag tgcgcgtatg      1320
tgccagtggg ttgagcccag cgctggtgcc gagggtgctg gtaagggtgt tctgttcttc      1380
cgcaaccgca acaacgtggg cacccccccc gctgttatca agcccgttgc ttaa            1434
```

<210> SEQ ID NO 41
<211> LENGTH: 477
<212> TYPE: PRT
<213> ORGANISM: Fusarium monoliforme

<400> SEQUENCE: 41

```
Met Ala Ser Thr Ser Ala Leu Pro Lys Gln Asn Pro Ala Leu Arg Arg
1               5                   10                  15

Thr Val Thr Ser Thr Val Thr Asp Ser Glu Ser Ala Ala Val Ser
            20                  25                  30

Pro Ser Asp Ser Pro Arg His Ser Ala Ser Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205

Arg Thr Arg Glu Gln Gln Ala Thr Arg Leu Gly Lys Met Thr His Glu
    210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Val Asn His Phe Asp Pro Arg Ser
        275                 280                 285

Pro Leu Tyr Glu Asn Ser Asp Ala Lys Leu Ile Val Leu Ser Asp Ile
    290                 295                 300

Gly Ile Gly Leu Met Ala Thr Ala Leu Tyr Phe Leu Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350
```

```
Leu Pro His Tyr Thr Asn Asp Glu Trp Asn Phe Val Arg Gly Ala Ala
        355                 360                 365

Ala Thr Ile Asp Arg Glu Met Gly Phe Ile Gly Arg His Leu Leu His
    370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
            405                 410                 415

Lys His Tyr Arg Ala Asp Val Gln Asp Gly Pro Arg Gly Phe Ile Arg
        420                 425                 430

Ala Met Tyr Arg Ser Ala Arg Met Cys Gln Trp Val Glu Pro Ser Ala
            435                 440                 445

Gly Ala Glu Gly Ala Gly Lys Gly Val Leu Phe Phe Arg Asn Arg Asn
    450                 455                 460

Asn Val Gly Thr Pro Pro Ala Val Ile Lys Pro Val Ala
465                 470                 475
```

<210> SEQ ID NO 42
<211> LENGTH: 39
<212> TYPE: DNA
<213> ORGANISM: Artificial Sequence
<220> FEATURE:
<223> OTHER INFORMATION: Primer 515

<400> SEQUENCE: 42
cttttcggta ctggtctctg gattattgcc catgagtgc                                39

<210> SEQ ID NO 43
<211> LENGTH: 39
<212> TYPE: DNA
<213> ORGANISM: Artificial Sequence
<220> FEATURE:
<223> OTHER INFORMATION: Primer 516

<400> SEQUENCE: 43
gcactcatgg gcaataatcc agagaccagt accgaaaag                                39

<210> SEQ ID NO 44
<211> LENGTH: 39
<212> TYPE: DNA
<213> ORGANISM: Artificial Sequence
<220> FEATURE:
<223> OTHER INFORMATION: Primer 517

<400> SEQUENCE: 44
ctgttctgca ccggtgtctg ggttctcggc catgagtgc                                39

<210> SEQ ID NO 45
<211> LENGTH: 39
<212> TYPE: DNA
<213> ORGANISM: Artificial Sequence
<220> FEATURE:
<223> OTHER INFORMATION: Primer 518

<400> SEQUENCE: 45
gcactcatgg ccgagaaccc agacaccggt gcagaacag                                39

<210> SEQ ID NO 46
<211> LENGTH: 15
<212> TYPE: PRT
<213> ORGANISM: Artificial Sequence
<220> FEATURE:

```
<223> OTHER INFORMATION: Fungal Delta-15 Desaturase Motif "A"
<220> FEATURE:
<221> NAME/KEY: MISC_FEATURE
<222> LOCATION: (2)..(2)
<223> OTHER INFORMATION: Xaa = Ile or Leu or Val or Met or Pro
<220> FEATURE:
<221> NAME/KEY: MISC_FEATURE
<222> LOCATION: (6)..(6)
<223> OTHER INFORMATION: Xaa = Ala or Gly or Ser
<220> FEATURE:
<221> NAME/KEY: MISC_FEATURE
<222> LOCATION: (9)..(9)
<223> OTHER INFORMATION: Xaa = Ala or Cys
<220> FEATURE:
<221> NAME/KEY: MISC_FEATURE
<222> LOCATION: (12)..(12)
<223> OTHER INFORMATION: Xaa = Gly or Ser

<400> SEQUENCE: 46

Gly Xaa Trp Ile Leu Xaa His Glu Xaa Gly His Xaa Ala Phe Ser
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Fungal Delta-15 Desaturase Motif "B"
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa = Ala or Cys
<220> FEATURE:
<221> NAME/KEY: misc_feature
<222> LOCATION: (12)..(12)
<223> OTHER INFORMATION: Xaa can be any naturally occurring amino acid

<400> SEQUENCE: 47

Gly Xaa Trp Ile Leu Xaa His Glu Xaa Gly His Xaa Ala Phe Ser
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Fungal Delta-15 Desaturase Motif "C"
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid

<400> SEQUENCE: 48

Gly Xaa Trp Ile Xaa Xaa His Glu Xaa Gly His Xaa Xaa Xaa Ser
```

-continued

<210> SEQ ID NO 49
<211> LENGTH: 477
<212> TYPE: PRT
<213> ORGANISM: Gibberella fujikuroi
<220> FEATURE:
<221> NAME/KEY: MISC_FEATURE
<222> LOCATION: (1)..(477)
<223> OTHER INFORMATION: delta-12 desaturase; GenBank Accession No. DQ272515

<400> SEQUENCE: 49

Met Ala Ser Thr Ser Ala Leu Pro Lys Gln Asn Pro Ala Leu Arg Arg
1               5                   10                  15

Thr Val Thr Ser Thr Thr Val Thr Asp Ser Glu Ser Ala Ala Val Ser
            20                  25                  30

Pro Ser Asp Ser Pro Arg His Ser Ala Ser Thr Ser Leu Ser Ser
        35                  40                  45

Met Ser Glu Val Asp Ile Ala Lys Pro Lys Ser Glu Tyr Gly Val Met
50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205

Arg Thr Arg Glu Gln Gln Ala Thr Arg Leu Gly Lys Met Thr His Glu
    210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Val Asn His Phe Asp Pro Arg Ser
        275                 280                 285

Pro Leu Tyr Glu Asn Ser Asp Ala Lys Leu Ile Val Leu Ser Asp Ile
    290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr

```
                340                 345                 350
Leu Pro His Tyr Thr Asn Asp Glu Trp Asn Phe Val Arg Gly Ala Ala
            355                 360                 365

Ala Thr Ile Asp Arg Glu Met Gly Phe Ile Gly Arg His Leu Leu His
        370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
                405                 410                 415

Lys His Tyr Arg Ala Asp Val Gln Asp Gly Pro Arg Gly Phe Ile Arg
            420                 425                 430

Ala Met Tyr Arg Ser Ala Arg Met Cys Gln Trp Val Glu Pro Ser Ala
        435                 440                 445

Gly Ala Glu Gly Ala Gly Lys Gly Val Leu Phe Phe Arg Asn Arg Asn
    450                 455                 460

Asn Val Gly Thr Pro Pro Ala Val Ile Lys Pro Val Ala
465                 470                 475

<210> SEQ ID NO 50
<211> LENGTH: 402
<212> TYPE: PRT
<213> ORGANISM: Gibberella fujikuroi
<220> FEATURE:
<221> NAME/KEY: MISC_FEATURE
<222> LOCATION: (1)..(402)
<223> OTHER INFORMATION: delta-15 desaturase; GenBank Accession No.
      DQ272516

<400> SEQUENCE: 50

Met Ala Thr Arg Gln Arg Thr Ala Thr Thr Val Val Val Glu Asp Leu
1               5                   10                  15

Pro Lys Val Thr Leu Glu Ala Lys Ser Glu Pro Val Phe Pro Asp Ile
            20                  25                  30

Lys Thr Ile Lys Asp Ala Ile Pro Ala His Cys Phe Gln Pro Ser Leu
        35                  40                  45

Val Thr Ser Phe Tyr Tyr Val Phe Arg Asp Phe Ala Met Val Ser Ala
    50                  55                  60

Leu Val Trp Ala Ala Leu Thr Tyr Ile Pro Ser Ile Pro Asp Gln Thr
65                  70                  75                  80

Leu Arg Val Ala Ala Trp Met Val Tyr Gly Phe Val Gln Gly Leu Phe
                85                  90                  95

Cys Thr Gly Val Trp Ile Leu Gly His Glu Cys Gly His Gly Ala Phe
            100                 105                 110

Ser Leu His Gly Lys Val Asn Asn Val Thr Gly Trp Phe Leu His Ser
        115                 120                 125

Phe Leu Leu Val Pro Tyr Phe Ser Trp Lys Tyr Ser His Arg His His
    130                 135                 140

His Arg Phe Thr Gly His Met Asp Leu Asp Met Ala Phe Val Pro Lys
145                 150                 155                 160

Thr Glu Pro Lys Pro Ser Lys Ser Leu Met Ile Ala Gly Ile Asp Val
                165                 170                 175

Ala Glu Leu Val Glu Asp Thr Pro Ala Ala Gln Met Val Lys Leu Ile
            180                 185                 190

Phe His Gln Leu Phe Gly Trp Gln Ala Tyr Leu Phe Phe Asn Ala Ser
        195                 200                 205

Ser Gly Lys Gly Ser Lys Gln Trp Glu Pro Lys Thr Gly Leu Ser Lys
```

```
                    210                 215                 220
Trp Phe Arg Val Ser His Phe Glu Pro Thr Ser Ala Val Phe Arg Pro
225                 230                 235                 240

Asn Glu Ala Ile Phe Ile Leu Ile Ser Asp Ile Gly Leu Ala Leu Met
                245                 250                 255

Gly Thr Ala Leu Tyr Phe Ala Ser Lys Gln Val Gly Val Ser Thr Ile
                260                 265                 270

Leu Phe Leu Tyr Leu Val Pro Tyr Leu Trp Val His His Trp Leu Val
                275                 280                 285

Ala Ile Thr Tyr Leu His His His Thr Glu Leu Pro His Tyr Thr
290                 295                 300

Ala Glu Gly Trp Thr Tyr Val Lys Gly Ala Leu Ala Thr Val Asp Arg
305                 310                 315                 320

Glu Phe Gly Phe Ile Gly Lys His Leu Phe His Gly Ile Ile Glu Lys
                325                 330                 335

His Val Val His His Leu Phe Pro Lys Ile Pro Phe Tyr Lys Ala Asp
                340                 345                 350

Glu Ala Thr Glu Ala Ile Lys Pro Val Ile Gly Asp His Tyr Cys His
                355                 360                 365

Asp Asp Arg Ser Phe Leu Gly Gln Leu Trp Thr Ile Phe Gly Thr Leu
                370                 375                 380

Lys Tyr Val Glu His Asp Pro Ala Arg Pro Gly Ala Met Arg Trp Asn
385                 390                 395                 400

Lys Asp

<210> SEQ ID NO 51
<211> LENGTH: 426
<212> TYPE: PRT
<213> ORGANISM: Aspergillus nidulans FGSC A4
<220> FEATURE:
<221> NAME/KEY: MISC_FEATURE
<222> LOCATION: (1)..(426)
<223> OTHER INFORMATION: delta-12 desaturase; GenBank Accession No.
      XP_658641

<400> SEQUENCE: 51

Met Ala Ser Asp Ala Gly Lys Gly Asp Leu Gly Lys Met Leu Asp Thr
1               5                   10                  15

Tyr Gly Asn Glu Phe Lys Ile Pro Asp Tyr Thr Ile Lys Asp Ile Arg
                20                  25                  30

Asp Ala Ile Pro Ser His Cys Tyr Asn Arg Ser Ala Ile Arg Ser Leu
                35                  40                  45

Ser Tyr Val Phe Arg Asp Leu Ala Val Leu Ala Ser Val Phe Tyr Val
            50                  55                  60

Phe His Lys Tyr Val Thr Pro Glu Thr Val Pro Ser Tyr Pro Ala Arg
65                  70                  75                  80

Val Ala Leu Trp Thr Leu Tyr Thr Val Gln Gly Leu Phe Gly Thr
                85                  90                  95

Gly Ile Trp Val Leu Ala His Glu Cys Gly His Gln Ala Phe Ser Thr
                100                 105                 110

Ser Lys Val Leu Asn Asp Thr Val Gly Trp Ile Leu His Ser Ala Leu
                115                 120                 125

Leu Val Pro Tyr Phe Ser Trp Lys Ile Ser His Gly Lys His His Lys
                130                 135                 140

Ala Thr Gly Asn Leu Ala Arg Asp Met Val Phe Val Pro Lys Thr Arg
145                 150                 155                 160
```

Glu Val Tyr Ala Ser Arg Ile Lys Lys Thr Ile Tyr Asp Leu Asn Glu
            165                 170                 175

Val Met Glu Glu Thr Pro Leu Ala Thr Ala Thr His Ser Ile Leu Gln
        180                 185                 190

Gln Leu Phe Gly Trp Pro Leu Tyr Leu Leu Thr Asn Val Thr Gly His
    195                 200                 205

Asp Asn His Glu Arg Gln Pro Glu Gly Arg Gly Lys Gly Lys Arg Asn
210                 215                 220

Gly Tyr Phe Thr Gly Val Asn His Phe Asn Pro Asn Ser Pro Leu Phe
225                 230                 235                 240

Glu Ala Lys Asp Ala Lys Leu Ile Ile Leu Ser Asp Ile Gly Leu Ala
                245                 250                 255

Ile Thr Ala Ser Ile Leu Tyr Leu Ile Gly Ser Lys Phe Gly Trp Met
                260                 265                 270

Asn Leu Leu Val Trp Tyr Gly Ile Pro Tyr Leu Trp Val Asn His Trp
            275                 280                 285

Leu Val Ala Ile Thr Tyr Leu Gln His Thr Asp Pro Thr Leu Pro His
    290                 295                 300

Tyr Gln Pro Glu Ser Trp Thr Phe Ala Arg Gly Ala Ala Ala Thr Ile
305                 310                 315                 320

Asp Arg Glu Phe Gly Phe Ile Gly Arg His Ile Leu His Gly Ile Ile
                325                 330                 335

Glu Thr His Val Leu His His Tyr Val Ser Thr Ile Pro Phe Tyr His
                340                 345                 350

Ala Asp Glu Ala Ser Glu Ala Ile Lys Lys Val Met Gly Ser His Tyr
            355                 360                 365

Arg Ser Glu Ala His Thr Gly Pro Leu Gly Phe Leu Lys Ala Leu Trp
    370                 375                 380

Thr Ser Ala Arg Val Cys His Trp Val Glu Pro Thr Glu Gly Thr Lys
385                 390                 395                 400

Gly Glu Asn Ala Gly Val Leu Phe Phe Arg Asn Thr Asn Gly Ile Gly
                405                 410                 415

Val Pro Pro Ile Lys Leu Thr Lys Pro Asn
            420                 425

<210> SEQ ID NO 52
<211> LENGTH: 394
<212> TYPE: PRT
<213> ORGANISM: Aspergillus nidulans FGSC A4
<220> FEATURE:
<221> NAME/KEY: MISC_FEATURE
<222> LOCATION: (1)..(394)
<223> OTHER INFORMATION: delta-15 desaturase; GenBank Accession No.
      XP_664808

<400> SEQUENCE: 52

Met Ala Ala Thr Ala Thr Thr Leu Ala Glu Ile Glu Lys Thr Ile Lys
1               5                   10                  15

Asn Ala Ile Pro Lys His Cys Phe Asn Arg Ser Leu Leu Ile Ser Ser
            20                  25                  30

Ala Tyr Val Val Arg Asp Leu Leu Tyr Ala Ser Val Leu Phe Tyr Phe
        35                  40                  45

Ala Leu His Ile Asp Thr Leu Phe Ser Ser Gln Leu Leu Arg Ile Leu
    50                  55                  60

Ala Trp Thr Ala Tyr Gly Phe Met Gln Gly Cys Val Gly Thr Gly Ile
65                  70                  75                  80

```
Trp Ile Leu Ala His Glu Cys Gly His Gly Ala Phe Ser Pro Tyr Gln
            85                  90                  95

Thr Trp Asn Asp Val Val Gly Trp Thr Leu His Ser Leu Leu Met Val
        100                 105                 110

Pro Tyr Phe Ser Trp Lys Ile Thr His Ala Arg His Arg Tyr Thr
        115                 120                 125

Asn Asn Thr Glu Arg Asp Thr Ala Phe Val Pro Trp Thr Glu Lys Glu
    130                 135                 140

Tyr Asp Thr Arg Pro Arg Tyr Phe Pro Ala Trp Phe Glu Met Phe Glu
145                 150                 155                 160

Asp Thr Pro Val Tyr Asn Leu Ile Ser Leu Leu Ala His Gln Ile Ala
                165                 170                 175

Gly Trp Gln Met Tyr Leu Cys Phe Tyr Val Ser Ala Gly Ala Lys Ser
            180                 185                 190

Lys Pro Val Pro Gln Gly Lys Gln Ser Gly Trp Phe Gly Gly Gln Gln
        195                 200                 205

Ser Ala Ser His Phe Asp Pro Gly Ser Ser Leu Trp Thr Glu Asn Gln
    210                 215                 220

Arg His Leu Ile Ala Ile Ser Asp Leu Gly Leu Leu Val Ala Ala
225                 230                 235                 240

Ala Asn Trp Tyr Leu Ala Gln Gln Val Gly Val Leu Arg Met Val Leu
                245                 250                 255

Ile Tyr Val Val Pro Tyr Phe Trp Val His His Trp Leu Val Ala Ile
            260                 265                 270

Thr Tyr Leu His His Thr His Pro Ser Ile Pro His Tyr Thr Asp Ser
        275                 280                 285

Thr Trp Thr Phe Thr Lys Gly Ala Leu Ser Thr Val Asp Arg Asp Phe
    290                 295                 300

Gly Phe Ile Gly Arg His Phe His His Ile Ile Asp His His Val
305                 310                 315                 320

Val His His Leu Phe Asn Arg Ile Pro Phe Tyr His Ala Glu Glu Ala
                325                 330                 335

Thr Asn Ala Ile Ile Pro Val Leu Gly Asp Met Tyr His Arg Glu Glu
            340                 345                 350

Thr Gly Phe Leu Trp Ser Leu Met Glu Thr Tyr Lys Asn Cys Arg Phe
        355                 360                 365

Val Gly Val Glu Asn Asp Val Gly Lys Glu Gly Val Leu His Trp Val
    370                 375                 380

Phe Glu Glu Lys Lys Gly Ala Lys Ala Glu
385                 390

<210> SEQ ID NO 53
<211> LENGTH: 551
<212> TYPE: PRT
<213> ORGANISM: Magnaporthe grisea 70-15
<220> FEATURE:
<221> NAME/KEY: MISC_FEATURE
<222> LOCATION: (1)..(551)
<223> OTHER INFORMATION: delta-12 desaturase; GenBank Accession No.
      XP_365283

<400> SEQUENCE: 53

Met Pro Ser Thr Arg Ser Thr Thr Ser Gly Ile Ala Gln Glu Lys Thr
1               5                   10                  15

Pro Met Arg Arg Thr Thr Thr Ser Ala Thr Val Glu Ser Asp Val Ser
            20                  25                  30
```

```
Ala Pro Gly Thr Ala Val Gln Ser Pro Met Asp Ser Pro Arg His Ser
        35                  40                  45

Ala Ser Ser Thr Ser Leu Ser Ser Leu Ser Ser Val Asp Ala Ala Ala
    50                  55                  60

Glu Lys Lys Ser Asn Glu Ser Val Gly Lys Leu Val Asp Thr Tyr Gly
65                  70                  75                  80

Asn Thr Phe Glu Ile Pro Asp Phe Thr Ile Lys Asp Ile His Asp Ala
                85                  90                  95

Ile Pro Lys His Cys Phe Glu Arg Ser Ala Ile Arg Ser Leu Ser Tyr
                100                 105                 110

Val Ala Arg Asp Met Val Leu Leu Ala Thr Thr Phe Tyr Val Phe His
            115                 120                 125

Asn Tyr Val Thr Pro Glu Tyr Ile Pro Ser Lys Pro Ala Arg Ala Gly
        130                 135                 140

Leu Trp Ala Ile Tyr Thr Val Leu Gln Gly Leu Phe Gly Thr Gly Ile
145                 150                 155                 160

Trp Val Leu Ala His Glu Cys Gly His Gln Ala Phe Ser Pro Ser Lys
                165                 170                 175

Thr Ile Asn Asn Thr Val Gly Trp Ile Leu His Ser Ser Leu Leu Val
                180                 185                 190

Pro Tyr Phe Ser Trp Gln Met Ser His Ser Lys His His Lys Ala Thr
        195                 200                 205

Gly His Ile Glu Arg Asp Met Val Phe Val Pro Arg Thr Arg Glu Glu
    210                 215                 220

His Ala Ser Arg Ile Gly Arg Met Val His Glu Leu Ser Glu Leu Thr
225                 230                 235                 240

Glu Glu Thr Pro Ile Ala Thr Leu Ile His Leu Val Gly Gln Gln Leu
                245                 250                 255

Ile Gly Trp Pro Leu Tyr Ile Ile Thr Asn Lys Thr Gly His Asn Tyr
                260                 265                 270

His Glu Arg Gln Arg Glu Gly Arg Gly Lys Gly Lys Lys Asn Gly Leu
            275                 280                 285

Phe Thr Gly Val Asn His Phe Asn Pro Ser Ser Pro Leu Tyr Glu Asn
        290                 295                 300

Lys Asp Ala Gly Lys Val Leu Leu Ser Asp Leu Gly Val Gly Leu Val
305                 310                 315                 320

Ile Ala Gly Leu Val Tyr Leu Cys Gln Thr Phe Gly Thr Gln Asn Met
                325                 330                 335

Leu Val Trp Tyr Phe Ile Pro Tyr Leu Trp Val Asn His Trp Leu Val
            340                 345                 350

Ala Ile Thr Phe Leu Gln His Thr Asp Pro Ser Leu Pro His Tyr Thr
        355                 360                 365

Ala Glu Glu Trp Asn Phe Val Arg Gly Ala Ala Ala Thr Ile Asp Arg
    370                 375                 380

Glu Phe Gly Phe Val Gly Arg His Leu Leu His Gly Ile Ile Glu Thr
385                 390                 395                 400

His Val Leu His His Tyr Val Ser Thr Ile Pro Phe Tyr Asn Ala Asp
                405                 410                 415

Glu Ala Thr Asp Ala Ile Lys Lys Val Met Gly Lys His Tyr Arg Ser
            420                 425                 430

Asp Thr Ala Gly Gly Pro Ala Gly Phe Leu Lys Ser Leu Trp Thr Ser
        435                 440                 445
```

```
Ser Arg Met Cys Gln Trp Val Glu Pro Ser Ala Glu Ala Glu Gly Ser
    450                 455                 460

Gly Lys Gly Val Leu Phe Phe Arg Asn His Asn Lys Ile Gly Thr Pro
465                 470                 475                 480

Pro Ile Lys Met Ser Ala Gln Lys Ile Arg Leu Cys Asn Asp Leu Leu
                485                 490                 495

Gly Met His Lys Gly Lys Asn Gln Met Asn Gly Ser Arg Glu Arg Arg
                500                 505                 510

Gly Gly Gln Ser Ser Leu Lys Arg Val Arg Asn Gln Arg Ser Thr Asn
                515                 520                 525

Met Asn Glu Ser His Met Thr Val Phe Arg Ala Phe Arg Thr Trp Ser
530                 535                 540

Ser Cys Thr Arg Ala Ser Thr
545                 550

<210> SEQ ID NO 54
<211> LENGTH: 394
<212> TYPE: PRT
<213> ORGANISM: Magnaporthe grisea 70-15
<220> FEATURE:
<221> NAME/KEY: MISC_FEATURE
<222> LOCATION: (1)..(394)
<223> OTHER INFORMATION: delta-15 desaturase; GenBank Accession No.
      XP_362963

<400> SEQUENCE: 54

Met Ser Thr Thr Val Thr Gln Arg Pro Gly Ala Ala Ser Arg Ala Glu
1               5                   10                  15

Ala Lys Pro Lys Glu Gln Gln Phe Pro Asp Ile Asn Thr Ile Arg Asn
                20                  25                  30

Ala Ile Pro Ala His Cys Phe Glu Ala Ser Leu Val Thr Ser Val Gly
            35                  40                  45

Tyr Leu Val Arg Asp Val Ala Leu Ile Thr Ala Leu Gly Trp Ala Ala
        50                  55                  60

Leu Thr Tyr Ile Pro Gln Ile Pro Asp Ser Thr Leu Arg Trp Thr Ala
65                  70                  75                  80

Trp Ala Ala Tyr Gly Phe Val Gln Gly Leu Phe Gly Thr Gly Leu Trp
                85                  90                  95

Ile Leu Ala His Glu Cys Gly His Gly Ala Phe Ser Lys His Thr Arg
                100                 105                 110

Ile Asn Asn Ile Leu Gly Trp Ala Ala His Ser Ala Leu Leu Val Pro
            115                 120                 125

Tyr Phe Ser Trp Lys Phe Ser His His Arg His His Asn Phe Thr Gly
        130                 135                 140

His Met Glu Lys Asp Met Ala Phe Val Pro Pro Gln Ala Ala Asp Arg
145                 150                 155                 160

Glu Ser Arg Ala Ser Leu Leu Ser Arg Phe Gly Ile Asp Leu Glu Val
                165                 170                 175

Phe Glu Asp Thr Pro Ile Phe Gln Leu Ala Arg Leu Val Ser His Gln
                180                 185                 190

Leu Phe Gly Trp Gln Thr Tyr Leu Leu Phe Asn Ala Thr Cys Gly Lys
            195                 200                 205

Glu Ser Leu Gln Asn Lys Gly Ala Ala Trp Phe Arg Gln Ser His Phe
        210                 215                 220

Glu Pro Thr Ser Ala Val Phe Arg Ser Ser Glu Ala Leu Tyr Ile Ala
225                 230                 235                 240
```

```
Ile Ser Asp Ile Gly Leu Ala Ile Val Ala Ala Ile Tyr Trp Gly
                245                 250                 255

Ser Thr Lys Val Gly Ala Gly Thr Met Phe Leu Leu Tyr Ala Val Pro
        260                 265                 270

Tyr Met Trp Val His His Trp Leu Val Ala Ile Thr Tyr Leu His His
275                 280                 285

Thr Asn Lys Glu Val His His Tyr Glu Ala Asp Ser Trp Thr Phe Val
    290                 295                 300

Lys Gly Ala Val Ala Thr Val Asp Arg Asp Phe Gly Phe Ile Asp Arg
305                 310                 315                 320

His Leu Phe His Gly Ile Ile Gly Thr His Val Ala His His Leu Phe
                325                 330                 335

Pro Arg Ile Pro Phe Tyr Lys Ala Glu Glu Ala Thr Glu Ala Ile Lys
            340                 345                 350

Pro Val Leu Gly Asp Leu Tyr His Ser Asp Asn Arg Pro Phe Met Gln
        355                 360                 365

Ala Leu Trp Ser Asn Phe Thr Thr Cys Lys Tyr Val Lys Asp Pro
    370                 375                 380

Lys Val Pro Gly Ala Met Arg Trp Ala Asp
385                 390

<210> SEQ ID NO 55
<211> LENGTH: 429
<212> TYPE: PRT
<213> ORGANISM: Neurospora crassa
<220> FEATURE:
<221> NAME/KEY: MISC_FEATURE
<222> LOCATION: (1)..(429)
<223> OTHER INFORMATION: delta-15 desaturase; GenBank Accession No.
      XP_329856

<400> SEQUENCE: 55

Met Thr Val Thr Thr Arg Ser His Lys Ala Ala Ala Thr Glu Pro
1               5                   10                  15

Glu Val Val Ser Thr Gly Val Asp Ala Val Ser Ala Ala Pro Ser
                20                  25                  30

Ser Ser Ser Ser Ser Ser Gln Lys Ser Ala Glu Pro Ile Glu Tyr
                35                  40                  45

Pro Asp Ile Lys Thr Ile Arg Asp Ala Ile Pro Asp His Cys Phe Arg
    50                  55                  60

Pro Arg Val Trp Ile Ser Met Ala Tyr Phe Ile Arg Asp Phe Ala Met
65                  70                  75                  80

Ala Phe Gly Leu Gly Tyr Leu Ala Trp Gln Tyr Ile Pro Leu Ile Ala
                85                  90                  95

Ser Thr Pro Leu Arg Tyr Gly Ala Trp Ala Leu Tyr Gly Tyr Leu Gln
            100                 105                 110

Gly Leu Val Cys Thr Gly Ile Trp Ile Leu Ala His Glu Cys Gly His
        115                 120                 125

Gly Ala Phe Ser Arg His Thr Trp Phe Asn Asn Val Met Gly Trp Ile
    130                 135                 140

Gly His Ser Phe Leu Leu Val Pro Tyr Phe Ser Trp Lys Phe Ser His
145                 150                 155                 160

His Arg His His Arg Phe Thr Gly His Met Glu Lys Asp Met Ala Phe
                165                 170                 175

Val Pro Ala Thr Glu Ala Asp Arg Asn Gln Arg Lys Leu Ala Asn Leu
            180                 185                 190
```

-continued

```
Tyr Met Asp Lys Glu Thr Ala Glu Met Phe Glu Asp Val Pro Ile Val
            195                 200                 205
Gln Leu Val Lys Leu Ile Ala His Gln Leu Ala Gly Trp Gln Met Tyr
        210                 215                 220
Leu Leu Phe Asn Val Ser Ala Gly Lys Gly Ser Lys Gln Trp Glu Thr
225                 230                 235                 240
Gly Lys Gly Gly Met Gly Trp Leu Arg Val Ser His Phe Glu Pro Ser
                245                 250                 255
Ser Ala Val Phe Arg Asn Ser Glu Ala Ile Tyr Ile Ala Leu Ser Asp
            260                 265                 270
Leu Gly Leu Met Ile Met Gly Tyr Ile Leu Tyr Gln Ala Ala Gln Val
        275                 280                 285
Val Gly Trp Gln Met Val Gly Leu Leu Tyr Phe Gln Gln Tyr Phe Trp
    290                 295                 300
Val His His Trp Leu Val Ala Ile Thr Tyr Leu His His Thr His Glu
305                 310                 315                 320
Glu Val His His Phe Asp Ala Asp Ser Trp Thr Phe Val Lys Gly Ala
                325                 330                 335
Leu Ala Thr Val Asp Arg Asp Phe Gly Phe Ile Gly Lys His Leu Phe
            340                 345                 350
His Asn Ile Ile Asp His His Val Val His His Leu Phe Pro Arg Ile
        355                 360                 365
Pro Phe Tyr Tyr Ala Glu Glu Ala Thr Asn Ser Ile Arg Pro Met Leu
    370                 375                 380
Gly Pro Leu Tyr His Arg Asp Arg Ser Phe Met Gly Gln Leu Trp
385                 390                 395                 400
Tyr Asn Phe Thr His Cys Lys Trp Val Val Pro Asp Pro Gln Val Pro
                405                 410                 415
Gly Ala Leu Ile Trp Ala His Thr Val Gln Ser Thr Gln
            420                 425

<210> SEQ ID NO 56
<211> LENGTH: 481
<212> TYPE: PRT
<213> ORGANISM: Neurospora crassa
<220> FEATURE:
<221> NAME/KEY: MISC_FEATURE
<222> LOCATION: (1)..(481)
<223> OTHER INFORMATION: delta-12 desaturase; GenBank Accession No.
      XP_330985

<400> SEQUENCE: 56

Met Ala Ser Val Ser Ser Ala Leu Pro Glu Gly Asn Lys Pro Ala Leu
1               5                   10                  15
Arg Arg Thr Gln Thr Glu Ala Thr Ser Asp Ser Tyr Pro Gly Thr Ala
            20                  25                  30
Asp Ala Ser Pro Phe Asp Ser Pro Leu Glu Arg Ser Ala Ser Asn Thr
        35                  40                  45
Ser Leu Ser Ser Gln Ala Ser Asp Asn Val Lys Thr Asp Lys Ala Glu
    50                  55                  60
Phe Gly Lys Leu Leu Asp Thr Tyr Gly Asn Glu Phe Glu Val Pro Asp
65                  70                  75                  80
Phe Thr Ile Lys Asp Ile Arg Asp Ala Ile Pro Ala His Cys Phe Glu
                85                  90                  95
Arg Ser Ala Leu His Ser Leu Ala His Val Val Arg Asp Ile Ile Tyr
            100                 105                 110
```

Leu Thr Val Thr Phe Tyr Val Trp Asn Lys Tyr Val Thr Pro Glu Tyr
            115                 120                 125

Ile Pro Met Lys Ala Ala Arg Val Val Leu Trp Gly Leu Tyr Thr Phe
130                 135                 140

Met Gln Gly Leu Phe Gly Thr Gly Leu Trp Val Leu Ala His Glu Cys
145                 150                 155                 160

Gly His Gln Ala Phe Ser Pro Ser Arg Leu Ile Asn Asp Thr Val Gly
                165                 170                 175

Trp Val Leu His Ser Ala Leu Leu Val Pro Tyr Phe Ser Trp Lys Phe
            180                 185                 190

Ser His Ser Lys His His Lys Ala Thr Gly Asn Ile Glu Arg Asp Met
        195                 200                 205

Val Phe Val Pro Arg Thr Arg Glu Gln Phe Ala Ser Arg Ile Gly Arg
    210                 215                 220

Phe Val His Glu Ile Ser Glu Leu Thr Glu Thr Pro Ile Tyr Thr
225                 230                 235                 240

Leu Ile His Leu Ile Gly Gln Gln Leu Ile Gly Trp Pro Asn Tyr Leu
                245                 250                 255

Met Thr Asn Val Thr Gly His Asn Phe His Glu Arg Gln Arg Glu Gly
            260                 265                 270

Arg Gly Lys Gly Lys Lys Asn Gly Trp Phe Thr Gly Val Asn His Phe
        275                 280                 285

Asn Pro Ser Ser Pro Leu Tyr Glu Glu Arg Glu Ala Pro Trp Ile Ile
    290                 295                 300

Val Ser Asp Ile Gly Ile Ala Ile Ala Ala Thr Ala Leu Ile Tyr Leu
305                 310                 315                 320

Gly Asn Thr Phe Gly Trp Ser Asn Met Phe Val Trp Tyr Phe Leu Pro
                325                 330                 335

Tyr Leu Trp Val Asn His Trp Leu Val Ala Ile Thr Tyr Leu Gln His
            340                 345                 350

Thr Asp Pro Ser Leu Pro His Tyr Thr Pro Asp Gln Trp Asn Phe Val
        355                 360                 365

Arg Gly Ala Ala Ala Thr Ile Asp Arg Glu Phe Gly Phe Ile Gly Arg
    370                 375                 380

His Leu Leu His Gly Ile Ile Glu Thr His Val Leu His His Tyr Val
385                 390                 395                 400

Ser Thr Ile Pro Phe Tyr His Ala Asp Glu Ala Ser Glu Ala Ile Lys
                405                 410                 415

Lys Val Met Gly Arg His Tyr Arg Ala Asp Val Gln Asp Gly Pro Ile
            420                 425                 430

Gly Phe Ile Lys Ala Met Trp Lys Ala Ala Arg Trp Cys Gln Trp Val
        435                 440                 445

Glu Pro Thr Glu Gly Ala Glu Gly Lys Gly Lys Gly Val Leu Phe Tyr
    450                 455                 460

Arg Asn Gln Asn Gly Leu Gly Val Lys Pro Ala Lys Leu Pro Lys Thr
465                 470                 475                 480

Asn

<210> SEQ ID NO 57
<211> LENGTH: 475
<212> TYPE: PRT
<213> ORGANISM: Gibberella zeae PH-1
<220> FEATURE:
<221> NAME/KEY: MISC_FEATURE
<222> LOCATION: (1)..(475)

<223> OTHER INFORMATION: delta-12 desaturase; GenBank Accession No. EAA75859

<400> SEQUENCE: 57

```
Met Ala Ser Thr Ser Ala Leu Pro Lys Gln Asn Pro Ala Leu Arg Arg
1               5                   10                  15

Thr Val Thr Ser Thr Thr Ala Thr Asp Thr Glu Ser Ala Ala Val Ser
            20                  25                  30

Pro Ser Asp Ser Pro Arg His Ser Ala Ser Ser Thr Ser Leu Ser Ser
        35                  40                  45

Leu Ser Glu Ile Asp Ile Ala Lys Pro Lys Ala Glu Tyr Gly Val Met
    50                  55                  60

Leu Asp Thr Tyr Gly Asn Lys Phe Glu Val Pro Asp Phe Thr Ile Lys
65                  70                  75                  80

Glu Ile Tyr Asn Ala Ile Pro Lys His Cys Phe Gln Arg Ser Ala Leu
                85                  90                  95

Lys Gly Tyr Gly Tyr Ile Leu Arg Asp Ile Val Leu Leu Ala Thr Thr
            100                 105                 110

Phe Ser Ile Trp Tyr Asn Tyr Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Leu Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205

Arg Thr Arg Glu Gln Gln Ala Thr Arg Leu Gly Lys Met Thr His Glu
    210                 215                 220

Leu Ala His Leu Thr Glu Glu Thr Pro Val Phe Thr Leu Ile Met Leu
225                 230                 235                 240

Val Leu Gln Gln Leu Val Gly Trp Pro Asn Tyr Leu Met Thr Asn Val
                245                 250                 255

Thr Gly His Asn Tyr His Glu Arg Gln Lys Glu Gly Arg Gly Lys Gly
            260                 265                 270

Lys His Asn Gly Leu Gly Gly Val Asn His Phe Asp Pro Arg Ser
        275                 280                 285

Pro Leu Tyr Glu His Ser Asp Ala Lys Leu Ile Val Leu Ser Asp Ile
    290                 295                 300

Gly Ile Gly Leu Met Gly Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350

Leu Pro His Tyr Thr Asn Asp Glu Trp Asn Phe Val Arg Gly Ala Ala
        355                 360                 365

Ala Thr Ile Asp Arg Glu Met Gly Phe Ile Gly Arg His Leu Leu His
    370                 375                 380

Gly Ile Ile Glu Thr His Val Leu His His Tyr Val Ser Ser Ile Pro
385                 390                 395                 400
```

Phe Tyr Asn Ala Asp Glu Ala Thr Glu Ala Ile Lys Pro Val Met Gly
            405                 410                 415

Lys His Tyr Arg Ala Asp Val Gln Asp Gly Pro Arg Gly Phe Ile Arg
            420                 425                 430

Ala Met Tyr Arg Ser Ala Arg Met Cys Gln Trp Val Glu Pro Ser Ala
            435                 440                 445

Glu Ala Glu Gly Ala Gly Lys Gly Val Leu Phe Phe Arg Asn Arg Asn
450                 455                 460

Lys Val Gly Thr Ala Pro Ala Val Leu Lys Ala
465                 470                 475

<210> SEQ ID NO 58
<211> LENGTH: 193
<212> TYPE: PRT
<213> ORGANISM: Gibberella zeae
<220> FEATURE:
<221> NAME/KEY: MISC_FEATURE
<222> LOCATION: (1)..(193)
<223> OTHER INFORMATION: delta-15 desaturase; GenBank Accession No.
      BAA33772

<400> SEQUENCE: 58

Asp Leu Asp Met Ala Phe Val Pro Arg Thr Ser Pro Lys Pro Ser Leu
1               5                   10                  15

Ser Phe Arg Ile Ala Gly Met Asp Val Ala Glu Leu Ile Glu Asp Thr
            20                  25                  30

Pro Ile Ala Gln Ala Val Lys Leu Ile Phe His Gln Leu Phe Gly Trp
        35                  40                  45

Gln Val Tyr Thr Phe Phe Asn Ala Ser Ser Gly Lys Gly Ser Lys Gln
    50                  55                  60

Trp Glu Pro Lys Ser Gly Leu Ala Ser Trp Phe Arg Val Ser His Phe
65                  70                  75                  80

Glu Pro Thr Ser Ala Val Phe Arg Pro Ala Glu Ala Pro Phe Ile Leu
                85                  90                  95

Ile Ser Asp Ile Gly Leu Ala Leu Thr Gly Thr Ala Leu Tyr Phe Ala
            100                 105                 110

Ser Lys Glu Val Gly Val Ser Thr Val Leu Tyr Leu Tyr Leu Val Pro
        115                 120                 125

Tyr Leu Trp Val His His Trp Leu Val Ala Ile Thr Tyr Leu His His
    130                 135                 140

His His Thr Glu Leu Pro His Tyr Thr Ala Glu Gly Trp Thr Tyr Val
145                 150                 155                 160

Lys Gly Ala Leu Ala Thr Val Asp Arg Glu Phe Gly Phe Ile Gly Lys
                165                 170                 175

His Leu Phe His Gly Ile Ile Glu Lys His Val Ile His His Leu Phe
            180                 185                 190

Pro

<210> SEQ ID NO 59
<211> LENGTH: 400
<212> TYPE: PRT
<213> ORGANISM: Mortierella alpina
<220> FEATURE:
<221> NAME/KEY: MISC_FEATURE
<222> LOCATION: (1)..(400)
<223> OTHER INFORMATION: delta-12 desaturase; GenBank Accession No.
      BAA81754

<400> SEQUENCE: 59

Met Ala Pro Pro Asn Thr Ile Asp Ala Gly Leu Thr Gln Arg His Ile
1               5                   10                  15

Ser Thr Ser Ala Ala Pro Thr Ser Ala Lys Pro Ala Phe Glu Arg Asn
            20                  25                  30

Tyr Gln Leu Pro Glu Phe Thr Ile Lys Glu Ile Arg Glu Cys Ile Pro
        35                  40                  45

Ala His Cys Phe Glu Arg Ser Gly Leu Arg Gly Leu Cys His Val Ala
    50                  55                  60

Ile Asp Leu Thr Trp Ala Ser Leu Leu Phe Leu Ala Ala Thr Gln Ile
65                  70                  75                  80

Asp Lys Phe Glu Asn Pro Leu Ile Arg Tyr Leu Ala Trp Pro Ala Tyr
                85                  90                  95

Trp Ile Met Gln Gly Ile Val Cys Thr Gly Ile Trp Val Leu Ala His
            100                 105                 110

Glu Cys Gly His Gln Ser Phe Ser Thr Ser Lys Thr Leu Asn Asn Thr
        115                 120                 125

Val Gly Trp Ile Leu His Ser Met Leu Leu Val Pro Tyr His Ser Trp
    130                 135                 140

Arg Ile Ser His Ser Lys His His Lys Ala Thr Gly His Met Thr Lys
145                 150                 155                 160

Asp Gln Val Phe Val Pro Lys Thr Arg Ser Gln Val Gly Leu Pro Pro
                165                 170                 175

Lys Glu Asn Val Ala Val Ala Val Gln Glu Glu Asp Met Ser Val His
            180                 185                 190

Leu Asp Glu Glu Ala Pro Ile Val Thr Leu Phe Trp Met Val Ile Gln
        195                 200                 205

Phe Leu Phe Gly Trp Pro Ala Tyr Leu Ile Met Asn Ala Ser Gly Gln
    210                 215                 220

Asp Tyr Gly Arg Trp Thr Ser His Phe His Thr Tyr Ser Pro Ile Phe
225                 230                 235                 240

Glu Pro Arg Asn Phe Phe Asp Ile Ile Ile Ser Asp Leu Gly Val Leu
                245                 250                 255

Ala Ala Leu Gly Thr Leu Ile Tyr Ala Ser Met Gln Leu Ser Leu Leu
            260                 265                 270

Thr Val Thr Lys Tyr Tyr Ile Val Pro Tyr Leu Phe Val Asn Phe Trp
        275                 280                 285

Leu Val Leu Ile Thr Phe Leu Gln His Thr Asp Pro Lys Leu Pro His
    290                 295                 300

Tyr Arg Glu Gly Ala Trp Asn Phe Gln Arg Gly Ala Leu Cys Thr Val
305                 310                 315                 320

Asp Arg Ser Phe Gly Lys Phe Leu Asp His Met Phe His Gly Ile Val
                325                 330                 335

His Thr His Val Ala His His Leu Phe Ser Gln Met Pro Phe Tyr His
            340                 345                 350

Ala Glu Glu Ala Thr His His Leu Lys Lys Leu Leu Gly Glu Tyr Tyr
        355                 360                 365

Val Tyr Asp Pro Ser Pro Ile Val Val Ala Val Trp Arg Ser Phe Arg
    370                 375                 380

Glu Cys Arg Phe Val Glu Asp His Gly Asp Val Val Phe Lys Lys
385                 390                 395                 400

<210> SEQ ID NO 60
<211> LENGTH: 403

```
<212> TYPE: PRT
<213> ORGANISM: Mortierella alpina
<220> FEATURE:
<221> NAME/KEY: MISC_FEATURE
<222> LOCATION: (1)..(403)
<223> OTHER INFORMATION: delta-15 desaturase; GenBank Accession No.
      AB182163

<400> SEQUENCE: 60
```

| | | | | | | | | | | | | | | |
|---|---|---|---|---|---|---|---|---|---|---|---|---|---|---|
| Met | Ala | Pro | Pro | His | Val | Val | Asp | Glu | Gln | Val | Arg | Arg | Ile | Val |
| 1 | | | | 5 | | | | | 10 | | | | | 15 |
| Val | Glu | Asp | Glu | Ile | Lys | Ser | Lys | Lys | Gln | Phe | Glu | Arg | Asn | Tyr | Val |
| | | | 20 | | | | | 25 | | | | | 30 | |
| Pro | Met | Asp | Phe | Thr | Ile | Lys | Glu | Ile | Arg | Asp | Ala | Ile | Pro | Ala | His |
| | | 35 | | | | | 40 | | | | | 45 | | |
| Leu | Phe | Ile | Arg | Asp | Thr | Thr | Lys | Ser | Ile | Leu | His | Val | Val | Lys | Asp |
| | 50 | | | | | 55 | | | | | 60 | | | | |
| Leu | Val | Thr | Ile | Ala | Ile | Val | Phe | Tyr | Cys | Ala | Thr | Phe | Ile | Glu | Thr |
| 65 | | | | | 70 | | | | | 75 | | | | | 80 |
| Leu | Pro | Ser | Leu | Ala | Leu | Arg | Val | Pro | Ala | Trp | Ile | Thr | Tyr | Trp | Ile |
| | | | | 85 | | | | | 90 | | | | | 95 | |
| Ile | Gln | Gly | Thr | Val | Met | Val | Gly | Pro | Trp | Ile | Leu | Ala | His | Glu | Cys |
| | | | 100 | | | | | 105 | | | | | 110 | | |
| Gly | His | Gly | Ala | Phe | Ser | Asp | Ser | Lys | Thr | Ile | Asn | Thr | Ile | Phe | Gly |
| | | 115 | | | | | 120 | | | | | 125 | | | |
| Trp | Val | Leu | His | Ser | Ala | Leu | Leu | Val | Pro | Tyr | Gln | Ala | Trp | Ala | Met |
| | 130 | | | | | 135 | | | | | 140 | | | | |
| Ser | His | Ser | Lys | His | His | Lys | Gly | Thr | Gly | Ser | Met | Thr | Lys | Asp | Val |
| 145 | | | | | 150 | | | | | 155 | | | | | 160 |
| Val | Phe | Ile | Pro | Ala | Thr | Arg | Ser | Tyr | Lys | Gly | Leu | Pro | Ala | Leu | Glu |
| | | | | 165 | | | | | 170 | | | | | 175 | |
| Lys | Pro | Ala | Val | Glu | Glu | Glu | Val | Ser | Glu | Gln | Glu | His | His | His | His |
| | | | 180 | | | | | 185 | | | | | 190 | | |
| Glu | Glu | Ser | Ile | Phe | Ala | Glu | Thr | Pro | Ile | Tyr | Thr | Leu | Gly | Ala | Leu |
| | | 195 | | | | | 200 | | | | | 205 | | | |
| Leu | Phe | Val | Leu | Thr | Phe | Gly | Trp | Pro | Leu | Tyr | Leu | Ile | Val | Asn | Phe |
| | 210 | | | | | 215 | | | | | 220 | | | | |
| Ser | Gly | His | Glu | Ala | Pro | His | Trp | Val | Asn | His | Phe | Gln | Thr | Val | Ala |
| 225 | | | | | 230 | | | | | 235 | | | | | 240 |
| Pro | Leu | Tyr | Glu | Pro | His | Gln | Arg | Lys | Asn | Ile | Phe | Tyr | Ser | Asn | Cys |
| | | | | 245 | | | | | 250 | | | | | 255 | |
| Gly | Ile | Val | Ala | Met | Gly | Ser | Ile | Leu | Thr | Tyr | Leu | Ser | Met | Val | Phe |
| | | | 260 | | | | | 265 | | | | | 270 | | |
| Ser | Pro | Leu | Thr | Val | Phe | Met | Tyr | Tyr | Gly | Ile | Pro | Tyr | Leu | Gly | Val |
| | | 275 | | | | | 280 | | | | | 285 | | | |
| Asn | Ala | Trp | Ile | Val | Cys | Ile | Thr | Tyr | Leu | Gln | His | Thr | Asp | Pro | Lys |
| | 290 | | | | | 295 | | | | | 300 | | | | |
| Val | Pro | His | Phe | Arg | Asp | Asn | Glu | Trp | Asn | Phe | Gln | Arg | Gly | Ala | Ala |
| 305 | | | | | 310 | | | | | 315 | | | | | 320 |
| Cys | Thr | Ile | Asp | Arg | Ser | Phe | Gly | Thr | Ile | Val | Asn | His | Leu | His | His |
| | | | | 325 | | | | | 330 | | | | | 335 | |
| His | Ile | Gly | Asp | Ser | His | Gln | Cys | His | His | Met | Phe | Ser | Gln | Met | Pro |
| | | | 340 | | | | | 345 | | | | | 350 | | |
| Phe | Tyr | Asn | Ala | Val | Glu | Ala | Thr | Lys | Tyr | Leu | Lys | Ala | Lys | Leu | Gly |
| | | 355 | | | | | 360 | | | | | 365 | | | |

```
Lys Tyr Tyr Ile Phe Asp Asp Thr Pro Ile Ala Lys Ala Leu Tyr Arg
    370                 375                 380

Asn Trp Arg Glu Cys Lys Phe Val Glu Asp Glu Gly Asp Val Val Phe
385                 390                 395                 400

Tyr Lys His

<210> SEQ ID NO 61
<211> LENGTH: 416
<212> TYPE: PRT
<213> ORGANISM: Saccharomyces kluyveri
<220> FEATURE:
<221> NAME/KEY: MISC_FEATURE
<222> LOCATION: (1)..(416)
<223> OTHER INFORMATION: delta-12 desaturase; GenBank Accession No.
      BAD08375

<400> SEQUENCE: 61

Met Ser Ala Val Thr Val Thr Gly Ser Asp Pro Lys Asn Arg Gly Ser
1               5                   10                  15

Ser Ser Asn Thr Glu Gln Glu Val Pro Lys Val Ala Ile Asp Thr Asn
            20                  25                  30

Gly Asn Val Phe Ser Val Pro Asp Phe Thr Ile Lys Asp Ile Leu Gly
        35                  40                  45

Ala Ile Pro His Glu Cys Tyr Glu Arg Arg Leu Ala Thr Ser Leu Tyr
    50                  55                  60

Tyr Val Phe Arg Asp Ile Phe Cys Met Leu Thr Thr Gly Tyr Leu Thr
65                  70                  75                  80

His Lys Ile Leu Tyr Pro Leu Leu Ile Ser Tyr Thr Ser Asn Ser Ile
                85                  90                  95

Ile Lys Phe Thr Phe Trp Ala Leu Tyr Thr Tyr Val Gln Gly Leu Phe
            100                 105                 110

Gly Thr Gly Ile Trp Val Leu Ala His Glu Cys Gly His Gln Ala Phe
        115                 120                 125

Ser Asp Tyr Gly Ile Val Asn Asp Phe Val Gly Trp Thr Leu His Ser
    130                 135                 140

Tyr Leu Met Val Pro Tyr Phe Ser Trp Lys Tyr Ser His Gly Lys His
145                 150                 155                 160

His Lys Ala Thr Gly His Met Thr Arg Asp Met Val Phe Val Pro Ala
                165                 170                 175

Thr Lys Glu Glu Phe Lys Lys Ser Arg Asn Phe Phe Gly Asn Leu Ala
            180                 185                 190

Glu Tyr Ser Glu Asp Ser Pro Leu Arg Thr Leu Tyr Glu Leu Leu Val
        195                 200                 205

Gln Gln Leu Gly Gly Trp Ile Ala Tyr Leu Phe Val Asn Val Thr Gly
    210                 215                 220

Gln Pro Tyr Pro Asp Val Pro Ser Trp Lys Trp Asn His Phe Trp Leu
225                 230                 235                 240

Thr Ser Pro Leu Phe Glu Gln Arg Asp Ala Leu Tyr Ile Phe Leu Ser
                245                 250                 255

Asp Leu Gly Ile Leu Thr Gln Gly Ile Val Leu Thr Leu Trp Tyr Lys
            260                 265                 270

Lys Phe Gly Gly Trp Ser Leu Phe Ile Asn Trp Phe Val Pro Tyr Ile
        275                 280                 285

Trp Val Asn His Trp Leu Val Phe Ile Thr Phe Leu Gln His Thr Asp
    290                 295                 300

Pro Thr Met Pro His Tyr Asn Ala Glu Glu Trp Thr Phe Ala Lys Gly
```

```
                305                 310                 315                 320
Ala Ala Ala Thr Ile Asp Arg Lys Phe Gly Phe Ile Gly Pro His Ile
                325                 330                 335

Phe His Asp Ile Ile Glu Thr His Val Leu His His Tyr Cys Ser Arg
            340                 345                 350

Ile Pro Phe Tyr Asn Ala Arg Pro Ala Ser Glu Ala Ile Lys Lys Val
            355                 360                 365

Met Gly Lys His Tyr Arg Ser Ser Asp Glu Asn Met Trp Lys Ser Leu
    370                 375                 380

Trp Lys Ser Phe Arg Ser Cys Gln Tyr Val Asp Gly Asp Asn Gly Val
385                 390                 395                 400

Leu Met Phe Arg Asn Ile Asn Asn Cys Gly Val Gly Ala Ala Glu Lys
                405                 410                 415

<210> SEQ ID NO 62
<211> LENGTH: 419
<212> TYPE: PRT
<213> ORGANISM: Saccharomyces kluyveri
<220> FEATURE:
<221> NAME/KEY: MISC_FEATURE
<222> LOCATION: (1)..(419)
<223> OTHER INFORMATION: delta-15 desaturase; GenBank Accession No.
      BAD11952

<400> SEQUENCE: 62

Met Ser Ile Glu Thr Val Gly Ser Ser Gly Val Ala Ile Asn Ser
1               5                   10                  15

Lys Ala Val Ser Ser Thr Ala Thr Val Val Gln Pro Lys Thr Ala
            20                  25                  30

Ile Asp Thr Asn Gly Asn Val Phe Lys Val Pro Asp Tyr Thr Ile Lys
            35                  40                  45

Asp Ile Leu Ser Ala Ile Pro Lys Glu Cys Tyr Lys Arg Asp Thr Leu
        50                  55                  60

Trp Ser Leu His Tyr Val Val Arg Asp Ile Ala Ala Ile Leu Val Ile
65                  70                  75                  80

Gly Tyr Leu Gly Thr Asn Tyr Ile Pro Val Leu Phe Pro Asn Ser Ala
                85                  90                  95

Leu Leu Arg Gly Ile Ala Tyr Ala Ile Gln Ser Tyr Leu Ile Gly Leu
            100                 105                 110

Phe Gly Phe Gly Leu Trp Ile Leu Ala His Glu Cys Gly His Ser Ala
        115                 120                 125

Phe Ser Glu Ser Asn Ala Val Asn Asp Thr Val Gly Trp Val Leu His
    130                 135                 140

Ser Trp Trp Met Val Pro Tyr Phe Pro Trp Lys Phe Ser His Ser Lys
145                 150                 155                 160

His His Lys Ala Thr Gly His Met Thr Arg Asp Met Val Phe Ile Pro
                165                 170                 175

Tyr Thr Lys Asp Glu Phe Ile Thr Met Lys Lys Ser Lys Phe Ala
            180                 185                 190

Glu Ile Thr Glu Glu Ala Pro Val Met Thr Leu Phe Asn Leu Ile Ala
        195                 200                 205

Gln Gln Val Gly Gly Leu Gln Leu Tyr Leu Ala Thr Asn Ala Thr Gly
    210                 215                 220

Gln Pro Tyr Pro Gly Val Lys Lys Phe Phe Lys Ser His Tyr Trp Pro
225                 230                 235                 240

Thr Ser Pro Val Phe Asp Ala Lys Asp Phe Trp Trp Ile Ile Met Ser
```

```
                    245                 250                 255
Asp Ile Gly Ile Val Ser Thr Leu Leu Ile Asn Tyr Leu Trp Tyr Arg
                260                 265                 270

Ala Tyr Gly Ala His Val Val Leu Ile Asn Trp Phe Ile Pro Trp Leu
            275                 280                 285

Trp Val Asn His Trp Leu Val Phe Val Thr Phe Leu Gln His Thr Asp
        290                 295                 300

Pro Thr Met Pro His Tyr Asp Ala Glu Glu Trp Thr Phe Ala Lys Gly
305                 310                 315                 320

Ala Ala Ala Thr Ile Asp Arg Asn Phe Gly Phe Val Gly Gln His Ile
                325                 330                 335

Phe His Asp Ile Ile Glu Thr His Val Leu His His Tyr Cys Ser Arg
            340                 345                 350

Ile Pro Phe Tyr Asn Ala Arg Lys Ala Thr Ser Ala Ile Lys Glu Val
        355                 360                 365

Met Gly Gln His Tyr Arg Tyr Glu Gly Glu Asn Met Trp Lys Ser Leu
    370                 375                 380

Trp Lys Val Ala Arg Ser Cys Gln Tyr Val Glu Gly Asp Asn Gly Val
385                 390                 395                 400

Arg Met Phe Arg Asn Thr Asn Gly Val Gly Val Lys Pro Glu Asp Gly
                405                 410                 415

Ser Ser Gln

<210> SEQ ID NO 63
<211> LENGTH: 410
<212> TYPE: PRT
<213> ORGANISM: Kluyveromyces lactis
<220> FEATURE:
<221> NAME/KEY: MISC_FEATURE
<222> LOCATION: (1)..(410)
<223> OTHER INFORMATION: delta-12 desaturase; GenBank Accession No.
      XP_455402

<400> SEQUENCE: 63

Met Ser Gln Ser Gln Tyr Val Thr Asp Ala Glu Thr Thr Glu Ser
1               5                   10                  15

Cys Lys Val Ala Ile Asp Thr His Gly Asn Val Phe Lys Val Pro Asp
                20                  25                  30

Tyr Thr Ile Lys Asp Ile Leu Ser Ala Ile Pro Pro Glu Cys Tyr Asn
            35                  40                  45

Arg Lys Leu Ala Val Ser Leu Tyr Tyr Val Phe Arg Asp Ile Ala Ile
        50                  55                  60

Met Ala Gly Ile Gly Tyr Phe Ala Asn Val Phe Ala Tyr Pro Tyr Val
65                  70                  75                  80

Lys Asp Leu His Val Ala Ala Arg Phe Val Tyr Trp Ala Phe Tyr Gly
                85                  90                  95

Tyr Val Gln Gly Leu Phe Gly Thr Gly Leu Trp Val Leu Ala His Glu
            100                 105                 110

Cys Gly His Gln Ala Phe Ser Asp Tyr Gly Ala Val Asn Asp Phe Val
        115                 120                 125

Gly Trp Val Leu His Ser Tyr Leu Leu Val Pro Tyr Phe Ser Trp Lys
    130                 135                 140

Tyr Thr His Ser Lys His His Lys Ala Thr Gly His Ile Thr Arg Asp
145                 150                 155                 160

Met Val Phe Val Pro Lys Thr Lys Glu Asp Phe Val Lys Ser Arg Gly
                165                 170                 175
```

Ile Leu Ala Asp Ile Asp Glu Phe Ser Glu Asp Ser Pro Ile Arg Thr
            180                 185                 190

Leu Ile Glu Leu Leu Thr Gln Gln Leu Gly Gly Trp Ile Tyr Tyr Leu
        195                 200                 205

Leu Thr Asn Val Thr Gly Gln Pro Tyr Pro Asp Val Pro Lys Trp Lys
    210                 215                 220

Trp Asn His Phe Trp Pro Ser Ser Pro Val Phe Asp Asp Lys Asp Tyr
225                 230                 235                 240

Ile Tyr Ile Leu Leu Ser Asp Leu Gly Ile Leu Thr Gln Ser Leu Val
                245                 250                 255

Leu Lys Ile Trp Tyr Asp Lys Phe Gly Gly Trp Ser Val Phe Ile Asn
            260                 265                 270

Trp Phe Val Pro Tyr Ile Trp Val Asn His Trp Leu Val Phe Ile Thr
        275                 280                 285

Tyr Leu Gln His Thr Asp Ala Ser Met Pro His Tyr Glu Ala Asp Gln
    290                 295                 300

Trp Ser Phe Ala Lys Gly Ala Ala Thr Ile Asp Arg Gln Phe Gly
305                 310                 315                 320

Phe Ile Gly Pro His Ile Phe His Asp Ile Ile Glu Thr His Val Leu
                325                 330                 335

His His Tyr Cys Ser Arg Ile Pro Phe Tyr Asn Ala Arg Pro Ala Ser
            340                 345                 350

Glu Ala Ile Lys Lys Val Met Gly Glu His Tyr Arg Phe Asn Asp Glu
        355                 360                 365

Asn Met Trp Val Ser Leu Trp Lys Ser Ala Arg Thr Cys Gln Tyr Val
    370                 375                 380

Asp Asp Ala Asp Ser Lys Gly Val Tyr Met Phe Arg Asn Val Asn Asn
385                 390                 395                 400

Val Gly Val Gly Thr Gly Lys Lys Lys Asn
                405                 410

<210> SEQ ID NO 64
<211> LENGTH: 415
<212> TYPE: PRT
<213> ORGANISM: Kluyveromyces lactis
<220> FEATURE:
<221> NAME/KEY: MISC_FEATURE
<222> LOCATION: (1)..(415)
<223> OTHER INFORMATION: delta-15 desaturase; GenBank Accession No.
      XP_451551

<400> SEQUENCE: 64

Met Ser Lys Ser Thr Gly Val Glu His His Ile Ser Gly Val Ala Thr
1               5                   10                  15

Thr Glu Thr Ala Thr Glu Thr Val Thr Val Pro Pro Ala Lys Thr Ala
            20                  25                  30

Ile Asp Thr His Gly Asn Ile Phe Lys Val Pro Asp Tyr Thr Ile Lys
        35                  40                  45

Asp Ile Leu Gly Ala Ile Pro Lys Glu Cys Tyr Lys Arg Asp Thr Leu
    50                  55                  60

Trp Ser Leu His Tyr Val Val Arg Asp Ile Ile Ala Ile Cys Ile Ile
65                  70                  75                  80

Gly Tyr Val Gly Thr Asn Tyr Ile Pro Val Trp Phe Pro Asn Ser Gly
                85                  90                  95

Leu Leu Arg Phe Val Ala Tyr Met Val Gln Ser Tyr Leu Ile Gly Leu
            100                 105                 110

```
Phe Gly Phe Gly Leu Trp Ile Leu Ala His Glu Cys Gly His Gly Ala
            115                 120                 125

Phe Ser Asp Ser Arg Leu Ile Asn Asp Thr Val Gly Trp Val Leu His
        130                 135                 140

Ser Trp Trp Met Val Pro Tyr Phe Ser Trp Lys Phe Ser His Ser Lys
145                 150                 155                 160

His His Lys Ala Thr Gly His Leu Thr Arg Asp Met Val Phe Val Pro
                165                 170                 175

Tyr Thr Lys Lys Glu Tyr Leu Glu Met Lys Gly Lys Ser Lys Leu Arg
            180                 185                 190

Glu Ile Thr Glu Glu Ala Pro Ile Val Thr Leu Leu Thr Leu Ile Gly
        195                 200                 205

Gln Gln Ile Gly Gly Leu Gln Leu Tyr Leu Ala Thr Asn Ala Thr Gly
    210                 215                 220

Gln Ser Tyr Pro Gly Val Pro Lys Phe Phe Lys Ser His Tyr Trp Pro
225                 230                 235                 240

Thr Ser Pro Val Phe Asp Thr Lys Asp Phe Trp Tyr Ile Ile Leu Ser
                245                 250                 255

Asp Ile Gly Ile Ile Ser Thr Leu Thr Ile Asn Tyr Leu Trp Ala Lys
            260                 265                 270

Thr Tyr Gly Ser His Val Met Leu Ile Asn Trp Phe Val Pro Trp Leu
        275                 280                 285

Trp Val Asn His Trp Leu Val Phe Val Thr Phe Leu Gln His Thr Asp
    290                 295                 300

Pro Thr Met Pro His Tyr Glu Ala Ser Glu Trp Thr Phe Ala Lys Gly
305                 310                 315                 320

Ala Ala Ala Thr Ile Asp Arg Asn Phe Gly Phe Val Gly Gln His Ile
                325                 330                 335

Phe His Asp Ile Ile Glu Thr His Val Leu His His Tyr Cys Ser Arg
            340                 345                 350

Ile Pro Phe Tyr Asn Ala Arg Val Ala Thr Glu Ala Ile Lys Lys Val
        355                 360                 365

Met Gly Glu His Tyr Arg Tyr Glu Gly Glu Asn Met Trp Gln Ser Leu
    370                 375                 380

Trp Lys Val Ala Arg Ser Cys Gln Phe Val Asp Gly Asp Asn Gly Val
385                 390                 395                 400

Leu Met Phe Arg Asn Thr Asn Gly Val Gly Ala Pro Cys Gln Glu
                405                 410                 415

<210> SEQ ID NO 65
<211> LENGTH: 436
<212> TYPE: PRT
<213> ORGANISM: Candida albicans SC5314
<220> FEATURE:
<221> NAME/KEY: MISC_FEATURE
<222> LOCATION: (1)..(436)
<223> OTHER INFORMATION: delta-12 desaturase; GenBank Accession No.
      EAK94955

<400> SEQUENCE: 65

Met Ala Ala Thr Thr Ser Phe Ser Ser Gly Phe Asn Asn Asn
1               5                   10                  15

Asn Ala Asp Gln Ser Thr Asp Ser Ser Ala Thr Ile Ser Lys Ser Gly
            20                  25                  30

Asn Val Ala Ser Phe Lys Thr Thr Ser Thr Thr Ser Thr Tyr Gln Thr
        35                  40                  45
```

```
Asn Leu Thr Ala Ile Asp Thr Tyr Gly Asn Glu Phe Lys Val Pro Asp
 50                  55                  60

Tyr Thr Ile Lys Asp Ile Leu Ser Ala Ile Pro Thr His Cys Tyr Glu
 65                  70                  75                  80

Arg Arg Leu Leu Gln Ser Leu Ser Tyr Val Phe Arg Asp Ile Phe Cys
                     85                  90                  95

Met Val Val Leu Gly Phe Ile Ala Asn Asn Tyr Ile His Leu Ile Pro
                100                 105                 110

Asn Gln Phe Ile Arg Phe Ala Ala Trp Thr Gly Tyr Val Trp Cys Gln
                115                 120                 125

Gly Leu Phe Gly Thr Gly Ile Trp Val Leu Ala His Glu Cys Gly His
            130                 135                 140

Gln Ala Phe Ser Asp Tyr Gly Ser Val Asn Asp Phe Val Gly Trp Val
145                 150                 155                 160

Leu His Ser Tyr Leu Leu Val Pro Tyr Phe Ser Trp Lys Phe Ser His
                165                 170                 175

Gly Lys His His Lys Ala Thr Gly His Leu Thr Arg Asp Met Val Phe
                180                 185                 190

Val Pro Lys Thr Lys Glu Glu Phe Leu Gln Asn Arg Gly Val Lys Asp
            195                 200                 205

Leu Asp Asp Leu Leu Gly Asp Ser Pro Met Tyr Ser Leu Leu Thr Leu
210                 215                 220

Ile Phe Gln Gln Thr Phe Gly Trp Ile Ser Tyr Leu Val Ala Asn Val
225                 230                 235                 240

Ser Gly Gln Lys Tyr Pro Gly Val Ser Phe Leu Lys Leu Asn His Phe
                245                 250                 255

Asn Pro Asn Ser Leu Ile Phe Asp Lys Lys Asp Tyr Trp Tyr Ile Leu
                260                 265                 270

Leu Ser Asp Leu Gly Ile Leu Leu Gln Phe Phe Asn Leu Tyr Val Trp
            275                 280                 285

Tyr Gln Ser Phe Gly Gly Phe Asn Leu Leu Val Asn Tyr Val Leu Pro
290                 295                 300

Tyr Phe Leu Val Asn His Trp Leu Val Phe Ile Thr Tyr Leu Gln His
305                 310                 315                 320

Ser Asp Pro Gln Met Pro His Tyr Glu Ala Ser Gln Trp Thr Phe Ala
                325                 330                 335

Arg Gly Ala Ala Ala Thr Ile Asp Arg Glu Phe Gly Phe Val Gly Lys
            340                 345                 350

His Ile Phe His Asp Ile Ile Glu Thr His Val Leu His His Tyr Val
            355                 360                 365

Ser Arg Ile Pro Phe Tyr Asn Ala Arg Glu Ala Ser Glu Ala Ile Lys
370                 375                 380

Lys Val Met Gly Ile His Tyr Gln His Ser Asp Glu Asn Met Trp Val
385                 390                 395                 400

Ser Leu Trp Lys Ser Ala Arg Trp Cys Gln Phe Val Asp Gly Asn Asn
                405                 410                 415

Gly Val Leu Met Tyr Arg Asn Thr Asn Gly Phe Gly Val Asp Pro Lys
            420                 425                 430

Lys Gln Thr His
            435

<210> SEQ ID NO 66
<211> LENGTH: 433
```

```
<212> TYPE: PRT
<213> ORGANISM: Candida albicans SC5314
<220> FEATURE:
<221> NAME/KEY: MISC_FEATURE
<222> LOCATION: (1)..(433)
<223> OTHER INFORMATION: delta-15 desaturase; GenBank Accession No.
      EAL03493

<400> SEQUENCE: 66
```

| | | | | | | | | | | | | | | |
|---|---|---|---|---|---|---|---|---|---|---|---|---|---|---|
| Met | Ser | Val | Val | Glu | Ala | Ser | Ser | Ser | Val | Val | Glu | Asp | Ser | Thr |
| 1 | | | | 5 | | | | | 10 | | | | | 15 |
| Ala | Ser | Asn | Val | Val | Gln | Arg | Gly | Asn | Ile | Ser | Ser | Phe | Ala | Ser | Thr |
| | | | 20 | | | | | 25 | | | | | 30 | |
| Thr | Ala | Ser | Ser | Asn | Leu | Thr | Thr | Ile | Asp | Thr | Asn | Gly | Lys | Val | Phe |
| | 35 | | | | | 40 | | | | | 45 | | | | |
| Lys | Val | Pro | Asp | Tyr | Ser | Ile | Lys | Asp | Ile | Leu | Gln | Ala | Ile | Pro | Lys |
| 50 | | | | | 55 | | | | | 60 | | | | | |
| His | Cys | Tyr | Glu | Arg | Ser | Leu | Ile | Arg | Ser | Leu | Gly | Tyr | Val | Val | Arg |
| 65 | | | | 70 | | | | | 75 | | | | | 80 | |
| Asp | Ile | Thr | Met | Met | Val | Ile | Ile | Gly | Tyr | Val | Gly | His | Thr | Phe | Ile |
| | | | | 85 | | | | | 90 | | | | | 95 | |
| Pro | Met | Val | Gln | Ile | Pro | Glu | Tyr | Pro | Ser | Leu | Ala | Tyr | Gly | Leu | Arg |
| | | | 100 | | | | | 105 | | | | | 110 | | |
| Gly | Ala | Leu | Trp | Met | Val | Gln | Ser | Tyr | Cys | Ile | Gly | Leu | Phe | Gly | Phe |
| | | 115 | | | | | 120 | | | | | 125 | | | |
| Gly | Leu | Trp | Ile | Leu | Ala | His | Glu | Cys | Gly | His | Gly | Ala | Phe | Ser | Asp |
| 130 | | | | | 135 | | | | | 140 | | | | | |
| Tyr | Gln | Asn | Ile | Asn | Asp | Phe | Ile | Gly | Trp | Val | Leu | His | Ser | Tyr | Leu |
| 145 | | | | | 150 | | | | | 155 | | | | | 160 |
| Ile | Val | Pro | Tyr | Phe | Ser | Trp | Lys | Phe | Ser | His | Ala | Lys | His | His | Lys |
| | | | | 165 | | | | | 170 | | | | | 175 | |
| Ala | Thr | Gly | His | Leu | Thr | Lys | Asp | Met | Val | Phe | Ile | Pro | Tyr | Thr | Lys |
| | | | 180 | | | | | 185 | | | | | 190 | | |
| Glu | Glu | Tyr | Leu | Glu | Lys | Asn | Lys | Val | Glu | Lys | Val | Ala | Asp | Leu | Met |
| | | 195 | | | | | 200 | | | | | 205 | | | |
| Glu | Glu | Ser | Pro | Ile | Tyr | Ser | Phe | Leu | Val | Leu | Val | Phe | Gln | Gln | Leu |
| 210 | | | | | 215 | | | | | 220 | | | | | |
| Gly | Gly | Leu | Gln | Leu | Tyr | Leu | Ala | Thr | Asn | Ala | Thr | Gly | Gln | Val | Tyr |
| 225 | | | | | 230 | | | | | 235 | | | | | 240 |
| Pro | Gly | Tyr | Ser | Lys | Ile | Ala | Lys | Ser | His | Tyr | Thr | Pro | Thr | Ser | Pro |
| | | | | 245 | | | | | 250 | | | | | 255 | |
| Val | Phe | Asp | Lys | His | Gln | Tyr | Trp | Tyr | Ile | Val | Leu | Ser | Asp | Ile | Gly |
| | | | 260 | | | | | 265 | | | | | 270 | | |
| Ile | Ile | Leu | Ala | Phe | Thr | Thr | Val | Tyr | Gln | Trp | Tyr | Lys | Asn | Phe | Gly |
| | | 275 | | | | | 280 | | | | | 285 | | | |
| Leu | Phe | Asn | Met | Met | Ile | Asn | Trp | Phe | Val | Pro | Trp | Leu | Trp | Val | Asn |
| 290 | | | | | 295 | | | | | 300 | | | | | |
| His | Trp | Leu | Val | Phe | Val | Thr | Phe | Leu | Gln | His | Thr | Asp | Pro | Thr | Met |
| 305 | | | | | 310 | | | | | 315 | | | | | 320 |
| Pro | His | Tyr | Thr | Ser | Lys | Glu | Trp | Thr | Phe | Ala | Arg | Gly | Ala | Ala | Ala |
| | | | | 325 | | | | | 330 | | | | | 335 | |
| Thr | Ile | Asp | Arg | Asn | Phe | Gly | Phe | Val | Gly | Gln | His | Ile | Phe | His | Asp |
| | | | 340 | | | | | 345 | | | | | 350 | | |
| Ile | Ile | Glu | Thr | His | Val | Leu | His | His | Tyr | Val | Ser | Arg | Ile | Pro | Phe |
| | | 355 | | | | | 360 | | | | | 365 | | | |

```
Tyr Asn Ala Arg Glu Ala Thr Asp Ala Ile Arg Lys Val Met Gly Glu
    370                 375                 380

His Tyr Arg Tyr Glu Gly Glu Ser Met Trp Tyr Ser Leu Trp Lys Cys
385                 390                 395                 400

Met Arg Met Cys Gln Phe Val Asp Asp Lys Glu Asp Ala Lys Gly
                405                 410                 415

Val Met Met Phe Arg Asn Val Asn Gly Trp Gly Pro Val Lys Pro Lys
                420                 425                 430

Asp

<210> SEQ ID NO 67
<211> LENGTH: 417
<212> TYPE: PRT
<213> ORGANISM: Candida guilliermondii
<220> FEATURE:
<221> NAME/KEY: MISC_FEATURE
<222> LOCATION: (1)..(417)
<223> OTHER INFORMATION: delta-12 desaturase

<400> SEQUENCE: 67

Met Ile Asn Ser Ala Thr Ser Thr Ala Thr Ser Ser Gly Tyr Gly Thr
1               5                   10                  15

Thr Ile Asn Arg Asn Gly Asn Val Ala Thr Leu Ser Ser Asn Val Lys
                20                  25                  30

Ala Ile Asp Thr Tyr Gly Asp Glu Phe Val Ala Pro Asp Tyr Ser Ile
            35                  40                  45

Lys Asp Ile Leu Lys Ala Ile Pro Ala His Cys Tyr Glu Arg Arg Val
    50                  55                  60

Ile Glu Ser Met Tyr Tyr Val Phe Arg Asp Ile Phe Trp Ile Gly Val
65                  70                  75                  80

Phe Met Tyr Val Ala Asn Asn Tyr Ile Gln Leu Leu Pro Ala Pro Trp
                85                  90                  95

Met Arg Phe Ala Ala Trp Gly Gly Tyr Val Trp Val Gln Gly Leu Leu
                100                 105                 110

His Thr Gly Leu Trp Val Leu Ala His Glu Cys Gly His Leu Ala Phe
            115                 120                 125

Ser Asp Tyr Lys Leu Val Asn Asp Thr Val Gly Trp Val Leu His Ser
    130                 135                 140

Tyr Leu Met Val Pro Tyr Phe Ser Trp Lys Phe Ser His Ser Lys His
145                 150                 155                 160

His Lys Ala Thr Gly Asn Leu Lys Arg Asp Thr Val Phe Ile Pro Lys
                165                 170                 175

Thr Lys Glu Glu Phe Leu Glu Ser Arg Asp His Asp His Asp Ile Asp
            180                 185                 190

Asp Ile Val Gly Asp Ser Pro Ile Tyr Thr Leu Tyr Gln Leu Ile Leu
    195                 200                 205

Gln Gln Phe Gly Gly Trp Ile Ala Tyr Leu Phe Thr Asn Val Ser Gly
210                 215                 220

Gln Lys Tyr Glu Gly Lys Lys Trp Tyr Gln Asn Asn His Phe Asn Pro
225                 230                 235                 240

Ala Ser Pro Ile Phe Glu Ser Arg Glu Tyr Trp Tyr Val Met Ser
                245                 250                 255

Asp Ile Gly Ile Leu Thr Gln Leu Ile Val Val Tyr Thr Trp Tyr Lys
                260                 265                 270

Lys Phe Gly Gly Phe Asn Leu Leu Val Asn Trp Ala Leu Pro Tyr Val
            275                 280                 285
```

```
Leu Val Asn His Trp Leu Val Phe Ile Thr Phe Leu Gln His Ser Asp
    290                 295                 300

Pro Arg Met Pro His Tyr Thr Pro Glu Gln Trp Asn Phe Ala Arg Gly
305                 310                 315                 320

Ala Ala Ala Thr Met Asp Arg Glu Phe Gly Phe Val Gly Lys Tyr Ile
                325                 330                 335

Phe His Asp Ile Ile Glu Thr His Val Leu His His Tyr Val Ser Arg
                340                 345                 350

Ile Pro Phe Tyr Asn Ala Arg Glu Ala Ser Glu Ala Ile Lys Lys Val
                355                 360                 365

Met Gly Ser His Tyr Gln His Ser Asp Glu Asn Met Trp Val Ser Leu
                370                 375                 380

Trp Lys Ser Gly Arg Trp Cys Gln Tyr Val Asp Gly Asp Asn Gly Val
385                 390                 395                 400

Met Met Tyr Arg Asn Val Asn Asn Lys Gly Val Gly Thr Gly Asn Lys
                405                 410                 415

Ala

<210> SEQ ID NO 68
<211> LENGTH: 370
<212> TYPE: PRT
<213> ORGANISM: Candida guilliermondii
<220> FEATURE:
<221> NAME/KEY: MISC_FEATURE
<222> LOCATION: (1)..(370)
<223> OTHER INFORMATION: delta-15 desaturase

<400> SEQUENCE: 68

Met Lys Asp Ile Leu Ser Ala Ile Pro Lys His Cys Tyr Glu Arg Ser
1               5                   10                  15

Leu Val Lys Ser Met Gly Tyr Val Val Arg Asp Ile Val Leu Met Cys
                20                  25                  30

Ala Ile Gly Tyr Val Gly His Lys Val Ile Pro Met Val Gln Ile Ala
                35                  40                  45

Asn His Asp Thr Leu Ser Met Val Val Arg Gly Gly Leu Trp Ser Leu
            50                  55                  60

Gln Ser Tyr Leu Ile Gly Leu Phe Gly Phe Gly Leu Trp Ile Leu Ala
65              70                  75                  80

His Glu Cys Gly His Gly Ala Phe Ser Asp Phe Gln Asn Val Asn Asp
                85                  90                  95

Phe Ile Gly Trp Val Leu His Ser Tyr Leu Met Val Pro Tyr Phe Ser
                100                 105                 110

Trp Lys Tyr Ser His Ser Lys His His Lys Ala Thr Gly His Leu Thr
                115                 120                 125

Arg Asp Met Val Phe Val Pro Tyr Thr Lys Asp Glu Phe Ala Glu Lys
                130                 135                 140

His Gly Val Ser Asn Val Ala Glu Ile Met Glu Ser Pro Ile Trp
145                 150                 155                 160

Thr Leu Leu Val Leu Ile Phe Gln Gln Leu Gly Gly Leu Gln Thr Tyr
                165                 170                 175

Leu Ala Thr Asn Ala Thr Gly Gln Pro Tyr Pro Gly Leu Ser Trp Leu
                180                 185                 190

Ala Lys Ser His Tyr Ala Pro Ser Ser Pro Val Phe Asp Pro His Gln
                195                 200                 205

Tyr Trp Phe Ile Val Leu Ser Asp Ile Gly Ile Leu Thr Thr Leu Thr
```

```
                210                 215                 220
Val Val Tyr Gln Trp Tyr Lys Asn Phe Gly Ala Phe Asn Met Phe Val
225                 230                 235                 240

Asn Trp Phe Met Pro Trp Leu Trp Val Asn His Trp Leu Val Phe Val
                245                 250                 255

Thr Phe Leu Gln His Thr Asp Pro Ser Met Pro His Tyr Lys Asp Thr
                260                 265                 270

Glu Trp Thr Phe Ala Arg Gly Ala Ala Thr Ile Asp Arg Asn Phe
            275                 280                 285

Gly Phe Val Gly Gln His Ile Phe His Asp Ile Ile Glu Thr His Val
        290                 295                 300

Leu His His Tyr Val Ser Arg Ile Pro Phe Tyr Asn Ala Arg Glu Ala
305                 310                 315                 320

Thr Asp Ala Ile Lys Lys Val Met Gly Ser His Tyr Arg Tyr Glu Gly
                325                 330                 335

Glu Ser Met Trp Tyr Ser Leu Trp Lys Val Met Arg Met Cys Gln Tyr
            340                 345                 350

Val Asp Asp Asn Val Asn Gly Val Met Met Phe Arg Asn Val Asn
        355                 360                 365

Gly Leu
    370

<210> SEQ ID NO 69
<211> LENGTH: 340
<212> TYPE: PRT
<213> ORGANISM: Candida tropicalis
<220> FEATURE:
<221> NAME/KEY: MISC_FEATURE
<222> LOCATION: (1)..(340)
<223> OTHER INFORMATION: delta-12 desaturase

<400> SEQUENCE: 69

Met Val Val Leu Gly Phe Ile Ala Asn Asn Tyr Ile Gln Phe Leu Pro
1               5                   10                  15

Asn Gln Tyr Leu Arg Phe Ala Ala Trp Ala Gly Tyr Ile Trp Cys Gln
                20                  25                  30

Gly Leu Phe Gly Thr Gly Ile Trp Val Leu Ala His Glu Cys Gly His
            35                  40                  45

Gln Ala Phe Ser Asp Tyr Gly Trp Val Asn Asp Leu Val Gly Trp Ile
        50                  55                  60

Leu His Ser Tyr Leu Leu Val Pro Tyr Phe Ser Trp Lys Tyr Ser His
65                  70                  75                  80

Gly Lys His His Lys Ala Thr Gly His Leu Thr Arg Asp Met Val Phe
                85                  90                  95

Val Pro Lys Thr Lys Glu Gln Phe Leu Ala Asn Arg Gly Ala Glu Asp
                100                 105                 110

Leu Asp Asp Leu Leu Gly Asp Ala Pro Leu Tyr Ser Leu Gly Thr Leu
            115                 120                 125

Ile Phe Gln Gln Thr Phe Gly Trp Ile Ser Tyr Leu Val Ser Asn Val
        130                 135                 140

Ser Gly Gln Lys Tyr Pro Gly Gln Gly Leu Phe Ser Val Asn His Phe
145                 150                 155                 160

Asn Pro Asn Ser Pro Ile Phe Glu Lys Arg Asp Tyr Trp Phe Ile Leu
                165                 170                 175

Leu Ser Asp Leu Gly Ile Leu Ile Gln Phe Thr Val Leu Tyr Thr Trp
            180                 185                 190
```

```
Tyr Gln Asn Phe Gly Leu Phe Asn Phe Met Val Asn Tyr Phe Leu Pro
            195                 200                 205

Tyr Leu Leu Val Asn His Trp Leu Val Phe Ile Thr Tyr Leu Gln His
        210                 215                 220

Ser Asp Pro Gln Met Pro His Tyr Glu Ala Ser Gln Trp Thr Phe Ala
225                 230                 235                 240

Arg Gly Ala Ala Ala Thr Ile Asp Arg Glu Phe Gly Phe Val Gly Lys
                245                 250                 255

His Ile Phe His Asp Ile Ile Glu Thr His Val Leu His His Tyr Val
            260                 265                 270

Ser Arg Ile Pro Phe Tyr Asn Ala Arg Glu Ala Ser Glu Cys Ile Lys
        275                 280                 285

Lys Val Met Gly Glu His Tyr Gln His Ser Asp Glu Asn Met Trp Val
290                 295                 300

Ser Leu Trp Lys Ser Ala Arg Trp Cys Gln Phe Val Asp Gly Asp Asn
305                 310                 315                 320

Gly Val Met Met Tyr Arg Asn Ile Asn Gly Phe Gly Val Asp Pro Lys
                325                 330                 335

Lys Lys Thr His
            340

<210> SEQ ID NO 70
<211> LENGTH: 349
<212> TYPE: PRT
<213> ORGANISM: Candida tropicalis
<220> FEATURE:
<221> NAME/KEY: MISC_FEATURE
<222> LOCATION: (1)..(349)
<223> OTHER INFORMATION: delta-15 desaturase

<400> SEQUENCE: 70

Met Met Val Leu Ile Ser Tyr Val Gly His Ser Phe Ile Pro Leu Val
1               5                   10                  15

Asp Ile Glu Asn His Glu Thr Leu Ser Thr Val Val Arg Gly Ser Leu
            20                  25                  30

Trp Met Val Gln Ser Tyr Leu Ile Gly Leu Phe Gly Phe Gly Leu Trp
        35                  40                  45

Ile Leu Ala His Glu Cys Gly His Gly Ala Phe Ser Asp Tyr Gln Asn
    50                  55                  60

Leu Asn Asp Leu Ile Gly Trp Val Ile His Ser Tyr Leu Met Val Pro
65                  70                  75                  80

Tyr Phe Ser Trp Lys Phe Ser His Ala Lys His His Lys Ala Thr Gly
                85                  90                  95

His Leu Thr Lys Asp Met Val Phe Ile Pro Tyr Thr Lys Glu Glu Tyr
            100                 105                 110

Leu Glu Lys Asn Lys Val Glu Lys Val Ser Glu Leu Val Glu Glu Ser
        115                 120                 125

Pro Ile Tyr Ser Leu Leu Val Leu Ile Phe Gln Gln Leu Gly Gly Leu
    130                 135                 140

Gln Leu Tyr Leu Ala Asn Asn Ala Thr Gly Gln Val Tyr Pro Gly Val
145                 150                 155                 160

Ser Trp Tyr Ala Arg Ser His Tyr Ser Pro Ile Ser Pro Val Phe Asp
                165                 170                 175

Lys Asn Gln Tyr Trp Phe Ile Val Leu Ser Asp Ile Gly Ile Ile Ser
            180                 185                 190
```

```
Thr Leu Thr Val Val Tyr Gln Trp Tyr Lys Asn Phe Gly Leu Phe Asn
        195                 200                 205

Met Met Ile Asn Trp Phe Val Pro Trp Leu Trp Val Asn His Trp Leu
    210                 215                 220

Val Phe Val Thr Phe Leu Gln His Thr Asp Pro Thr Met Pro His Tyr
225                 230                 235                 240

Ala Ala Asn Glu Trp Thr Phe Ala Arg Gly Ala Ala Thr Ile Asp
                245                 250                 255

Arg Asn Phe Gly Phe Val Gly Gln His Ile Phe His Asp Ile Ile Glu
                260                 265                 270

Thr His Val Leu His His Tyr Val Ser Arg Ile Pro Phe Tyr Asn Ala
        275                 280                 285

Arg Glu Ala Thr Glu Ala Ile Lys Lys Val Met Gly Glu His Tyr Arg
    290                 295                 300

Tyr Glu Gly Glu Asn Met Trp Phe Ser Leu Trp Lys Cys Val Arg Met
305                 310                 315                 320

Cys Gln Phe Val Asp Asp Asp Lys Glu Asp Ala Lys Gly Val Leu Met
                325                 330                 335

Phe Arg Asn Val Asn Gly Leu Gly Val Lys Pro Lys Asp
                340                 345

<210> SEQ ID NO 71
<211> LENGTH: 418
<212> TYPE: PRT
<213> ORGANISM: Candida lusitaniae
<220> FEATURE:
<221> NAME/KEY: MISC_FEATURE
<222> LOCATION: (1)..(418)
<223> OTHER INFORMATION: delta-12 desaturase

<400> SEQUENCE: 71

Met Ala Gln Val Thr Ser Phe Ser Thr Gly Asn Ser Glu Ser Ser Ser
1               5                   10                  15

Thr Ser Thr Thr Ile Lys Lys Lys Gly Asn Val Ala Thr Leu Thr Ser
            20                  25                  30

Gly Leu Thr Ala Thr Asn Thr Tyr Gly Glu Glu Phe Gln Val Pro Asp
        35                  40                  45

Tyr Thr Ile Lys Asp Ile Leu Ser Ala Ile Pro Ser Gln Cys Tyr Glu
    50                  55                  60

Arg Arg Ala Leu Glu Ser Leu Tyr Tyr Val Phe Arg Asp Ile Ala Cys
65                  70                  75                  80

Met Val Ala Ile Gly Tyr Val Ala Asn Asn Tyr Ile Gln Phe Leu Pro
                85                  90                  95

Asn Lys Ala Leu Arg Phe Thr Ala Trp Ala Leu Tyr Ser Tyr Val Gln
                100                 105                 110

Gly Leu Phe Gly Thr Gly Ile Trp Val Leu Ala His Glu Cys Gly His
        115                 120                 125

Gln Ala Phe Ser Asp Tyr Gly Trp Leu Asn Asp Leu Val Gly Trp Val
    130                 135                 140

Leu His Ser Tyr Trp Leu Val Pro Tyr Phe Ser Trp Lys Phe Ser His
145                 150                 155                 160

Gly Lys His His Lys Ala Thr Gly His Met Asp Arg Asp Met Val Phe
                165                 170                 175

Val Pro Lys Thr Arg Asp Gly Phe Val Glu Ser Arg His Ala His Thr
                180                 185                 190

Leu Glu Glu Ile Val Ala Asp Ser Pro Leu Ala Thr Phe Ile Gly Leu
```

```
            195                 200                 205
Leu Ser Gln Gln Leu Gly Gly Trp Leu Met Tyr Leu Ala Thr Asn Val
    210                 215                 220

Thr Gly Gln Pro Val Ala Glu Ser Gly Trp Gly Met Ser His Phe Asn
225                 230                 235                 240

Pro Ser Ser Ala Ile Phe Glu Thr Lys Asp Tyr Trp Tyr Ile Val Leu
                245                 250                 255

Ser Asp Ile Gly Leu Leu Ile Gln Gly Leu Val Leu Tyr Thr Trp Tyr
            260                 265                 270

Gln Lys Phe Gly Ala Phe Asn Leu Leu Val Asn Trp Leu Ile Pro Tyr
        275                 280                 285

Ile Gly Val Asn His Trp Leu Val Phe Ile Thr Phe Leu Gln His Ser
    290                 295                 300

Asp Pro Lys Met Pro His Tyr Glu Ala Ser Glu Trp Asn Phe Ala Arg
305                 310                 315                 320

Gly Ala Ala Thr Met Asp Arg Glu Phe Gly Phe Val Gly Lys His
                325                 330                 335

Ile Phe His Asp Ile Ile Glu Thr His Val Leu His His Tyr Cys Ser
            340                 345                 350

Arg Ile Pro Phe Tyr Asn Ala Arg Glu Ala Thr Glu Ala Ile Lys Lys
        355                 360                 365

Val Met Gly Lys His Tyr Gln Tyr Ser Asp Glu Asn Met Trp Val Ser
    370                 375                 380

Leu Trp Lys Ser Gly Arg Trp Cys Gln Phe Val Glu Gly Asp Asn Gly
385                 390                 395                 400

Val Leu Met Phe Arg Asn Ile Asn Gly Asn Gly Val Ala Pro Lys Lys
                405                 410                 415

Thr Gln

<210> SEQ ID NO 72
<211> LENGTH: 346
<212> TYPE: PRT
<213> ORGANISM: Candida lusitaniae
<220> FEATURE:
<221> NAME/KEY: MISC_FEATURE
<222> LOCATION: (1)..(346)
<223> OTHER INFORMATION: delta-15 desaturase

<400> SEQUENCE: 72

Met Met Val Leu Ile Gly Tyr Val Gly Met Thr Tyr Ile Pro Lys Val
1               5                   10                  15

Asp Ile Val Gly His Glu Thr Ala Ser Thr Val Ala Arg Ala Cys Leu
            20                  25                  30

Trp Met Val Gln Ser Tyr Leu Ile Gly Leu Phe Gly Phe Gly Leu Trp
        35                  40                  45

Ile Leu Ala His Glu Cys Gly His Gly Ala Phe Ser Asp Tyr Gln Asn
    50                  55                  60

Val Asn Asp Phe Ile Gly Trp Val Leu His Ser Tyr Leu Gly Val Pro
65                  70                  75                  80

Tyr Phe Ser Trp Lys Phe Ser His Ala Lys His His Lys Ala Thr Gly
                85                  90                  95

His Ile Ser Arg Asp Met Val Phe Ile Pro Tyr Thr Lys Glu Glu Phe
            100                 105                 110

Leu Glu Ser Arg Gly Val Thr Lys Val Ser Glu Leu Val Glu Asp Leu
        115                 120                 125
```

```
Pro Ile Trp Ser Leu Met Val Leu Val Phe Gln Gln Leu Gly Gly Leu
        130                 135                 140

Gln Leu Tyr Leu Ala Thr Asn Ala Thr Gly Gln Thr Ile Asp Leu Pro
145                 150                 155                 160

Trp Tyr Ala Lys Ser His Tyr Ala Pro Ser Pro Val Phe Asp Ala
                165                 170                 175

His Gln Tyr Trp Tyr Ile Val Leu Ser Asp Ile Gly Ile Leu Ser Thr
                180                 185                 190

Ile Phe Ala Val Tyr Gln Trp Tyr Lys His Phe Gly Leu Phe Asn Met
            195                 200                 205

Met Ile Asn Trp Phe Val Pro Trp Leu Trp Val Asn His Trp Leu Val
    210                 215                 220

Phe Val Thr Phe Leu Gln His Thr Asp Pro Ser Met Pro His Tyr Thr
225                 230                 235                 240

Ala Lys Glu Trp Thr Phe Ala Arg Gly Ala Ala Thr Ile Asp Arg
                245                 250                 255

Asp Tyr Gly Phe Ile Gly Gln His Ile Phe His Asp Ile Glu Thr
                260                 265                 270

His Val Leu His His Tyr Val Ser Arg Ile Pro Phe Tyr Asn Ala Arg
            275                 280                 285

Glu Ala Thr Ala Ala Ile Arg Glu Val Met Gly His Tyr Arg Tyr
    290                 295                 300

Asp Gly Glu Asn Met Trp Lys Ser Leu Trp Lys Val Met Arg Ser Cys
305                 310                 315                 320

Gln Phe Val Ser Asp Glu Glu Gly Asn Gly Val Leu Met Phe Arg Asn
                325                 330                 335

Ala Asn Gly Val Gly Val Thr Pro Lys Asn
            340                 345

<210> SEQ ID NO 73
<211> LENGTH: 416
<212> TYPE: PRT
<213> ORGANISM: Debaryomyces hansenii CBS767
<220> FEATURE:
<221> NAME/KEY: MISC_FEATURE
<222> LOCATION: (1)..(416)
<223> OTHER INFORMATION: delta-12 desaturase; GenBank Accession No.
      CAG90237

<400> SEQUENCE: 73

Met Ala Ser Gln Ile Ala Ser Ser Thr Lys Ser Ser Gly Ile Gly Gly
1               5                   10                  15

Ser Ser Ser Ile Gln Lys Arg Gly Asn Val Ala Thr Leu Gln Thr Asn
                20                  25                  30

Glu Asn Leu Thr Ala Ile Asp Ala His Gly Asn Val Phe Lys Val Pro
            35                  40                  45

Asp Tyr Thr Ile Lys Asp Ile Leu Lys Ala Ile Pro Ala His Cys Tyr
        50                  55                  60

Glu Arg Arg Val Ala Glu Ser Met Tyr Tyr Val Phe Arg Asp Ile Phe
65                  70                  75                  80

Trp Leu Leu Thr Ile Gly Tyr Val Ala Asn Asn Tyr Ile Gln Leu Leu
                85                  90                  95

Pro Asn Ala Phe Thr Arg Phe Val Ala Trp Ser Gly Tyr Val Tyr Val
            100                 105                 110

Gln Ser Leu Phe Leu Thr Gly Leu Trp Val Leu Ala His Glu Cys Gly
        115                 120                 125
```

```
His Gln Ala Phe Ser Asp Tyr Gly Trp Val Asn Asp Thr Val Gly Trp
    130                 135                 140

Val Leu His Ser Tyr Leu Met Val Pro Tyr Phe Ser Trp Lys Phe Ser
145                 150                 155                 160

His Ser Lys His His Lys Ala Thr Gly His Leu Thr Arg Asp Met Val
                165                 170                 175

Phe Val Pro Tyr Thr Lys Glu Glu Phe Val Ala Ser Lys Asn Ala His
            180                 185                 190

His Ile Asp Asp Ile Val Gly Asp Ser Pro Ile Tyr Thr Leu Tyr Gln
        195                 200                 205

Leu Val Val Gln Gln Phe Gly Gly Trp Ile Ala Tyr Leu Phe Thr Asn
210                 215                 220

Val Thr Gly Gln Gln Tyr Glu Asn Lys Ser Phe Trp Gly Val Ser His
225                 230                 235                 240

Phe Asn Pro Asn Ala Ala Ile Phe Glu Lys Lys Glu Gln Trp Tyr Val
                245                 250                 255

Leu Leu Ser Asp Ile Gly Ile Phe Ala Gln Gly Leu Val Leu His Thr
            260                 265                 270

Trp Tyr Lys Asn Phe Gly Gly Phe Asn Leu Leu Val Asn Trp Phe Leu
        275                 280                 285

Pro Tyr Ile Leu Val Asn His Trp Leu Val Phe Ile Thr Tyr Leu Gln
290                 295                 300

His Thr Asp Ser Gln Met Pro His Tyr Glu Ser His Gln Trp Asn Phe
305                 310                 315                 320

Ala Arg Gly Ala Ala Thr Ile Asp Arg Glu Phe Gly Phe Val Gly
                325                 330                 335

Lys Phe Met Phe His Asp Ile Ile Glu Thr His Val Leu His His Tyr
            340                 345                 350

Cys Ser Arg Ile Pro Phe Tyr Asn Gly Arg Glu Ala Ser Glu Ala Ile
        355                 360                 365

Lys Lys Val Met Gly Glu His Tyr Gln Tyr Ser Asp Glu Asn Met Trp
370                 375                 380

Val Ser Leu Trp Lys Ser Ala Arg Thr Cys Gln Tyr Val Asp Gly Asp
385                 390                 395                 400

Asn Gly Val Leu Met Phe Arg Asn Ala Ala Phe Lys Gly Pro Lys Ala
                405                 410                 415

<210> SEQ ID NO 74
<211> LENGTH: 435
<212> TYPE: PRT
<213> ORGANISM: Debaryomyces hansenii CBS767
<220> FEATURE:
<221> NAME/KEY: MISC_FEATURE
<222> LOCATION: (1)..(435)
<223> OTHER INFORMATION: delta-15 desaturase; GenBank Accession No.
      CAG88182

<400> SEQUENCE: 74

Met Ser Val Val Asp Leu Thr Ser Thr Thr Ser Gly Ser Ala Ile Asn
1               5                   10                  15

Ser Ser Asn Ile Ser Gln Arg Gly Asn Gly Ser Thr Ile Val Glu Thr
            20                  25                  30

Lys Lys Gly Pro Ser Ser Asn Leu Lys Ala Ile Asp Thr Phe Gly Asn
        35                  40                  45

Glu Phe Lys Val Pro Asp Tyr Thr Ile Lys Gln Ile Leu Ser Ala Ile
50                  55                  60
```

```
Pro Lys His Cys Tyr Glu Arg Ser Leu Val Arg Ser Leu Gly Tyr Val
 65                  70                  75                  80

Ala Arg Asp Ile Thr Met Met Cys Leu Ile Gly Tyr Val Gly Gln Lys
             85                  90                  95

Thr Ile Pro Met Val Gln Ile Ala Asp Gln Glu Gly Leu Ser Thr Ala
            100                 105                 110

Ile Arg Gly Gly Leu Trp Cys Val Tyr Ser Tyr Leu Leu Gly Leu Phe
        115                 120                 125

Gly Phe Gly Leu Trp Ile Leu Ala His Glu Cys Gly His Gly Ala Phe
    130                 135                 140

Ser Asp Tyr Gln Asn Val Asn Asp Val Val Gly Trp Ile Leu His Ser
145                 150                 155                 160

Tyr Leu Ile Val Pro Tyr Phe Ser Trp Lys Phe Ser His Ser Lys His
                165                 170                 175

His Lys Ala Thr Gly His Leu Thr Lys Asp Met Val Phe Ile Pro Tyr
            180                 185                 190

Thr Lys Asp Glu Phe Val Glu Lys Ser Gly Val Ser Lys Val Ser Glu
        195                 200                 205

Val Met Glu Asp Ser Pro Ile Trp Ser Leu Met Val Leu Ile Phe Gln
210                 215                 220

Gln Ile Gly Gly Leu Gln Leu Tyr Leu Ala Thr Asn Ala Thr Gly Gln
225                 230                 235                 240

Ser Tyr Gln Gly His Ser Lys Ile Ala Lys Ser His Tyr Ala Pro Ala
                245                 250                 255

Ser Pro Val Phe Asp Lys Glu His Tyr Trp Tyr Ile Ile Leu Ser Asp
            260                 265                 270

Ile Gly Ile Ile Thr Thr Ile Thr Val Val Tyr Gln Trp Tyr Lys Asn
        275                 280                 285

Phe Gly Phe Phe Asn Met Phe Val Asn Trp Phe Met Pro Trp Leu Trp
    290                 295                 300

Val Asn His Trp Leu Val Phe Val Thr Phe Leu Gln His Thr Asp Pro
305                 310                 315                 320

Thr Met Pro His Tyr Arg Asp Asn Glu Trp Thr Phe Ala Arg Gly Ala
                325                 330                 335

Ala Ala Thr Ile Asp Arg Asn Phe Gly Phe Ile Gly Gln His Ile Phe
            340                 345                 350

His Asp Ile Ile Glu Thr His Val Leu His His Tyr Val Ser Arg Ile
        355                 360                 365

Pro Phe Tyr Asn Ala Arg Glu Ala Thr Asp Ala Ile Arg Lys Val Met
    370                 375                 380

Gly Glu His Tyr Arg Tyr Glu Gly Glu Ser Met Trp Tyr Ser Leu Trp
385                 390                 395                 400

Lys Cys Met Arg Met Cys Gln Tyr Val Asp Asp Ala Asp Thr Asp Ala
                405                 410                 415

Lys Gly Val Leu Met Tyr Arg Asn Val Asn Gly Ala Gly Pro Val Lys
            420                 425                 430

Pro Ile Asp
        435

<210> SEQ ID NO 75
<211> LENGTH: 469
<212> TYPE: PRT
<213> ORGANISM: Aspergillus fumigatus Af293
<220> FEATURE:
<221> NAME/KEY: MISC_FEATURE
```

<222> LOCATION: (1)..(469)
<223> OTHER INFORMATION: delta-12 desaturase; GenBank Accession No. EAL90585

<400> SEQUENCE: 75

```
Met Ser Ser Thr Ala Leu Pro Lys Arg Val Ala Leu His Arg Asn Pro
1               5                   10                  15

Thr Thr Glu Ser Ser Val Pro Ser Ser Val Ser His Ser Pro Phe Asp
            20                  25                  30

Ser Pro Arg Gln Ser Pro Ser Ser Thr Ser Leu Ser Ser Met Ala Ser
        35                  40                  45

Asp Ala Glu Lys Thr Ser Ser Lys Met Ile Asp Thr Tyr Gly Asn Glu
    50                  55                  60

Phe Lys Ile Pro Asp Tyr Thr Ile Lys Gln Ile Arg Asp Ala Ile Pro
65                  70                  75                  80

Ala His Cys Tyr Gln Arg Ser Ala Ala Thr Ser Leu Tyr Tyr Val Phe
                85                  90                  95

Arg Asp Met Ala Ile Leu Ala Ser Val Phe Tyr Val Phe His Asn Tyr
            100                 105                 110

Val Thr Pro Glu Thr Val Pro Ser Met Pro Val Arg Val Val Leu Trp
        115                 120                 125

Thr Ile Tyr Thr Val Val Gln Gly Leu Val Gly Thr Gly Val Trp Val
    130                 135                 140

Leu Ala His Glu Cys Gly His Gln Ala Phe Ser Thr Ser Lys Val Leu
145                 150                 155                 160

Asn Asp Thr Val Gly Trp Ile Cys His Ser Leu Leu Leu Val Pro Tyr
                165                 170                 175

Phe Ser Trp Lys Ile Ser His Gly Lys His His Lys Ala Thr Gly Asn
            180                 185                 190

Ile Ala Arg Asp Met Val Phe Val Pro Lys Thr Arg Glu Glu Tyr Ala
        195                 200                 205

Thr Arg Ile Gly Arg Ala Ala His Glu Leu Ser Glu Leu Met Glu Glu
    210                 215                 220

Thr Pro Ile Leu Thr Ala Thr Asn Leu Val Leu Gln Gln Leu Phe Gly
225                 230                 235                 240

Trp Pro Met Tyr Leu Leu Thr Asn Val Thr Gly His Asn Asn His Glu
                245                 250                 255

Arg Gln Pro Glu Gly Arg Gly Lys Gly Lys Arg Asn Gly Tyr Phe Gly
            260                 265                 270

Gly Val Asn His Phe Asn Pro Ser Ser Pro Leu Tyr Glu Ala Lys Asp
        275                 280                 285

Ala Lys Leu Ile Val Leu Ser Asp Leu Gly Leu Phe Leu Val Gly Ser
    290                 295                 300

Leu Leu Tyr Tyr Ile Gly Ser Thr Tyr Gly Trp Leu Asn Leu Leu Val
305                 310                 315                 320

Trp Tyr Gly Ile Pro Tyr Leu Trp Val Asn His Trp Leu Val Ala Ile
                325                 330                 335

Thr Phe Leu Gln His Thr Asp Pro Thr Leu Pro His Tyr Gln Pro Glu
            340                 345                 350

Ala Trp Asp Phe Thr Arg Gly Ala Ala Thr Ile Asp Arg Asp Phe
        355                 360                 365

Gly Phe Val Gly Arg His Ile Phe His Gly Ile Ile Glu Thr His Val
    370                 375                 380

Leu His His Tyr Val Ser Thr Ile Pro Phe Tyr His Ala Asp Glu Ala
```

```
385                 390                 395                 400
Ser Glu Ala Ile Gln Lys Val Met Gly Pro His Tyr Arg Ser Glu Ala
                405                 410                 415

His Thr Gly Trp Thr Gly Phe Leu Lys Ala Leu Trp Thr Ser Ala Arg
            420                 425                 430

Thr Cys Gln Trp Val Glu Pro Thr Glu Gly Ala Lys Gly Glu Ser Gln
            435                 440                 445

Tyr Val Leu Phe Tyr Arg Asn Ile Asn Gly Ile Gly Val Pro Pro Ala
        450                 455                 460

Lys Ile Pro Ala Lys
465

<210> SEQ ID NO 76
<211> LENGTH: 396
<212> TYPE: PRT
<213> ORGANISM: Aspergillus fumigatus Af293
<220> FEATURE:
<221> NAME/KEY: MISC_FEATURE
<222> LOCATION: (1)..(396)
<223> OTHER INFORMATION: delta-15 desaturase; GenBank Accession No.
      EAL85733

<400> SEQUENCE: 76

Met Ala Gly Lys Met Ala Glu Val Arg Gln Arg Asp Val Gln Thr Glu
1               5                   10                  15

Thr Glu Val Val Gln Asp Ser Ile Pro Ser Leu Lys Ser Leu Lys Asp
            20                  25                  30

Ala Ile Pro Lys Glu Cys Phe Glu Ser Ser Leu Ala Ile Ser Phe Leu
        35                  40                  45

Tyr Leu Ala Arg Asp Ile Leu Tyr Cys Ala Ile Leu Thr Tyr Gly Ala
    50                  55                  60

Phe His Ile His Leu Leu Pro Ser Leu Pro Leu Arg Val Leu Ala Trp
65                  70                  75                  80

Ala Thr Tyr Gly Phe Phe Gln Gly Cys Val Gly Thr Gly Met Trp Ile
                85                  90                  95

Leu Ala His Glu Cys Gly His Gly Ala Phe Ser Pro Tyr Gln Gly Ile
            100                 105                 110

Asn Asp Phe Ile Gly Trp Ala Thr His Ser Phe Leu Leu Val Pro Tyr
        115                 120                 125

Phe Ser Trp Lys Ile Thr His Ala Arg His His Arg Tyr Thr Gly His
    130                 135                 140

Met Glu Lys Asp Thr Val Phe Val Pro Trp Thr Asp Glu Gln Leu Ala
145                 150                 155                 160

Lys Lys Arg Asn Val Arg Ile Glu Gln Leu Lys His Phe Ala Glu Glu
                165                 170                 175

Thr Pro Ile Val Ser Phe Leu Gln Leu Ile Gly His Gln Leu Gly Gly
            180                 185                 190

Trp Gln Leu Tyr Leu Leu Thr Asn Ala Thr Ala Gly Ala Gln Ser Trp
        195                 200                 205

Pro Glu Gly Lys Pro Lys Thr Gly Pro Ala Ser His Phe Asn Pro Val
    210                 215                 220

Gly Ala Leu Trp Thr Pro Ser Gln Arg Leu Ser Ile Ala Ile Ser Asp
225                 230                 235                 240

Leu Gly Leu Leu Ile Met Ala Ala Val Leu Tyr Tyr Ala Ser Thr Gln
                245                 250                 255

Ile Gly Ala Trp Asn Val Val Leu Leu Tyr Phe Val Pro Tyr Leu Trp
```

```
                        260                 265                 270
Val His His Trp Leu Ile Ala Ile Thr Tyr Leu Gln His Thr His Pro
            275                 280                 285

Ser Val Pro His Tyr Thr Pro Glu Ala Trp Thr Tyr Thr Lys Gly Ala
            290                 295                 300

Leu Ala Thr Val Asp Arg Thr Met Gly Phe Ile Gly Arg His Phe Phe
305                 310                 315                 320

His Glu Ile Ile Asp Tyr His Val Val His Leu Phe Ser Arg Ile
                    325                 330                 335

Pro Phe Tyr Lys Ala Glu Gln Ala Thr Trp Ala Ile Gln Pro Leu Leu
                340                 345                 350

Gly Ala Gln Tyr His Glu Glu Lys Glu Gln Ser Phe Leu Gly Ser Leu
            355                 360                 365

Val Thr Thr Phe Arg Lys Cys Ile Tyr Val Ser Ala Thr Gly Gln Pro
            370                 375                 380

Gly Val Leu His Phe Val Lys Ala Asp Glu Gly Asn
385                 390                 395

<210> SEQ ID NO 77
<211> LENGTH: 466
<212> TYPE: PRT
<213> ORGANISM: Aspergillus oryzae
<220> FEATURE:
<221> NAME/KEY: MISC_FEATURE
<222> LOCATION: (1)..(466)
<223> OTHER INFORMATION: delta-12 desaturase; GenBank Accession No.
      BAD04850

<400> SEQUENCE: 77

Met Ser Ser Thr Ala Ile Pro Lys Arg Met Ala Leu Asn Arg Asn Pro
1               5                   10                  15

Gly Thr Asp Ser Ser Val Pro Ser Val Ser Val Ser Pro Phe Asp Ser
                20                  25                  30

Pro Arg His Ser Pro Ser Ser Thr Ser Leu Ser Ser Leu Ala Ser Glu
            35                  40                  45

Ser Glu Asn Lys Gly Lys Met Leu Asp Thr Tyr Gly Asn Glu Phe Lys
        50                  55                  60

Ile Pro Asp Tyr Thr Ile Lys Gln Ile Arg Asp Ala Ile Pro Ala His
65                  70                  75                  80

Cys Tyr Glu Arg Lys Ala Leu Thr Ser Leu Tyr Tyr Val Phe Arg Asp
                85                  90                  95

Ile Ala Met Leu Gly Ser Ile Phe Tyr Val Phe His Asn Tyr Val Thr
            100                 105                 110

Pro Glu Thr Val Pro Ser Phe Pro Ala Arg Val Ala Leu Trp Ser Leu
        115                 120                 125

Tyr Thr Val Val Gln Gly Leu Ile Ala Thr Gly Val Trp Val Leu Ala
    130                 135                 140

His Glu Cys Gly His Gln Ala Phe Ser Pro Ser Lys Val Leu Asn Asp
145                 150                 155                 160

Thr Val Gly Trp Ile Cys His Ser Ala Leu Leu Val Pro Tyr Phe Ser
                165                 170                 175

Trp Lys Ile Ser His Gly Lys His His Lys Ala Thr Gly Asn Ile Ala
            180                 185                 190

Arg Asp Met Val Phe Val Pro Lys Thr Arg Glu Glu Tyr Ala Ser Arg
        195                 200                 205

Ile Gly Lys Thr Ile His Asp Leu Asn Glu Leu Met Glu Glu Thr Pro
```

```
            210                 215                 220
Ile Ala Thr Val Thr Asn Leu Ile Leu Gln Gln Leu Phe Gly Trp Pro
225                 230                 235                 240

Met Tyr Leu Leu Thr Asn Val Thr Gly His Asn Asn His Glu Arg Gln
                245                 250                 255

Pro Glu Gly Arg Gly Lys Gly Lys Arg Asn Gly Tyr Phe Gly Gly Val
                260                 265                 270

Asn His Phe Asn Pro Ser Ser Pro Leu Tyr Glu Ala Lys Asp Ala Lys
            275                 280                 285

Leu Ile Val Leu Ser Asp Leu Gly Leu Ala Ile Thr Gly Ser Val Leu
        290                 295                 300

Tyr Tyr Ile Gly Ser Thr Tyr Gly Trp Leu Asn Leu Leu Val Trp Tyr
305                 310                 315                 320

Gly Ile Pro Tyr Leu Trp Val Asn His Trp Leu Glu Ala Ile Thr Tyr
                325                 330                 335

Leu Gln His Thr Asp Pro Thr Leu Pro His Tyr Gln Pro Glu Val Trp
                340                 345                 350

Asn Phe Ala Arg Gly Ala Ala Ala Thr Ile Asp Arg Asp Phe Gly Phe
            355                 360                 365

Val Gly Arg His Ile Leu His Gly Ile Ile Glu Thr His Val Leu His
        370                 375                 380

His Tyr Val Ser Thr Ile Pro Phe Tyr His Ala Asp Glu Ala Ser Glu
385                 390                 395                 400

Ala Ile Gln Lys Val Met Gly Ser His Tyr Arg Thr Glu Ala His Thr
                405                 410                 415

Gly Trp Thr Gly Phe Phe Lys Ala Leu Phe Thr Ser Ala Arg Val Cys
                420                 425                 430

His Trp Val Glu Pro Thr Glu Gly Ala Arg Gly Glu Ser Glu Gly Val
            435                 440                 445

Leu Phe Tyr Arg Asn Thr Asn Gly Ile Gly Val Pro Pro Ala Lys Leu
        450                 455                 460

Ser Lys
465

<210> SEQ ID NO 78
<211> LENGTH: 392
<212> TYPE: PRT
<213> ORGANISM: Aspergillus oryzae
<220> FEATURE:
<221> NAME/KEY: MISC_FEATURE
<222> LOCATION: (1)..(392)
<223> OTHER INFORMATION: delta-15 desaturase; GenBank Accession No.
      BAE66531

<400> SEQUENCE: 78

Met Ala Glu Leu His Asn Arg Lys Ala Glu Lys Ala Ile Glu Lys Asp
1               5                   10                  15

Thr Thr Pro Thr Leu Lys Glu Leu Lys Asp Ala Ile Pro Lys Glu Cys
                20                  25                  30

Phe Glu Ser Ser Ala Val Thr Ser Leu Leu Tyr Leu Ala Arg Asp Ile
            35                  40                  45

Leu Tyr Cys Ala Ile Leu Thr Val Ala Ala Phe Gln Ile His Arg Ile
        50                  55                  60

Pro Ser Leu Pro Leu Arg Ile Ile Ala Trp Ala Thr Tyr Gly Phe Phe
65                  70                  75                  80

Gln Gly Cys Val Gly Thr Gly Ile Trp Ile Leu Ser His Glu Cys Gly
```

```
                85                  90                  95
His Gly Ala Phe Ser Pro Asn Gln Arg Leu Asn Asp Phe Val Gly Trp
            100                 105                 110

Ala Gly His Ser Phe Leu Met Val Pro Tyr Phe Ser Trp Lys Ile Thr
        115                 120                 125

His Ala Arg His His Arg Tyr Thr Gly His Met Glu Lys Asp Thr Val
    130                 135                 140

Tyr Val Pro Trp Thr Asp Glu Asp Leu Ala Gln Lys Lys Asn Val Arg
145                 150                 155                 160

Ile Glu Gln Leu Lys His Leu Thr Glu Thr Pro Ile Val Ser Phe
                165                 170                 175

Leu Gln Leu Ile Gly His Gln Leu Phe Gly Trp Gln Ile Tyr Leu Phe
            180                 185                 190

Leu Asn Ala Thr Ala Gly Thr Lys Ser Leu Pro Glu Gly Ala Gly Lys
        195                 200                 205

Met Gly Pro Ala Asn His Phe Asn Phe Met Gly Pro Leu Phe Thr Gly
    210                 215                 220

Ser Gln Arg Val Ser Ile Ala Leu Ser Asp Leu Gly Leu Leu Ile Met
225                 230                 235                 240

Gly Ser Ile Leu Tyr Tyr Ala Ser Thr Gln Ile Gly Ala Trp Asn Val
                245                 250                 255

Val Leu Leu Tyr Phe Ile Pro Tyr Phe Trp Val His Trp Leu Ile
            260                 265                 270

Ala Ile Thr Tyr Leu Gln His Thr His Pro Glu Val Pro His Tyr Thr
        275                 280                 285

Ala Glu Ala Trp Thr Tyr Thr Lys Gly Ala Leu Ala Thr Val Asp Arg
    290                 295                 300

Thr Ile Gly Phe Ile Gly Arg His Phe His Glu Ile Ile Asp Tyr
305                 310                 315                 320

His Val Val His His Leu Phe Ser Arg Ile Pro Phe Tyr Lys Ala Glu
                325                 330                 335

Glu Ala Thr Lys Ala Ile Gln Pro Leu Leu Gly Glu Lys Tyr His Glu
            340                 345                 350

Ser Lys Asp Glu Ser Phe Leu Tyr Ser Leu Met Thr Thr Phe Arg Lys
        355                 360                 365

Cys Ile Tyr Val Ser Ala Lys Gly Ser Ser Gln Pro Gly Val Leu His
    370                 375                 380

Phe Val Arg Ala Asp Asp Ser Lys
385                 390

<210> SEQ ID NO 79
<211> LENGTH: 348
<212> TYPE: PRT
<213> ORGANISM: Chaetomium globosum CBS 148.51
<220> FEATURE:
<221> NAME/KEY: MISC_FEATURE
<222> LOCATION: (1)..(348)
<223> OTHER INFORMATION: delta-12 desaturase; GenBank Accession No.
      EAQ83131

<400> SEQUENCE: 79

Met Ala Pro Thr Thr Ala Thr Ser Val Pro Ser Ala Asn Lys Pro Phe
1               5                   10                  15

Leu Arg Arg Asn Met Ala Ser Ser Thr Phe Asp Ser Asp Ser Ser Ala
            20                  25                  30

Val Val Ser Pro Met Asp Ser Pro Thr Asp Ser Pro Arg Gln Ser Pro
```

```
                35                  40                  45
Ser Ser Thr Ser Leu Ser Ser Leu Ala Ser Asp Asp Ala Ala Pro
 50                  55                  60

Thr Lys Tyr Gly Lys Leu Ile Asp Thr Tyr Gly Asn Glu Phe Gln Val
 65                  70                  75                  80

Pro Asp Phe Thr Ile Lys Glu Ile Arg Asp Ala Ile Pro Lys His Cys
                 85                  90                  95

Tyr Glu Arg Ser Ala Val Arg Ser Leu Ala Tyr Val Ala Arg Asp Met
                100                 105                 110

Val Tyr Leu Gly Thr Thr Phe Tyr Ile Trp Asn Thr Tyr Val Thr Pro
                115                 120                 125

Glu Phe Ile Pro Ser Gln Pro Leu Arg Val Val Leu Trp Gly Val Tyr
                130                 135                 140

Thr Phe Leu Gln Gly Leu Phe Gly Thr Gly Leu Trp Val Leu Ala His
145                 150                 155                 160

Glu Cys Gly His Gly Ala Phe Ser Pro Ser Gln Lys Leu Asn Asn Ile
                165                 170                 175

Val Gly Trp Val Leu His Ser Ala Leu Leu Val Pro Tyr Phe Ser Trp
                180                 185                 190

Gln Leu Ser His Ser Lys His His Lys Ala Thr Gly Asn Met Asp Arg
                195                 200                 205

Asp Met Val Phe Val Pro Arg Thr Arg Glu Gln Ala Ser Arg Ile
210                 215                 220

Gly Arg Leu Val His Glu Ile Ser Glu Leu Thr Glu Thr Pro Ile
225                 230                 235                 240

Tyr Thr Phe Ile His Leu Leu Gly Gln Gln Leu Ile Gly Trp Trp Asn
                245                 250                 255

Tyr Leu Leu Thr Asn Val Thr Gly His Asn Asn His Glu Arg Gln Arg
                260                 265                 270

Glu Gly Arg Gly Lys Gly Lys Lys Asn Gly Trp Gly Gly Gln Val Asn
                275                 280                 285

His Phe Asp Pro Arg Ser Pro Leu Tyr Glu Asn Arg Asp Ala Ser Tyr
290                 295                 300

Ile Leu Leu Ser Asp Leu Gly Leu Ala Ile Thr Ile Ser Ala Leu Val
305                 310                 315                 320

Tyr Leu Gly Lys Thr Phe Gly Trp Ser Asn Met Phe Val Trp Tyr Phe
                325                 330                 335

Leu Pro Tyr Leu Trp Val Asn His Trp Leu Gly Glu
                340                 345

<210> SEQ ID NO 80
<211> LENGTH: 400
<212> TYPE: PRT
<213> ORGANISM: Chaetomium globosum CBS 148.51
<220> FEATURE:
<221> NAME/KEY: MISC_FEATURE
<222> LOCATION: (1)..(400)
<223> OTHER INFORMATION: delta-15 desaturase; GenBank Accession No.
      EAQ88866

<400> SEQUENCE: 80

Met Ala Thr Thr Thr Thr Thr Thr Arg Ser Arg Arg Ala Ala Ser
 1               5                  10                  15

Glu Val Lys Ser Ala Pro Ile Lys Leu Val Glu Gly Pro Gln Tyr Pro
                 20                  25                  30

Asp Ile Gln Thr Ile Arg Asp Ala Ile Pro Ala His Cys Phe Val Pro
```

```
            35                  40                  45
Ser Thr Trp Arg Ser Leu Gly Tyr Val Phe Arg Asp Val Ser Met Ala
 50                  55                  60

Ala Ala Leu Gly Trp Ala Ala Phe Thr Tyr Ile Ser Gln Ile Glu Asp
 65                  70                  75                  80

Phe Thr Trp Arg Thr Ala Val Trp Ile Val Tyr Gly Tyr Leu Gln Gly
                 85                  90                  95

Leu Val Cys Thr Gly Ile Trp Ile Leu Ala His Glu Ala Gly His Gly
                100                 105                 110

Ala Phe Ser Val His Gln Lys Leu Asn Asp Val Val Gly Trp Thr Leu
            115                 120                 125

His Ser Ala Leu Leu Val Pro Tyr Phe Ser Trp Lys Phe Ser His His
130                 135                 140

Arg His His Arg Phe Thr Gly His Met Glu Lys Asp Met Ala Phe Val
145                 150                 155                 160

Pro His Thr Lys Ala Asp Arg Glu Lys Arg Arg Leu Ala Asp Leu Tyr
                165                 170                 175

Leu Asp Arg Glu Leu Phe Glu Asp Ile Pro Val Val Gln Leu Phe Lys
            180                 185                 190

Leu Leu Ala His Gln Leu Ala Gly Trp Gln Met Tyr Leu Leu Phe Asn
            195                 200                 205

Val Ser Ala Gly Ser Asp Ser Gln Gln Ser Lys Ala Ser Trp Trp Arg
210                 215                 220

Val Ser His Phe Glu Pro Thr Ser Ala Val Phe Arg Pro Ser Glu Ala
225                 230                 235                 240

Leu Tyr Val Ala Ile Thr Asp Ile Gly Leu Leu Ile Val Ala Gly Leu
                245                 250                 255

Leu Tyr Leu Ala Ser Thr Val Val Gly Trp Lys Met Val Phe Leu Met
            260                 265                 270

Tyr Gly Val Pro Tyr Phe Trp Val His His Trp Leu Val Ala Ile Thr
            275                 280                 285

Tyr Leu His His Thr His Pro Asp Val His His Phe Glu Ala Asp Ser
290                 295                 300

Trp Thr Phe Val Lys Gly Ala Leu Ala Thr Val Asp Arg Asp Phe Gly
305                 310                 315                 320

Phe Val Gly Arg His Leu Phe His Gly Ile Ile Asp Thr His Val Ile
                325                 330                 335

His His Leu Phe Pro Arg Ile Pro Phe Tyr Lys Ala Glu Ala Thr
            340                 345                 350

Glu Ala Ile Lys Pro Leu Leu Gly Asp Leu Tyr His Arg Glu Glu Arg
            355                 360                 365

Ser Phe Met Gly Gln Leu Trp Ser Thr Phe Thr Gln Cys Lys Tyr Val
            370                 375                 380

Glu Ala Asp Pro Ala Ala Pro Gly Ala Leu Lys Trp Ala Glu Lys Lys
385                 390                 395                 400

<210> SEQ ID NO 81
<211> LENGTH: 400
<212> TYPE: PRT
<213> ORGANISM: Mortierella isabellina
<220> FEATURE:
<221> NAME/KEY: MISC_FEATURE
<222> LOCATION: (1)..(400)
<223> OTHER INFORMATION: delta-12 desaturase; GenBank Accession No.
      AAL13301
```

<400> SEQUENCE: 81

```
Met Ala Pro Pro Asn Thr Ile Asp Ala Gly Leu Thr Gln Arg His Ile
1               5                   10                  15

Thr Thr Thr Ala Ala Pro Thr Ser Ala Lys Pro Ala Phe Glu Arg Asn
            20                  25                  30

Tyr Gln Leu Pro Glu Phe Thr Ile Lys Glu Ile Arg Glu Cys Ile Pro
        35                  40                  45

Ala His Cys Phe Glu Arg Ser Gly Leu Arg Gly Leu Cys His Val Ala
    50                  55                  60

Ile Asp Leu Thr Trp Ala Ser Leu Leu Phe Leu Ala Ala Thr Gln Ile
65                  70                  75                  80

Asp Lys Phe Glu Asn Pro Leu Ile Arg Tyr Leu Ala Trp Pro Ala Tyr
                85                  90                  95

Trp Ile Met Gln Gly Ile Val Cys Thr Gly Ile Trp Val Leu Ala His
            100                 105                 110

Glu Cys Gly His Gln Ser Phe Ser Thr Ser Lys Thr Leu Asn Asn Thr
        115                 120                 125

Val Gly Trp Ile Leu His Ser Met Leu Leu Val Pro Tyr His Ser Trp
    130                 135                 140

Arg Ile Ser His Ser Lys His His Lys Ala Thr Gly His Met Thr Lys
145                 150                 155                 160

Asp Gln Val Phe Val Pro Lys Thr Arg Ser Gln Val Gly Leu Pro Pro
                165                 170                 175

Lys Glu Ser Ala Ala Ala Ala Val Gln Glu Glu Asp Met Ser Val His
            180                 185                 190

Leu Asp Glu Glu Ala Pro Ile Val Thr Leu Phe Trp Met Val Ile Gln
        195                 200                 205

Phe Leu Phe Gly Trp Pro Ala Tyr Leu Ile Met Asn Ala Ser Gly Gln
    210                 215                 220

Asp Tyr Gly Arg Trp Thr Ser His Phe His Thr Tyr Ser Pro Ile Phe
225                 230                 235                 240

Glu Pro Arg Asn Phe Phe Asp Ile Ile Ile Ser Asp Leu Gly Val Leu
                245                 250                 255

Ala Ala Leu Gly Ala Leu Ile Tyr Ala Ser Met Gln Leu Ser Leu Leu
            260                 265                 270

Thr Val Thr Lys Tyr Tyr Ile Ile Pro Tyr Leu Phe Val Asn Phe Trp
        275                 280                 285

Leu Val Leu Ile Thr Phe Leu Gln His Thr Asp Pro Lys Leu Pro His
    290                 295                 300

Tyr Arg Glu Gly Ala Trp Asn Phe Gln Arg Gly Ala Leu Cys Thr Val
305                 310                 315                 320

Asp Arg Ser Phe Gly Lys Phe Leu Asp His Met Phe His Gly Ile Val
                325                 330                 335

His Thr His Val Ala His His Leu Phe Ser Gln Met Pro Phe Tyr His
            340                 345                 350

Ala Glu Glu Ala Thr Tyr His Leu Lys Lys Leu Leu Gly Glu Tyr Tyr
        355                 360                 365

Val Tyr Asp Pro Ser Pro Ile Val Val Ala Val Trp Arg Ser Phe Arg
    370                 375                 380

Glu Cys Arg Phe Val Glu Asp His Gly Asp Val Val Phe Phe Lys Lys
385                 390                 395                 400
```

<210> SEQ ID NO 82

```
<211> LENGTH: 445
<212> TYPE: PRT
<213> ORGANISM: Coccidioides immitis RS
<220> FEATURE:
<221> NAME/KEY: MISC_FEATURE
<222> LOCATION: (1)..(445)
<223> OTHER INFORMATION: delta-12 desaturase; GenBank Accession No.
      EAS31392

<400> SEQUENCE: 82

Met Glu Ser Pro Arg His Ser Pro Ser Thr Thr Ser Leu Ser Ser Leu
1               5                   10                  15

Ala Ser Glu Ala Leu Ala Glu Gly Ser Ser Lys Leu Leu Asp Thr Tyr
            20                  25                  30

Gly Asn Glu Phe Glu Ile Pro Asn Phe Thr Ile Lys Glu Ile Arg Asp
        35                  40                  45

Ala Ile Pro Ala His Cys Phe Lys Arg Asp Gly Ile Arg Gly Leu Leu
    50                  55                  60

Tyr Val Phe Arg Asp Leu Ala Cys Leu Gly Val Thr Phe Tyr Ala Phe
65                  70                  75                  80

His Asn Tyr Val Thr Pro Glu Asn Ile Pro Ser Thr Pro Ile Arg Ala
                85                  90                  95

Gly Leu Trp Ala Leu Tyr Thr Phe Val Gln Gly Leu Phe Gly Thr Gly
            100                 105                 110

Ile Trp Val Leu Ala His Glu Cys Gly His Gln Ser Phe Ser Pro Ser
        115                 120                 125

Lys Val Leu Asn Asp Thr Val Gly Trp Ile Leu His Ser Ser Leu Leu
    130                 135                 140

Val Pro Tyr Phe Ser Trp Lys Ile Ser His Gly Lys His His Lys Ala
145                 150                 155                 160

Thr Gly Asn Leu Glu Arg Asp Met Val Phe Val Pro Lys Thr Arg Glu
                165                 170                 175

Gln Tyr Ala Ser Arg Met Gly Tyr Phe Val His Gln Leu Asn Glu Val
            180                 185                 190

Met Glu Glu Thr Pro Ile Gln Ala Ala Thr Asn Leu Ile Leu Gln Gln
        195                 200                 205

Leu Phe Gly Trp Pro Met Tyr Leu Leu Ser Asn Val Thr Gly His Asn
    210                 215                 220

Asn His Glu Cys Gln Arg Glu Gly Arg Gly Lys Gly Lys Lys Asn Gly
225                 230                 235                 240

Met Phe Thr Gly Val Asn His Phe Asn Pro Ser Ser Pro Leu Tyr Glu
                245                 250                 255

Ala Lys Asp Ala Lys Leu Ile Val Leu Ser Asp Ile Gly Leu Leu Ile
            260                 265                 270

Met Gly Ser Ile Leu Tyr Ala Leu Gly Gln Arg Phe Gly Trp Thr Asn
        275                 280                 285

Leu Leu Val Trp Tyr Phe Ile Pro Tyr Leu Trp Val Asn His Trp Leu
    290                 295                 300

Val Ala Ile Thr Tyr Leu Gln His Thr Asp Pro Ser Leu Pro His Tyr
305                 310                 315                 320

His Ser Ser Val Trp Asn Phe Ala Arg Gly Ala Ala Ala Thr Ile Asp
                325                 330                 335

Arg Glu Phe Gly Phe Ile Gly Arg Gln Leu Phe His Gly Ile Ile Glu
            340                 345                 350

Thr His Val Leu His His Tyr Val Ser Thr Ile Pro Phe Tyr Asn Ala
        355                 360                 365
```

Asp Glu Ala Thr Glu Ala Ile Lys Lys Val Met Gly Lys His Tyr Arg
            370                 375                 380

Ser Asp Thr Lys Gly Gly Ser Leu Gly Phe Ile Arg Ala Leu Trp Arg
385                 390                 395                 400

Ser Thr Arg Met Cys Gln Trp Val Glu Pro Ser Glu Gly Ala Gln Gly
                405                 410                 415

Glu Gly Lys Asp Val Leu Phe Phe Arg Asn Arg Asn Gly Leu Gly Pro
            420                 425                 430

Arg Pro Leu Val Val Glu Pro Glu Gly Lys Ala Lys
            435                 440                 445

<210> SEQ ID NO 83
<211> LENGTH: 420
<212> TYPE: PRT
<213> ORGANISM: Pichia pastoris
<220> FEATURE:
<221> NAME/KEY: MISC_FEATURE
<222> LOCATION: (1)..(420)
<223> OTHER INFORMATION: delta-12 desaturase; GenBank Accession No.
      AAX20125

<400> SEQUENCE: 83

Met Ser Ala Val Thr Val Thr Gly Asn Asn Gly Asp Ala Ser Arg Ser
1               5                   10                  15

Asn Thr Thr Thr Thr Lys Arg Thr Gly Asn Val Ser Ser Phe Ser
                20                  25                  30

Gln Ser Lys Gly Leu Thr Ala Ile Asp Thr Trp Gly Asn Val Phe Lys
            35                  40                  45

Val Pro Asp Phe Thr Ile Lys Gln Ile Leu Asp Ala Ile Pro Lys His
50                  55                  60

Cys Tyr Glu Arg Arg Leu Thr Thr Ser Phe Tyr Val Phe Arg Asp
65                  70                  75                  80

Ile Phe Leu Ile Gly Cys Thr Met Phe Met Gly Ser Phe Ile Pro Met
                85                  90                  95

Ile Glu Asn Val Phe Leu Arg Gly Ala Ala Tyr Ala Ala Leu Val Phe
            100                 105                 110

Leu Leu Ser Val Glu Tyr Thr Gly Leu Trp Val Leu Ala His Glu Cys
        115                 120                 125

Gly His Gln Ala Phe Ser Asp Tyr Gly Trp Val Asn Asp Thr Val Gly
    130                 135                 140

Trp Ile Leu His Ser Tyr Leu Leu Val Pro Tyr Phe Ser Trp Lys Tyr
145                 150                 155                 160

Ser His Gly Lys His His Lys Ala Thr Gly His Leu Thr Arg Asp Met
                165                 170                 175

Val Phe Val Pro Ala Thr Lys Glu Lys Phe Leu Glu Lys Arg Asn Ala
            180                 185                 190

Ser Lys Leu Gly Glu Leu Gly Glu Asp Ala Pro Ile Phe Thr Leu Tyr
        195                 200                 205

Gln Leu Val Ala Gln Gln Leu Gly Gly Trp Ile Leu Tyr Leu Phe Thr
    210                 215                 220

Asn Val Thr Gly Gln Pro Tyr Pro Asn Thr Pro Lys Trp Met Gln Asn
225                 230                 235                 240

His Phe Val Pro Ser Ser Pro Ile Phe Glu Lys Lys Asp Tyr Trp Phe
                245                 250                 255

Ile Ile Leu Ser Asp Leu Gly Ile Leu Ala Gln Leu Met Val Leu Tyr
            260                 265                 270

```
Val Trp Arg Gln Gln Met Gly Asn Trp Asn Leu Phe Ile Tyr Trp Phe
        275                 280                 285

Leu Pro Tyr Val Leu Thr Asn His Trp Leu Val Phe Ile Thr Phe Leu
    290                 295                 300

Gln His Ser Asp Pro Thr Met Pro His Tyr Glu Ala Glu Gln Trp Thr
305                 310                 315                 320

Phe Ala Arg Gly Ala Ala Thr Ile Asp Arg Glu Phe Gly Phe Ile
                325                 330                 335

Gly Pro Phe Phe His Asp Ile Ile Glu Thr His Val Leu His His
            340                 345                 350

Tyr Val Ser Arg Ile Pro Phe Tyr Asn Ala Arg Glu Ala Ser Glu Gly
        355                 360                 365

Ile Lys Lys Val Met Gly Glu His Tyr Arg Tyr Ser Gly Glu Asn Met
    370                 375                 380

Trp Val Ser Leu Trp Lys Ser Gly Arg Ser Cys Gln Phe Val Asp Gly
385                 390                 395                 400

Glu Asn Gly Val Lys Met Tyr Arg Asn Ile Asn Asn Trp Gly Ile Gly
                405                 410                 415

Thr Gly Glu Lys
            420

<210> SEQ ID NO 84
<211> LENGTH: 413
<212> TYPE: PRT
<213> ORGANISM: Ashbya gossypii ATCC #10895
<220> FEATURE:
<221> NAME/KEY: MISC_FEATURE
<222> LOCATION: (1)..(413)
<223> OTHER INFORMATION: delta-12 desaturase; GenBank Accession No.
      AAS53960

<400> SEQUENCE: 84

Met Ala Ser Met Ser Ala Ala Gly Gly Ser Ser Thr Ala Thr Glu Thr
1               5                   10                  15

Val Arg Gln Lys Val Ala Val Asp Thr Asn Gly Asn Val Phe Lys Val
            20                  25                  30

Pro Asp Tyr Thr Ile Lys Glu Leu Leu Arg Ala Ile Pro Ala His Cys
        35                  40                  45

Tyr Glu Arg Ser Leu Val Arg Ser Met Gly Tyr Val Leu Arg Asp Ile
    50                  55                  60

Ala Cys Ile Leu Thr Thr Gly Tyr Leu Ala Gln Cys Val Leu Tyr Pro
65                  70                  75                  80

Tyr Val Ala Asp Met His Val Ser Val Arg Phe Val Phe Trp Phe Ala
                85                  90                  95

Tyr Ser Leu Ala Gln Gly Leu Phe Cys Thr Gly Leu Trp Val Leu Ala
            100                 105                 110

His Glu Cys Gly His Gln Ala Phe Ser Asp Tyr Gly Ala Ile Asn Asp
        115                 120                 125

Leu Thr Gly Trp Ile Leu His Ser Tyr Leu Leu Val Pro Tyr Phe Ser
    130                 135                 140

Trp Lys Tyr Ser His Ala Lys His His Lys Gly Asn Gly His Met Ser
145                 150                 155                 160

Arg Asp Met Val Phe Val Pro Pro Arg Ala Gln Glu Tyr Arg Glu Lys
                165                 170                 175

Arg Gly Ile Ile Gly Glu Leu Ala Glu His Ser Gly Asp Ser Pro Leu
            180                 185                 190
```

```
Arg Thr Leu Ser Asp Leu Val Thr Gln Gln Leu Phe Gly Trp Leu Met
            195                 200                 205

Tyr Leu Thr Thr Asn Val Thr Gly Gln Lys Tyr Pro Gly Arg Ser Lys
    210                 215                 220

Trp Thr Gln Asn His Phe Trp Pro Phe Ser Pro Val Phe Glu Lys Arg
225                 230                 235                 240

Asp Ala Leu Phe Ile Leu Leu Ser Asp Leu Gly Ile Leu Thr Gln Leu
                245                 250                 255

Leu Val Leu Arg Val Trp Tyr Leu Asp Phe Gly Ala Trp Ser Val Phe
            260                 265                 270

Ile His Trp Phe Val Pro Tyr Ile Trp Val Asn His Trp Leu Val Phe
        275                 280                 285

Val Thr Phe Leu Gln His Thr Asp Thr Thr Ile Gly Arg Tyr Glu Thr
    290                 295                 300

Glu Glu Trp Thr Phe Ala Arg Gly Ala Ala Cys Thr Ile Asp Arg Glu
305                 310                 315                 320

Leu Pro Phe Ile Gly Pro His Leu Phe His Asp Ile Ile Glu Thr His
                325                 330                 335

Val Val His His Tyr Ser Ser Arg Ile Pro Phe Tyr Asn Ala Arg Glu
            340                 345                 350

Ala Ser Glu Ala Ile Gln Lys Val Met Gly Glu His Tyr Arg Lys Ser
        355                 360                 365

Thr Glu Ser Met Trp Val Thr Leu Trp Arg Ala Ala Arg Gly Cys Gln
    370                 375                 380

Tyr Val Asp Gly Asp Asn Gly Val Met Met Tyr Arg Asn Ile Asn Gly
385                 390                 395                 400

Ile Gly Val Gly Thr Gly Pro Glu Ala Lys Lys Thr Lys
                405                 410

<210> SEQ ID NO 85
<211> LENGTH: 466
<212> TYPE: PRT
<213> ORGANISM: Aspergillus parasiticus
<220> FEATURE:
<221> NAME/KEY: MISC_FEATURE
<222> LOCATION: (1)..(466)
<223> OTHER INFORMATION: delta-12 desaturase; GenBank Accession No.
      AAP23194

<400> SEQUENCE: 85

Met Ser Ser Thr Ala Ile Pro Lys Arg Met Ala Leu Asn Arg Asn Pro
1               5                   10                  15

Gly Thr Asp Ser Ser Val Pro Ser Val Ser Val Ser Pro Phe Asp Ser
                20                  25                  30

Pro Arg His Ser Pro Ser Ser Thr Leu Ser Ser Leu Ala Ser Glu
        35                  40                  45

Ser Glu Asn Lys Gly Lys Met Leu Asp Thr Tyr Gly Asn Glu Phe Lys
    50                  55                  60

Ile Pro Asp Tyr Thr Ile Lys Gln Ile Arg Asp Ala Ile Pro Ala His
65                  70                  75                  80

Cys Tyr Glu Arg Lys Ala Leu Thr Ser Leu Tyr Tyr Val Phe Arg Asp
                85                  90                  95

Ile Ala Met Leu Gly Ser Ile Phe Tyr Val Phe His Asn Tyr Val Thr
                100                 105                 110

Pro Glu Thr Val Pro Ser Phe Pro Ala Arg Val Ala Leu Trp Ser Leu
            115                 120                 125
```

Tyr Thr Val Val Gln Gly Leu Ile Ala Thr Gly Val Trp Val Leu Ala
            130                 135                 140

His Glu Cys Gly His Gln Ala Phe Ser Pro Ser Lys Val Leu Asn Asp
145                 150                 155                 160

Thr Val Gly Trp Ile Cys His Ser Ala Leu Leu Val Pro Tyr Phe Ser
                165                 170                 175

Trp Lys Ile Ser His Gly Lys His His Lys Ala Thr Gly Asn Ile Ala
            180                 185                 190

Arg Asp Met Val Phe Val Pro Lys Thr Arg Glu Glu Tyr Ala Ser Arg
        195                 200                 205

Ile Gly Lys Thr Ile His Asp Leu Asn Glu Leu Met Glu Glu Thr Pro
210                 215                 220

Ile Ala Thr Val Thr Asn Leu Ile Leu Gln Gln Leu Phe Gly Trp Pro
225                 230                 235                 240

Met Tyr Leu Leu Thr Asn Val Thr Gly His Asn Asn His Glu Arg Gln
                245                 250                 255

Pro Glu Gly Arg Gly Lys Gly Lys Arg Asn Gly Tyr Phe Gly Gly Val
            260                 265                 270

Asn His Phe Asn Pro Ser Ser Pro Leu Tyr Glu Ala Lys Asp Ala Lys
        275                 280                 285

Leu Ile Val Leu Ser Asp Leu Gly Leu Ala Ile Thr Gly Ser Val Leu
290                 295                 300

Tyr Tyr Ile Gly Ser Thr Tyr Gly Trp Leu Asn Leu Leu Val Trp Tyr
305                 310                 315                 320

Gly Ile Pro Tyr Leu Trp Val Asn His Trp Leu Val Ala Ile Thr Tyr
                325                 330                 335

Leu Gln His Thr Asp Pro Thr Leu Pro His Tyr Gln Pro Glu Val Trp
            340                 345                 350

Asn Phe Ala Arg Gly Ala Ala Ala Thr Ile Asp Arg Asp Phe Gly Phe
        355                 360                 365

Val Gly Arg His Ile Leu His Gly Ile Ile Glu Thr His Val Leu His
370                 375                 380

His Tyr Val Ser Thr Ile Pro Phe Tyr His Ala Asp Glu Ala Ser Glu
385                 390                 395                 400

Ala Ile Gln Lys Val Met Gly Ser His Tyr Arg Thr Glu Ala His Thr
                405                 410                 415

Gly Trp Thr Gly Phe Phe Lys Ala Leu Phe Thr Ser Ala Arg Val Cys
            420                 425                 430

His Trp Val Glu Pro Thr Glu Gly Ala Lys Gly Glu Ser Glu Gly Val
        435                 440                 445

Leu Phe Tyr Arg Asn Thr Asn Gly Val Gly Val Pro Pro Ala Lys Leu
450                 455                 460

Ser Lys
465

<210> SEQ ID NO 86
<211> LENGTH: 446
<212> TYPE: PRT
<213> ORGANISM: Cryptococcus curvatus
<220> FEATURE:
<221> NAME/KEY: MISC_FEATURE
<222> LOCATION: (1)..(446)
<223> OTHER INFORMATION: delta-12 desaturase; GenBank Accession No.
      AAU12575

<400> SEQUENCE: 86

-continued

```
Met Ser Ala Ala Thr Leu Arg Gln Arg Asn Val Asp Lys Pro Gly Ala
1               5                   10                  15

Ala Asp Lys Ala Glu Leu Leu Arg Glu Ala Glu Asp Leu Glu Leu Thr
            20                  25                  30

Glu Gly Gln Lys Phe Val Val Pro Asn Phe Thr Val Lys Gln Leu Leu
        35                  40                  45

Asp Ala Ile Pro Ala His Cys Tyr Lys Arg Ser Ala Phe Lys Ser Ser
    50                  55                  60

Leu Tyr Val Leu Gln Asp Phe Val Leu Leu Ala Ala Leu Val Tyr Gly
65                  70                  75                  80

Ala Tyr His Ile Asp Ser Phe Leu Ser Arg Phe Asn Leu Gly Ser Val
                85                  90                  95

Ala His Thr Ala Ala Lys Ile Gly Leu Trp Phe Thr Tyr Gln Val Leu
            100                 105                 110

Ala Gly Met Val Gly Thr Gly Ile Trp Val Ile Ala His Glu Cys Gly
        115                 120                 125

His Gln Ala Tyr Ser Glu Ser Lys Thr Ile Asn Asn Ala Val Gly Trp
    130                 135                 140

Val Leu His Ser Ile Leu Leu Val Pro Tyr His Ser Trp Arg Ile Ser
145                 150                 155                 160

His Gly Arg His His Ala Ala Thr Gly His Leu Thr Arg Asp Glu Val
                165                 170                 175

Phe Val Pro Arg Thr Arg Glu Gln Leu Gly Ile Gln Ala Pro Lys Thr
            180                 185                 190

Glu Glu Glu Lys Lys Gly Ile Asn Val Pro Ala Trp Arg Gln Ala Glu
        195                 200                 205

Leu Arg Glu Ala Leu Glu Glu Ser Pro Ile Gly Ala Leu Tyr Gly Ala
    210                 215                 220

Ile Leu His Gln Leu Phe Gly Trp Pro Met Tyr Leu Ile Arg Asn Ala
225                 230                 235                 240

Ser Gly Gln Leu Trp Tyr Pro Lys Met Thr Asn His Phe Gln Pro Ser
                245                 250                 255

Ser Ile Ile Phe Lys Pro Ser His Phe Trp Gln Ile Ile Ala Ser Asp
            260                 265                 270

Ile Gly Val Val Leu Thr Ala Ala Leu Gly Val Phe Val Tyr Tyr
        275                 280                 285

Arg Gly Phe Ala Glu Met Ala Arg Ile Tyr Leu Ile Pro Tyr Leu Trp
    290                 295                 300

Val Asn His Trp Leu Val Phe Ile Thr Phe Leu Gln His Thr Asp Pro
305                 310                 315                 320

Val Leu Pro His Tyr Ser Glu Lys Thr Trp Thr Phe Ala Arg Gly Ala
                325                 330                 335

Leu Ala Thr Ile Asp Arg Asn Cys Leu Gly Pro Val Gly Pro Tyr Leu
            340                 345                 350

Phe His Gly Ile Thr Glu Thr His Val Ala His His Thr Ser Ser Arg
        355                 360                 365

Ile Pro His Tyr Asn Ala Trp Glu Ala Thr Glu Ala Leu Lys Lys Phe
    370                 375                 380

Leu Gly Pro His Tyr His Tyr Asn Pro Glu Asn Met Phe Val Ser Phe
385                 390                 395                 400

Trp Lys Ala His Arg Tyr Cys Lys Phe Ile Glu Ala Gly Glu Asp Val
                405                 410                 415
```

```
Ala Phe Tyr Arg Asn Ala Ala Gly Val Ala Gln Lys Val Gly Ile Ile
                420                 425                 430

Glu Glu Asn Gly Ala Val Ser Asp Ser Gly Val Glu His Lys
            435                 440                 445

<210> SEQ ID NO 87
<211> LENGTH: 448
<212> TYPE: PRT
<213> ORGANISM: Cryptococcus neoformans var. neoformans B-3501A
<220> FEATURE:
<221> NAME/KEY: MISC_FEATURE
<222> LOCATION: (1)..(448)
<223> OTHER INFORMATION: delta-12 desaturase; GenBank Accession No.
      EAL21306

<400> SEQUENCE: 87

Met Thr Ser Thr Leu Arg Gln Arg Ala Val Thr Pro Pro Ala Gly Gln
1               5                   10                  15

Val Glu Lys Asp Gln Leu Leu Arg Glu Ala Glu Glu Lys Glu Ile Ser
            20                  25                  30

Gln Gly Gln Gln Phe Ile Val Pro Asn Phe Thr Ile Lys Gln Leu Leu
        35                  40                  45

Asp Ala Ile Pro Ala His Cys Tyr Lys Arg Ser Ala Leu Arg Ser Ser
    50                  55                  60

Leu Tyr Val Val Gln Asp Val Val Ile Ala Ala Leu Val Tyr Gly
65                  70                  75                  80

Ala Phe His Ile Asp Ser Leu Leu Gly Arg Phe Ser Leu Ser Pro Val
                85                  90                  95

Ala Tyr Tyr Ala Ala Lys Phe Ala Leu Trp Ser Ala Tyr Trp Phe Ile
            100                 105                 110

Thr Gly Leu Phe Gly Thr Gly Ile Trp Val Ile Ala His Glu Ala Gly
        115                 120                 125

His Gln Ala Tyr Ser Ser Ser Lys Ala Ile Asn Asn Ala Val Gly Trp
    130                 135                 140

Val Leu His Ser Ala Leu Leu Val Pro Tyr His Ser Trp Arg Ile Ser
145                 150                 155                 160

His Gly Arg His His Ala Ala Thr Gly His Leu Thr Arg Asp Glu Val
                165                 170                 175

Phe Val Pro Arg Thr Arg Lys Gln Leu Gly Tyr Pro Glu Val Glu Glu
            180                 185                 190

Glu Gly Glu Ile Leu Gly Ile Asn Val Ser Lys Glu Arg Gln Asn Gln
        195                 200                 205

Leu Arg Glu Ala Leu Glu Asp Ser Pro Ile Val Val Cys Tyr Asn Leu
    210                 215                 220

Phe Leu Gln Gln Leu Phe Gly Trp Pro Met Tyr Leu Ile Arg Asn Ala
225                 230                 235                 240

Ser Gly Gln Leu His Tyr Pro Glu Lys Thr Asn His Phe Ser Pro His
                245                 250                 255

Ser Phe Ile Phe Lys Ala Asn Gln Tyr Trp Gln Ile Ile Trp Ser Asp
            260                 265                 270

Ile Gly Ile Val Leu Val Phe Ala Ala Leu Ala Phe Trp Ala Ser Gln
        275                 280                 285

Arg Gly Ile Lys Glu Val Ala Thr Ile Tyr Gly Ile Pro Tyr Leu Trp
    290                 295                 300

Val Asn His Trp Leu Val Phe Ile Thr Phe Leu Gln His Thr Asp Pro
305                 310                 315                 320
```

```
Val Leu Pro His Tyr Ser Ala Asn Lys Trp Thr Phe Pro Arg Gly Ala
                325                 330                 335

Leu Ala Thr Ile Asp Arg Asp Phe Leu Gly Pro Val Gly Ala Tyr Ala
            340                 345                 350

Phe His Gly Ile Thr Glu Thr His Val Ala His His Ile Ser Ser Lys
        355                 360                 365

Ile Pro His Tyr Asn Ala Trp Glu Ala Thr Glu Ala Leu Lys Lys Phe
    370                 375                 380

Leu Gly Pro Ala Tyr His Lys Ser Asn Glu Asn Met Phe Val Ser Cys
385                 390                 395                 400

Tyr Lys Cys Tyr Arg Asp Cys Leu Phe Val Glu Asp Gly Gln Asp Ile
                405                 410                 415

Val Phe Tyr Lys Asn Ala Ser Gly Leu Ala Gln Arg Val Pro Val Glu
            420                 425                 430

Glu Asn Gly Asn Ile Ser Asp Ser Gly Ile Asp Met Ala Glu Ser Lys
        435                 440                 445
```

<210> SEQ ID NO 88
<211> LENGTH: 393
<212> TYPE: PRT
<213> ORGANISM: Saprolegnia diclina
<220> FEATURE:
<221> NAME/KEY: MISC_FEATURE
<222> LOCATION: (1)..(393)
<223> OTHER INFORMATION: delta-12 desaturase; GenBank Accession No. AAR20443

<400> SEQUENCE: 88

```
Met Cys Lys Gly Gln Ala Pro Ser Lys Ala Asp Val Phe His Ala Ala
1               5                   10                  15

Gly Tyr Arg Pro Val Ala Gly Thr Pro Glu Pro Leu Pro Leu Glu Pro
            20                  25                  30

Pro Thr Ile Thr Leu Lys Asp Leu Arg Ala Ala Ile Pro Ala His Cys
        35                  40                  45

Phe Glu Arg Ser Ala Ala Thr Ser Phe Tyr His Leu Ala Lys Asn Leu
    50                  55                  60

Ala Ile Cys Ala Gly Val Phe Ala Val Gly Leu Lys Leu Ala Ala Ala
65                  70                  75                  80

Asp Leu Pro Leu Ala Ala Lys Leu Val Ala Trp Pro Ile Tyr Trp Phe
                85                  90                  95

Val Gln Gly Thr Tyr Phe Thr Gly Ile Trp Val Ile Ala His Glu Cys
            100                 105                 110

Gly His Gln Ala Phe Ser Ala Ser Glu Ile Leu Asn Asp Thr Val Gly
        115                 120                 125

Ile Ile Leu His Ser Leu Leu Phe Val Pro Tyr His Ser Trp Lys Ile
    130                 135                 140

Thr His Arg Arg His His Ser Asn Thr Gly Ser Cys Glu Asn Asp Glu
145                 150                 155                 160

Val Phe Thr Pro Thr Pro Arg Ser Val Val Glu Ala Lys His Asp His
                165                 170                 175

Ser Leu Leu Glu Glu Ser Pro Leu Tyr Asn Leu Tyr Gly Ile Val Met
            180                 185                 190

Met Leu Leu Val Gly Trp Met Pro Gly Tyr Leu Phe Phe Asn Ala Thr
        195                 200                 205

Gly Pro Thr Lys Tyr Ala Gly Leu Ala Lys Ser His Phe Asn Pro Tyr
    210                 215                 220
```

```
Ala Ala Phe Phe Leu Pro Lys Glu Arg Leu Ser Ile Trp Trp Ser Asp
225                 230                 235                 240

Leu Cys Phe Leu Ala Ala Leu Tyr Gly Phe Gly Tyr Gly Val Ser Val
                245                 250                 255

Phe Gly Leu Leu Asp Val Ala Arg His Tyr Ile Val Pro Tyr Leu Ile
            260                 265                 270

Cys Asn Ala Tyr Leu Val Leu Ile Thr Tyr Leu Gln His Thr Asp Thr
        275                 280                 285

Tyr Val Pro His Phe Arg Gly Asp Glu Trp Asn Trp Leu Arg Gly Ala
    290                 295                 300

Leu Cys Thr Val Asp Arg Ser Phe Gly Ala Trp Ile Asp Ser Ala Ile
305                 310                 315                 320

His His Ile Ala Asp Thr His Val Thr His His Ile Phe Ser Lys Thr
                325                 330                 335

Pro Phe Tyr His Ala Ile Glu Ala Thr Asp Ala Ile Thr Pro Leu Leu
            340                 345                 350

Gly Lys Tyr Tyr Leu Ile Asp Pro Thr Pro Ile Pro Leu Ala Leu Trp
                355                 360                 365

Arg Ser Phe Thr His Cys Lys Tyr Val Glu Asp Asp Gly Asn Val Val
370                 375                 380

Phe Tyr Lys Arg Lys Leu Glu Glu Lys
385                 390

<210> SEQ ID NO 89
<211> LENGTH: 419
<212> TYPE: PRT
<213> ORGANISM: Yarrowia lipolytica CLIB122
<220> FEATURE:
<221> NAME/KEY: MISC_FEATURE
<222> LOCATION: (1)..(419)
<223> OTHER INFORMATION: delta-12 desaturase; GenBank Accession No.
      CAG82952

<400> SEQUENCE: 89

Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
                20                  25                  30

Val Tyr Asp Thr Phe Gly Asn Glu Phe Thr Pro Pro Asp Tyr Ser Ile
            35                  40                  45

Lys Asp Ile Leu Asp Ala Ile Pro Gln Glu Cys Tyr Lys Arg Ser Tyr
    50                  55                  60

Val Lys Ser Tyr Ser Tyr Val Ala Arg Asp Cys Phe Phe Ile Ala Val
65                  70                  75                  80

Phe Ala Tyr Met Ala Tyr Ala Tyr Leu Pro Leu Ile Pro Ser Ala Ser
                85                  90                  95

Gly Arg Ala Val Ala Trp Ala Met Tyr Ser Ile Val Gln Gly Leu Phe
            100                 105                 110

Gly Thr Gly Leu Trp Val Leu Ala His Glu Cys Gly His Ser Ala Phe
        115                 120                 125

Ser Asp Ser Asn Thr Val Asn Asn Val Thr Gly Trp Val Leu His Ser
130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
                165                 170                 175
```

```
Asp Arg Lys Glu Phe Met Glu Asn Arg Gly Ala His Asp Trp Ser Glu
            180                 185                 190

Leu Ala Glu Asp Ala Pro Leu Met Thr Leu Tyr Gly Leu Ile Thr Gln
        195                 200                 205

Gln Val Phe Gly Trp Pro Leu Tyr Leu Leu Ser Asn Val Thr Gly Gln
    210                 215                 220

Lys Tyr Pro Lys Leu Asn Lys Trp Ala Val Asn His Phe Asn Pro Asn
225                 230                 235                 240

Ala Pro Leu Phe Glu Lys Lys Asp Trp Phe Asn Ile Trp Ile Ser Asn
            245                 250                 255

Val Gly Ile Gly Ile Thr Met Ser Val Ile Ala Tyr Ser Ile Asn Arg
        260                 265                 270

Trp Gly Leu Ala Ser Val Thr Leu Tyr Tyr Leu Ile Pro Tyr Leu Trp
    275                 280                 285

Val Asn His Trp Leu Val Ala Ile Thr Tyr Leu Gln His Thr Asp Pro
290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
            325                 330                 335

His Asp Ile Ile Glu Thr His Val Leu His His Tyr Val Ser Arg Ile
        340                 345                 350

Pro Phe Tyr Asn Ala Arg Ile Ala Thr Glu Lys Ile Lys Lys Val Met
    355                 360                 365

Gly Lys His Tyr Arg His Asp Asp Thr Asn Phe Ile Lys Ser Leu Tyr
370                 375                 380

Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
            405                 410                 415

Ser Lys Lys

<210> SEQ ID NO 90
<211> LENGTH: 435
<212> TYPE: PRT
<213> ORGANISM: Lentinula edodes
<220> FEATURE:
<221> NAME/KEY: MISC_FEATURE
<222> LOCATION: (1)..(435)
<223> OTHER INFORMATION: delta-12 desaturase; GenBank Accession No.
      BAD51484

<400> SEQUENCE: 90

Met Gly Ala Gln Arg Glu Ile Val Val Glu Gln Glu Pro Val Val Ile
1               5                   10                  15

Pro Asp Phe Ser Val Lys Asp Leu Leu Gly Val Ile Pro Ala His Cys
            20                  25                  30

His Lys Arg Ser Ala Phe Arg Ser Ser Leu Tyr Ile Val Met Asp Val
        35                  40                  45

Ala Val Ile Thr Ala Val Tyr Asn Ile Ala Thr Phe Val Asp Ser Phe
    50                  55                  60

Leu Asn Pro Glu Ser Leu Ser Leu Pro His Pro Leu Leu Phe Pro Leu
65                  70                  75                  80

Ala Arg Phe Ala Ile Trp Ala Leu Tyr Gly Phe Trp Thr Gly Leu Phe
            85                  90                  95

Ala Thr Gly Leu Trp Val Val Ala His Glu Cys Gly His Gln Ala Phe
```

```
            100                 105                 110
Ser Glu Ser Lys Phe Val Asn Asn Ala Val Gly Trp Val Leu His Ser
            115                 120                 125

Ala Leu Gly Val Pro Tyr His Ser Trp Arg Ile Thr His Gly Gln His
            130                 135                 140

His Ala Ser Thr Gly His Met Thr Lys Asp Gln Val Phe Val Pro Pro
145                 150                 155                 160

Thr Arg Ser Gln Trp Gly Leu Lys Pro Phe Asn Pro Glu Gln Glu Asn
                165                 170                 175

Leu Leu Gly Ser Arg Val Ser Glu Val Ser Lys Glu Leu Trp Asp
            180                 185                 190

Ala Leu Gly Asp Ser Pro Ile Gly Ala Met Ile Gly Ser Ala Thr Tyr
            195                 200                 205

Leu Leu Gly Gly Trp Pro Ala Tyr Leu Ile Leu Asn Ala Ser Gly Gln
            210                 215                 220

Lys Tyr Pro Lys Gly Ser Asn His Phe Asn Pro Gly Ala Ile Met Phe
225                 230                 235                 240

Lys Asp Arg Glu Trp Gly Gln Ile Ile Met Ser Asp Val Gly Ile Ile
                245                 250                 255

Leu Trp Ile Ala Gly Val Ile Ala Ser Ile Ser Val Tyr Gly Phe Thr
            260                 265                 270

Asn Val Phe Val Leu Tyr Leu Ile Pro Tyr Leu Trp Val Asn His Trp
            275                 280                 285

Leu Val Leu Ile Thr Phe Leu Gln His Thr Asp Pro Leu Leu Pro His
            290                 295                 300

Tyr Arg Ala Arg Glu His Thr Phe Pro Arg Gly Ala Leu Ala Thr Leu
305                 310                 315                 320

Asp Arg Ser Leu Leu Gly Asp Leu Gly Ser Phe Met Gly Trp Ile Gly
                325                 330                 335

Ala Leu Ala Thr His Gly Ile Ser Glu Thr His Ile Cys His His Val
            340                 345                 350

Ala Ser Lys Ile Pro His Tyr His Ala Trp Glu Ala Gly Glu His Leu
            355                 360                 365

Lys Arg Lys Leu Glu Ala Ala Gly Met Arg Thr Glu Gly Ala Pro Ala
            370                 375                 380

Gly Trp Ala Glu Val Tyr Arg Val Phe Lys Glu Cys Lys Phe Val Glu
385                 390                 395                 400

Asp Glu Gly Asp Ile Val Phe Phe Lys Asp Ala Arg Gly Leu Ala Lys
                405                 410                 415

Ala Arg Pro Val Tyr Asn Ser Asp Ser Pro Ser Asp Ser Gly Ile Glu
            420                 425                 430

Leu Glu Lys
        435

<210> SEQ ID NO 91
<211> LENGTH: 553
<212> TYPE: PRT
<213> ORGANISM: Ustilago maydis 521
<220> FEATURE:
<221> NAME/KEY: MISC_FEATURE
<222> LOCATION: (1)..(553)
<223> OTHER INFORMATION: delta-12 desaturase; GenBank Accession No.
      XP_757193

<400> SEQUENCE: 91

Met Lys Gln Arg Lys Pro Ser Gln Asp Leu Phe Thr Leu Ser Cys Asp
```

-continued

```
1               5                   10                  15
Ser Gly Met Gln Phe Lys Arg Glu Cys Trp Ser Lys Arg Arg Ala Arg
            20                  25                  30
Gly Ala Cys Ser Glu Ile Ser Pro Pro Gln Asn His Glu Cys Leu His
            35                  40                  45
Gln Ser Pro Val Leu Ala Thr Asp Ser His Ser Arg Ser Val Asp Met
        50                  55                  60
Ser Ser Ala Val Ala Pro Asn Val Thr Ala Ala Gly Gln Arg Ala Gly
65                  70                  75                  80
Lys Lys Ala Ala Ala Ser Thr Ala Ala Lys Ala Ser Lys Thr Glu
            85                  90                  95
Thr Ile Arg Tyr Ser His Arg Lys Ala Ala Thr Tyr Asp Glu Lys Asp
            100                 105                 110
Ile Pro Thr Phe Asp Val Pro Gln Phe Thr Val Lys Asp Leu Leu Ser
            115                 120                 125
Ala Ile Pro Ala His Cys Phe Glu Arg Ser Ala Phe Lys Ser Phe Thr
            130                 135                 140
Tyr Val Phe Ala Asp Phe Ala Met Ile Ala Ala Leu Gly Tyr Ala Ala
145                 150                 155                 160
Ser Phe Ile Asp Pro Thr Val Ala Ser Thr Phe Ser Gly Leu Lys Ser
                165                 170                 175
Asn Ala Leu Ser Pro Tyr Val Ser Leu Gly Val Gln Gln Ala Ala Thr
            180                 185                 190
Arg Phe Ala Ala Trp Ser Ala Tyr Trp Ile Leu Gln Gly Met Val Phe
            195                 200                 205
Thr Gly Val Trp Val Ile Ala His Glu Cys Gly His Gln Ser Phe Ser
    210                 215                 220
Thr Ser Lys Thr Leu Asn Asn Ala Val Gly Trp Val Leu His Ser Ala
225                 230                 235                 240
Leu Leu Val Pro Tyr His Ser Trp Arg Ile Ser His Ala Arg His His
                245                 250                 255
Ala Ala Thr Gly His Leu Thr Arg Asp Glu Val Phe Val Pro Arg Thr
            260                 265                 270
Arg Gln Gln Arg Gly Arg Leu Pro Leu Gln Pro Ala Pro Lys Ser Ala
        275                 280                 285
Asp Asp Ser Asn Asp Glu Asp Ala Val Glu Lys Glu Val Gly Ala Ile
    290                 295                 300
Lys Val Asp Glu Thr Phe Gly Glu Trp Leu Ala Glu Val Leu Glu Asp
305                 310                 315                 320
Ala Pro Ala Tyr Asn Leu Leu Tyr Ile Phe Ile Gln Gln Leu Leu Gly
                325                 330                 335
Trp Pro Leu Tyr Leu Leu Arg Asn Ala Ser Gly Gln Leu His Tyr Pro
            340                 345                 350
Lys Phe Thr Asn His Phe Asn Pro Asp Ala Ile Phe Asp Lys Arg
            355                 360                 365
His Arg Met Gln Ile Ile Val Ser Asp Ile Gly Ile Ala Ala Thr Leu
            370                 375                 380
Ser Ala Leu Thr Ala Trp Gly Leu Leu Ser Lys Gly Gly Phe Ser Asp
385                 390                 395                 400
Val Phe Arg Tyr Tyr Val Ile Pro Tyr Leu Trp Cys Asn His Trp Leu
                405                 410                 415
Val Met Ile Thr Tyr Leu Gln His Thr Asp Pro Ala Leu Pro His Tyr
            420                 425                 430
```

Lys Ala Glu Ala Trp Thr Phe Pro Arg Gly Ala Leu Cys Thr Ile Asp
            435                 440                 445

Arg Asn Trp Leu Gly Pro Val Gly Pro Tyr Leu Phe His Gly Ile Ala
        450                 455                 460

Glu Thr His Val Leu His His Val Ser Ser Lys Ile Pro His Tyr Asn
465                 470                 475                 480

Ala Trp Glu Ala Thr Glu Ala Leu Lys Ala Arg Leu Gly His His Tyr
                485                 490                 495

Val Lys Ser Thr Glu Asn Val Phe Val Ser Leu Trp Lys Ser Ile Asn
            500                 505                 510

Thr Cys Lys Phe Val Asp Glu Asn Asp Gln Val Ala Phe Tyr Arg Thr
        515                 520                 525

Val Asp Gly Val Pro His Arg Val Ile Ser Pro Asp Ser Ala Tyr Ala
530                 535                 540

Ser Asp Ser Gly Ile Ala Met Ser Glu
545                 550

<210> SEQ ID NO 92
<211> LENGTH: 396
<212> TYPE: PRT
<213> ORGANISM: Mucor circinelloides
<220> FEATURE:
<221> NAME/KEY: MISC_FEATURE
<222> LOCATION: (1)..(396)
<223> OTHER INFORMATION: delta-12 desaturase; GenBank Accession No.
      BAB69056

<400> SEQUENCE: 92

Met Ala Thr Lys Arg Asn Val Thr Ser Asn Ala Pro Ala Ala Glu Asp
1               5                   10                  15

Ile Ser Ile Ser Asn Lys Ala Val Ile Asp Glu Ala Ile Glu Arg Asn
            20                  25                  30

Trp Glu Ile Pro Asn Phe Thr Ile Lys Glu Ile Arg Asp Ala Ile Pro
        35                  40                  45

Ala His Cys Phe Arg Arg Asp Thr Phe Arg Ser Phe Thr His Val Leu
    50                  55                  60

His Asp Ile Ile Ile Met Ser Ile Leu Ala Ile Gly Ala Ser Tyr Ile
65                  70                  75                  80

Asp Ser Ile Pro Asn Thr Tyr Ala Arg Ile Ala Leu Trp Pro Leu Tyr
                85                  90                  95

Trp Ile Ala Gln Gly Ile Val Gly Thr Gly Val Trp Val Ile Gly His
            100                 105                 110

Glu Cys Gly His Gln Ala Phe Ser Pro Ser Lys Thr Ile Asn Asn Ser
        115                 120                 125

Val Gly Tyr Val Leu His Thr Ala Leu Leu Val Pro Tyr His Ser Trp
    130                 135                 140

Arg Phe Ser His Ser Lys His His Lys Ala Thr Gly His Met Ser Lys
145                 150                 155                 160

Asp Gln Val Phe Val Pro Ser Thr Arg Lys Glu Tyr Gly Leu Pro Pro
                165                 170                 175

Arg Glu Gln Asp Pro Glu Val Asp Gly Pro His Asp Ala Leu Asp Glu
            180                 185                 190

Ala Pro Ile Val Val Leu Tyr Arg Met Phe Leu Gln Phe Thr Phe Gly
        195                 200                 205

Trp Pro Leu Tyr Leu Phe Thr Asn Val Ser Gly Gln Asp Tyr Pro Gly
    210                 215                 220

```
Trp Ala Ser His Phe Asn Pro Lys Cys Ala Ile Tyr Asp Glu Asn Gln
225                 230                 235                 240

Phe Trp Asp Val Met Ser Ser Thr Ala Gly Val Leu Gly Met Ile Gly
                245                 250                 255

Phe Leu Ala Tyr Cys Gly Gln Val Phe Gly Ser Leu Ala Val Ile Lys
            260                 265                 270

Tyr Tyr Val Ile Pro Tyr Leu Asn Val Asn Phe Trp Leu Val Leu Ile
        275                 280                 285

Thr Tyr Leu Gln His Thr Asp Pro Lys Leu Pro His Tyr Arg Glu Asn
    290                 295                 300

Val Trp Asn Phe Gln Arg Gly Ala Ala Leu Thr Val Asp Arg Ser Tyr
305                 310                 315                 320

Gly Phe Leu Leu Asp Tyr Phe His His Ile Ser Asp Thr His Val
                325                 330                 335

Ala His His Phe Phe Ser Thr Met Pro His Tyr His Ala Glu Glu Ala
                340                 345                 350

Thr Val His Ile Lys Lys Ala Leu Gly Lys His Tyr His Cys Asp Asn
                355                 360                 365

Thr Pro Val Pro Ile Ala Leu Trp Lys Val Trp Lys Ser Cys Arg Phe
                370                 375                 380

Val Glu Asp Glu Gly Asp Val Val Phe Phe Lys Asn
385                 390                 395
```

<210> SEQ ID NO 93
<211> LENGTH: 396
<212> TYPE: PRT
<213> ORGANISM: Mucor rouxii
<220> FEATURE:
<221> NAME/KEY: MISC_FEATURE
<222> LOCATION: (1)..(396)
<223> OTHER INFORMATION: delta-12 desaturase; GenBank Accession No. AAD55982

<400> SEQUENCE: 93

```
Met Ala Thr Lys Arg Asn Val Thr Ser Asn Ala Pro Ala Ala Glu Asp
1               5                   10                  15

Ile Ser Ile Ser Asn Lys Ala Val Ile Asp Glu Ala Ile Glu Arg Asn
                20                  25                  30

Trp Glu Ile Pro Asn Phe Thr Ile Lys Glu Ile Arg Asp Ala Ile Pro
            35                  40                  45

Ala His Cys Phe Arg Arg Asp Thr Phe Arg Ser Phe Thr His Val Leu
        50                  55                  60

His Asp Ile Ile Ile Met Pro Ile Leu Ala Ile Gly Ala Ser Tyr Ile
65                  70                  75                  80

Asp Ser Ile Pro Asn Thr Tyr Ala Arg Ile Ala Leu Trp Pro Leu Tyr
                85                  90                  95

Trp Ile Ala Gln Gly Ile Val Gly Thr Gly Val Trp Val Ile Gly His
            100                 105                 110

Glu Cys Gly His Gln Ala Phe Ser Pro Ser Lys Thr Ile Asn Asn Ser
        115                 120                 125

Val Gly Tyr Val Leu His Thr Ala Leu Leu Val Pro Tyr His Ser Trp
    130                 135                 140

Arg Phe Ser His Ser Lys His His Lys Ala Thr Gly His Met Ser Lys
145                 150                 155                 160

Asp Gln Val Phe Val Pro Ser Thr Arg Lys Glu Tyr Gly Leu Pro Pro
                165                 170                 175
```

```
Arg Glu Gln Asp Pro Glu Val Asp Gly Pro His Asp Ala Leu Asp Glu
            180                 185                 190

Val Pro Leu Leu Ser Cys Ile Ala Cys Ser Phe Asn Leu Pro Leu Ala
            195                 200                 205

Gly Leu Phe Ile Ser Ser Pro Met Ser Leu Val Lys Ile Thr Pro Val
            210                 215                 220

Gly Leu Leu Ile Ser Thr Pro Ser Val Leu Ser Thr Ile Glu Asn Gln
225                 230                 235                 240

Phe Trp Asp Val Met Ser Ser Thr Ala Gly Val Leu Gly Met Ile Gly
                    245                 250                 255

Phe Leu Ala Tyr Cys Gly Gln Val Leu Ala Leu Leu Leu Ser Ser Ser
                260                 265                 270

Thr Met Leu Phe Pro Tyr Leu Asn Val Asn Phe Trp Leu Val Leu Ile
            275                 280                 285

Thr Tyr Leu Gln His Thr Asp Pro Lys Leu Pro His Tyr Arg Glu Asn
            290                 295                 300

Val Trp Asn Phe Gln Arg Gly Ala Ala Leu Thr Val Asp Arg Ser Tyr
305                 310                 315                 320

Gly Phe Leu Leu Asp Tyr Phe His His Ile Ser Asp Thr His Val
                    325                 330                 335

Ala His His Phe Phe Ser Thr Met Pro His Tyr His Ala Glu Glu Ala
                340                 345                 350

Thr Val His Ile Lys Lys Ala Leu Gly Lys Tyr His Cys Asp Asn
                355                 360                 365

Thr Pro Val Pro Ile Ala Leu Trp Lys Val Trp Lys Ser Cys Arg Phe
            370                 375                 380

Val Glu Asp Glu Gly Asp Val Val Phe Phe Lys Asn
385                 390                 395

<210> SEQ ID NO 94
<211> LENGTH: 389
<212> TYPE: PRT
<213> ORGANISM: Rhizopus oryzae
<220> FEATURE:
<221> NAME/KEY: MISC_FEATURE
<222> LOCATION: (1)..(389)
<223> OTHER INFORMATION: delta-12 desaturase; GenBank Accession No.
      AAT58363

<400> SEQUENCE: 94

Met Ala Thr Lys Arg Asn Ile Ser Ser Asn Glu Pro Glu Asn Lys Pro
1               5                   10                  15

Val Ile Asp Glu Ala Val Ala Arg Asn Trp Glu Ile Pro Asp Phe Thr
                20                  25                  30

Ile Lys Glu Ile Arg Asp Ala Ile Pro Ser His Cys Phe Arg Arg Asp
            35                  40                  45

Thr Phe Arg Ser Phe Thr Tyr Val Ile His Asp Phe Ala Ile Ile Ala
            50                  55                  60

Val Leu Gly Tyr Leu Ala Thr Tyr Ile Asp Gln Val His Ser Ala Ala
65                  70                  75                  80

Leu Arg Leu Leu Leu Trp Ser Tyr Trp Thr Ala Gln Gly Ile Val
                85                  90                  95

Gly Thr Gly Val Trp Val Val Gly His Glu Cys Gly His Gln Ala Phe
                100                 105                 110

Ser Pro Ser Lys Ala Val Asn Asn Ser Val Gly Phe Val Leu His Thr
            115                 120                 125
```

```
Leu Leu Leu Val Pro Tyr His Ser Trp Arg Phe Ser His Ser Lys His
        130                 135                 140

His Lys Ala Thr Gly His Met Ser Lys Asp Gln Val Phe Leu Pro Lys
145                 150                 155                 160

Thr Arg Glu Lys Val Gly Leu Pro Pro Arg Asp Lys Asp Pro Gln Ala
                165                 170                 175

Asp Gly Pro His Asp Val Leu Asp Glu Thr Pro Ile Val Val Leu Tyr
            180                 185                 190

Arg Met Phe Leu Met Phe Leu Phe Gly Trp Pro Leu Tyr Leu Phe Thr
        195                 200                 205

Asn Val Thr Gly Gln Asp Tyr Pro Gly Trp Ala Ser His Phe Asn Pro
    210                 215                 220

Ser Cys Asp Ile Tyr Glu Glu Gly Gln Tyr Trp Asp Val Val Ser Ser
225                 230                 235                 240

Ser Val Gly Val Val Gly Met Val Gly Leu Leu Gly Tyr Cys Gly Gln
                245                 250                 255

Ile Phe Gly Ser Leu Asn Met Ile Lys Tyr Val Ile Pro Tyr Leu
            260                 265                 270

Cys Val Asn Phe Trp Leu Val Leu Ile Thr Tyr Leu Gln His Thr Asp
        275                 280                 285

Pro Lys Leu Pro His Tyr Arg Glu Asn Val Trp Asn Phe Gln Arg Gly
    290                 295                 300

Ala Ala Leu Thr Val Asp Arg Ser Tyr Gly Ala Leu Ile Asn Tyr Phe
305                 310                 315                 320

His His Ile Ser Asp Thr His Val Ala His His Phe Phe Ser Thr
                325                 330                 335

Met Pro Tyr His Ala Glu Glu Ala Thr Val His Ile Lys Lys Ala
            340                 345                 350

Leu Gly Lys His Tyr His Cys Asp Asn Thr Pro Ile Pro Ile Ala Leu
        355                 360                 365

Trp Lys Val Trp Lys Ser Cys Arg Phe Val Glu Ser Glu Gly Asp Val
370                 375                 380

Val Phe Tyr Lys Asn
385

<210> SEQ ID NO 95
<211> LENGTH: 466
<212> TYPE: PRT
<213> ORGANISM: Aspergillus flavus
<220> FEATURE:
<221> NAME/KEY: MISC_FEATURE
<222> LOCATION: (1)..(466)
<223> OTHER INFORMATION: delta-12 desaturase; GenBank Accession No.
      AAP33789

<400> SEQUENCE: 95

Met Ser Ser Thr Ala Ile Pro Lys Arg Met Ala Leu Asn Arg Asn Pro
1               5                   10                  15

Gly Thr Asp Ser Ser Val Pro Ser Val Ser Val Ser Pro Phe Asp Ser
                20                  25                  30

Pro Arg His Ser Pro Ser Ser Thr Ser Leu Ser Ser Leu Ala Ser Glu
            35                  40                  45

Ser Glu Asn Lys Gly Lys Met Leu Asp Thr Tyr Gly Asn Glu Phe Lys
        50                  55                  60

Ile Pro Asp Tyr Thr Ile Lys Gln Ile Arg Asp Ala Ile Pro Ala His
65                  70                  75                  80
```

```
Cys Tyr Glu Arg Lys Ala Leu Thr Ser Leu Tyr Tyr Val Phe Arg Asp
                85                  90                  95

Ile Ala Met Leu Gly Ser Ile Phe Tyr Val Phe His Asn Tyr Val Thr
            100                 105                 110

Pro Glu Thr Val Pro Ser Phe Pro Ala Arg Val Ala Leu Trp Ser Leu
        115                 120                 125

Tyr Thr Val Val Gln Gly Leu Ile Ala Thr Gly Val Trp Val Leu Ala
    130                 135                 140

His Glu Cys Gly His Gln Ala Phe Ser Pro Ser Lys Val Leu Asn Asp
145                 150                 155                 160

Thr Val Gly Trp Ile Cys His Ser Ala Leu Leu Val Pro Tyr Phe Ser
                165                 170                 175

Trp Lys Ile Ser His Gly Lys His His Lys Ala Thr Gly Asn Ile Ala
            180                 185                 190

Arg Asp Met Val Phe Val Pro Lys Thr Arg Glu Glu Tyr Ala Ser Arg
        195                 200                 205

Ile Gly Lys Thr Ile His Asp Leu Asn Glu Leu Met Glu Glu Thr Pro
    210                 215                 220

Ile Ala Thr Val Thr Asn Leu Ile Leu Gln Gln Leu Phe Gly Trp Pro
225                 230                 235                 240

Met Tyr Leu Leu Thr Asn Val Thr Gly His Asn Asn His Glu Arg Gln
                245                 250                 255

Pro Glu Gly Arg Gly Lys Gly Lys Arg Asn Gly Tyr Phe Gly Gly Val
            260                 265                 270

Asn His Phe Asn Pro Ser Ser Pro Leu Tyr Glu Ala Lys Asp Ala Lys
        275                 280                 285

Leu Ile Val Leu Ser Asp Leu Gly Leu Ala Ile Thr Gly Ser Val Leu
    290                 295                 300

Tyr Tyr Ile Gly Ser Thr Tyr Gly Trp Leu Asn Leu Leu Val Trp Tyr
305                 310                 315                 320

Gly Ile Pro Tyr Leu Trp Val Asn His Trp Leu Val Ala Ile Thr Tyr
                325                 330                 335

Leu Gln His Thr Asp Pro Thr Leu Pro His Tyr Gln Pro Glu Val Trp
            340                 345                 350

Asn Phe Ala Arg Gly Ala Ala Ala Thr Ile Asp Arg Asp Phe Gly Phe
        355                 360                 365

Val Gly Arg His Ile Leu His Gly Ile Ile Glu Thr His Val Leu His
    370                 375                 380

His Tyr Val Ser Thr Ile Pro Phe Tyr His Ala Asp Glu Ala Ser Glu
385                 390                 395                 400

Ala Ile Gln Lys Val Met Gly Ser His Tyr Arg Thr Glu Ala His Thr
                405                 410                 415

Gly Trp Thr Gly Phe Phe Lys Ala Leu Phe Thr Ser Ala Arg Val Cys
            420                 425                 430

His Trp Val Glu Pro Thr Glu Gly Ala Arg Gly Glu Ser Glu Gly Val
        435                 440                 445

Leu Phe Tyr Arg Asn Thr Asn Gly Ile Gly Val Pro Pro Ala Lys Leu
    450                 455                 460

Ser Lys
465

<210> SEQ ID NO 96
<211> LENGTH: 40
```

```
<212> TYPE: DNA
<213> ORGANISM: Artificial Sequence
<220> FEATURE:
<223> OTHER INFORMATION: Primer 631

<400> SEQUENCE: 96
ctatttgggt tggcttgtg ggttttggcc catgaatgtg                              40

<210> SEQ ID NO 97
<211> LENGTH: 40
<212> TYPE: DNA
<213> ORGANISM: Artificial Sequence
<220> FEATURE:
<223> OTHER INFORMATION: Primer 632

<400> SEQUENCE: 97
cacattcatg ggccaaaacc cacaagccaa acccaaatag                             40

<210> SEQ ID NO 98
<211> LENGTH: 9099
<212> TYPE: DNA
<213> ORGANISM: Artificial Sequence
<220> FEATURE:
<223> OTHER INFORMATION: Plasmid pY28

<400> SEQUENCE: 98
tcgacgcagt aggatgtcct gcacgggtct ttttgtgggg tgtggagaaa ggggtgcttg       60
gagatggaag ccggtagaac cgggctgctt gtgcttggag atggaagccg gtagaaccgg      120
gctgcttggg gggatttggg gccgctgggc tccaaagagg ggtaggcatt tcgttggggt      180
tacgtaattg cggcatttgg gtcctgcgcg catgtcccat tggtcagaat tagtccggat      240
aggagactta tcagccaatc acagcgccgg atccacctgt aggttgggtt gggtgggagc      300
accccctccac agagtagagt caaacagcag cagcaacatg atagttgggg gtgtgcgtgt      360
taaaggaaaa aaaagaagct tgggttatat tcccgctcta tttagaggtt gcgggataga      420
cgccgacgga gggcaatggc gctatggaac cttgcgcgata tccatacgcc gcggcggact      480
gcgtccgaac cagctccagc agcgtttttt ccgggccatt gagccgactg cgaccccgcc      540
aacgtgtctt ggcccacgca ctcatgtcat gttggtgttg ggaggccact ttttaagtag      600
cacaaggcac ctagctcgca gcaaggtgtc cgaaccaaag aagcggctgc agtggtgcaa      660
acggggcgga acggcgggga aaagccacg ggggcacgaa ttgaggcacg ccctcgaatt       720
tgagacgagt cacggcccca ttcgcccgcg caatggctcg ccaacgcccg gtcttttgca      780
ccacatcagg ttaccccaag ccaaaccttt gtgttaaaaa gcttaacata ttataccgaa      840
cgtaggtttg ggcgggcttg ctccgtctgt ccaaggcaac atttatataa gggtctgcat      900
cgccggctca attgaatctt ttttcttctt ctcttctcta tattcattct tgaattaaac      960
acacatcaac catggattcg accacgcaga ccaacaccgg caccggcaag gtggccgtgc     1020
agccccccac ggccttcatt aagcccattg agaaggtgtc cgagcccgtc tacgacacct     1080
ttggcaacga gttcactcct ccagactact ctatcaagga tattctggat gccattcccc     1140
aggagtgcta caagcggtcc tacgttaagt cctactcgta cgtggcccga gactgcttct     1200
ttatcgccgt ttttgcctac atggcctacg cgtacctgcc tcttattccc tcggcttccg     1260
gccgagctgt ggcctgggcc atgtactcca ttgtccaggg tctgtttggc accggtctgt     1320
gggttcttgc ccacgagtgt ggccactctg ctttctccga ctctaacacc gtcaacaacg     1380
tcaccggatg ggttctgcac tcctccatgc tggtcccctta ctacgcctgg aagctgaccc     1440
```

```
actccatgca ccacaagtcc actggtcacc tcacccgtga tatggtgttt gtgcccaagg    1500
accgaaagga gtttatggag aaccgaggcg cccatgactg gtctgagctt gctgaggacg    1560
ctcccctcat gaccctctac ggcctcatca cccagcaggt gtttggatgg cctctgtatc    1620
tgctgtctta cgttaccgga cagaagtacc ccaagctcaa caaatgggct gtcaaccact    1680
tcaaccccaa cgcccgctg tttgagaaga aggactggtt caacatctgg atctctaacg    1740
tcggtattgg tatcaccatg tccgtcatcg catactccat caaccgatgg ggcctggctt    1800
ccgtcacct ctactacctg atcccctacc tgtgggtcaa ccactggctc gtggccatca    1860
cctacctgca gcacaccgac cccactctgc ccactacca cgccgaccag tggaacttca    1920
cccgaggagc cgccgccacc atcgaccgag agtttggctt catcggctcc ttctgcttcc    1980
atgacatcat cgagacccac gttctgcacc actacgtgtc tcgaattccc ttctacaacg    2040
cccgaatcgc cactgagaag atcaagaagg tcatgggcaa gcactaccga cacgacgaca    2100
ccaacttcat caagtctctt tacactgtcg cccgaacctg ccagtttgtt gaaggtaagg    2160
aaggcattca gatgtttaga aacgtcaatg gagtcggagt tgctcctgac ggcctgcctt    2220
ctaaaaagta ggcggccgca tgagaagata aatatataaa tacattgaga tattaaatgc    2280
gctagattag agagcctcat actgctcgga gagaagccaa gacgagtact caaaggggat    2340
tacaccatcc atatccacag acacaagctg gggaaaggtt ctatatacac tttccggaat    2400
accgtagttt ccgatgttat caatgggggc agccaggatt tcaggcactt cggtgtctcg    2460
gggtgaaatg gcgttcttgg cctccatcaa gtcgtaccat gtcttcattt gcctgtcaaa    2520
gtaaaacaga agcagatgaa gaatgaactt gaagtgaagg aatttaaatg taacgaaact    2580
gaaatttgac cagatattgt gtccgcggtg gagctccagc ttttgttccc tttagtgagg    2640
gttaatttcg agcttggcgt aatcatggtc atagctgttt cctgtgtgaa attgttatcc    2700
gctcacaagc ttccacacaa cgtacgagcc ggaagcataa agtgtaaagc ctggggtgcc    2760
taatgagtga gctaactcac attaattgcg ttgcgctcac tgcccgcttt ccagtcggga    2820
aacctgtcgt gccagctgca ttaatgaatc ggccaacgcg cggggagagg cggtttgcgt    2880
attgggcgct cttccgcttc ctcgctcact gactcgctgc gctcggtcgt tcggctgcgg    2940
cgagcggtat cagctcactc aaaggcggta atacggttat ccacagaatc aggggataac    3000
gcaggaaaga acatgtgagc aaaaggccag caaaaggcca ggaaccgtaa aaaggccgcg    3060
ttgctggcgt ttttccatag gctccgcccc cctgacgagc atcacaaaaa tcgacgctca    3120
agtcagaggt ggcgaaaccc gacaggacta taaagatacc aggcgtttcc ccctggaagc    3180
tccctcgtgc gctctcctgt tccgaccctg ccgcttaccg gatacctgtc cgcctttctc    3240
ccttcgggaa gcgtggcgct ttctcatagc tcacgctgta ggtatctcag ttcggtgtag    3300
gtcgttcgct ccaagctggg ctgtgtgcac gaaccccccg ttcagcccga ccgctgcgcc    3360
ttatccggta actatcgtct tgagtccaac ccggtaagac acgacttatc gccactggca    3420
gcagccactg gtaacaggat tagcagagcg aggtatgtag gcggtgctac agagttcttg    3480
aagtggtggc ctaactacgg ctacactaga aggacagtat ttggtatctg cgctctgctg    3540
aagccagtta ccttcggaaa aagagttggt agctcttgat ccggcaaaca aaccaccgct    3600
ggtagcggtg gtttttttgt ttgcaagcag cagattacgc gcagaaaaaa aggatctcaa    3660
gaagatcctt tgatcttttc tacggggtct gacgctcagt ggaacgaaaa ctcacgttaa    3720
gggattttgg tcatgagatt atcaaaaagg atcttcacct agatcctttt aaattaaaaa    3780
tgaagtttta aatcaatcta agtatatat gagtaaactt ggtctgacag ttaccaatgc    3840
```

```
ttaatcagtg aggcacctat ctcagcgatc tgtctatttc gttcatccat agttgcctga   3900
ctccccgtcg tgtagataac tacgatacgg gagggcttac catctggccc cagtgctgca   3960
atgataccgc gagacccacg ctcaccggct ccagatttat cagcaataaa ccagccagcc   4020
ggaagggcca agcgcagaag tggtcctgca actttatccg cctccatcca gtctattaat   4080
tgttgccggg aagctagagt aagtagttcg ccagttaata gtttgcgcaa cgttgttgcc   4140
attgctacag gcatcgtggt gtcacgctcg tcgtttggta tggcttcatt cagctccggt   4200
tcccaacgat caaggcgagt tacatgatcc cccatgttgt gcaaaaaagc ggttagctcc   4260
ttcggtcctc cgatcgttgt cagaagtaag ttggccgcag tgttatcact catggttatg   4320
gcagcactgc ataattctct tactgtcatg ccatccgtaa gatgcttttc tgtgactggt   4380
gagtactcaa ccaagtcatt ctgagaatag tgtatgcggc gaccgagttg ctcttgcccg   4440
gcgtcaatac gggataatac cgcgccacat agcagaactt taaaagtgct catcattgga   4500
aaacgttctt cggggcgaaa actctcaagg atcttaccgc tgttgagatc cagttcgatg   4560
taacccactc gtgcacccaa ctgatcttca gcatctttta ctttcaccag cgtttctggg   4620
tgagcaaaaa caggaaggca aaatgccgca aaaaagggaa taaggcgac acggaaatgt    4680
tgaatactca tactcttcct ttttcaatat tattgaagca tttatcaggg ttattgtctc   4740
atgagcggat acatatttga atgtatttag aaaataaac aaatagggggt ccgcgcaca    4800
tttccccgaa aagtgccacc tgacgcgccc tgtagcggcg cattaagcgc ggcgggtgtg   4860
gtggttacgc gcagcgtgac cgctacactt gccagcgccc tagcgcccgc tcctttcgct   4920
ttcttccctt cctttctcgc cacgttcgcc ggctttcccc gtcaagctct aaatcggggg   4980
ctccctttag ggttccgatt tagtgcttta cggcacctcg accccaaaaa acttgattag   5040
ggtgatggtt cacgtagtgg gccatcgccc tgatagacgg ttttcgccc tttgacgttg    5100
gagtccacgt tctttaatag tggactcttg ttccaaactg gaacaacact caaccctatc   5160
tcggtctatt cttttgattt ataagggatt ttgccgattt cggcctattg gttaaaaaat   5220
gagctgattt aacaaaaatt taacgcgaat tttaacaaaa tattaacgct tacaatttcc   5280
attcgccatt caggctgcgc aactgttggg aagggcgatc ggtgcgggcc tcttcgctat   5340
tacgccagct ggcgaaaggg ggatgtgctg caaggcgatt aagttgggta acgccaggt    5400
tttcccagtc acgacgttgt aaaacgacgg ccagtgaatt gtaatacgac tcactatagg   5460
gcgaattggg taccgggccc ccctcgagg tcgatggtgt cgataagctt gatatcgaat    5520
tcatgtcaca caaaccgatc ttcgcctcaa ggaaacctaa ttctacatcc gagagactgc   5580
cgagatccag tctacactga ttaattttcg ggccaataat ttaaaaaaat cgtgttatat   5640
aatattatat gtattatata tacatcat gatgatactg acagtcatgt cccattgcta    5700
aatagacaga ctccatctgc cgcctccaac tgatgttctc aatatttaag gggtcatctc   5760
gcattgttta ataataaaca gactccatct accgcctcca aatgatgttc tcaaaatata   5820
ttgtatgaac ttatttttat tacttagtat tattagacaa cttacttgct ttatgaaaaa   5880
cacttcctat ttaggaaaca atttataatg gcagttcgtt catttaacaa tttatgtaga   5940
ataaatgtta taaatgcgta tgggaaatct taaaatatgga tagcataaat gatatctgca   6000
ttgcctaatt cgaaatcaac agcaacgaaa aaaatcccct gtacaacata aatagtcatc   6060
gagaaatatc aactatcaaa gaacagctat tcacacgtta ctattgagat tattattgga   6120
cgagaatcac acactcaact gtctttctct cttctagaaa tacaggtaca agtatgtact   6180
```

```
attctcattg ttcatacttc tagtcatttc atcccacata ttccttggat ttctctccaa    6240
tgaatgacat tctatcttgc aaattcaaca attataataa gatataccaa agtagcggta    6300
tagtggcaat caaaaagctt ctctggtgtg cttctcgtat ttatttttat tctaatgatc    6360
cattaaaggt atatatttat ttcttgttat ataatccttt tgtttattac atgggctgga    6420
tacataaagg tattttgatt taattttttg cttaaattca atccccccctc gttcagtgtc    6480 aactgtaatg gtaggaaatt accatacttt tgaagaagca aaaaaaatga aagaaaaaaa    6540
aaatcgtatt tccaggttag acgttccgca gaatctagaa tgcggtatgc ggtacattgt    6600
tcttcgaacg taaaagttgc gctccctgag atattgtaca ttttgctttt tacaagtaca    6660
agtacatcgt acaactatgt actactgttg atgcatccac aacagtttgt tttgtttttt    6720
tttgtttttt ttttttctaa tgattcatta ccgctatgta tacctacttg tacttgtagt    6780
aagccgggtt attggcgttc aattaatcat agacttatga atctgcacgg tgtgcgctgc    6840
gagttacttt tagcttatgc atgctacttg ggtgtaatat tgggatctgt tcggaaatca    6900
acggatgctc aaccgatttc gacagtaata atttgaatcg aatcggagcc taaaatgaac    6960
ccgagtatat ctcataaaat tctcggtgag aggtctgtga ctgtcagtac aaggtgcctt    7020
cattatgccc tcaaccttac catacctcac tgaatgtagt gtacctctaa aaatgaaata    7080
cagtgccaaa agccaaggca ctgagctcgt ctaacggact tgatatacaa ccaattaaaa    7140
caaatgaaaa gaaatacagt tctttgtatc atttgtaaca attaccctgt acaaactaag    7200
gtattgaaat cccacaatat tcccaaagtc caccccttct caaattgtca tgcctacaac    7260
tcatatacca agcactaacc taccaaacac cactaaaacc ccacaaaata tatcttaccg    7320
aatatacagt aacaagctac caccacactc gttgggtgca gtcgccagct taaagatatc    7380
tatccacatc agccacaact ccccttcctttt aataaaccga ctacacccctt ggctattgag    7440 gttatgagtg aatatactgt agacaagaca ctttcaagaa gactgtttcc aaaacgtacc    7500
actgtcctcc actacaaaca cacccaatct gcttcttcta gtcaaggttg ctacaccggt    7560
aaattataaa tcatcatttc attagcaggg cagggcccctt tttatagagt cttatacact    7620 agcggacccct gccggtagac caacccgcag gcgcgtcagt ttgctccttc catcaatgcg    7680
tcgtagaaac gacttactcc ttcttgagca gctccttgac cttgttggca acaagtctcc    7740
gacctcggag gtgaggaag agcctccgat atcggcggta gtgataccag cctcgacgga    7800
ctccttgacg gcagcctcaa cagcgtcacc ggcgggcttc atgttaagag agaacttgag    7860
catcatggcg gcagacagaa tggtggcaat ggggttgacc ttctgcttgc cgagatcggg    7920
ggcagatccg tgacagggct cgtacagacc gaacgcctcg ttggtgtcgg gcagagaagc    7980
cagagaggcg gagggcagca gacccagaga accggggatg acggaggcct cgtcggagat    8040
gatatcgcca aacatgttgg tggtgatgat gataccattc atcttggagg gctgcttgat    8100
gaggatcatg gcggccgagt cgatcagctg gtggttgagc tcgagctggg ggaattcgtc    8160
cttgaggact cgagtgacag tctttcgcca agtcgagag gaggccagca cgttggcctt    8220
gtcaagagac cacacgggaa gagggggggtt gtgctgaagg gccaggaagg cggccattcg    8280
ggcaattcgc tcaacctcag gaacggagta ggtctcggtg tcgaagcga cgccagatcc    8340 gtcatcctcc tttcgctctc caaagtagat acctccgacg agctctcgga caatgatgaa    8400
gtcggtgccc tcaacgtttc ggatggggga gagatcggcg agcttgggcg acagcagctg    8460
gcagggtcgc aggttggcgt acaggttcag gtcctttcgc agcttgagga gaccctgctc    8520
gggtcgcacg tcggttcgtc cgtcgggagt ggtccatacg gtgttggcag cgcctccgac    8580
```

```
agcaccgagc ataatagagt cagcctttcg gcagatgtcg agagtagcgt cggtgatggg    8640
ctcgccctcc ttctcaatgg cagctcctcc aatgagtcgg tcctcaaaca caaactcggt    8700
gccggaggcc tcagcaacag acttgagcac cttgacggcc tcggcaatca cctcggggcc    8760
acagaagtcg ccgccgagaa gaacaatctt cttggagtca gtcttggtct tcttagtttc    8820
gggttccatt gtggatgtgt gtggttgtat gtgtgatgtg gtgtgtggag tgaaaatctg    8880
tggctggcaa acgctcttgt atatatacgc acttttgccc gtgctatgtg gaagactaaa    8940
cctccgaaga ttgtgactca ggtagtgcgg tatcggctag ggacccaaac cttgtcgatg    9000
ccgatagcgc tatcgaacgt accccagccg gccgggagta tgtcggaggg gacatacgag    9060
atcgtcaagg gtttgtggcc aactggtatt taaatgatg                           9099
```

<210> SEQ ID NO 99
<211> LENGTH: 40
<212> TYPE: DNA
<213> ORGANISM: Artificial Sequence
<220> FEATURE:
<223> OTHER INFORMATION: Primer 633

<400> SEQUENCE: 99

```
ctgtttggca ccggtctgtg gattcttgcc cacgagtgtg                            40
```

<210> SEQ ID NO 100
<211> LENGTH: 40
<212> TYPE: DNA
<213> ORGANISM: Artificial Sequence
<220> FEATURE:
<223> OTHER INFORMATION: Primer 634

<400> SEQUENCE: 100

```
cacactcgtg ggcaagaatc cacagaccgg tgccaaacag                            40
```

<210> SEQ ID NO 101
<211> LENGTH: 6267
<212> TYPE: DNA
<213> ORGANISM: Artificial Sequence
<220> FEATURE:
<223> OTHER INFORMATION: Plasmid pY137

<400> SEQUENCE: 101

```
taactttggc cggcctttac ctgcaggata acttcgtata atgtatgcta tacgaagtta     60
tgaattctgt aatattggga tctgttcgga aatcaacgga tgctcaaccg atttcgacag    120
taataatttg aatcgaatcg gagcctaaaa tgaacccgag tatatctcat aaaattctcg    180
gtgagaggtc tgtgactgtc agtacaaggt gccttcatta tgccctcaac cttaccatac    240
ctcactgaat gtagtgtacc tctaaaaatg aaatacagtg ccaaaagcca aggcactgag    300
ctcgtctaac ggacttgata tacaaccaat taaacaaat gaaagaaat acagttcttt      360 gtatcatttg taacaattac cctgtacaaa ctaaggtatt gaaatcccac aatattccca    420
aagtccaccc ctttccaaat tgtcatgcct acaactcata taccaagcac taacctacca    480
aacaccacta aaaccccaca aaatatatct taccgaatat acagtaacaa gctaccacca    540
cactcgttgg gtgcagtcgc cagcttaaag atatctatcc acatcagcca caactcccct    600
cctttaataa accgactaca cccttggcta ttgaggttat gagtgaatat actgtagaca    660
agacactttc aagaagactg tttccaaaac gtaccactgt cctccactac aaacacaccc    720
aatctgcttc ttctagtcaa ggttgctaca ccggtaaatt ataaatcatc atttcattag    780
```

```
cagggcaggg ccctttttat agagtcttat acactagcgg accctgccgg tagaccaacc   840
cgcaggcgcg tcagtttgct ccttccatca atgcgtcgta gaaacgactt actccttctt   900
gagcagctcc ttgaccttgt tggcaacaag tctccgacct cggaggtgga ggaagagcct   960
ccgatatcgg cggtagtgat accagcctcg acggactcct tgacggcagc ctcaacagcg  1020
tcaccggcgg gcttcatgtt aagagagaac ttgagcatca tggcggcaga cagaatggtg  1080
gcaatggggt tgaccttctg cttgccgaga tcggggcag atccgtgaca gggctcgtac  1140
agaccgaacg cctcgttggt gtcgggcaga gaagccagag aggcggaggg cagcagaccc  1200
agagaaccgg ggatgacgga ggcctcgtcg gagatgatat cgccaaacat gttggtggtg  1260
atgatgatac cattcatctt ggagggctgc ttgatgagga tcatggcggc cgagtcgatc  1320
agctggtggt tgagctcgag ctgggggaat tcgtccttga ggactcgagt gacagtcttt  1380
cgccaaagtc gagaggaggc cagcacgttg gccttgtcaa gagaccacac gggaagaggg  1440
gggttgtgct gaagggccag gaaggcggcc attcgggcaa ttcgctcaac ctcaggaacg  1500
gagtaggtct cggtgtcgga agcgacgcca gatccgtcat cctcctttcg ctctccaaag  1560
tagataccctc cgacgagctc tcggacaatg atgaagtcgg tgccctcaac gtttcggatg  1620
ggggagagat cggcgagctt gggcgacagc agctggcagg gtcgcaggtt ggcgtacagg  1680
ttcaggtcct ttcgcagctt gaggagaccc tgctcgggtc gcacgtcggt tcgtccgtcg  1740
ggagtggtcc atacggtgtt ggcagcgcct ccgacagcac cgagcataat agagtcagcc  1800
tttcggcaga tgtcgagagt agcgtcggtg atgggctcgc cctccttctc aatggcagct  1860
cctccaatga gtcggtcctc aaacacaaac tcggtgccgg aggcctcagc aacagacttg  1920
agcaccttga cggcctcggc aatcacctcg ggccacagag agtcgccgcc gagaagaaca  1980
atcttcttgg agtcagtctt ggtcttctta gtttcgggtt ccattgtgga tgtgtgtggt  2040
tgtatgtgtg atgtggtgtg tggagtgaaa atctgtggct ggcaaacgct cttgtatata  2100
tacgcacttt tgcccgtgct atgtggaaga ctaaacctcc gaagattgtg actcaggtag  2160
tgcggtatcg gctagggacc caaaccttgt cgatgccgat agcgctatcg aacgtacccc  2220
agccggccgg gagtatgtcg gaggggacat acgagatcgt caagggtttg tggccaactg  2280
gtatttaaat gatgtcgact catcgatata acttcgtata atgtatgcta tacgaagtta  2340
tcctaggtat agatctgtta ccggacagaa gtacccaag ctcaacaaat gggctgtcaa  2400
ccacttcaac cccaacgccc cgctgtttga gaagaaggac tggttcaaca tctggatctc  2460
taacgtcggt attggtatca ccatgtccgt catcgcatac tccatcaacc gatgggggcct  2520
ggcttccgtc accctctact acctgatccc ctacctgtgg gtcaaccact ggctcgtggc  2580
catcacctac ctgcagcaca ccgaccccac tctgccccac taccacgccg accagtggaa  2640
cttcacccga ggagccgccg ccaccatcga ccgagagttt ggcttcatcg gctccttctg  2700
cttccatgac atcatcgaga cccacgttct gcaccactac gtgtctcgaa ttcccttcta  2760
caacgcccga atcgccactg agaagatcaa gaaggtcatg gcaagcact accgacacga  2820
cgacaccaac ttcatcaagt ctcttttacac tgtcgcccga acctgccagt tgttgaagg  2880
taaggaaggc attcagatgt ttagaaacgt caatggagtc ggagttgctc ctgacggcct  2940
gccttctaaa ggcgcgccag ctgcattaat gaatcggcca acgcgcgggg agaggcggtt  3000
tgcgtattgg gcgctcttcc gcttcctcgc tcactgactc gctgcgctcg gtcgttcggc  3060
tgcggcgagc ggtatcagct cactcaaagg cggtaatacg ttatccaca gaatcagggg  3120
ataacgcagg aaagaacatg tgagcaaaag gccagcaaaa ggccaggaac cgtaaaaagg  3180
```

```
ccgcgttgct ggcgtttttc cataggctcc gcccccctga cgagcatcac aaaaatcgac    3240
gctcaagtca gaggtggcga acccgacag gactataaag ataccaggcg tttcccctg     3300 gaagctccct cgtgcgctct cctgttccga ccctgccgct taccggatac ctgtccgcct    3360
ttctcccttc gggaagcgtg gcgctttctc atagctcacg ctgtaggtat ctcagttcgg    3420
tgtaggtcgt tcgctccaag ctgggctgtg tgcacgaacc ccccgttcag cccgaccgct    3480
gcgccttatc cggtaactat cgtcttgagt ccaacccggt aagacacgac ttatcgccac    3540
tggcagcagc cactggtaac aggattagca gagcgaggta tgtaggcggt gctacagagt    3600
tcttgaagtg gtggcctaac tacgctaca ctagaagaac agtatttggt atctgcgctc     3660
tgctgaagcc agttaccttc ggaaaaagag ttggtagctc ttgatccggc aaacaaacca    3720
ccgctggtag cggtggtttt tttgtttgca agcagcagat tacgcgcaga aaaaaggat     3780 ctcaagaaga tcctttgatc ttttctacgg ggtctgacgc tcagtggaac gaaaactcac    3840
gttaagggat tttggtcatg agattatcaa aaaggatctt cacctagatc cttttaaatt    3900
aaaaatgaag ttttaaatca atctaaagta tatatgagta aacttggtct gacagttacc    3960
aatgcttaat cagtgaggca cctatctcag cgatctgtct atttcgttca tccatagttg    4020
cctgactccc cgtcgtgtag ataactacga tacgggaggg cttaccatct ggccccagtg    4080
ctgcaatgat accgcgagac ccacgctcac cggctccaga tttatcagca ataaaccagc    4140
cagccggaag ggccgagcgc agaagtggtc ctgcaacttt atccgcctcc atccagtcta    4200
ttaattgttg ccgggaagct agagtaagta gttcgccagt taatagtttg cgcaacgttg    4260
ttgccattgc tacaggcatc gtggtgtcac gctcgtcgtt tggtatggct tcattcagct    4320
ccggttccca acgatcaagg cgagttacat gatcccccat gttgtgcaaa aaagcggtta    4380
gctccttcgg tcctccgatc gttgtcagaa gtaagttggc cgcagtgtta tcactcatgg    4440
ttatggcagc actgcataat tctcttactg tcatgccatc cgtaagatgc ttttctgtga    4500
ctggtgagta ctcaaccaag tcattctgag aatagtgtat gcggcgaccg agttgctctt    4560
gcccggcgtc aatacgggat aataccgcgc cacatagcag aactttaaaa gtgctcatca    4620
ttggaaaacg ttcttcgggg cgaaaactct caaggatctt accgctgttg agatccagtt    4680
cgatgtaacc cactcgtgca cccaactgat cttcagcatc ttttactttc accagcgttt    4740
ctgggtgagc aaaaacagga aggcaaaatg ccgcaaaaaa gggaataagg gcgacacgga    4800
aatgttgaat actcatactc ttcctttttc aatattattg aagcatttat cagggttatt    4860
gtctcatgag cggatacata tttgaatgta tttagaaaaa taaacaaata ggggttccgc    4920
gcacatttcc ccgaaaagtg ccacctgatg cggtgtgaaa taccgcacag atgcgtaagg    4980
agaaaatacc gcatcaggaa attgtaagcg ttaatatttt gttaaaattc gcgttaaatt    5040
tttgttaaat cagctcattt tttaaccaat aggccgaaat cggcaaaatc ccttataaat    5100
caaaagaata accgagata gggttgagtg ttgttccagt ttggaacaag agtccactat    5160
taaagaacgt ggactccaac gtcaagggc gaaaaccgt ctatcagggc gatggcccac     5220
tacgtgaacc atcaccctaa tcaagttttt tggggtcgag gtgccgtaaa gcactaaatc    5280
ggaaccctaa agggagcccc cgatttagag cttgacggg aaagccggcg aacgtggcga    5340
gaaaggaagg gaagaaagcg aaaggagcgg gcgctagggc gctggcaagt gtagcggtca    5400
cgctgcgcgt aaccaccaca cccgccgcgc ttaatgcgcc gctacagggc gcgtccattc    5460
gccattcagg ctgcgcaact gttgggaagg gcgatcggtg cgggcctctt cgctattacg    5520
```

| | |
|---|---|
| ccagctggcg aaaggggqat gtgctgcaag gcgattaagt tgggtaacgc cagggttttc | 5580 |
| ccagtcacga cgttgtaaaa cgacggccag tgaattgtaa tacgactcac tatagggcga | 5640 |
| attgggcccg acgtcgcatg catggattcg accacgcaga ccaacaccgg caccggcaag | 5700 |
| gtggccgtgc agccccccac ggccttcatt aagcccattg agaaggtgtc cgagcccgtc | 5760 |
| tacgacacct ttggcaacga gttcactcct ccagactact ctatcaagga tattctggat | 5820 |
| gccattcccc aggagtgcta caagcggtcc tacgttaagt cctactcgta cgtggcccga | 5880 |
| gactgcttct ttatcgccgt ttttgcctac atggcctacg cgtacctgcc tcttattccc | 5940 |
| tcggcttccg gccgagctgt ggcctgggcc atgtactcca ttgtccaggg tctgtttggc | 6000 |
| accggtctgt gggttcttgc ccacgagtgt ggccactctg ctttctccga ctctaacacc | 6060 |
| gtcaacaacg tcaccggatg ggttctgcac tcctccatgc tggtccctta ctacgcctgg | 6120 |
| aagctgaccc actccatgca ccacaagtcc actggtcacc tcacccgtga tatggtgttt | 6180 |
| gtgcccaagg accgaaagga gtttatggag aaccgaggcg cccatgactg gtctgagctt | 6240 |
| gctgaggacg ctcccctcat gattaat | 6267 |

<210> SEQ ID NO 102
<211> LENGTH: 9570
<212> TYPE: DNA
<213> ORGANISM: Artificial Sequence
<220> FEATURE:
<223> OTHER INFORMATION: Plasmid pY117

<400> SEQUENCE: 102

| | |
|---|---|
| ggccgccacc gcggcccgag attccggcct cttcggccgc caagcgaccc gggtggacgt | 60 |
| ctagaggtac ctagcaatta acagatagtt tgccggtgat aattctctta acctcccaca | 120 |
| ctcctttgac ataacgattt atgtaacgaa actgaaattt gaccagatat tgtgtccgcg | 180 |
| gtggagctcc agcttttgtt ccctttagtg agggtttaaa cgagcttggc gtaatcatgg | 240 |
| tcatagctgt ttcctgtgtg aaattgttat ccgctcacaa ttccacacaa cgtacgagcc | 300 |
| ggaagcataa agtgtaaagc ctggggtgcc taatgagtga gctaactcac attaattgcg | 360 |
| ttgcgctcac tgcccgcttt ccagtcggga aacctgtcgt gccagctgca ttaatgaatc | 420 |
| ggccaacgcg cggggagagg cggtttgcgt attgggcgct cttccgcttc ctcgctcact | 480 |
| gactcgctgc gctcggtcgt tcggctgcgg cgagcggtat cagctcactc aaaggcggta | 540 |
| atacggttat ccacagaatc aggggataac gcaggaaaga acatgtgagc aaaaggccag | 600 |
| caaaaggcca ggaaccgtaa aaaggccgcg ttgctggcgt ttttccatag gctccgcccc | 660 |
| cctgacgagc atcacaaaaa tcgacgctca agtcagaggt ggcgaaaccc gacaggacta | 720 |
| taaagatacc aggcgtttcc ccctggaagc tccctcgtgc gctctcctgt tccgaccctg | 780 |
| ccgcttaccg gatacctgtc cgcctttctc ccttcgggaa gcgtggcgct ttctcatagc | 840 |
| tcacgctgta ggtatctcag ttcggtgtag gtcgttcgct ccaagctggg ctgtgtgcac | 900 |
| gaaccccccg ttcagcccga ccgctgcgcc ttatccggta actatcgtct tgagtccaac | 960 |
| ccggtaagac acgacttatc gccactggca gcagccactg gtaacaggat tagcagagcg | 1020 |
| aggtatgtag gcggtgctac agagttcttg aagtggtggc ctaactacgg ctacactaga | 1080 |
| aggacagtat ttggtatctg cgctctgctg aagccagtta ccttcggaaa aagagttggt | 1140 |
| agctcttgat ccggcaaaca aaccaccgct ggtagcggtg gtttttttgt ttgcaagcag | 1200 |
| cagattacgc gcagaaaaaa aggatctcaa gaagatcctt tgatcttttc tacggggtct | 1260 |
| gacgctcagt ggaacgaaaa ctcacgttaa gggattttgg tcatgagatt atcaaaaagg | 1320 |

```
atcttcacct agatccttt  aaattaaaaa tgaagttta  aatcaatcta aagtatatat   1380
gagtaaactt ggtctgacag ttaccaatgc ttaatcagtg aggcacctat ctcagcgatc   1440
tgtctatttc gttcatccat agttgcctga ctccccgtcg tgtagataac tacgatacgg   1500
gagggcttac catctggccc cagtgctgca atgataccgc gagacccacg ctcaccggct   1560
ccagatttat cagcaataaa ccagccagcc ggaagggccg agcgcagaag tggtcctgca   1620
actttatccg cctccatcca gtctattaat tgttgccggg aagctagagt aagtagttcg   1680
ccagttaata gtttgcgcaa cgttgttgcc attgctacag gcatcgtggt gtcacgctcg   1740
tcgtttggta tggcttcatt cagctccggt tcccaacgat caaggcgagt tacatgatcc   1800
cccatgttgt gcaaaaaagc ggttagctcc ttcggtcctc cgatcgttgt cagaagtaag   1860
ttggccgcag tgttatcact catggttatg gcagcactgc ataattctct tactgtcatg   1920
ccatccgtaa gatgcttttc tgtgactggt gagtactcaa ccaagtcatt ctgagaatag   1980
tgtatgcggc gaccgagttg ctcttgcccg gcgtcaatac gggataatac cgcgccacat   2040
agcagaactt taaaagtgct catcattgga aaacgttctt cggggcgaaa actctcaagg   2100
atcttaccgc tgttgagatc cagttcgatg taacccactc gtgcacccaa ctgatcttca   2160
gcatctttta ctttcaccag cgtttctggg tgagcaaaaa caggaaggca aaatgccgca   2220
aaaaagggaa taagggcgac acggaaatgt tgaatactca tactcttcct ttttcaatat   2280
tattgaagca tttatcaggg ttattgtctc atgagcggat acatatttga atgtatttag   2340
aaaaataaac aaataggggt tccgcgcaca tttccccgaa aagtgccacc tgacgcgccc   2400
tgtagcggcg cattaagcgc ggcgggtgtg gtggttacgc gcagcgtgac cgctacactt   2460
gccagcgccc tagcgcccgc tcctttcgct ttcttccctt cctttctcgc cacgttcgcc   2520
ggctttcccc gtcaagctct aaatcggggg ctccctttag ggttccgatt tagtgcttta   2580
cggcacctcg accccaaaaa acttgattag ggtgatggtt cacgtagtgg gccatcgccc   2640
tgatagacgg ttttcgccc  tttgacgttg gagtccacgt tctttaatag tggactcttg   2700
ttccaaactg gaacaacact caaccctatc tcggtctatt cttttgattt ataagggatt   2760
ttgccgattt cggcctattg gttaaaaaat gagctgattt aacaaaaatt taacgcgaat   2820
tttaacaaaa tattaacgct tacaatttcc attcgccatt caggctgcgc aactgttggg   2880
aagggcgatc ggtgcgggcc tcttcgctat tacgccagct ggcgaaaggg ggatgtgctg   2940
caaggcgatt aagttgggta acgccagggt tttcccagtc acgacgttgt aaaacgacgg   3000
ccagtgaatt gtaatacgac tcactatagg gcgaattggg taccgggccc ccctcgagg   3060
tcgatggtgt cgataagctt gatatcgaat tcatgtcaca caaaccgatc ttcgcctcaa   3120
ggaaacctaa ttctacatcc gagagactgc cgagatccag tctacactga ttaattttcg   3180
ggccaataat ttaaaaaaat cgtgttatat aatattatat gtattatata tacatcat    3240
gatgatactg acagtcatgt cccattgcta aatagacaga ctccatctgc cgcctccaac   3300
tgatgttctc aatatttaag gggtcatctc gcattgttta ataataaaca gactccatct   3360
accgcctcca aatgatgttc tcaaaatata ttgtatgaac ttatttttat tacttagtat   3420
tattagacaa cttacttgct ttatgaaaaa cacttcctat ttaggaaaca atttataatg   3480
gcagttcgtt catttaacaa tttatgtaga ataaatgtta taaatgcgta tgggaaatct   3540
taaatatgga tagcataaat gatatctgca ttgcctaatt cgaaatcaac agcaacgaaa   3600
aaaatcccctt gtacaacata aatagtcatc gagaaatatc aactatcaaa gaacagctat   3660
```

```
tcacacgtta ctattgagat tattattgga cgagaatcac acactcaact gtctttctct    3720
cttctagaaa tacaggtaca agtatgtact attctcattg ttcatacttc tagtcatttc    3780
atcccacata ttccttggat ttctctccaa tgaatgacat tctatcttgc aaattcaaca    3840
attataataa gatataccaa agtagcggta tagtggcaat caaaaagctt ctctggtgtg    3900
cttctcgtat ttattttat tctaatgatc cattaaaggt atatatttat ttcttgttat    3960
ataatccttt tgtttattac atgggctgga tacataaagg tattttgatt taattttttg    4020
cttaaattca atccccctc gttcagtgtc aactgtaatg gtaggaaatt accatacttt    4080
tgaagaagca aaaaaatga aagaaaaaaa aaatcgtatt tccaggttag acgttccgca    4140
gaatctagaa tgcggtatgc ggtacattgt tcttcgaacg taaaagttgc gctccctgag    4200
atattgtaca tttttgcttt tacaagtaca agtacatcgt acaactatgt actactgttg    4260
atgcatccac aacagtttgt tttgttttt tttgtttttt tttttctaa tgattcatta    4320 ccgctatgta tacctacttg tacttgtagt aagccgggtt attggcgttc aattaatcat    4380
agacttatga atctgcacgg tgtgcgctgc gagttacttt tagcttatgc atgctacttg    4440
ggtgtaatat tgggatctgt tcggaaatca acggatgctc aaccgatttc gacagtaatt    4500
aattaattcc ctagtcccag tgtacacccg ccgatatcgc ttaccctgca gccgattaa    4560 ggttggcaat ttttcacgtc cttgtctccg caattactca ccgggtggtt tataagattg    4620
caagcgtctt gatttgtctc tgtatactaa catgcaatcg cgactcgccc gacgggccac    4680
taacctggcc agaatctcca gatccaagta ttctcttggt ctgcgatatg tttccaacac    4740
aaaagcccct gctgcccagc cggcaactgc tgagtgagta ttccttgcca taaacgaccc    4800
agaaccactg tatagtgttt ggaagcacta gtcagaagac cagcgaaaac aggtggaaaa    4860
aactgagacg aaaagcaacg accagaaatg taatgtgtgg aaaagcgaca cacacagagc    4920
agataaagag gtgacaaata acgacaaatg aaatatcagt atcttcccac aatcactacc    4980
tctcagctgt ctgaaggtgc ggctgatata tccatcccac gtctaacgta tggagtgtga    5040
tagaatatga cgacacaagc atgagaactc gctctctatc caaccaccga aacactgtca    5100
ctacagccgt tcttgttgct ccattcgctt ttgtgattcc atgccttctc tggtgactga    5160
caacattcct tcctttttctc cagccctgtt gttatctgct catgacctac ggccactctc    5220
tatcgcatac taacatagac gatcccagcc cgctccccac ttccagggca ccgttggcaa    5280
gcctcctatc ctcaagaagg ctgaggctgc caacgctgac atggacgagt ccttcatcgg    5340
aatgtctgga ggagagatct tccacgagat gatgctgcga cacaacgtcg acactgtctt    5400
cggttacccc ggtggagcca ttctcccgt ctttgacgcc attcacaact ctgagtactt    5460
caactttgtg ctccctcgac acgagcaggg tgccggccac atggccgagg ctacgctcg    5520 agcctctggt aagcccggtg tcgttctcgt cacctctggc cccggtgcca ccaacgtcat    5580 caccccatg caggacgctc tttccgatgg taccccatg gttgtcttca ccggtcaggt    5640
cctgacctcc gttatcggca ctgacgcctt ccaggaggcc gatgttgtcg gcatctcccg    5700
atcttgcacc aagtggaacg tcatggtcaa gaacgttgct gagctccccc gacgaatcaa    5760
cgaggccttt gagattgcta cttccggccg accggtccc gttctcgtcg atctgccaa    5820 ggatgttact gctgccatcc tgcgagagcc catcccacc aagtccacca ttccctcgca    5880
ttctctgacc aacctcacct ctgccgccgc caccgagttc cagaagcagg ctatccagcg    5940
agccgccaac ctcatcaacc agtccaagaa gcccgtcctt tacgtcggac agggtatcct    6000
tggctccgag gagggtccta agctgcttaa ggagctggct gagaaggccg agattcccgt    6060
```

```
caccactact ctgcagggtc ttggtgcctt tgacgagcga gaccccaagt ctctgcacat   6120
gctcggtatg cacggttccg gctacgccaa catggccatg cagaacgctg actgtatcat   6180
tgctctcggc gcccgatttg atgaccgagt taccggctcc atccccaagt ttgccccga    6240
ggctcgagcc gctgccccttg agggtcgagg tggtattgtt cactttgaga tccaggccaa   6300
gaacatcaac aaggttgttc aggccaccga agccgttgag ggagacgtta ccgagtctgt   6360
ccgacagctc atcccctca tcaacaaggt ctctgccgct gagcgagctc cctggactga    6420
gactatccag tcctggaagc agcagttccc cttcctcttc gaggctgaag gtgaggatgg   6480
tgttatcaag ccccagtccg tcattgctct gctctctgac ctgacagaga caacaagga    6540
caagaccatc atcaccaccg tgttggtca gcatcagatg tggactgccc agcatttccg    6600
atggcgacac cctcgaacca tgatcacttc tggtggtctt ggaactatgg gttacggcct   6660
gcccgccgct atcggcgcca aggttgcccg acctgactgc gacgtcattg acatcgatgg   6720
tgacgcttct ttcaacatga ctctgaccga gctgtccacc gccgttcagt tcaacattgg   6780
cgtcaaggct attgtcctca caacgagga acagggtatg gtcacccagc tgcagtctct    6840
cttctacgag aaccgatact gccacactca tcagaagaac cccgacttca tgaagctggc   6900
cgagtccatg ggcatgaagg gtatccgaat cactcacatt gaccagctgg aggccggtct   6960
caaggagatg ctcgcataca agggcccgt gctcgttgag gttgttgtcg acaagaagat    7020
ccccgttctt cccatggttc ccgctggtaa ggctttgcat gagttccttg tctacgacgc   7080
tgacgccgag gctgcttctc gacccgatcg actgaagaat gccccgccc ctcacgtcca    7140
ccagaccacc tttgagaact aagtggaaag gaacacaagc aatccgaacc aaaaataatt   7200
ggggtcccgt gccacagag tctagtgcag acctaaaatg accacagtaa attatagctg    7260
ttattaaaca tgagattttg accaacaaga gcgtaggaat gttattagct actacttgta   7320
catacacagc atttgtttta aataatgttg cctccagggg cagtgagatc aggacccaga   7380
tccgtggcca gctctctgac ttcagaccgc ttgtacttaa gcagctcgca acactgttgt   7440
cgaggattga acttgccata ttcgattttg tggtcatgaa tccagcacac ctcatttaaa   7500
tgtagctaac ggtagcaggc gaactactgg tacatacctc ccccggaata tgtacaggca   7560
taatgcgtat ctgtgggaca tgtggtcgtt gcgccattat gtaagcagcg tgtactcctc   7620
tgactgtcca tatggtttgc tccatctcac cctcatcgtt ttcattgttc acaggcggcc   7680
acaaaaaaac tgtcttctct ccttctctct tcgccttagt ctactcggac cagttttagt   7740
ttagcttggc gccactggat aaatgagacc tcaggccttg tgatgaggag gtcacttatg   7800
aagcatgtta ggaggtgctt gtatggatag agaagcaccc aaaataataa gaataataat   7860
aaaacagggg gcgttgtcat ttcatatcgt gttttcacca tcaatacacc tccaaacaat   7920
gcccttcatg tggccagccc caatattgtc ctgtagttca actctatgca gctcgtatct   7980
tattgagcaa gtaaaactct gtcagccgat attgcccgac ccgcgacaag ggtcaacaag   8040
gtggtgtaag gccttcgcag aagtcaaaac tgtgccaaac aaacatctag agtctctttg   8100
gtgtttctcg catatatttw atcggctgtc ttacgtattt gcgcctcggt accggactaa   8160
tttcggatca tccccaatac gcttttctct tcgcagctgt aacagtgtcc atgatctatc   8220
cacctaaatg ggtcatatga ggcgtataat ttcgtggtgc tgataataat tcccatatat   8280
ttgacacaaa acttcccccc ctagacatac atctcacaat ctcacttctt gtgcttctgt   8340
cacacatctc ctccagctga cttcaactca cacctctgcc ccagttggtc tacagcggta   8400
```

| | |
|---|---|
| taaggtttct ccgcatagag gtgcaccact cctcccgata cttgtttgtg tgacttgtgg | 8460 |
| gtcacgacat atatatctac acacattgcg ccacccttg gttcttccag cacaacaaaa | 8520 |
| acacgacacg ctaaccatgg ccaatttact gaccgtacac caaaatttgc ctgcattacc | 8580 |
| ggtcgatgca acgagtgatg aggttcgcaa gaacctgatg gacatgttca gggatcgcca | 8640 |
| ggcgttttct gagcatacct ggaaaatgct tctgtccgtt tgccggtcgt gggcggcatg | 8700 |
| gtgcaagttg aataaccgga aatggtttcc cgcagaacct gaagatgttc gcgattatct | 8760 |
| tctatatctt caggcgcgcg gtctggcagt aaaaactatc cagcaacatt tgggccagct | 8820 |
| aaacatgctt catcgtcggt ccgggctgcc acgaccaagt gacagcaatg ctgtttcact | 8880 |
| ggttatgcgg cggatccgaa aagaaaacgt tgatgccggt gaacgtgcaa aacaggctct | 8940 |
| agcgttcgaa cgcactgatt tcgaccaggt tcgttcactc atggaaaata gcgatcgctg | 9000 |
| ccaggatata cgtaatctgg catttctggg gattgcttat aacaccctgt tacgtatagc | 9060 |
| cgaaattgcc aggatcaggg ttaaagatat ctcacgtact gacggtggga gaatgttaat | 9120 |
| ccatattggc agaacgaaaa cgctggttag caccgcaggt gtagagaagg cacttagcct | 9180 |
| ggggggtaact aaactggtcg agcgatggat ttccgtctct ggtgtagctg atgatccgaa | 9240 |
| taactacctg ttttgccggg tcagaaaaaa tggtgttgcc gcgccatctg ccaccagcca | 9300 |
| gctatcaact cgcgccctgg aagggatttt tgaagcaact catcgattga tttacggcgc | 9360 |
| taaggatgac tctggtcaga gatacctggc ctggtctgga cacagtgccc gtgtcggagc | 9420 |
| cgcgcgagat atggcccgcg ctggagtttc aataccggag atcatgcaag ctggtggctg | 9480 |
| gaccaatgta aatattgtca tgaactatat ccgtaacctg gatagtgaaa caggggcaat | 9540 |
| ggtgcgcctg ctggaagatg gcgattaagc | 9570 |

<210> SEQ ID NO 103
<211> LENGTH: 1260
<212> TYPE: DNA
<213> ORGANISM: Saccharomyces kluyveri

<400> SEQUENCE: 103

| | |
|---|---|
| atgtctattg aaacagtcgg atcatcgtct ggtgttgcta ttaactccaa ggcagtttcc | 60 |
| tctactgcta ctgccgttgt tcagccaaaa acagccattg ataccaatgg caacgtcttt | 120 |
| aaggttcctg actacactat taaagacatt ctttctgcta ttccaaaaga gtgctacaaa | 180 |
| agggacactt tatggtcatt acattatgtt gtcagagaca tcgctgctat tcttgttatt | 240 |
| ggctacatag gtaccaatta cattcctgtt ttattcccta cagtgcgtt gttgagaggg | 300 |
| attgcctatg cgatccaatc ctacttgatt ggtctatttg ggtttggctt gtggattttg | 360 |
| gcccatgaat gtgccactc cgcttttcg gaatccaata ctgtcaacga taccgttggc | 420 |
| tgggttttgc actcttggtg gatggttcct tacttttctt ggaagttttc acacagcaag | 480 |
| catcataaag ctactggcca tatgactagg gacatggttt tcattcctta caccaaggat | 540 |
| gagtttatca caatgaagaa gaaatcaaag cttgctgaga tcacagagga ggcacccgtg | 600 |
| atgacgcttt tcaatctgat tgctcagcag gttggaggt tacaattgta tttagctact | 660 |
| aatgctaccg ccagcctta tcctggagtc aaaaagttct tcaagtccca ttattggcca | 720 |
| acttctccag tgttcgacgc taaggacttt tggtggatca tcatgagtga tatcggtatc | 780 |
| gtatcaactc tgcttatcaa ttatttatgg taccgtgcct acggtgctca cgtcgtcctg | 840 |
| attaactggt ttatcccatg gctatggggt taaccactggt tagttttgt cactttttg | 900 |
| caacataccg atccaaccat gccgcactac gatgccgagg aatggacttt tgccaaaggt | 960 |

```
gctgctgcta ccatcgatag aaactttggc tttgttggac aacatatctt ccatgacatt   1020
atcgaaacgc atgtttaca ccattattgt agcagaattc ccttctacaa cgcacgcaaa   1080
gctacctcgg ccatcaagga ggttatgggt caacactacc gttacgaagg cgagaacatg   1140
tggaaatctc tctggaaagt tgctagatca tgtcaatatg ttgagggcga caacggtgtt   1200
agaatgttta gaaacaccaa tggcgttggt gtcaagccgg aagatggttc cagtcaatga   1260
```